US008609935B2

(12) United States Patent
Kinney et al.

(10) Patent No.: US 8,609,935 B2
(45) Date of Patent: Dec. 17, 2013

(54) SOYBEAN EVENT DP-305423-1 AND COMPOSITIONS AND METHODS FOR THE IDENTIFICATION AND/OR DETECTION THEREOF

(75) Inventors: Anthony J. Kinney, Wilmington, DE (US); Keven L. Stecca, New Castle, DE (US); Knut Meyer, Wilmington, DE (US); Kent Brink, Newark, DE (US); Robert F. Cressman, Jr., Wilmington, DE (US); Natalie N. Weber, Hockessin, DE (US); Cathy Xiaoyan Zhong, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 1237 days.

(21) Appl. No.: 11/927,884

(22) Filed: Oct. 30, 2007

(65) Prior Publication Data

US 2008/0312082 A1   Dec. 18, 2008

Related U.S. Application Data

(60) Provisional application No. 60/863,721, filed on Oct. 31, 2006, provisional application No. 60/942,676, filed on Jun. 8, 2007.

(51) Int. Cl.
*C12N 15/82* (2006.01)

(52) U.S. Cl.
USPC .......................................... 800/300; 800/281

(58) Field of Classification Search
None
See application file for complete search history.

(56) References Cited

U.S. PATENT DOCUMENTS

| 5,981,781 A | 11/1999 | Knowlton |
| 2003/0226166 A1 | 12/2003 | Falco et al. |

FOREIGN PATENT DOCUMENTS

| EP | 0 730 030 | 8/1987 |
| WO | WO 04/001001 | 12/2003 |
| WO | WO 2004/062351 | 7/2004 |
| WO | WO 2005/089198 | * 9/2005 |

OTHER PUBLICATIONS

Weising et al., Foreign Genes in Plants: Transfer, Structure, Expression, and Applications, Ann. Rev. Genet., 1988, vol. 22:421-477.
Gailliard, Degradation of Acyl Lipids: Hydrolytic and Oxidative Enzymes, The Biochemistry of Plants, 1980, vol. 4:85-116.
Mensink et al., Effect of Dietary Trans Fatty Acids on High-Density and Low-Density Lipoprotein Cholesterol Levels in Healthy Subjects, New England J. Medicine, 1990, vol. 323:439-445.
Fehr et al., Inheritance of Reduced Linolenic Acid Content in Soybean Genotypes A16 and A17, Crop Science, 1992, vol. 32:903-906.
Martin et al., Relationship Between Fatty Acid Composition of Vegetative and Reproductive Structures of Six Soybean Genotypes, Crop Science, 1985, vol. 25:1055-1058.
Heppard, E. P. et al., Developmental and Growth Temperature Regulation of Two Different Microsomal Omega-6 Desaturase Genes in Soybeans, Plant Physiol., vol. 110: 311-319, 1996.
Database Accession No. BH131218, Loftus et al., Determination of Clone End Sequences From *Entamoeba histolytica* HM1:IMSS Sheared DNA Library, Aug. 8, 2001.
Database Accession No. AQ329480, Wing et al., A BAC End Sequencing Framework to Sequence the Rice Genome, Jan. 11, 1999.
Database Accession No. AAD51498, Huber et al., Insect Resistant Cotton Plants, Tissues and Seeds That Include the MON15985 Event, Useful in Plant Insect Protection and Plant Breeding, Apr. 16, 2003.
Database Accession No. AW471666, Shoemaker et al., Public Soybean EST Project, Mar. 2, 2004.
International Search Report, PCT/US2007/022920.

* cited by examiner

*Primary Examiner* — David H Kruse

(57) ABSTRACT

Compositions and methods related to transgenic high oleic acid/ALS inhibitor-tolerant soybean plants are provided. Specifically, the present invention provides soybean plants having a DP-305423-1 event which imparts a high oleic acid phenotype and tolerance to at least one ALS-inhibiting herbicide. The soybean plant harboring the DP-305423-1 event comprises genomic/transgene junctions having at least the polynucleotide sequence of SEQ ID NO:8, 9, 14, 15, 20, 21, 83 or 84. The characterization of the genomic insertion site of the DP-305423-1 event provides for an enhanced breeding efficiency and enables the use of molecular markers to track the transgene insert in the breeding populations and progeny thereof. Various methods and compositions for the identification, detection, and use of the soybean DP-305423-1 events are provided.

11 Claims, 12 Drawing Sheets

SEQUENCE LISTING

```
<160> NUMBER OF SEQ ID NOS: 94

<210> SEQ ID NO 1
<211> LENGTH: 2924
<212> TYPE: DNA
<213> ORGANISM: Artificial
<220> FEATURE:
<223> OTHER INFORMATION: PHP19340A fragment

<400> SEQUENCE: 1
cgcgccaagc ttggatcctc gaagagaagg gttaataaca cacttttta  acatttttaa      60 cacaaatttt agttatttaa aaatttatta aaaaatttaa aataagaaga ggaactcttt     120
aaataaatct aacttacaaa atttatgatt tttaataagt tttcaccaat aaaaaatgtc     180
ataaaaatat gttaaaaagt atattatcaa tattctcttt atgataaata aaaagaaaaa     240
aaaaataaaa gttaagtgaa aatgagattg aagtgactt  aggtgtgtat aaatatatca     300
accccgccaa caatttattt aatccaaata tattgaagta tattattcca tagcctttat     360
ttatttatat atttattata taaaagcttt atttgttcta ggttgttcat gaaatatttt     420
tttggtttta tctccgttgt aagaaaatca tgtgctttgt gtcgccactc actattgcag     480 cttttttcatg cattggtcag attgacggtt gattgtattt ttgttttta tggttttgtg     540 ttatgactta agtcttcatc tctttatctc ttcatcaggt ttgatggtta cctaatatgg     600
tccatgggta catgcatggt taaattaggt ggccaacttt gttgtgaacg atagaatttt     660
tttttatatt aagtaaacta tttttatatt atgaaataat aataaaaaaa atattttatc     720
attattaaca aaatcatatt agttaatttg ttaactctat aataaaagaa atactgtaac     780
attcacatta catggtaaca tcttttccacc ctttcatttg  ttttttgttt gatgactttt    840
tttcttgttt aaatttattt cccttctttt aaatttggaa tacattatca tcatatataa     900
```

| | |
|---|---|
| actaaaatac taaaaacagg attacacaaa tgataaataa taacacaaat atttataaat | 960 |
| ctagctgcaa tatatttaaa ctagctatat cgatattgta aaataaaact agctgcattg | 1020 |
| atactgataa aaaaatatca tgtgctttct ggactgatga tgcagtatac ttttgacatt | 1080 |
| gcctttattt tattttttcag aaaagctttc ttagttctgg gttcttcatt atttgtttcc | 1140 |
| catctccatt gtgaattgaa tcatttgctt cgtgtcacaa atacatttag ctaggtacat | 1200 |
| gcattggtca gattcacggt ttattatgtc atgacttaag ttcatggtag tacattacct | 1260 |
| gccacgcatg cattatattg gttagatttg ataggcaaat ttggttgtca acaatataaa | 1320 |
| tataaataat gttttatat tacgaaataa cagtgatcaa acaaacagt tttatcttta | 1380 |
| ttaacaagat tttgtttttg tttgatgacg tttttaatg tttacgcttt cccccttctt | 1440 |
| ttgaatttag aacactttat catcataaaa tcaaatacta aaaaaattac atatttcata | 1500 |
| aataataaca caaatatttt taaaaaatct gaaataataa tgaacaatat tacatattat | 1560 |
| cacgaaaatt cattaataaa aatattatat aaataaaatg taatagtagt tatatgtagg | 1620 |
| aaaaaagtac tgcacgcata atatatacaa aaagattaaa atgaactatt ataaataata | 1680 |
| acactaaatt aatggtgaat catatcaaaa taatgaaaaa gtaaataaaa tttgtaatta | 1740 |
| acttctatat gtattacaca cacaaataat aaataatagt aaaaaaaatt atgataaata | 1800 |
| tttaccatct cataaagata tttaaaataa tgataaaaat atagattatt ttttatgcaa | 1860 |
| ctagctagcc aaaaagagaa cacgggtata tataaaaaga gtacctttaa attctactgt | 1920 |
| acttcctta ttcctgacgt ttttatatca agtggacata cgtgaagatt ttaattatca | 1980 |
| gtctaaatat ttcattagca cttaatactt ttctgtttta ttcctatcct ataagtagtc | 2040 |
| ccgattctcc caacattgct tattcacaca actaactaag aaagtcttcc atagcccccc | 2100 |
| aagcggccgc tgagtgattg ctcacgagtg tggtcaccat gccttcagca agtaccaatg | 2160 |
| ggttgatgat gttgtgggtt tgacccttca ctcaacactt ttagtccctt atttctcatg | 2220 |
| gaaaataagc catcgccgcc atcactccaa cacaggttcc cttgaccgtg atgaagtgtt | 2280 |
| tgtcccaaaa ccaaaatcca aagttgcatg gttttccaag tacttaaaca accctctagg | 2340 |
| aagggctgtt tctcttctcg tcacactcac aatagggtgg cctatgtatt tagccttcaa | 2400 |
| tgtctctggt agaccctatg atagttttgc aagccactac cacccttatg ctcccatata | 2460 |
| ttctaaccgt gagaggcttc tgatctatgt ctctgatgtt gctttgtttt ctgtgactta | 2520 |
| ctctctctac cgtgttgcaa ccctgaaagg gttggtttgg ctgctatgtg tttatggggt | 2580 |
| gcctttgctc attgtgaacg gttttcttgt gactatcaca tatttgcagc acacacactt | 2640 |
| tgccttgcct cattacgatt catcagaatg ggactggctg aagggagctt tggcaactat | 2700 |
| ggacagagat aagcggccgc gacacaagtg tgagagtact aaataaatgc tttggttgta | 2760 |
| cgaaatcatt acactaaata aaataatcaa agcttatata tgccttccgc taaggccgaa | 2820 |
| tgcaaagaaa ttggttcttt ctcgttatct tttgccactt ttactagtac gtattaatta | 2880 |
| ctacttaatc atctttgttt acggctcatt atatccgtcg acgg | 2924 |

<210> SEQ ID NO 2
<211> LENGTH: 4512
<212> TYPE: DNA
<213> ORGANISM: Artificial
<220> FEATURE:
<223> OTHER INFORMATION: PHP17752A fragment

<400> SEQUENCE: 2

| | |
|---|---|
| cgcgccaagc ttggatcccc cctcgaggtc gacggtatcg ataagcttct gcaggaattc | 60 |

```
tgagctagcg aagttcctat tccgaagttc ctattcttca aaaagtatag gaacttcaga    120
cgtcctcgag tccgtcctgt agaaacccca acccgtgaaa tcaaaaaact cgacggcctg    180
tgggcattca gtctggatcg cgaaaactgt ggaattgatc cagaattcgc tagcgaagtt    240
cctattccga agttcctatt ctctagaaag tataggaact tcagatccag aattcggtcc    300
gggccatcgt ggcctcttgc tcttcaggat gaagagctat gtttcgcgcc aagcttggat    360
cctagaacta gaaacgtgat gccacttgtt attgaagtcg attacagcat ctattctgtt    420
ttactattta aactttgcc atttctgact tttgaaaact atctctggat ttcggtatcg    480
ctttgtgaag atcgagcaaa agagacgttt tgtggacgca atggtccaaa tccgttctac    540
atgaacaaat tggtcacaat ttccactaaa agtaaataaa tggcaagtta aaaaggaat    600 atgcatttta ctgattgcct aggtgagctc aagagaagt tgaatctaca cgtctaccaa    660
ccgctaaaaa aagaaaaaca ttgaatatgt aacctgattc cattagcttt tgacttcttc    720
aacagattct ctactagat ttctaacaga aatattatta ctagcacatc attttcagtc    780
tcactacagc aaaaaatcca acggcacaat acagacaaca ggagatatca gactacagag    840
atagatagat gctactgcat gtagtaagtt aaataaaagg aaataaaat gtcttgctac    900 caaaactact acagactatg atgctcacca caggccaaat cctgcaacta ggacagcatt    960
atcttatata tattgtacaa aacaagcatc aaggaacatt tggtctaggc aatcagtacc   1020
tcgttctacc atcacctca gttatcacat ccttgaagga tccattactg gaatcatcg   1080 gcaacacatg ctcctgatgg ggcacaatga catcaagaag gtaggggcca gggtgtcca   1140 acattctctg aattgccgct ctaagctctt ccttcttcgt cactcgcgct gccggtatcc   1200
cacaagcatc agcaaacttg agcatgtttg ggaatatctc gctctcgcta gacggatctc   1260
caagataggt gtgagctcta ttggacttgt agaacctatc ctccaactga ccaccatac   1320 ccaaatgctg attgttcaac aacaatatct taactgggag attctccact cttatagtgg   1380
ccaactcctg aacattcatg atgaaactac catcccatc aatgtcaacc acaacagccc   1440
cagggttagc aacagcagca ccaatagccg caggcaatcc aaaacccatg ctccaagac   1500 cccctgaggt caaccactgc ctcggtctct tgtacttgta aaactgcgca gcccacattt   1560
gatgctgccc aaccccagta ctaacaatag catctccatt agtcaactca tcaagaacct   1620
cgatagcatg ctgcggagaa atcgcgtcct ggaatgtctt gtaacccaat ggaaacttgt   1680
gtttctgcac attaatctct tctctccaac ctccaagatc aaacttaccc tccactcctt   1740
tctcctccaa aatcatatta attcccttca aggccaactt caaatccgcg caaaccgaca   1800
cgtgcgcctg cttgttcttc ccaatctcgg cagaatcaat atcaatgtga acaatcttag   1860
ccctactagc aaaagcctca agcttcccag taacacggtc atcaaacctt accccaaagg   1920
caagcaacaa atcactattg tcaacagcat agttagcata acagtacca tgcatacca   1980 gcatctgaag ggaatattca tcaccaatag gaaaagttcc aagaccccatt aaagtgctag   2040 caacgggaat accagtgagt tcaacaaagc gcctcaattc agcactggaa ttcaaactgc   2100
caccgccgac gtagagaacg ggcttttggg cctccatgat gagtctgaca atgtgttcca   2160
attgggcctc ggcgggggc ctgggcagcc tggcgaggta accggggagg ttaacgggct   2220
cgtcccaatt aggcacggcg agttgctgct gaacgtcttt ggaatgtcg atgaggaccg   2280 gaccggggcg gccggaggtg gcgacgaaga aagcctcggc gacgacgcgg gggatgtcgt   2340
cgacgtcgag gatgaggtag ttgtgcttcg tgatggatct gctcacctcc acgatcgggg   2400
tttcttggaa ggcgtcggtg ccgatcatcc ggcgggcgac ctggcggtg atggcgacga   2460
```

```
ctgggacgct gtccattaaa gcgtcggcga ggccgctcac gaggttggtg gcgccggggc    2520
cggaggtggc aatgcagacg ccggggaggc cggaggaacg cgcgtagcct tcggcggcga    2580
agacgccgcc ctgctcgtgg cgcgggagca cgttgcggat ggcggcggag cgcgtgagcg    2640
cctggtggat ctccatcgac gcaccgccgg ggtacgcgaa caccgtcgtc acgccctgcc    2700
tctccagcgc ctccacaagg atgtccgcgc ccttgcgagg ttcgccggag gcgaaccgtg    2760
acacgaaggg ctccgtggtc ggcgcttcct tggtgaaggg cgccgccgtg ggggtttgg     2820 agatggaaca tttgattttg agagcgtggt tgggtttggt gagggtttga tgagagagag    2880
ggagggtgga tctagtaatg cgtttgggga aggtggggtg tgaagaggaa gagagaatc    2940 gggtggttct ggaagcggtg gccgccattg tgttgtgtgg catggttata cttcaaaaac    3000
tgcacaacaa gcctagagtt agtacctaaa cagtaaattt acaacagaga gcaaagacac    3060
atgcaaaaat ttcagccata aaaaagtta taatagaatt taaagcaaaa gtttcatttt      3120
ttaaacatat atacaaacaa actggatttg aaggaaggga ttaattcccc tgctcaaagt    3180
ttgaattcct attgtgacct atactcgaat aaaattgaag cctaaggaat gtatgagaaa    3240
caagaaaaca aaacaaaact acagacaaac aagtacaatt acaaaattcg ctaaaattct    3300
gtaatcacca accccatct cagtcagcac aaggcccaag gtttatttg aaataaaaaa       3360 aaagtgatt tatttctcat aagctaaaag aaagaaggc aattatgaaa tgatttcgac       3420
tagatctgaa agtcaaacgc gtattccgca gatattaaag aaagagtaga gtttcacatg    3480
gatcctagat ggacccagtt gaggaaaaag caaggcaaag caaaccgaaa gtgcaagatc    3540
cgaaattgaa ccacggaatc taggatttgg tagagggaga agaaaagtac cttgagaggt    3600
agaagagaag agaagagcag agagatatat gaacgagtgt gtcttggtct caactctgaa    3660
gcgatacgag tttagagggg agcattgagt tccaatttat agggaaaccg ggtggcaggg    3720
gtgagttaat gacggaaaag cccctaagta acgagattgg attgtgggtt agattcaacc    3780
gtttgcatcc gcggcttaga ttggggaagt cagagtgaat ctcaaccgtt gactgagttg    3840
aaaattgaat gtagcaacca attgagccaa ccccagcctt tgccctttga ttttgatttg    3900
tttgttgcat acttttttatt tgtcttctgg ttctgactct cttctctcg tttcaatgcc     3960 aggttgccta ctcccacacc actcacaaga agattctact gttagtatta aatatttttt    4020
aatgtattaa atgatgaatg cttttgtaaa cagaacaaga ctatgtctaa taagtgtctt    4080
gcaacatttt ttaagaaatt aaaaaaaata tatttattat caaaatcaaa tgtatgaaaa    4140
atcatgaata atataatttt atacattttt ttaaaaaatc ttttaatttc ttaattaata    4200
tcttaaaaat aatgattaat atttaacccca aaataattag tatgattggt aaggaagata    4260
tccatgttat gtttggatgt gagtttgatc tagagcaaag cttactagag tcgaccgatc    4320
cgtcgacggc gcgcgcgcct ctagttgaag acacgttcat gtcttcatcg taagaagaca    4380
ctcagtagtc ttcggccaga atgggccgga ccgaagcttc tgcaggaatt ctgagctagc    4440
gaagttccta ttccgaagtt cctattctct agaaagtata ggaacttcag atccactagg    4500
atccgtcgac gg                                                        4512
```

<210> SEQ ID NO 3
<211> LENGTH: 5438
<212> TYPE: DNA
<213> ORGANISM: Artificial
<220> FEATURE:
<223> OTHER INFORMATION: PHP19340 Expression Vector

<400> SEQUENCE: 3

-continued

```
ggccgcgaca caagtgtgag agtactaaat aaatgctttg gttgtacgaa atcattacac      60
taaataaaat aatcaaagct tatatatgcc ttccgctaag gccgaatgca aagaaattgg     120
ttctttctcg ttatcttttg ccacttttac tagtacgtat taattactac ttaatcatct    180
ttgtttacgg ctcattatat ccgtcgacgg cgcgcccgat catccggata tagttcctcc    240
tttcagcaaa aaacccctca agacccgttt agaggcccca aggggttatg ctagttattg    300
ctcagcggtg gcagcagcca actcagcttc ctttcgggct tgttagcag ccggatcgat     360
ccaagctgta cctcactatt cctttgccct cggacgagtg ctggggcgtc ggtttccact    420
atcggcgagt acttctacac agccatcggt ccagacggcc gcgcttctgc gggcgatttg    480
tgtacgcccg acagtcccgg ctccggatcg gacgattgcg tcgcatcgac cctgcgccca    540
agctgcatca tcgaaattgc cgtcaaccaa gctctgatag agttggtcaa gaccaatgcg    600
gagcatatac gcccggagcc gcggcgatcc tgcaagctcc ggatgcctcc gctcgaagta    660
gcgcgtctgc tgctccatac aagccaacca cggcctccag aagaagatgt tggcgacctc    720
gtattgggaa tccccgaaca tcgcctcgct ccagtcaatg accgctgtta tgcggccatt    780
gtccgtcagg acattgttgg agccgaaatc cgcgtcacg aggtgccgga cttcggggca    840
gtcctcggcc caaagcatca gctcatcgag agcctgcgcg acggacgcac tgacggtgtc    900
gtccatcaca gtttgccagt gatacacatg gggatcagca atcgcgcata tgaaatcacg    960
ccatgtagtg tattgaccga ttccttgcgg tccgaatggg ccgaacccgc tcgtctggct   1020
aagatcggcc gcagcgatcg catccatagc ctccgcgacc ggctgcagaa cagcgggcag   1080
ttcggtttca ggcaggtctt gcaacgtgac accctgtgca cggcgggaga tgcaataggt   1140
caggctctcg ctgaattccc caatgtcaag cacttccgga atcgggagcg cggccgatgc   1200
aaagtgccga taaacataac gatctttgta gaaaccatcg gcgcagctat ttacccgcag   1260
gacatatcca cgccctccta catcgaagct gaaagcacga gattcttcgc cctccgagag   1320
ctgcatcagg tcggagacgc tgtcgaactt ttcgatcaga aacttctcga cagacgtcgc   1380
ggtgagttca ggcttttcca tgggtatatc tccttcttaa agttaaacaa aattatttct   1440
agagggaaac cgttgtggtc tccctatagt gagtcgtatt aatttcgcgg gatcgagatc   1500
tgatcaacct gcattaatga atcggccaac gcgcggggag aggcggtttg cgtattgggc   1560
gctcttccgc ttcctcgctc actgactcgc tgcgctcggt cgttcggctg cggcgagcgg   1620
tatcagctca ctcaaaggcg gtaatacggt tatccacaga atcagggdat aacgcaggaa   1680
agaacatgtg agcaaaaggc cagcaaaagg ccaggaaccg taaaaaggcc gcgttgctgg   1740
cgttttccca taggctccgc cccctgacg agcatcacaa aaatcgacgc tcaagtcaga   1800
ggtggcgaaa cccgacagga ctataaagat accaggcgtt tccccctgga agctccctcg   1860
tgcgctctcc tgttccgacc ctgccgctta ccggatacct gtccgccttt ctcccttcgg   1920
gaagcgtggc gctttctcaa tgctcacgct gtaggtatct cagttcggtg taggtcgttc   1980
gctccaagct gggctgtgtg cacgaacccc ccgttcagcc cgaccgctgc gccttatccg   2040
gtaactatcg tcttgagtcc aacccggtaa gacacgactt atcgccactg gcagcagcca   2100
ctggtaacag gattagcaga gcgaggtatg taggcggtgc tacagagttc ttgaagtggt   2160
ggcctaacta cggctacact agaagaacag tatttggtat ctgcgctctg ctgaagccag   2220
ttaccttcgg aaaaagagtt ggtagctctt gatccggcaa acaaaccacc gctggtagcg   2280
gtggtttttt tgtttgcaag cagcagatta cgcgcagaaa aaaaggatct caagaagatc   2340
ctttgatctt ttctacgggg tctgacgctc agtggaacga aaactcacgt taagggattt   2400
```

-continued

```
tggtcatgac attaacctat aaaaataggc gtatcacgag gcccttcgt ctcgcgcgtt    2460 tcggtgatga cggtgaaaac ctctgacaca tgcagctccc ggagacggtc acagcttgtc    2520
tgtaagcgga tgccgggagc agacaagccc gtcagggcgc gtcagcgggt gttggcgggt    2580 gtcgggctg gcttaactat gcggcatcag agcagattgt actgagagtg caccatatgg    2640
acatattgtc gttagaacgc ggctacaatt aatacataac cttatgtatc atacacatac    2700
gatttaggtg acactataga acggcgcgcc aagcttggat cctcgaagag aagggttaat    2760
aacacacttt tttaacattt ttaacacaaa ttttagttat ttaaaaattt attaaaaaat    2820
ttaaaataag aagaggaact ctttaaataa atctaactta caaaatttat gatttttaat    2880 aagtttcac caataaaaaa tgtcataaaa atatgttaaa aagtatatta tcaatattct    2940
ctttatgata aataaaaaga aaaaaaaat aaaagttaag tgaaaatgag attgaagtga    3000
ctttaggtgt gtataaatat atcaacccg ccaacaattt atttaatcca aatatattga    3060
agtatattat tccatagcct ttatttattt atatatttat tatataaaag ctttatttgt    3120
tctaggttgt tcatgaaata ttttttggt tttatctccg ttgtaagaaa atcatgtgct    3180
ttgtgtcgcc actcactatt gcagctttt catgcattgg tcagattgac ggttgattgt    3240 attttgttt tttatggttt tgtgttatga cttaagtctt catctcttta tctcttcatc    3300
aggtttgatg gttacctaat atggtccatg ggtacatgca tggttaaatt aggtggccaa    3360
ctttgttgtg aacgatagaa ttttttttta tattaagtaa actatttta tattatgaaa    3420 taataataaa aaaatatttt tatcattatt aacaaaatca tattagttaa tttgttaact    3480
ctataataaa agaaatactg taacattcac attacatggt aacatctttc cacccttca    3540 tttgttttt gttgatgac ttttttctt gtttaaattt atttcccttc ttttaaattt    3600
ggaatacatt atcatcatat ataaactaaa atactaaaaa caggattaca caaatgataa    3660
ataataacac aaatatttat aaatctagct gcaatatatt taaactagct atatcgatat    3720
tgtaaaataa aactagctgc attgatactg ataaaaaaat atcatgtgct ttctggactg    3780
atgatgcagt atacttttga cattgccttt attttatttt tcagaaaagc tttcttagtt    3840
ctgggttctt cattatttgt ttcccatctc cattgtgaat tgaatcattt gcttcgtgtc    3900
acaaatacat ttagctaggt acatgcattg gtcagattca cggtttatta tgtcatgact    3960
taagttcatg gtagtacatt acctgccacg catgcattat attggttaga tttgataggc    4020
aaatttggtt gtcaacaata taaatataaa taatgttttt atattacgaa ataacagtga    4080 tcaaacaaa cagtttatc tttattaaca agatttgtt tttgtttgat gacgtttttt    4140
aatgtttacg ctttcccct tcttttgaat ttagaacact ttatcatcat aaaatcaaat    4200
actaaaaaaa ttacatattt cataaataat aacacaaata ttttaaaaa atctgaaata    4260 ataatgaaca atattacata ttatcacgaa aattcattaa taaaaatatt atataaataa    4320
aatgtaatag tagttatatg taggaaaaaa gtactgcacg cataatatat acaaaaagat    4380
taaaatgaac tattataaat aataacacta aattaatggt gaatcatatc aaaataatga    4440 aaagtaaat aaaatttgta attaacttct atatgtatta cacacacaaa taataaataa    4500 tagtaaaaa aattatgata aatatttacc atctcataaa gatatttaaa ataatgataa    4560
aaatatagat tattttttat gcaactagct agccaaaaag agaacacggg tatatataaa    4620
aagagtacct ttaaattcta ctgtacttcc tttattcctg acgttttat atcaagtgga    4680 catacgtgaa gattttaatt atcagtctaa atatttcatt agcacttaat acttttctgt    4740
tttattccta tcctataagt agtcccgatt ctcccaacat tgcttattca cacaactaac    4800
```

| | |
|---|---|
| taagaaagtc ttccatagcc ccccaagcgg ccgctgagtg attgctcacg agtgtggtca | 4860 |
| ccatgccttc agcaagtacc aatgggttga tgatgttgtg ggtttgaccc ttcactcaac | 4920 |
| acttttagtc ccttatttct catggaaaat aagccatcgc cgccatcact ccaacacagg | 4980 |
| ttcccttgac cgtgatgaag tgtttgtccc aaaaccaaaa tccaaagttg catggttttc | 5040 |
| caagtactta aacaaccctc taggaagggc tgtttctctt ctcgtcacac tcacaatagg | 5100 |
| gtggcctatg tatttagcct tcaatgtctc tggtagaccc tatgatagtt ttgcaagcca | 5160 |
| ctaccaccct tatgctccca tatattctaa ccgtgagagg cttctgatct atgtctctga | 5220 |
| tgttgctttg ttttctgtga cttactctct ctaccgtgtt gcaaccctga aagggttggt | 5280 |
| ttggctgcta tgtgtttatg ggtgcctttt gctcattgtg aacggttttc ttgtgactat | 5340 |
| cacatatttg cagcacacac actttgcctt gcctcattac gattcatcag aatgggactg | 5400 |
| gctgaaggga gctttggcaa ctatggacag agataagc | 5438 |

<210> SEQ ID NO 4
<211> LENGTH: 7026
<212> TYPE: DNA
<213> ORGANISM: Artificial
<220> FEATURE:
<223> OTHER INFORMATION: PHP17752 Expression Vector

<400> SEQUENCE: 4

| | |
|---|---|
| gatccgtcga cggcgcgccc gatcatccgg atatagttcc tcctttcagc aaaaaacccc | 60 |
| tcaagacccg tttagaggcc ccaaggggtt atgctagtta ttgctcagcg gtggcagcag | 120 |
| ccaactcagc ttcctttcgg gctttgttag cagccggatc gatccaagct gtacctcact | 180 |
| attcctttgc cctcggacga gtgctggggc gtcggtttcc actatcggcg agtacttcta | 240 |
| cacagccatc ggtccagacg gccgcgcttc tgcgggcgat ttgtgtacgc ccgacagtcc | 300 |
| cggctccgga tcggacgatt gcgtcgcatc gaccctgcgc ccaagctgca tcatcgaaat | 360 |
| tgccgtcaac caagctctga tagagttggt caagaccaat gcggagcata tacgcccgga | 420 |
| gccgcggcga tcctgcaagc tccggatgcc tccgctcgaa gtagcgcgtc tgctgctcca | 480 |
| tacaagccaa ccacggcctc cagaagaaga tgttggcgac ctcgtattgg gaatccccga | 540 |
| acatcgcctc gctccagtca atgaccgctg ttatgcggcc attgtccgtc aggacattgt | 600 |
| tggagccgaa atccgcgtgc acgaggtgcc ggacttcggg gcagtcctcg gcccaaagca | 660 |
| tcagctcatc gagagcctgc gcgacggacg cactgacggt gtcgtccatc acagtttgcc | 720 |
| agtgatacac atggggatca gcaatcgcgc atatgaaatc acgccatgta gtgtattgac | 780 |
| cgattccttg cggtccgaat gggccgaacc cgctcgtctg gctaagatcg gccgcagcga | 840 |
| tcgcatccat agcctccgcg accggctgca gaacagcggg cagttcggtt tcaggcaggt | 900 |
| cttgcaacgt gacaccctgt gcacggcggg agatgcaata ggtcaggctc tcgctgaatt | 960 |
| ccccaatgtc aagcacttcc ggaatcggga gcgcggccga tgcaaagtgc cgataaacat | 1020 |
| aacgatcttt gtagaaacca tcggcgcagc tatttacccg caggacatat ccacgccctc | 1080 |
| ctacatcgaa gctgaaagca cgagattctt cgccctccga gagctgcatc aggtcggaga | 1140 |
| cgctgtcgaa cttttcgatc agaaacttct cgacagacgt cgcggtgagt tcaggctttt | 1200 |
| ccatgggtat atctccttct taaagttaaa caaaattatt tctagaggga aaccgttgtg | 1260 |
| gtctccctat agtgagtcgt attaatttcg cgggatcgag atctgatcaa cctgcattaa | 1320 |
| tgaatcggcc aacgcgcggg gagaggcggt ttgcgtattg ggcgctcttc cgcttcctcg | 1380 |
| ctcactgact cgctgcgctc ggtcgttcgg ctgcggcgag cggtatcagc tcactcaaag | 1440 |

```
gcggtaatac ggttatccac agaatcaggg gataacgcag gaaagaacat gtgagcaaaa   1500
ggccagcaaa aggccaggaa ccgtaaaaag gccgcgttgc tggcgttttt ccataggctc   1560
cgcccccctg acgagcatca caaaaatcga cgctcaagtc agaggtggcg aaacccgaca   1620
ggactataaa gataccaggc gtttccccct ggaagctccc tcgtgcgctc tcctgttccg   1680
accctgccgc ttaccggata cctgtccgcc tttctccctt cgggaagcgt ggcgctttct   1740
caatgctcac gctgtaggta tctcagttcg gtgtaggtcg ttcgctccaa gctgggctgt   1800
gtgcacgaac cccccgttca gcccgaccgc tgcgccttat ccggtaacta tcgtcttgag   1860
tccaacccgg taagacacga cttatcgcca ctggcagcag ccactggtaa caggattagc   1920
agagcgaggt atgtaggcgg tgctacagag ttcttgaagt ggtggcctaa ctacggctac   1980
actagaagga cagtatttgg tatctgcgct ctgctgaagc cagttacctt cggaaaaaga   2040
gttggtagct cttgatccgg caaacaaacc accgctggta gcggtggttt ttttgtttgc   2100
aagcagcaga ttacgcgcag aaaaaaagga tctcaagaag atcctttgat cttttctacg   2160
gggtctgacg ctcagtggaa cgaaaactca cgttaaggga ttttggtcat gacattaacc   2220
tataaaaata ggcgtatcac gaggcccttt cgtctcgcgc gtttcggtga tgacggtgaa   2280
aacctctgac acatgcagct cccggagacg gtcacagctt gtctgtaagc ggatgccggg   2340
agcagacaag cccgtcaggg cgcgtcagcg ggtgttggcg ggtgtcgggg ctggcttaac   2400
tatgcggcat cagagcagat tgtactgaga gtgcaccata tggacatatt gtcgttagaa   2460
cgcggctaca attaatacat aaccttatgt atcatacaca tacgatttag gtgacactat   2520
agaacggcgc gccaagcttg atccccccct cgaggtcgac ggtatcgata agcttctgca   2580
ggaattctga gctagcgaag ttcctattcc gaagttccta ttcttcaaaa agtataggaa   2640
cttcagacgt cctcgagtcc gtcctgtaga accccaacc cgtgaaatca aaaaactcga   2700
cggcctgtgg gcattcagtc tggatcgcga aaactgtgga attgatccag aattcgctag   2760
cgaagttcct attccgaagt tcctattctc tagaaagtat aggaacttca gatccagaat   2820
tcggtccggg ccatcgtggc ctcttgctct tcaggatgaa gagctatgtt tcgcgccaag   2880
cttggatcct agaactagaa acgtgatgcc acttgttatt gaagtcgatt acagcatcta   2940
ttctgtttta ctatttataa ctttgccatt tctgactttt gaaaactatc tctggatttc   3000
ggtatcgctt tgtgaagatc gagcaaaaga gacgttttgt ggacgcaatg gtccaaatcc   3060
gttctacatg aacaaattgg tcacaatttc cactaaaagt aaataaatgg caagttaaaa   3120
aaggaatatg cattttactg attgcctagg tgagctccaa gagaagttga atctacacgt   3180
ctaccaaccg ctaaaaaaag aaaaacattg aatatgtaac ctgattccat tagcttttga   3240
cttcttcaac agattctcta cttagatttc taacagaaat attattacta gcacatcatt   3300
ttcagtctca ctacagcaaa aaatccaacg gcacaataca gacaacagga gatatcagac   3360
tacagagata gatagatgct actgcatgta gtaagttaaa taaaaggaaa ataaaatgtc   3420
ttgctaccaa aactactaca gactatgatg ctcaccacag gccaaatcct gcaactagga   3480
cagcattatc ttatatatat tgtacaaaac aagcatcaag gaacatttgg tctaggcaat   3540
cagtacctcg ttctaccatc accctcagtt atcacatcct tgaaggatcc attactggga   3600
atcatcggca acacatgctc ctgatggggc acaatgacat caagaaggta ggggccaggg   3660
gtgtccaaca ttctctgaat tgccgctcta agctcttcct tcttcgtcac tcgcgctgcc   3720
ggtatcccac aagcatcagc aaacttgagc atgtttggga atatctcgct ctcgctagac   3780
ggatctccaa gataggtgtg agctctattg gacttgtaga acctatcctc caactgaacc   3840
```

```
accatacccca aatgctgatt gttcaacaac aatatcttaa ctgggagatt ctccactctt    3900
atagtggcca actcctgaac attcatgatg aaactaccat ccccatcaat gtcaaccaca    3960
acagccccag ggttagcaac agcagcacca atagccgcag gcaatccaaa acccatggct    4020
ccaagacccc ctgaggtcaa ccactgcctc ggtctcttgt acttgtaaaa ctgcgcagcc    4080
cacatttgat gctgcccaac cccagtacta acaatagcat ctccattagt caactcatca    4140
agaacctcga tagcatgctg cggagaaatc gcgtcctgga atgtcttgta acccaatgga    4200
aacttgtgtt tctgcacatt aatctcttct ctccaacctc caagatcaaa cttaccctcc    4260
actcctttct cctccaaaat catattaatt cccttcaagg ccaacttcaa atccgcgcaa    4320
accgacacgt gcgcctgctt gttcttccca atctcggcag aatcaatatc aatgtgaaca    4380
atcttagccc tactagcaaa agcctcaagc ttcccagtaa cacggtcatc aaaccttacc    4440
ccaaaggcaa gcaacaaatc actattgtca acagcatagt tagcataaac agtaccatgc    4500
atacccagca tctgaaggga atattcatca ccaataggaa aagttccaag acccattaaa    4560
gtgctagcaa cgggaatacc agtgagttca acaaagcgcc tcaattcagc actggaattc    4620
aaactgccac cgccgacgta gagaacgggc ttttgggcct ccatgatgag tctgacaatg    4680
tgttccaatt gggcctcggc gggggcctg gcagcctgg cgaggtaacc ggggaggtta    4740
acgggctcgt cccaattagg cacggcgagt tgctgctgaa cgtctttggg aatgtcgatg    4800
aggaccggac cggggcggcc ggaggtggcg acgaagaaag cctcggcgac dacgcggggg    4860
atgtcgtcga cgtcgaggat gaggtagttg tgcttcgtga tggatctgct cacctccacg    4920
atcggggttt cttggaaggc gtcggtgccg atcatccggc gggcgacctg gccggtgatg    4980
gcgacgactg ggacgctgtc cattaaagcg tcggcgaggc cgctcacgag gttggtggcg    5040
ccggggccgg aggtggcaat gcagacgccg gggaggccgg aggaacgcgc gtagccttcg    5100
gcggcgaaga cgccgccctg ctcgtggcgc gggagcacgt tgcggatggc ggcggagcgc    5160
gtgagcgcct ggtggatctc catcgacgca ccgccggggt acgcgaacac cgtcgtcacg    5220
ccctgcctct ccagcgcctc cacaaggatg tccgcgccct tgcgaggttc gccggaggcg    5280
aaccgtgaca cgaagggctc cgtggtcggc gcttccttgg tgaagggcgc cgccgtgggg    5340
ggtttggaga tggaacattt gattttgaga gcgtggttgg gtttggtgag ggtttgatga    5400
gagagaggga gggtggatct agtaatgcgt ttggggaagg tggggtgtga agaggaagaa    5460
gagaatcggg tggttctgga agcggtggcc gccattgtgt tgtgtggcat ggttatactt    5520
caaaaactgc acaacaagcc tagagttagt acctaaacag taaatttaca acagagagca    5580
aagacacatg caaaaatttc agccataaaa aaagttataa tagaatttaa agcaaaagtt    5640
tcatttttta aacatatata caaacaaact ggatttgaag gaagggatta attcccctgc    5700
tcaaagtttg aattcctatt gtgacctata ctcgaataaa attgaagcct aaggaatgta    5760
tgagaaacaa gaaaacaaaa caaaactaca gacaaacaag tacaattaca aaattcgcta    5820
aaattctgta atcaccaaac cccatctcag tcagcacaag gcccaaggtt tatttttgaaa   5880
taaaaaaaaa gtgattttat ttctcataag ctaaaagaaa gaaaggcaat tatgaaatga    5940
tttcgactag atctgaaagt caaacgcgta ttccgcagat attaaagaaa gagtagagtt    6000
tcacatggat cctagatgga cccagttgag gaaaaagcaa ggcaaagcaa accagaagtg    6060
caagatccga aattgaacca cggaatctag gatttggtag agggagaaga aaagtacctt    6120
gagaggtaga agagaagaga agagcagaga gatatatgaa cgagtgtgtc ttggtctcaa    6180
ctctgaagcg atacgagttt agaggggagc attgagttcc aatttatagg gaaaccgggt    6240
```

```
ggcagggtg agttaatgac ggaaaagccc ctaagtaacg agattggatt gtgggttaga    6300
ttcaaccgtt tgcatccgcg gcttagattg gggaagtcag agtgaatctc aaccgttgac    6360
tgagttgaaa attgaatgta gcaaccaatt gagccaaccc cagcctttgc cctttgattt    6420
tgatttgttt gttgcatact ttttatttgt cttctggttc tgactctctt tctctcgttt    6480
caatgccagg ttgcctactc ccacaccact cacaagaaga ttctactgtt agtattaaat    6540
attttttaat gtattaaatg atgaatgctt ttgtaaacag aacaagacta tgtctaataa    6600
gtgtcttgca acattttta agaaattaaa aaaatatat ttattatcaa atcaaatgt    6660 atgaaaaatc atgaataata taattttata cattttttta aaaatctttt taatttctta    6720
attaatatct aaaaataat gattaatatt taacccaaaa taattagtat gattggtaag    6780
gaagatatcc atgttatgtt tggatgtgag tttgatctag agcaaagctt actagagtcg    6840
accgatccgt cgacggcgcg cgcgcctcta gttgaagaca cgttcatgtc ttcatcgtaa    6900
gaagacactc agtagtcttc ggccagaatg gcccggaccg aagcttctgc aggaattctg    6960
agctagcgaa gttcctattc cgaagttcct attctctaga aagtatagga acttcagatc    7020
cactag                                                               7026

<210> SEQ ID NO 5
<211> LENGTH: 39499
<212> TYPE: DNA
<213> ORGANISM: Artificial
<220> FEATURE:
<223> OTHER INFORMATION: Contig-1

<400> SEQUENCE: 5
tccccaaaca agcttgcaag tatttgtggt ggtacctgtc tgctgccttt tatttctctt      60
acttttgttt ctattgattc ttttatttag tctaacttta agtttagtta gtgaacttac     120
ttttgttttt attggttctt ttaatttagt ccaactttaa ctttaattat tgattagtga     180
tgctcacacg gagtttgttc ttttcgtttt accacatata cttccacgta acaactttca     240
cttttcacat tgcagttttc gtcctttcac atctaaattt tgaaattcta gttaatatta     300
attaagcctc tgtgatcgac agaaaagaga atcactaatc attgtacatg gtttgagacc     360
atgagtttat aaactaattt tgaggaaatt ttttcatcat tgtacatgtt ttgtgaccat     420
gagttcaacc ctacctttac gtttaactac atgaccacat gagcgaactc gtaaattatt     480 atatttatt ttattatcat catgcactac atgaaaaaag agaattaacg ggagttttat     540
tttttaacgt tttattgttg atataataat atacatatca actagttaaa tatagtttta     600
aattattagt ttcttaaaag gattttaaaa ttgtgacttt ataaaatcgg taacaataaa     660
tcagtcattc ttgacaatat gacacaatta ttacaatgac aattttataa aattatgatt     720 gaattttgt taccagctaa aacatttaac cttta tttcg tttagtaaac aataattta     780 tatgtgcttt acataaaaga ataaaaaaat aatttaattt gatgtattta gttacattga     840
tttcactagt tgtaagagtt caagtaataa aaattgcata tcttatccct tgaagtgaga     900
aataaaaagt aaaaaaaatt ctgagtgatt ctaaagaaa tgatttttta aatcatgtta     960
atgaataaga taatacaaac aaaaataaaa acaaaaacgt aatattataa aaaatgtcat    1020
atgaacatta ttatttaaaa cgcacaaata atgtctcaat ggagttgagt tggagggatt    1080
gtctcttctt tatatttctc ttattgtgat gtagagggag tgtgctcttt cttctacttc    1140
ttttatatga tgcaatgtcc atgtgaaagc ttgaatgttc ataagtttta ttataagttt    1200
tatgtttctt tcttctccag ctaaacaacc catgttcaca gtactcttac caattttacc    1260
```

```
taatatttag gtactgaaca taacttacat taagctcctg ctatttact attgcttttc      1320 attaaaataa tttaagagaa atcatagtaa attttaacaa gtgaaaatat ttatatgtta      1380
tgaaccaatt aataattata ataaatataa tctttaagat aagttttaat tatagttttg      1440
atccctaatt aatatttaat ttttgtattt aatttataa taaatatttc ttttacgact      1500
ttagagtcat taaaaaaatt attataactt taagttgta tttaaaaaaa tgaaaaaaaa      1560
tataaaagtt ataattttt tcacgatttt agtgtaaaaa aacatgttac aaccttttag      1620
aatattaatt taaattttat cctcatattg taaatttgac aaaaaaattc ttgattggtc      1680
atttggcccc tttgggtctc atgtggtccc aaaagctttt ataccgtgtc agtttgattt      1740
tgtgttcgat aattgatttt aaatttaaaa ttgattttga atatatttct acttgtttgg      1800
tttgatgtta gagaagaatt cataattaat tttgagttca taatttctag ttaggttgaa      1860
gtaactttga ataggttttg tattggatcc aaaattttat attgaatttt aatttatttt      1920
taacttaatt ttataataaa atatttaaac ataagacaca ttaattcaaa attaatttta      1980
atcaaaatca attttactaa cacccaacca aacacacttg aacaatccat ccctcatgca      2040
aaccaacatt cattttttaa ccctttcgta tctcaggttg tgcccagtat tcatttgaat      2100
taaattggaa ctctctccaa acatgattta tttgattttt ctacttcatg tatcaattt      2160 attgttttag tttttctctt taaaatgcat tttgtaattt gtaaaaacct tcatacttct      2220 gtgaaggga taatcagttt tagcaagtag ttgtatggaa tgaaataata ttaataaact      2280
aaataatttg ccaattaaaa aagaatacac taatagaatt atatagttta tataatttag      2340
aacttacata tataattggt atgtgtatcc ccaaaagttt agaaatcata atcgcattaa      2400
attagccaaa gaaatcttgc aaatgagttt gttaattggg ttgattataa tttgcttatt      2460
tattagtata aaacaaagca aatatcatca atggagagaa tgagagggat agaaagtatg      2520
ttgtgggtga gtagaggttt ctttagccaa aaagtttgac acaaagtttc caattttcta      2580
cccgtgcaaa acgttgctat agtgtctttt gttttgcatt gacttggaag tcaatttatg      2640
caaagatgga ttcaactacc ttcccaatag cgcagaaatt aagtgcattg agagtgagag      2700
acaagcactc ctcaacttca aacatggcct catagatgac tctggcatgc tgtctacatg      2760
gagggacgat ggcaataaca gagactgttg caaatggaaa gacattcaat gcaacaatca      2820
aactggtcat gttgagatgc ttcatctccg tggtcatgat acacaatatt tgataggtgc      2880
aatcaatatc tcttcattga ttgcccttga aaatattgaa cacttggatc tcagctataa      2940 tgatttgaa gtgagtttga tttatgctat tgaacacttg caatcaatat ctcttcattg      3000
attttgaaca cttgaaaaat tccgtcattt ttactacaag cttctgggct gatgctctct      3060 gaaataatt tttcagattt gttttcattc ttatgtgacc aaagcacagc ttcaaatttg      3120
gcaactttag atgtatcacg caatcaaata aagggcaac tgccagattg ttggaaatca      3180
gtaaagcaat tactgttcct tgatttaagc agcaataaat tgtcagggaa gattcctatg      3240
tccatgggcg cccttgttaa tatggaagcc ttggttttac gaaacaatgg tttaatgggt      3300
gagttgcctt cttcttttgaa gaattgcagc agtttattta tgctggacct gagtgaaaat      3360
atgttgtcgg gtccaatacc atcatggatt ggagaaagta tgcatcaatt gataatcttg      3420
aacatgcgag gaaatcacct ctcaggaaat gtacccattc atctctgtta tttgaaccgt      3480
attcaattgt tgggatcttt caaggaataa cttgtcaagc ggaaattcca tcatgcttaa      3540
agaatttcac tgcaatgtct gaacagagca tcaactcaag tgacactatg tctcgtatat      3600
attggtataa taacacttat catgatattt atggtgttta ctcattcgga ggttatacgc      3660
```

```
ttgacataac atggatgtgg aaaggtgtgg aacgggggtt caagaatcca gagttagagc      3720
tcaagagcat tgatctttcc agtaacaatt taatgggtga aataccaaag gaggtcggat      3780
atttgcttgg gttagtttct ttgaatctat caagaaacaa tttgagtgga gaaattcctt      3840
ctcggattgg gaatttaagg tcactagaat cacttgactt gtcaagaaat cacatctctc      3900
ggagaattcc ttcttctctt tctgaaattg attatttgca aaaattagac ttgtcacaca      3960
actctctgtc tggaagaatc ccatcaggaa gacattttga aacctttgaa gcctctagtt      4020
ttgaaggaaa cattgatctt tgtggtgaac aacttaacaa aacttgtcct ggggatggag      4080
atcagacaac agaagagcat caagaaccac cagtcaaagg tgatgattca gttttctatg      4140
agggattata catcagcttg gggattggat acttcactgg attttggggc ttattagggc      4200
cattactact gtggcctcct tggagaattg cttacatcag gtttctgaac agattaacag      4260
actatttata tgtatgctta ttgtgaatgt gggaattgtt gctgatcgct ccaaggcaaa      4320
aatgtatgtt ctagatttat ttgtcaattt catggtttat gttctgactt tgttttattt      4380
tacatatatc aagaaattgc ttcactgatc aaaaagagca atatggattt cacttagagg      4440
aggccaagaa taataataat aatttaatct aattattatt taacttgaat ttttttttata      4500 ttttttacaa agaaaaaata tacaactata ttaagcataa aaacattact atctaattaa      4560
ttttatcatt tatatgaaaa taaataaata attttttttat tcctaaatac tagaaacata      4620
aactctttca aatatattat tagacatttg tagaagaaac aaatagatgc atttttaaa      4680 atgattttcc ataattataa atgtacactt acacattaca aatattttat tattatcttt      4740
aatttctttt tatctcactt tttactatca cattatatta cctattatac atacacttct      4800
cttctttttt ttttcttttt gtctccttaa gtgtcaacta agatgacatg tattattttt      4860 caatatttt tttcataaat tttaagggga ccgtaattct tttaacatgg tattttaatt      4920
acactttgtg aaaaaacttg ggggccatgg tccctgcatg tatacttcca ttttcaattt      4980
tatatgaaaa aatataattc tgtttatatc ttgtaattaa tccagcacat taattgttgt      5040
acaaaaaaat gctgattgtt gcagatgtgc tgcacgcttc tgatcagaga agaaaccatt      5100
gttggcagct acaaatgcga gataattctt tagtatagga gtttacattg ttttgtattt      5160
aagtaatgaa ctgcaaaatc ttgtttccag aaacttagta tgctattgct gtatttattg      5220
tataatatat ttgtaatgct gtttgttttt cattattgtg cttagatctg taatatctaa      5280
aatttcacca cttcatattc atcttcaaca atgctttcta ctatattctg ctagtgcagc      5340
tatacgttac tgtgaatcaa atttgtgcat gagaagaaga atgcaagata ccctatttgt      5400
tcctagttac taccagtatg tttgcatcct tgtgttagac cccttctgta catgcactta      5460
tgttttgcca aaagtagcaa gcagagcatt aaaaattgca tcaagctagt gttaggttgc      5520
tggtcttatc acattttatc tatttatctc acaattatca cgaagataga aaagggtaca      5580
tctgtaaatg aaattcacac aatgaatgct aatttgaaat tctctctctt ccgtagcacc      5640
aatatgagag tgccaattag atcccatcat ctagtcctta ttttaggaat aagtttcgta      5700
agaaaaggga aaggatcata ggtagtctca aacacaactt catttcatgc agttttgcca      5760
tttcttttgc aattttcatt tttttatttg tattctgcca tttaaattga tacacttttc      5820
taaatgttgt aaactatcaa acttctagtt ttataagaag tctgtctgca ataaatggta      5880
tcattagtaa ttagtacata ttctcactgg tatcactgaa aatatctctt ggagactaac      5940
ttttcaagat aggagtggac cacgtatggt tcatcatggg cttagcctgt caaatcatga      6000
tcatgattcg ttgaaggttc accacaagta tttacaataa atctattgca atactaattt      6060
```

```
ttcttttttc tgcagcttta ggcgaagtct ccctaattta ggaataaatg ccttaattct    6120
aatcactagt tagcaattac tctatcatca ccatccatct tatatctttt gtattctcta    6180
ttctctttcg ttttatttaa agagattctc aatcctaaaa tagtgttctc catctctagt    6240
cttcatattt ttctctatat tcaatgagat ttcgggtaaa gccagttgaa tacatttata    6300
aactaaatgt caatgttggt agtccctaat ttaggagatc gtggtgattt tgaggttgct    6360
atttatgtga ccacatggag gaattgatgg tggtatacgc agcaatattt gtttcctaga    6420
cagtagacac tatcctcaat cacctactga agacgtttga accaaaagat ttttcaaaaa    6480
aatggatatt aatcaactca acttatttat aattatgcta ctattttttt aacattcatt    6540
tttataaaat tgatgttaaa ataatgacat taaatgtata ttttctagtg ttatagaaag    6600
ggttcgacaa gctagattga gagaaattca gaatctgact tgctatttca ttgatcaagg    6660
gtcctatcat cttggctcat cggtatgctt ctctcattta aaatattcag aatatgtctt    6720
tacctaaaaa tattaattaa tatgtgacac ttacacccaa ctaagaatag taaatttgtc    6780
gaagtgcttt gcacacttga aaaataaaat tattagagac atttataaag acatgacaat    6840
ataatgaatt aatggttgtt tgttagtccc tgataaaatt gagtggagct tcgagaccaa    6900
taagtatatt acaggaaatt agttaaaaga atctctcaat caattatata gttgagaatt    6960
tgatttttat ttgagtctaa taataataga atatgaatat tgtaaatgtt atagttatat    7020
aataatgata tataataa taattagaca aattatagtg tttattatat ttatactaat    7080
tgtatgagta tgaaataatg atattttgt attataatat aaagattata ttttaaataa    7140
atagcctata aattataatt ttttaaaatt tttcacatgt attaaaatat attagtactt    7200
ttaaataatg ataaaaaaaa tgatattgtc gtctttttg ttttctaact cctttaatgg    7260
gttagaaaat taaacataca atcacatcca aatttaaaag taaaaccaat gtataaactt    7320
tgaaattatt agtctttgtg gaatttttat atcaagacaa attaattaag tttacatttt    7380
ctgctcttta gccaaatgac aaatgatatt tattcatctt agttcttagt agatttttca    7440
cataatgata tcaaccctag aaagacttgg aaatactcta acctgcaagg acttttttat    7500
ttattgggga caagtgcaaa gattgtgcaa aaacattagt gtaaagataa attagtattg    7560
cattcctgat actttgacaa aataacactt catattttg gtgggtttaa ataattgttt    7620
tttgtcctta taaaattaag gatttttta ctttaatata taaagatttt tttatatatt    7680
ttagtgcttg taattttaat atttgaattt attgtttgct atcaactatc aataggttac    7740
tgattatgta agagtgatgt tggtagttca ttgtcctctc gacaatatca atagtttgac    7800
atggtattat atgtaaagtt tttggtaaat tgaattatta cattttcata tgtttaaaat    7860
aattgatgat gttagattaa ccgatgagaa atttaaaaaa acataattta ctaaaaataa    7920
ttgcatatta tttattgtta aaatttttat aagttaatta acggttaatg taattccatg    7980
ttatgtcgtc aattaatatt tttacttgac aataaaaact aatttttttt ttttagtttg    8040
accagcacta aaataaaaaa ctttgaaaaa ctaaagcaga aaacacacta atttatagta    8100
gctaaaatga tgtttaagcc ttgttgtgt tagttttaca tagactttt ctaagcatgg    8160 tgctcgttaa agtgacaaac tcaaatacct tttatgggca cctcacgtgt catttaatga    8220
cattacaaaa attcccttga taatgtaaaa atagaatcat atttatattt tttatttatt    8280 aaattttta catcatttt ttgtcgaatt atctgatgaa atttagtta ttacaacatg    8340 ttgctacaat atgaagtata tcttcatgaa cctgtaatta atataggaaa tcatttatt    8400 acacaattat ataattagat ttttttaat tttaaattct aatttttttc ttgaagaatg    8460
```

```
gtaagatttt gtaagagtaa ttttttaaaa accatgtctt aattaaagaa aaaaaatcaa   8520
atcacaacat ataagaaaat atttattaga cgtgattgat taacatggca gtatcaaatg   8580
aaacaagaat ggtttccctc tcatatttttt cttttaaaaa atttatatat acaggttaat   8640
taatttttta tataaatat agttatgaaa tttcttaatt aacataattt tgtatgttta    8700
agcttgttat tattttactc ctccactgct tattttctgg atatgttcat gttaattaat   8760
ccctattaaa tattttaatc cccagcatat gaacacggaa gattccagcc aaaagatata   8820
attgaacaca gggaatacca ccttttttt ttttttggtc tagaagaata ccacctgttt    8880
aagagaagat gcatctacaa gttattggtg gttttttctt cttcttatga tagcatagaa   8940
gaatattatt gtgaaaattc agaagttaat ttgtcgtatc acatgaaagt ttgaggacac   9000
aatttctgcc caaacataa gctcccatca ctatctactt catcaacaga ctacatatat    9060
gtgatatgat tctaaaaaca aaacacttat aaacagccag ttcagttaaa tccaagcaat   9120
tgttttccaa gtctgccaac ccttgaaata tgggttagaa aacacgtcca caaaatatt    9180 taaatcaaaa gaaaattaaa ggaaactcac gctgatacat tagtttgtgg aaaaattctg   9240
tcttcacttt ttccatacta gggtccgttg actgatacat cagctaatcg ctatcaagtt   9300
tccaatatat caaccaaata ttgagataaa tgccacaaaa taaaaaataa aaaagaaccc   9360
gtgcatttac attatctgaa attctttgaa tggtatctgg tccaagagaa aattccaaaa   9420
gcaaagaact cttagagctt caatagtcat tttcatgagg ttaatcgtta ctgcaatagt   9480 cttcaatag tctttctctc attttgtgtt tctcccacat gttagccttt ccctcaagcg    9540
gaagtcattt tcaatccaag aatatttcat ggtgacccctt agagcttaat cgttactgcc  9600
cccggcttgt ctagccattg ccacaatatg ttctagtatc ttgtactatt gcaacacctg   9660
caactctgct acctgacatt catgcatgaa ttcacccgtc agaaagactt ttgatgcaaa   9720
gaactctata tccatgaatc catcaacgcc atcttactcg tctaagctag tcactaagtc   9780 aaaatcattga ctctgatatc aaatttttt gaaaaatcca agagagtaaa taatagagaa   9840
atttttcaca ataggtcacc aaacaaatta cataagtaaa cttgatatca tatcttagag   9900
ttccaacact tattttttgaa taaaaaaact gtaggtggat tctagaataa ttttaatagc  9960
ataagagata ggcaaaacca aaacatagtt ttagttcaca tgtctatcct gagactgctc  10020
agcaccagat acccacttat gaaggcatat ggcagcagag taatttgaac cacatgcaat  10080
atatttcaca tgtctatcct ttaatgcttc aaccaaagcc ggtgttttac gatcttcaat  10140
atctccatga cccagtctcc catttgcacc tttcccccaa gtataaactt cattttgga   10200 tgttaataca gctacatgat atgctccaca agcaatttct tcaatcgatt ccctggcaat  10260
cttgtctccg accaagcatg gaacctttcc gtcagattga ggattccaa gctgaccata   10320 aacagtactt cccatagtga aaacacgtcc agattttgtc aggcctgctg tcaaactgtg  10380
cccacaagca attttatgaa aattggaatc aataagtgca gccacacaag ttggtttaag  10440
gcgtgcctcc ttgtccccat gtccaaggcg attttttgtct ccatcacccc aagtaaacaa  10500
tttacctgat gatatgcttg tactggagtg tgttgcgata acctctacaa cagctgcagt  10560
atgccacact ccacaagcaa cagctattgt tctcaacccc aataaggatt ctacttctct  10620
aggatatgaa acattttgcc tatctccatg gcccaagaca ccgaatgttc catcaccaaa  10680
tgtaaacagc tgccctgttg aagttaccaa ggctgtgtgc catggaccac aagcaacaaa  10740
tgcaatttga agtccctcta atggaccagc aattctcttt ggtatccaat gactgacatc  10800
actgccatga ccaagaagcc cagcattatg ggtaccatca ccccatgtat atagttcccc  10860
```

```
agccattgta acagcacagg aatggaactc accacaggca acaaaatcaa cagttgtaga    10920
agtcaatgct tcaactagac gaggttgaac cacattcttc ccaacaccat gaccaaggca    10980
tcctcctgat tcttcgcccc atgtaaaaac ttcaccttgc ctagtgacta gagaagcatg    11040
tctaacacca catgctatat gatgtacatc taaaactacg ctggattcca gtggtctggg    11100
gagaagtaca tctgccctgg ggctgacata atttacattt ttatcagcac caactttaac    11160
attttcacag gtaacctctc cccatatgta tacatccccc aaagcatcac agtcatcagg    11220
tgcagatcca tgactagatg tacttggggc actggaaaca ctgacacgaa atacatctga    11280
agcagatcct ttcacttgca tgtttgttgg gtctggtggc gcatgtgacc tttcagaaat    11340
tgtattgtca gaccgaaagg actttggtga agtatttgga agagtcacag aaatgtcagg    11400
agaacaaatg cctcgtgacg tgctagccaa acttacactt ggattatttg atgttaagtc    11460
tctgctatcc tgatattatt tgagacacag agaattgtaa gcaacttatc atgtatttca    11520
tcagtagcta tggaagcata atggcaacag caaaggtaca ggaattagga aagcttgtat    11580
aaaatcagtt caccttttca caaaaaaatc acatcatata aaataaaacc ataatcaaca    11640
caatcaccaa ttagcaaccg aagcagagaa tgagtgagag gtaatctctt tcagatataa    11700
ataaatatat aaaataaaac cacaatttat atcctttcag gttaagctgc gatctgagaa    11760
aataaatact agttttcctt agaggaaaca acaaataatc aatcttataa tggagcaaat    11820
aagttctctc cattttgatt ggttcaaaat atacactcta ttgtagcatt ttggtgtgca    11880
gacagaaaaa agaattgaaa aaacagaaca aaatgaaatg attccgcttt attttgttct    11940
tggtaccacc atctttagta gaaccaaaat gtaccacttc ttaacctcat gtctaatacc    12000
attccgtttt taaaatgcac aatacataga acaacaccca tatgttctcc cattcccttc    12060
tagcatgcct atcaaatgct gcctaaggaa aatggcatga cgactattaa cctaagacta    12120
agatctatca cctttccagc ttatagaagt agaacaactt acaagaaaca taatgtgacc    12180
aaaatgaatt taactacaaa aaccacaagt tagtatattt acattaagaa tgagaccccc    12240
atcactccat ccatcaattt tggaccgacc accttgacca gaagctatca gtgctttgag    12300
gccagcaatc cacacttctg cctcaacttt atctctgcaa atctgaatag caatacacag    12360
aaattattat aataatgaaa atacagaaaa tgaaaagaaa taatgattta gtgatgcatg    12420
aaatcacata atttgccact aaccaaatca agcgatcgct ttccgttact gtaaataagt    12480
gaaaaagaca aatagtcctt ctcaggacgc aagtaacgtt ggaaaacagc ctgccaaaag    12540
attaagggaa tgaaaacaag aacaagtaag agtaagtttg tgaaacaatt tttagatcac    12600
tttattaata acagagaatg tcaaggtatc atatgcaatt agattttaa gggaagaaat    12660
ctcacagttc tttgtccagg aataattcta gagacagaag atagcttcag atttctttct    12720
ccactacttg taatccagat taaggatgat tcatcctgca gtttacagat aacgtttata    12780
catagaaata actcaagagt ttaaaatttc aagcctacta tatataaatg ttcaactctt    12840
agtctacaat caaggaagaa tagaaaagat gcatttttat tagcattttt gaatttataa    12900
atacaaccgt aaaggcatac accaaataag aaatatgttt tccagcgata aagctacact    12960
acctctactt gttagcagta gcactaatta ctaaaataag aaaactcagc atggatatta    13020
ataaaaatct atgcaaaatc ataaagatct ggatagtaat aatactaatt aacctgaatt    13080
gtgccactat aatgcagtga acccagagaa ttcgcagtgc caactcaggt aagtaccaat    13140
tttagccaca cagtgaaatt taagtggcat ataagtaaaa gtaaaatact tcaaggtgca    13200
gtcatctatt tcctatgcat taagaagttg cagaaaatag gtataaaaag tttaggaggc    13260
```

```
tatacaatac agtcaacaca cgaaagttag ttagagatta caatttaaag ggaactccct    13320
actacaaagt gtcgaaattt caatcccgat aaagaacaaa atgacacctc atcggacgta    13380
gggcatataa aataaggaca atacaaatta acagtctttc catactatat tgctcatata    13440
gttatagcat aaaaaacatg caatatcagc tatttgtcat gagcacataa tcaatcaaga    13500
actgtccaac caggcagtta acaaagatgt gatgtagaga atccaaaaac actcttgaaa    13560
aggctttcag ttaacttaca tgggaaagtc taaatggaca aaacttgggc tttcctttac    13620
gaccatattt aagaagttga gcaccctttt tcaaagcaat caatacctgc acaatgaaaa    13680
gttacaatat aaacaccagt aaagatcaaa cagacacagc agtatatata gtcaaatgaa    13740
actaaatatg agtaacaagt taaaaaatct atattgataa ccaagatttg tatattcccc    13800
ttcatatgat gatgagtcat gagccttaca aaaaaatact caaaggcatc attttataat    13860
ctaagcactt tctcttctta caaaagatcc caaaacagga taaattgtta tgttttggaa    13920
cgagtgtttg caaacttgat tttaggtaat cttaattgtg tagaattgtt tttgttaaaa    13980
ttgattttga aataaagtga tttgtggttt aatggctggt ttatacgctg gtttaatggc    14040
aattaagctt ctaagtacta gaggggcctg ccttcaatcc cttgctagac caaaattttct    14100 ctcttgaggg cgagccctgg tgcagcggta aagttgtgcc ttggtgacct gttggtcatg    14160
ggttcgaatc cggaaacagc ctctttgcat atgcaagggt aaggctgcgt acaatatccc    14220
tcccccatac cttcgcatag cgaagagcct ctgggcaatg gggtacgaag tgtggtttat    14280
gtttgaaagt tttattgcaa aagcaaattt acagtgaaac ttaatgttaa tgctaaagct    14340
acctttttca attctagtca aacacatatt ttagtgtgtt tggaaacctg tttgcacccct   14400 tttaaacgga agtttagagc ttccaatacc aaaggtggaa gcaatctaaa gggtagattg    14460
acgttacatt gaaacaacag atttctaaat acactttgtt gttggttaag gtggtttgaa    14520
tatttgcaaa agtcactaga agaaacaata aggagagcat attgtataca ctttgttttt    14580
tagccctgtg aaaaagggta gaaggaaacc aagaaggaca aatagaggaa attgttaaga    14640
agaatctcat ggggaataat attctggaga atttggtctt taaccaaacc caatggtctt    14700
gtgcaaccta tgcaactgac ctcacctaat gggataaggc tttagttgtt gcagtcaaat    14760 acactttttag gagaaaactt tattttagat agcggaaatc aaataaggca ataattgtt     14820 aatattttaa catgattttt tgtgagtgtt aaagaaatga ttttttgtaa agtaaattac    14880
tcttttgtgc cttgagaaaa tgtttaaatt acacccccccc cacccccccct cctatcattt   14940 taaaatactc ttctcgctta aaagtgtata caatatgctc tacatttggt cattttcaat    15000
gtaaacaaac ctcttaaaag tggtaaataa ttaagaatgt gcctcccaat gatattttct    15060
cttcttttac aactttttgc gtcaccacca actaatattg actatcctat tataaacttt    15120
agtattttaa aggatagaat gaagttttaa aaacatttat tattggcttt gaaatttcac    15180
ctaatatctt tatttcatat tctaaagcta caagatttgt attagatgtt taaaattaac    15240
tattaatcat gttgagcaca aaagggaaaa aaatctctaa aaagctcatt tacattaaaa    15300
tagactcaaa tgaaacacat ttatctttca agggagggaa gcgtatcttt taaaaaaga     15360 ctggaggaga atgtaatata agcatgtacc aagagaagtg aatataattt acattttttt    15420
taagtattag tgtcctttga ttgcccagcc atatggaaga attgactcaa gtgtgtacgc    15480 tgaattttt taaaatttttt tttaattcga tacataatga ttaatgtcca acacatgaca    15540
taaaatgtca gtgttggaag catgcccaa catgtttata aaacttgcga gtaaactcct     15600
atagttgaat gggtttactt ttccacatgg atgaaatgag ttgaattgca tgaaaactca    15660
```

```
ttggttagta gacttgggtg gaattaggta aacttgggtt atacattggc gagtttgaga    15720
ttttgctgga tcacattagt ttttcccaaa ccaaaatgca acattttag cttaaaatgc     15780 tttggccaac tttggtaaaa tgattttat atgcttcacc tttaagtgta gaagctagcc     15840
caaaaacaca aatcaatctg cctcattcat tggttccttg tcatcactgt tttggtttgc    15900
tttgacataa aattagaatg attgaatatt tacaatgcat atggcattaa attatgtttt    15960 aatacttta taggcattat aaatattatt tatttattag gcatactctt gtgagtttag     16020
aagtaaggtt tacaaaagct tcacaagttt acataatctc tcgagtttga caacattgat    16080
tcccagttta gaaactccaa cacctcaagc agaagtgtcc atatttcaaa ctccgcaaga    16140
aatatagcag ataggggagga atgataatgt aagccacctt atactataag ttatgtgaaa  16200
atccataaga aatccagtac atcccaacat tgattcaatt tctatgagaa gcctatctct    16260
cttcttaata ttttgaccca aattacaggt tagagatgtt gtagtaacta cagatatttc    16320
taggtacaca gtacctgtta gtgttgtcca aaaaataaat aaacagtggc tgcgggctaa    16380
atttcactag atgaattttg atttagtcag cttctattta gaactagatc ataaaatgtt    16440
tggtcagtac aatcaaccct gtgcacaaaa gattctatga agatttaagg tactaaaaga   16500
tattaaaaat aaataacatt gatgcaagct tcaatttcct gcttgaaacg atccaagaca   16560
actataaaat gctgcactat caagatatta tctctaaaac atggtctcaa aaggcatcca    16620
ctgactaagc tgttaataat tcaaaaacaa gtcacccctc cattcaaaca caaacatgca   16680
tgcaatcata tctccaatt ccatattcca cagagcatta actcgtttag tcaactaaac    16740
cctacaaggt tcgaaaatca cacttcttat tcacaagatg aaaatgtcaa aaaaaaaaa    16800 caacgacaat acacaagtat atctctcatc tccctccaaa caagaaaag aaacacacac    16860 gcatgatcat aattcataac cttgagcatc tccaaaggta caatcaaggt ggagttgctt    16920
aactcacttt tgatggactc tataatgtca cttgagattt aagaacttca acaagttttc   16980
tccaatggtg caattcttaa gaacttaaaa taggttctac aattgtttcg cgattcttac    17040
caactgttaa aaacagttgt taatataagc aaaactacga catcaattac tccaagggtg    17100
aaattacata agaactggtt ctcaaattga agaacctcag aagcaacttc cattgaagat   17160
gctcttaacc accacaaagc aatttaacaa aaaaaaaaa aaaaagcat ttcccacatt     17220 agaacaaaaa ctaatacaaa caatcaaaat ttgaggaaaa aaattgtaac ttgccaccaa    17280
acttataact tccaacatat agaaagagag agacagagag aaagaaagaa ataccgtact    17340
tgttgttcaa tgtcacggta ggccttcccg tagctagcaa gatctgccat tccatgtgag    17400
agattcaccg acgcgccacc accctctccg atcactcgcc gcagttccgg tcatcataga    17460
aaactccaac ctcttcttct ctccacaacc attcaccctc acatgaaaac caaaacctct    17520
ctctctctct ctaaaaaacc aacaaagccc acttcgtatt ctctctctag aaccttcctg    17580
gatccgcacc tcttcgcaga acccaaaaaa aaatcccttc aactccactc acggttccaa    17640
gtcaaagacc aaaccagttt tcccgaatcg ggaaaaaac cggactttcg agcttgttga    17700
acagggctct caaaagggtc gcggtggctc gcaacgaaag agcagcttca gaaaggaaac    17760
accggcgacg aaagtgggct ccggcgggga gacagaggag agagagagaa aaaaacact    17820 gaaaggtgaa gagagagaga atcggaggat gtaaagtaca cctagtcaaa gattaagaaa    17880
gacggaaaat tgttaaaata ataaaattaa taatttagaa taatttagac ttgcgacttg    17940
gaatatgcat gcggtaaaaa aatcaatata aatcaaaaaa acattttcg agtttatttt    18000 tttttatatt tttagtgtcc gttaatttt ttaaaaaag gtattcattt tctaaaaaac      18060
```

```
tatataaaga aaatatttct ataaaaatat ttatttatca attatattct tatataaaag    18120
ttgtgcatat attcaaaatt tatgtttata attttaataa aatcaaaatt gttaatattt    18180
attaaaggga taaattaaat ttttacttaa taaatcatgt aaacattaaa aaattattcc    18240
tggtgacaag tacttgttta tttttatata ttttttcttt ggtgaaatca tgcttacttt    18300
tgtgatggga ccatttcgga tgaaaataat aattttattt atttatctat ccaatactag    18360
caaaagaaaa agaaattata cggaacaatg aaaaattgta gttgaaaaag aaaccagata    18420
acattttcta aaatacaact ctgactttt cttttaaaac tatcagttga ttaaaaagtg    18480
acataatttt gaaagatgat taatgaacaa gtaattacta gtgtgaacca agaaaaagta    18540
cttgatattg gtgatgtcac attacaagtg agatgtcatc acacaactct gacttagtta    18600
atcacaagta ctaaataaat taatccaagc ttggtactaa catacgaaat cattaagtag    18660
taattaatac gtactagtaa aagtggcaaa agataacgag aaagaaccaa tttctttgca    18720
ttcggcctta gcggaaggca tatataagct ttgattattt tatttagtgt aatgatttcg    18780
tacaaccaaa gcatttattt agtactctca cacttgtgtc gcggccgctt atctctgtcc    18840
atagttgcca aagctccctt cagccagtcc cattctgatg aatcgtaatg aggcaaggca    18900
aagtgtgtgt gctgcaaata tgtgatagtc acaagaaaac cgttcacaat gagcaaaggc    18960
accccataaa cacatagcag ccaaaccaac cctttcaggg ttgcaacacg gtagagagag    19020
taagtcacag aaaacaaagc aacatcagag acatagatca gaagcctctc acggttagaa    19080
tatatgggag cataagggtg gtagtggctt gcaaaactat cataggtct accagagaca     19140 ttgaaggcta aatacatagg ccaccctatt gtgagtgtga cgagaagaga aacagcccctt   19200 cctagagggt tgtttaagta cttggaaaac catgcaactt tggattttgg ttttgggaca    19260
aacacttcat cacggtcaag ggaacctgtg ttggagtgat ggcggcgatg gcttatttttc   19320 catgagaaat aagggactaa aagtgttgag tgaagggtca aacccacaac atcatcaacc    19380
cattggtact tgctgaaggc atggtgacca cactcgtgag caatcactca gcggccgctt    19440 gggggggctat ggaagacttt cttagttagt tgtgtgaata agcaatgttg ggagaatcgg   19500
gactacttat aggataggaa taaaacagaa aagtattaag tgctaatgaa atatttagac    19560
tgataattaa aatcttcacg tatgtccact tgatataaaa acgtcaggaa taaaggaagt    19620
acagtagaat ttaaaggtac tcttttata tatacccgtg ttctcttttt ggctagctag     19680
ttgcataaaa aataatctat atttttatca ttatttaaa tatctttatg agatggtaaa     19740
tatttatcat aatttttttt actattattt attatttgtg tgtgtaatac atatagaagt    19800
taattacaaa ttttatttac tttttcatta ttttgatatg attcaccatt aatttagtgt    19860
tattatttat aatagttcat tttaatcttt ttgtatatat tatgcgtgca gtactttttt    19920
cctacatata actactatta catttttattt atataatatt tttattaatg aattttcgtg   19980
ataatatgta atattgttca ttattatttc agatttttta aaaatatttg tgttattatt    20040
tatgaaatat gtaatttttt tagtatttga ttttatgatg ataaagtgtt ctaaattcaa    20100 aagaagggg aaagcgtaaa cattaaaaaa cgtcatcaaa caaaaacaaa atcttgttaa     20160
taaagataaa actgtttgtt ttgatcactg ttatttcgta atataaaaac attatttata    20220
tttatattgt tgacaaccaa atttgcctat caaatctaac caatataatg catgcgtggc    20280
aggtaatgta ctaccatgaa cttaagtcat gacataataa accgtgaatc tgaccaatgc    20340
atgtacctag ctaaatgtat ttgtgacacg aagcaaatga ttcaattcac aatggagatg    20400
ggaaacaaat aatgaagaac ccagaactaa gaaagctttt ctgaaaaata aaataaaggc    20460
```

```
aatgtcaaaa gtatactgca tcatcagtcc agaaagcaca tgatattttt ttatcagtat   20520
caatgcagct agttttattt tacaatatcg atatagctag tttaaatata ttgcagctag   20580
atttataaat atttgtgtta ttatttatca tttgtgtaat cctgttttta gtattttagt   20640
ttatatatga tgataatgta ttccaaattt aaaagaaggg aaataaattt aaacaagaaa   20700
aaaagtcatc aaacaaaaaa caaatgaaag ggtggaaaga tgttaccatg taatgtgaat   20760
gttacagtat ttcttttatt atagagttaa caaattaact aatatgattt tgttaataat   20820
gataaaatat ttttttatt attatttcat aatataaaaa tagtttactt aatataaaaa   20880
aaaattctat cgttcacaac aaagttggcc acctaattta accatgcatg tacccatgga   20940
ccatattagg taaccatcaa acctgatgaa gagataaaga gatgaagact aagtcataa    21000 cacaaaacca taaaaaacaa aaatacaatc aaccgtcaat ctgaccaatg catgaaaaag   21060
ctgcaatagt gagtggcgac acaaagcaca tgattttctt acaacggaga taaaaccaaa   21120
aaaatatttc atgaacaacc tagaacaaat aaagctttta tataataaat atataaataa   21180
ataaaggcta tggaataata tacttcaata tatttggatt aaataaattg ttggcggggt   21240
tgatatattt atacacacct aaagtcactt caatctcatt ttcacttaac ttttattttt   21300
tttttctttt tatttatcat aaagagaata ttgataatat acttttttaac atattttat   21360 gacatttttt attggtgaaa acttattaaa aatcataaat tttgtaagtt agatttattt   21420
aaagagttcc tcttcttatt ttaaatttt taataaattt ttaaataact aaaatttgtg   21480
ttaaaaatgt taaaaagtg tgttattaac ccttctcttc gaggatccaa gcttggcgcg   21540
ccgtcgacgg atataatgag ccgtaaacaa agatgattaa gtagtaatta atacgtacta   21600 gtaaagtgg caaaagataa cgagaaagaa ccaatttctt tgcattcggc cttagcggaa   21660
ggcatatata agctttgatt attttattta gtgtaatgat ttcgtacaac caaagcattt   21720
atttagtact ctcacacttg tgtcgcggcc gcttatctct gtccatagtt gccaaagctc   21780
ccttcagcca gtcccattct gatgaatcgt aatgaggcaa ggcaaagtgt gtgtgctgca   21840
aatatgtgat agtcacaaga aaaccgttca caatgagcaa aggcaccccca taaacacata   21900 gcagccaaac caacccttc agggttgcaa cacggtagag agagtaagtc acagaaaaca   21960
aagcaacatc agagacatag atcagaagcc tctcacggtt agaatatatg ggagcataag   22020
ggtggtagtg gcttgcaaaa ctatcatagg gtctaccaga gacattgaag gctaaataca   22080
taggccaccc tattgtgagt gtgacgagaa gagaaacagc ccttcctaga gggttgttta   22140
agtacttgga aaaccatgca actttggatt ttggttttgg gacaaacact tcatcacggt   22200
caagggaacc tgtgttggag tgatggcggc gatggcttat tttccatgag aaataaggga   22260
ctaaaagtgt tgagtgaagg gtcaaaccca caacatcatc aacccattgg tacttgctga   22320
aggcatggtg accacactcg tgagcaatca ctcagcggcc gcttgggggg ctatggaaga   22380
cttttcttag tagttgtgtg aataagcaat gttgggagaa tcgggactac ttataggata   22440
ggaataaaac agaaaagtat taagtgctaa tgaaatattt agactgataa ttaaaatctt   22500
cacgtatgtc cacttgatat aaaaacgtca ggaataaagg aagtacagta gaatttaaag   22560
gtactctttt tatatatacc cgtgttctct ttttggctag ctagttgcat aaaaaataat   22620 ctatatttt atcattattt taaatatctt tatgagatgg taaatatta tcataatttt   22680 ttttactatt atttattatt tgtgtgtgta atacatatag aagttaatta caaattttat   22740 ttacttttc attattttga tatgattcac cattaattta gtgttattat ttataatagt   22800
tcattttaat cttttttgtat atattatgcg tgcagtactt ttttcctaca tataactact   22860
```

```
attacatttt atttatataa tatttttatt aatgaattt cgtgataata tgtaatattg    22920
ttcattatta tttcagattt tttaaaaata tttgtgttat tatttatgaa atatgtaatt   22980
tttttagtat ttgattttat gatgataaag tgttctaaat tcaaagaag ggggaaagcg    23040
taaacattaa aaaacgtcat caaacaaaaa caaaatcttg ttaataaaga taaaactgtt   23100
tgttttgatc actgttattt cgtaatataa aaacattatt tatatttata ttgttgacaa   23160
ccaaatttgc ctatcaaatc taaccaatat aatgcatgcg tggcaggtaa tgtactacca   23220
tgaacttaag tcatgacata ataaaccgtg aatctgacca atgcatgtac ctagctaaat   23280
gtatttgtga cacgaagcaa atgattcaat tcacaatgga gatgggaaac aaataatgaa   23340
gaacccagaa ctaagaaagc ttttctgaaa aataaaataa aggcaatgtc aaaagtatac   23400
tgcatcatca gtccagaaag cacatgatat ttttttatca gtatcaatgc agctagtttt   23460
attttacaat atcgatatag ctagttttaaa tatattgcag ctagatttat aaatatttgt   23520
gttattattt atcatttgtg taatcctgtt tttagtattt tagtttatat atgatgataa   23580
tgtattccaa atttaaaaga agggaaataa atttaaacaa gaaaaaaagt catcaaacaa   23640
aaaacaaatg aaagggtgga aagatgttac catgtaatgt gaatgttaca gtatttcttt   23700
tattatagag ttaacaaatt aactaatatg attttgttaa taatgataaa atatttttt    23760
tattattatt tcataatata aaaatagttt acttaatata aaaaaaaatt ctatcgttca   23820
caacaaagtt ggccacctaa tttaaccatg catgtaccca tggaccatat taggtaacca   23880
tcaaacctga tgaagagata aagagatgaa gacttaagtc ataacacaaa accataaaaa   23940
acaaaaatac aatcaaccgt caatctgacc aatgcatgaa aaagctgcaa tagtgagtgg   24000
cgacacaaag cacatgattt tcttacaacg gagataaaac caaaaaaata tttcatgaac   24060
aacctagaac aaataaagct tttatataat aaatatataa ataaataaag gctatggaat   24120
aatatacttc aatatatttg gattaaataa attgttggcg gggttgatat attttataaac  24180
acctaaagtc acttcaatct cattttcact taacttttat tttttttttc tttttattta   24240
tcataaagag aatattgata atatacttt taacatattt ttatgacatt ttttattggt    24300
gaaaacttat taaaaatcat aaattttgta agttagattt atttaaagag ttcctcttct   24360
tatttttaaat ttttttaataa atttttaaat aactaaaatt tgtgttaaaa atgttaaaaa  24420
agtgtgttat taacccttct cttcgaggat ccaagcttgg cgcgccgtcg acggatccta   24480
gtggatctga agttcctata ctttctagag aataggaact tcggaatagg aacttcgcta   24540
gctcagaatt cctgcagaag cttcggtccg ggccattctg gccgaagact actgagtgtc   24600
ttcttacgat gaagacatga acgtgtcttc aactagaggc gcgcgcgccg tcgacggatc   24660
ggtcgactct agtaagcttt gctctagatc aaactcacat ccaaacataa catgggatatc  24720
ttccttacca atcatactaa ttattttggg ttaaatatta atcattattt ttaagatatt   24780
aattaagaaa ttaaaagatt ttttaaaaaa atgtataaaa ttatattatt catgattttt   24840
catacatttg attttgataa taaatatatt tttttaatt tcttaaaaaa tgttgcaaga    24900
cacttattag acatagtctt gttctgttta caaaagcatt catcatttaa tacattaaaa   24960
aatatttaat actaacagta gaatcttctt gtgagtggtg tgggagtagg caacctggca   25020
ttgaaacgag agaagagag tcagaaccag aagacaaata aaaagtatgc aacaaacaaa    25080
tcaaaatcaa agggcaaagg ctggggttgg ctcaattggt tgctacattc aattttcaac   25140
tcagtcaacg gttgagattc actctgactt ccccaatcta agccgcggat gcaaacggtt   25200
gaatctaacc cacaatccaa tctcgttact taggggcttt tccgtcatta actcacccct   25260
```

```
gccacccggt ttccctataa attggaactc aatgctcccc tctaaactcg tatcgcttca    25320
gagttgagac caagacacac tcgttcatat atctctctgc tcttctcttc tcttctacct    25380
ctcaaggtac ttttcttctc cctctaccaa atcctagatt ccgtggttca atttcggatc    25440
ttgcacttct ggtttgcttt gccttgcttt ttcctcaact gggtccatct aggatccatg    25500
tgaaactcta ctctttcttt aatatctgcg gaatacgcgt ttgactttca gatctagtcg    25560
aaatcatttc ataattgcct ttcttctttt tagcttatga gaaataaaat cactttttt    25620 ttatttcaaa ataaaccttg ggccttgtgc tgactgagat ggggtttggt gattacagaa    25680
ttttagcgaa ttttgtaatt gtacttgttt gtctgtagtt ttgttttgtt ttcttgtttc    25740
tcatacattc cttaggcttc aattttattc gagtataggt cacaatagga attcaaactt    25800
tgagcagggg aattaatccc ttccttcaaa tccagtttgt ttgtatatat gtttaaaaaa    25860
tgaaactttt gctttaaatt ctattataac tttttttatg gctgaaattt ttgcatgtgt    25920
ctttgctctc tgttgtaaat ttactgttta ggtactaact ctaggcttgt tgtgcagttt    25980
ttgaagtata accatgccac acaacacaat ggcggccacc gcttccagaa ccacccgatt    26040
ctcttcttcc tcttcacacc ccaccttccc caaacgcatt actagatcca ccctccctct    26100
ctctcatcaa accctcacca aacccaacca cgctctcaaa atcaaatgtt ccatctccaa    26160 acccccacg gcggcgccct tcaccaagga agcgccgacc acggagccct tcgtgtcacg    26220
gttcgcctcc ggcgaacctc gcaagggcgc ggacatcctt gtggaggcgc tggagaggca    26280
gggcgtgacg acggtgttcg cgtaccccgg cggtgcgtcg atggagatcc accaggcgct    26340
cacgcgctcc gccgccatcc gcaacgtgct cccgcgccac gagcagggcg gcgtcttcgc    26400
cgccgaaggc tacgcgcgtt cctccggcct cccgcggcgtc tgcattgcca cctccggccc    26460
cggcgccacc aacctcgtga gcggcctcgc cgacgcttta atggacagcg tcccagtcgt    26520
cgccatcacc ggccaggtcg cccgccggat gatcggcacc gacgccttcc aagaaacccc    26580
gatcgtggag gtgagcagat ccatcacgaa gcacaactac ctcatcctcg acgtcgacga    26640 catccccgc gtcgtcgccg aggctttctt cgtcgccacc tccggccgcc ccggtccggt    26700
cctcatcgac attcccaaag acgttcagca gcaactcgcc gtgcctaatt gggacgagcc    26760
cgttaacctc cccggttacc tcgccaggct gcccaggccc cccgccgagg cccaattgga    26820
acacattgtc agactcatca tggaggccca aaagcccgtt ctctacgtcg gcggtggcag    26880
tttgaattcc agtgctgaat tgaggcgctt tgttgaactc actggtattc ccgttgctag    26940
cactttaatg ggtcttggaa cttttcctat tggtgatgaa tattcccttc agatgctggg    27000
tatgcatggt actgtttatg ctaactatgc tgttgacaat agtgatttgt tgcttgcctt    27060 tgggtaagt tttgatgacc gtgttactgg gaagcttgag gcttttgcta gtagggctaa    27120
gattgttcac attgatattg attctgccga gattgggaag aacaagcagg cgcacgtgtc    27180
ggtttgcgcg gatttgaagt tggccttgaa gggaattaat atgatttttgg aggagaaagg    27240 agtggagggt aagtttgatc ttggaggttg gagagaagag attaatgtgc agaaacacaa    27300
gtttccattg ggttacaaga cattccagga cgcgatttct ccgcagcatg ctatcgaggt    27360
tcttgatgag ttgactaatg gagatgctat tgttagtact ggggttgggc agcatcaaat    27420
gtgggctgcg cagttttaca agtacaagag accgaggcag tggttgacct caggggtct    27480 tggagccatg ggttttggat tgcctgcggc tattggtgct gctgttgcta accctggggc    27540
tgttgtggtt gacattgatg gggatggtag tttcatcatg aatgttcagg agttggccac    27600
tataagagtg gagaatctcc cagttaagat attgttgttg aacaatcagc atttgggtat    27660
```

```
ggtggttcag ttggaggata ggttctacaa gtccaataga gctcacacct atcttggaga    27720
tccgtctagc gagagcgaga tattcccaaa catgctcaag tttgctgatg cttgtgggat    27780
accggcagcg cgagtgacga agaaggaaga gcttagagcg gcaattcaga gaatgttgga    27840
cacccctggc ccctaccttc ttgatgtcat tgtgccccat caggagcatg tgttgccgat    27900
gattcccagt aatggatcct tcaaggatgt gataactgag ggtgatggta gaacgaggta    27960
ctgattgcct agaccaaatg ttccttgatg cttgttttgt acaatatata taagataatg    28020
ctgtcctagt tgcaggattt ggcctgtggt gagcatcata gtctgtagta gttttggtag    28080
caagacattt tattttcctt ttatttaact tactacatgc agtagcatct atctatctct    28140
gtagtctgat atctcctgtt gtctgtattg tgccgttgga ttttttgctg tagtgagact    28200
gaaaatgatg tgctagtaat aatatttctg ttagaaatct aagtagagaa tctgttgaag    28260
aagtcaaaag ctaatggaat caggttacat attcaatgtt tttctttttc tagcggttgg    28320
tagacgtgta gattcaactt ctcttggagc tcacctaggc aatcagtaaa atgcatattc    28380
cttttttaac ttgccattta tttactttta gtggaaattg tgaccaattt gttcatgtag    28440
aacggatttg gaccattgcg tccacaaaac gtctcttttg ctcgatcttc acaaagcgat    28500
accgaaatcc agagatagtt ttcaaaagtc agaaatggca aagttataaa tagtaaaaca    28560
gaatagatgc tgtaatcgac ttcaataaca agtggcatca cgtttctagt tctaggatcc    28620
aagcttggcg cgaaacatag cttatcatcc tgaagagcaa gaggccacga tggcccggac    28680
cgaattctgg atctgaagtt cctatacttt ctagagaata ggaacttcgg aataggaact    28740
tcgctagcga attctggatc aattccacag ttttcgcgat ccagactgaa tgcccacagg    28800
ccgtcgagtt ttttgatttc acgggttggg gtttctacag gacggactcg aggacgtctg    28860
aagttcctat acttttgaa gaataggaac ttcggaatag gaacttcgct agctcagaat    28920
tcctgcagaa gctatcgat accgtcgacc tcgaggggg atccaagctt ggaagtatgt    28980
atacatgtac aatattgctg aaggcatggt gaccacactc gtgagcaatc actcagcggc    29040
cgcttggggg gctatggaag actttcttag ttagttgtgt gaataagcaa tgttgggaga    29100
atcgggacta cttataggat aggaataaaa cagaaaagta ttaagtgcta atgaaatatt    29160
tagactgata attaaaatct tcacgtatgt ccacttgata taaaaacgtc aggaataaag    29220
gaagtacagt agaatttaaa ggtactcttt ttatatatac ccgtgttctc tttttggcta    29280
gctagttgca taaaaaataa tctatatttt tatcattatt ttaaatatct ttatgagatg    29340
gtaaatattt atcataattt tttttactat tatttattat ttgtgtgtgt aatacatata    29400
gaagttaatt acaaatttta ttttacttttt cattatttg atatgattca ccattaattt    29460
agtgttatta tttataatag ttcattttaa tcttttgta tatattatgc gtgcagtact    29520
tttttcctac atataactac tattacattt tatttatata atattttat taatgaattt    29580 tcgtgataat atgtaatatt gttcattatt atttcagatt ttttaaaaat atttgtgtta    29640
ttatttatga aatatgtaat tttttagta tttgatttta tgatgataaa gtgttctaaa    29700
ttcaaaagaa gggggaaagc gtaaacatta aaaacgtca tcaaacaaaa acaaatcttt    29760
gttaataaag ataaaactgt ttgttttgat cactgttatt tcgtaatata aaaacattat    29820
ttatatttat attgttgaca accaaatttg cctatcaaat ctaaccaata taatgcatgc    29880
gtggcaggta atgtactacc atgaacttaa gtcatgacat aataaaccgt gaatctgacc    29940
aatgcatgta cctagctaaa tgtatttgtg acacgaagca aatgattcaa ttcacaatgg    30000
agatgggaaa caaataatga agaacccaga actaagaaag ctttttctgaa aaataaaata    30060
```

```
aaggcaatgt caaaagtata ctgcatcatc agtccagaaa gcacatgata tttttttatc   30120
agtatcaatg cagctagttt tattttacaa tatcgatata gctagtttaa atatattgca   30180
gctagattta taaatatttg tgttattatt tatcatttgt gtaatcctgt ttttagtatt   30240
ttagtttata tatgatgata atgtattcca aatttaaaag aagggaaata aatttaaaca   30300
agaaaaaaag tcatcaaaca aaaacaaat gaaagggtgg aaagatgtta ccatgtaatg    30360
tgaatgttac agtatttctt ttattataga gttaacaaat taactaatat gattttgtta   30420
ataatgataa aatatttttt ttattattat ttcataatat aaaaatagtt tacttaatat   30480
aaaaaaaaat tctatcgttc acaacaaagt tggccaccta atttaaccat gcatgtaccc   30540
atggaccata ttaggtaacc atcaaacctg atgaagagat aaagagatga agacttaagt   30600
cataacacaa aaccataaaa aacaaaaata caatcaaccg tcaatctgac caatgcatga   30660
aaaagctgca atagtgagtg gcgacacaaa gcacatgatt ttcttacaac ggagataaaa   30720
ccaaaaaaat atttcatgaa caacctagaa caaataaagc ttttatataa taaatatata   30780
aataaataaa ggctatggaa taatatactt caatatattt ggattaaata aattgttggc   30840
ggggttgata tatttataca cacctaaagt cacttcaatc tcattttcac ttaacttttta  30900 tttttttttt ctttttattt atcataaaga gaatattgat aatatacttt ttaacatatt   30960
tttatgacat tttttattgg tgaaaactta ttaaaaatca taaattttgt aagttagatt   31020
tatttaaaga gttcctcttc ttattttaaa ttttttaata aattttttaaa taactaaaat  31080 ttgtgttaaa aatgttaaaa aagtgtgtta ttaaccccttc tcttcgagga tccaagcttg  31140
gattttggtt ttgggacaaa cacttcatca cggtcaaggg aacctgtgtt ggagtgatgg   31200
cggcgatggc ttattttcca tgagaaataa gggactaaaa gtgttgagtg aagggtcaaa   31260
cccacaacat catcaaccca ttggtacttg ctgaaggcat ggtgaccaca ctcgtgagca   31320
atcactcagc ggccgcttgg ggggctatgg aagactttct tagttagttg tgtgaataag   31380
caatgttggg agaatcggga ctacttatag gataggaata aaacagaaaa gtattaagtg   31440
ctaatgaaat atttagactg ataattaaaa tcttcacgta tgtccacttg atataaaaac   31500
gtcaggaata aaggaagtac agtagaattt aaaggtactc tttttatata tacccgtgtt   31560 ctcttttttgg ctagctagtg ttttttttctc gacttttgta tgaaaatcat ttgtgtcaat  31620
agtttgtgtt atgtattcat tggtcacata aatcaacttc caaatttcaa tattaactat   31680
agcagccagg ttagaaattc agaatcatgt tactctatac gcatccttta gggcatttgg   31740
ttgagagaag aaatagatag gaaaagtagg tagatgcgaa aagaaaaaaa aaagagaaat   31800
aggaaaaaaa ataaaggttt tttatagaaa aaaataaagt gaaaatgaat gaaaaatatt   31860
tgaattaaaa tggtttggta tgtaaaaaaa aaataaagaa aattatgatg aaaatacttt   31920
taatcccttg catctgtgtg gatgattttt tgggctttaa tttcaagcgg aagacaacac   31980
ggtagctttg tgtcaacgat gcaaatttttt attgctttct catcggttaa aaggtgattc  32040
actctggggt gttgttaggt gcacccaaca ctattgctgg tgcacccagc attttacttg   32100
aatggtcaaa aatgtccttg ggctaatttt aaaaagaaaa agcccaccca gcaacaccct   32160
tttcttcttt ttccgcgaat gcttttttctt cttcttccgc gaatgcttct tcttcttctg   32220
cgaacgcttc ttcttcttct ccgctggtgc tctcctctag gcttcatctt ctcgagcttt   32280
cggtgccatt gacgacctgc attggtgcat tttgttgctg ctccgccgtc gaggtaagtt   32340
tattccttat tcctccattt cctttggtgg ttttttgatga tttacagatg tagggtagac   32400
gacgtaggta gttgttcata tggatgtaat tcatccgtat ttaggattga attggtaacg   32460
```

```
ttcatacgga tgaacttctt tcatatgaag aacacttcat tcgtatgaag aaaacttcat   32520
ctgtatgagt catacggatg aacttcaatt gtatgagtca tacgaaagaa gttcatccgt   32580
atgattcatc cagatattgt ttgtcattta gcttaagggt attgtatatt ctggttttta   32640
gcgttgcaaa atcacaagcg ttaggtactt gaatgggtac tggagtggaa gtttgaaagt   32700
aaacaccact atcattgtga ataatcgatc catttggaaa aataaaaccc aatgtggagt   32760
tcacaatcgt ctgactgcta gtttctccca aaaatgtcat actttgttct aaaaattggg   32820
ttgagagaga atgtgtgatt ttttagagtg ttgttgtgtc tcatatatat agatggtttt   32880
cactaatatt gcttcacttt tagaagaata gagacgcgtg cagatgcttt gtgtttgtgt   32940
ttccaactaa accaatgtgg tgtcaagctg tatcgtgcat cagaatgtgt tgtcaagtct   33000
gtcaatgtcg tgtcacgctc aaactttaat acgcatgcat ttgacaatgt gttatcaatt   33060
atgacaacga tgtatcatac atacgtgatc gaaagtcata tttaactaaa tagcaatcaa   33120
taacttcaac gaatcaaaca agacaacaat atagaggcag aggcagaggt tggtgttgtt   33180
cgctgagcct gagtggatga agccatttct ttgttatcat acgaaccatg aactatttta   33240
ttaacaaatc acaaaaatga ttttcaatgt caatcaattg tacaatatta ggccctccac   33300
aacaattttt atcacataat taataaaatt agataaacac atgtcaaagt ccataacaac   33360
catgcatgtt cagtcttcat ttatgtcgac ataqtctctt ttgaacatca tgaagcttat   33420
gtacttctgc attctactaa tatatggagc tgaccactgc tttgcctgag gatgagaatt   33480
cctagaccat aacaatgcta gaggcgataa aggacaacgg tctttcaaat aaacctgttg   33540
tacgtgaaca acattatta actcaaatga acacaaatga ttgcataaat ttaaaaataa   33600
gactaactat cttcaatgta cctaaacaaa atgatttcca aacacatgat cgacacatat   33660
aatgcggtgc atagaagaat ctgttggtgg ttgacttcta agaggaaaaa atgtcatgct   33720
ttgttgtcgg gacaatgata caaggattac attatacctt gatgcaatga catatcccat   33780
ctccgttata tccatccacg tatccacact aacctgaatc aaacaaatat acacatcaaa   33840
gttatttaaa gttagttctt aaaaaagaaa acctaaacaa atataccttg gaaaacccat   33900
caacaagtag ggaccgcctt aattcatcaa atctgtctgt gccaccgaag aggttgatat   33960
agtcatccga ccatttgcca agttctttaa ccaattggtt gcgcaccaac gaccaagaat   34020
cttcgcccat acctaataaa gcggcaatgg accgatatct tcaattaccg tccgctttca   34080
catccacaat gttgtcaatg aaaccctgta taaatggctc aaattgatcc aacatcggga   34140
tgatccttgt tggcttttggc tggttagaag atgatgtact atgcttcact gaagagttgc   34200
tactttgaac agaatgaaaa acatcaacat acttctagta agatgggtca cgctttgttg   34260
atctttggtt tctattcatc ggtttctttg gtgcaccttt agtgttgacc tttgacggag   34320
gaggacacat agagttttga tcagggtatg caatttctcg aagtttattc ttgagagtaa   34380
ctttaccata aacatcaagt tcctcaaata ttttagatat ggtctcgatc tcttccttga   34440
tggtgacttc ggcctcacat aacccttggt ctgaaaaact aagtctcctc caaaacatat   34500
gtattgaatc tagagggatg ctgccaacaa catacctaca tagctcacat gcacaaggaa   34560
gaccgtgtgt ggttctcata acacaatcac aagaagaagg attcttgcca gcataatgca   34620
catgctcaaa ctcagcaaca atctcattta aagcatacct tgaaaccatt ccaagaagct   34680
tcttgtataa ggttttttta aatacatgtc caaccacatg tgtacttgtt tcaaatgatg   34740
ctttaatttg agtgttgtag cgtgatcatg ttgttcatgg catcccaaac actatacagg   34800
tctccaagac tattatgtaa tactcttttt aaagctcaat gagcagattc aaccctacat   34860
```

```
gtgaaacaca caaaaaacaa taaacagata caataattaa attccatgaa ttcataaacc   34920
ttactagaaa aacttgaaca ttttaatacc tgtttgttgt tgtgttgcct aagtgcatca   34980
ccttattcat ccaggctgta acaaatttt ccttgtgtgg gattatccat gttaccttaa   35040
catagtcaac gaacattagt caaggtgaac aagccatttc aaacttctga aggcactcat   35100
ggaactattg ttcaaaagga caatcaacca gactacccca gacatccatg acatactccc   35160
aagcattttt ttgaccaatt agggatttgt atttggcctt gacattcttg tcaatgtgaa   35220
acctgcacaa caagtttgta cactcgggga acacaaattc cactgcattc atcaatgcta   35280
ggtctctgtc agttacaata attacaggga ggctatcatg tcttaaaaat agacctcgaa   35340
accgtttcaa agcccataca acattattaa cacgttcacc ctccagatat acaaacccaa   35400
tagagaatgt catctccgtt ggtgttaccc caacaaagtc aagtagtgag agtctgtacc   35460
tgttaatttt gtagggtact gtctataaaa aacaccaaat gacatgcatt gcataacttc   35520
actacatcag ggtgacacca aaaaagatca cgtaccacta cttcatcctt taatttatgt   35580
caatgaatat attgattccg ttcaagaagt tttattagat gttgtatttc agtatcactt   35640
cctctaatgg aagaacggta tgcacttctt gcattgtata tttgttttat tgttgtacaa   35700
ctattgacat tgtgttcctt caatgttagc aggatgtttc ttggtttcac cattgacttt   35760
gtcatatcag caataattgt cttctcatcc ttagtcaatc gcccaacgta tggatgacca   35820
actaatgatt tcgccaattc atgattatga atcccacaaa tcaacttaac catccaacct   35880
tgccctccaa tcactagttt cccatgaagc ttgaagggac aaccacattt tctactccta   35940
gtgctcttct aacaaattct ttcttcctat atttatactg accaccctt tcacaaccaa   36000 ttaacacaaa tgaacttctt tctctactac cagtatgtgt gtcagacatc ataatgacta   36060
caacaaattc gttttcatga gcaaccgatc gagcccactg caaaacatca tctcgggtaa   36120
caaagaccta caacacaacc cagacaattt atgttttcta caacacatac attcaatcat   36180
atgactcaaa ataatgaaca ttattaccta agaagtatta aaagcatctg aacaatcaac   36240
atgtggttca ttcacaccac attcttgttc attttcataa tccatatcaa cttcttcaga   36300
cattatatta ttatacatgc attgatcttc gtctatctta acaacaaatc aaaaatttat   36360
acatcataca caagtcattt tgttacaaaa aaaactacac aataaggact acaaaaaaaa   36420
actaaataaa actttaggga caactaatt taacataaga atacttcaaa taaatacaag   36480
ttttgcacct aaataatatc attttttact tatactatat ttaacatgta ataatttaat   36540
aattcctaat taacaaaaaa aaaaattcac tatagggact acaaaataaa atatcaaaat   36600
ctataactaa caactaattt aacatattac tacttcaaat aaatacaatt tttgtaccta   36660
aataatttaa ttttttactt acactatata caatttgaaa taaataaaca attcataatt   36720
tcataaatat aagcaataaa aaatataaca tattaataat taaaacaaat ataaattatt   36780
cacaatttaa aaataaatct aaaaaaaaca aaaatttatg gatgaagttc atccgtataa   36840
agcatatgga tgtactacat ctatatgctt tatacaggtg tactacatcc atatgcttta   36900 tacgatgta cttcatccgt aaggttcaaa atataacata ggatgaagta catccgtata   36960
aagcttacag atgaactaca tctgtattct ttatacgaat gaactatatt tgtatgttgt   37020
aattttgtct tacggatgta cttcattcgt atacaactta tgaatttagt tcatctgtat   37080
cttaaaaata acagatctac tagaacacca gttacccaaa aacgtcagaa aatgtgtacc   37140
tccgccgaaa taaaccatc actggtaaca ctttcacctc catcgaaccg ctacctctct   37200
caacacttac aaaacgacca ccaacgagag aaaccagacc acaataacaa aaatcaagca   37260
```

```
ttcaacacaa aacgaacaca acaatactgg tgttaattta aagaaaaaca atgaggggca    37320
ttattgtcat ttttaaaata tgttggatgc accaacaata gtgttggatg cacctaacaa    37380
gtctcttcag tgtgccgtgg gatccataga aatatcatgg tttttaaaatc tagactgggt   37440
tggccaatcc aatgatttca aaaaattgat gtgttcttaa attagcttaa aacatttaaa    37500
tcggttgaaa agggttaagg gatttaatcg attttgctta aaactttttt tttacccaaa    37560
acaaaacttt caaaaagata tcatttcgat tttaaaaaaa ttataactta tgagatcttt    37620
aaatgaaatt tacatttttta ttactattaa tttatgcata ttatgttatt tttttcaata   37680
ttactaaaat attatattaa aatactaaaa aaatatttta tcaaaatcga ttcgatctag    37740
aataaatcat ttaccgttga actagtactt ttaccgatct aataattggt ctgattataa    37800
aaatattgtg caatattcaa atattatgtt cctaattcac tgctcccaaa ccgtcgaaat    37860
gcgtggaatc tcataagttt tgtgcctcaa acaaggataa agaaaattga gaaattaaaa    37920
actattaaac tataagtgat cattattaaa aaaataagtg agataaaaaa gaattgtaat    37980
tttaacaaat tttagttaat aatgtggtca caagttgttt ctttattttt taaacaattt    38040
tctagcataa attactttat tttaaattta atttgagtta aaattaattt tgcaaaacga    38100
aagtgacgtt gaaaaacgta gattcacaag ttgtttcgag gttcacatca ttgacatcaa    38160
tgaattggat atttttgccg tcttgagtaa accgtgaaca gtcgaatatg atcaatcagc    38220
attgaagaat agaatttaaa ttccatgcta actagccaac gacatgagaa aaaggtacta    38280
tttcattttat atcacaatgg tacggtggtt ttctaaccc acgaaatatt cgcctatttt    38340
ggcttgtagt tatgatattt tgttagcaaa acttaaatgc ttcactatta cacttctaac    38400
cttctatatt ctatcgatta gtaaatgcaa atggttgtag aatctctgac tatacagtaa    38460
taaaactcag tcataaacac aaaacacacc cgtttttaac aacgaggaac atggataaga    38520
aaaatctaat taattaatat gtcaattttta agaaaattatt ttcacctaat attatattat   38580
aatcttacca acaagggatt taacttactt aattaaacat gagagttatt ataatctttc    38640
tcgtacttat cttcgatttt tacaaatata tttttttata atcttaccgc ttttgaaaaa    38700
agaaaacaaa agtccttttct gagaataatt tttggatagt gtaacatgga tattggataa    38760
tacttacgtg ggttaattga ctttgaggaa gaaaaatcac cataacttat catattttttg   38820
gtagagtgga gaaggagaga aatagacaag aaataagata ggtctcatgt gcctctcata    38880
ccttctacta cactttaccct taatttaaac tagctttgtg tcaaatgtct tttaagggta   38940
ttaaatttat ttttttatatt ttatatgagt atttttttaat attattttaa atttttaaata   39000
tattattaat tatttagtttt aaatttcaat aaatttatttt tagtagatat gttaataaac   39060
atttaaatat attttttatat acacacatca caataataac ctccataaaa atgaaaatag    39120
aaatagaaaa ggatgtcatt tgcatgacca taatgattat acatagaaga actaattcta    39180
gggagaaaaa aactaatatt aaagaaaaaa taatacaaat caaaacttag aggaagcaaa    39240
aaaaatcgag agaaaatgaa atgataaaat ttatgatcaa ataagagaag agaagaaaaa    39300
aaaggtgtgt taaaaaatgt tgataatgaa aattttcacc cacacatata taatataaat    39360
ataaataatt atttaataaa aatatattga atatatattt ttgaatcaat caattaacat    39420
atatatatca tattaatgaa gatttaatga aattattaac agaatgataa ataaaatatt    39480
taattaatttt gaattaatc                                                39499
```

<210> SEQ ID NO 6
<211> LENGTH: 25843
<212> TYPE: DNA

<213> ORGANISM: Artificial
<220> FEATURE:
<223> OTHER INFORMATION: Contig-2

<400> SEQUENCE: 6

```
ccggggatca tgttgtgttt cttggttttg tagtgagttc caaaggggtt taagttgatg      60
aagaaaaggt caaggctatc caagagtggc ctacacctaa aagtgtgacc gaggtgagaa     120
tttttcatgg cctagtgagt ttttataggc gatttgtgaa ggattttagt acctcggcag     180
cacctttgaa tgtgataatt aagaaaaatg tagttttcaa atgggggagag aaacaagaag     240
aagctttcaa tgctcttaag caaaagttaa ccaatgctcc catacttgct ttgccaaaat     300
tttcaaaatc ttttgaaatt gaatgtgatg cttcaaatgt tgggattagg gttgtattgt     360
tacaaaaagg tcatccaatt gcttatttta gtgaaaaatt aagtggtcct acccttaact     420
attctactta tgataaggag ttgtattcct tagtgagagc gttgaaaaca tgacaacact     480
atctttatcc caaggaattt gtgatccata gtgaccatga gtccctaaaa taattaaatg     540
gacaaggtaa gctaaacaaa aggcattcca ataggtggaa atttcttaag caatttcctt     600
atgttattaa acataaaaag ggaaaaggaa atattgttgt ggatgccttg tcaaggaggc     660
acttttttgct ttctatgctt gaaacaaaaa tgattggatt tgattgcttg aaagaaatgt     720
atgaaggaga tgacacattt ggtgaaatct caaaaattg tgaaaagttt tctaaagatg     780
gttttatag atatgagggc taactcttca aagaaaataa attatgtgtg cccaagtgtt     840
ctactagaaa cttgcttgtg tgtgaagccc atgaaggtgg ttgatgggg cattttgggg     900
tccaaaagac cttagataca ttgaaagagc atttttattg gcctaacatg aagaaagatg     960
tgcagaaatt ttatgagcat tgtattgttt gcaaaaaggc caagtcaaag gtaatgcctc    1020
atggtttgta taccccttta ccaatttcgg attctccgta gattgattta tcaatgaact    1080
ttgttttagg gctgcctaga acaagtaatg gtaaggattc catatttgtt gttgttgata    1140
ggttttctaa aatgactcat tttattcctt gtaggaaatt tgatgatact aatcatgtgg    1200
cggatttgtt cttcaaagaa gtggtgaaac tccatggatt accaagaagc attttagtg    1260
atagggactc caagttccta agccattttt ggaggaacctt atggggaaag ctgggtactg    1320
agttactatt ttctactact tgtcaccctc aaacagatgg acaaacagag gtcatgaata    1380
gaactttggg taccttgcta aggaccgttt tgaaaaagaa tcttaaaaat tgggaagttt    1440
gcttacttca cattgaattt gcttataata aggttgtgca taacaccact aattgttctc    1500
cttttgaggt tatttatggt ttcaatctac taactcctct tgatttgttg ccaatgccta    1560
atatttttgt ttttaagcat aaggaaggat aagccaaagc agactatgtg aaaaagctcc    1620
atgaaagagt caaggcccaa attaaaaaga agaatgagag ctttgctaga caagcaaaca    1680
aggggcacaa aaaggttgtt ttccaatccg gagattgggt ttgggttcac atgagaaatg    1740
agaggttttc ggagcaaaga aaatccaagc ttcaaccaag aggggatggt ccattttatg    1800
tacttgaaag gataaatgag aatgcataca gaatgaatt gcccggtgag tataatgtga    1860
gtactacatt taatgtgtct gacttaactc ttttgatgt aaatgaagaa gccgatttga    1920
ggacaaatcc ttttgaagag ggagagactg atgaggacat ggcaatgact aagggcaaag    1980
aaccttaga aggacttgga ggacctatgc caagggctag aacaaagaag gccaaggaag    2040
ctcttcaaca agtgttatcc atgctatttg aatttaggcc caagttacaa gtggagaagc    2100
ttcagattgt caattgcacc atgttccaag aaaagtatag ggtgccacct ttgttgagcg    2160
gttttattag cattttgtta gttgaaataa aggcccaaac ttgtgttaaa gtggttgtca    2220
```

```
attctctttg gattttcacc acctatgggc ttgttttaat ttaaagaaat taaggtttaa    2280
taaggtgaaa actctaggct tgtggctgcc tcttggctga ccaagagcta tgcattttc     2340 cacatgtttt tgtgtcttaa ttctagttta attaggtata atgacatcat caattgttgt    2400
tattggtgat catttgtctt aattctagtt ttaattaggt ataatgacac catcaattgt    2460
tgttattagt gatcatttca tcttctcact tgtgtaacca acttgatgtc attcctattt    2520
atgggttgca cattttctaa taaaaaaaca gaccttgaat tgagttttaa tcaccttcta    2580
aagtatgaga gttgaagaag aaaagctatc ctaatgtttt gatgatgcca aggaacatg     2640 cttttcaagt tttattcaag acaataatcc aagatatcca agaaattcaa gaaatatgat    2700
caagataatt tctagagtct taggatgaaa atttcaagtt gaaacaacaa aaggtttggc    2760
caaaggattt aacttaaaat gttttttaaa gaatttact  ctctggtaat tgattaccaa    2820
aagatgtaat cgattaccag tggtcaatgt gctttctaaa aagcttttaa atgttttaaa    2880
atattttaga aagcatgtaa ttgattacca gaggtttgga acgttttaaa acagccttaa    2940
agaaatttga atttaaatta caagttatgt aatcgattac aatgaattgg taatcgatta    3000
ccagtcttaa aaattcaaat ttcaaagtga agagtcataa ctcttcaaat aaataattgt    3060
gtaatcgatt acaccacaat ggtaatcgat taccactgag aattttttgaa aatggttccc    3120 aacagtcaca tctttgcatt taacttttga atggccatca aaggcctata tatatgtgac    3180
ttggacatga aatttttctca gagttttttac tgaccaaaaa gtcttatcct ctcaaaagaa    3240
caaattgtct tatcttctaa aaattccttg gccaaaacat tttgaattca ataagaaatt    3300
atttgagtgc ttcattgtac aatctgtctc ttgcaagaga gatttcttct tctttttctt    3360
cttgctcaag aaaagtgatt aagagatcga gggtctcttg ttgtaaagtg atctgaacac    3420
aaaggaaggg ttgtccttgt gtggttcgga gattgtaaat ttttttttaca agatagttaa    3480 aatctcaagc gggttgcttg aggactggac gtaggcacat ggtgtggccg aatcagtata    3540
aactgagttt gcactttctc ttcccttaaa cttcttttatt tattgttatt tatctttttgc   3600 attaaggaag tttagtttga attgtcttat aataattcat aataagggta cattgaaact    3660
ttcattaaag aagagtaaaa ttttttaattg gggaaatagt ttgtgatatc ttaattcaac    3720 ccccccccc  tcttaagata tttgagacca cttgtctaac aagagtgaat ctccatagtt    3780
acttaagtga ttcaagaaat tggtttatca aggaacacca ccttgtgtgt gacactaatt    3840
ccgaaggagt gattcttcca accactttct tcattctcct tatccattcc atttctaaa     3900 tttcatacaa aaaaaaaga aaataaaacc tttgaagatc catcctcaac tcttgtgcac    3960
atgggtttac atcatttttg tgacaccctc tatcccaaca tatatataaa taaataaaat    4020
atattggtaa acaaaatcac atgggtaaaa ggttcacatt cacttcaatt accaaataaa    4080
actcattaaa aacatattcg gctcaaaata aggccgtcaa aatttacaaa atatttttgg    4140
taaatcactg aggtgaaata aaatagacta acatcataaa attaacataa aaatttatat    4200
cccaatgtca catcttatca gagtgttgtg tcccgacgtc cttcaacaca atattcctta    4260
aaacagttca cctagtcatc tgctcccccg aacacaaagt tcaagatcat cacaggatcc    4320
aaacacaaat agcaaactgg gagtgagtta tcacattcct aactaataga gaaacaagac    4380
aactagatat acatatcata taaacaaaat aaaacttact tacacgtaat tccaccactt    4440
tgtcattcaa agttcacttt tcatccatca atcacacttt tcaatcatca atcacattaa    4500
acaagaatca cacgctctga tcaagacata ataacccctc aatttcataa taaacaatta    4560
gcaagcgcat gagacaatta tgctaagact caagcctaca tgcaatgtgg taccatgtca    4620
```

```
atgaaaaacc accatgggac gcttaggagt atataacaag acacaccaca caatgggttt    4680
gtcaggtcac tctcactaag taagatcata gggagaccag tcagggtcac gatgttttgc    4740
gagaatgctc caaccatatg ggatcagcat aggcttaaag gagcactcaa acccggtgac    4800
ccccaaggcc tacactccga agagtccgtc agggcctctc ccttctaatt gaggtccaac    4860
ccctaaaatc attttagcac acagacactg cttgtgaatt atacaatatc cacgacctca    4920
cactcgtgtc ttaaacacgt acaacatatt gcgctacaat ttaacactgg ttcctaaata    4980
ggaacctaca ctttctcttt acactgcgca tttacacttt tctcaagata acactggtcg    5040
actttgatat gtaactgggg taaatgtttt tatgtcccag ttatgtctg ctttgcccac     5100 agttgaattg gaccctccta caatttccat gacttttggt gtaaacgact ccccattggc    5160
tggtcgtgat ggctctcatg taattggtgt ttgttttgtt ttacttttac tttcttttgc    5220
ctccttcatt tgcttgtgta aaaacattg ggttgggtat gcttctcaaa tcccagttca     5280
gaactaccct tttgttgtct ttgaaggttc attctctagt ttttgcataa acagtttttt    5340 atgttttac ttattggtta tcttatagag taaatagact aatattgaac ttttttgtagt    5400 tgactggggg gagaattggt gaccgattga tggctgaagc tgaaaccaac ctcgccataa    5460
atgtgcttcc aggcttatca gaatcatttg aagttcaggg aagaggagag ctacagctgg    5520
gtttgttcct gtttctttga aattgcatga tctgatgatc ctcactgtta ttatatgcat    5580
ataaaaaccc catgatttgc tgtgcttaca cagctgatta tggcatcttt attaacaggt    5640
attttaattg agaatatgag acgtgaaggg tttgagttat ctgtctcacc acccaaagta    5700
atgtgagttt tcaaggactg aacaaggctc caaatatttt gtctcattat cagttttttac   5760 acaatgtggt tttgcttgcc tagtgctaca tatggatgtg gcatgctatt taaatattga    5820
ggaaatgttt taatggaaac tttgtatgca ttatttcatg ttttaatgga agcttgaatt    5880
tttaaactcc caagaaaact taagctattt ggtggaggct tgggttatgt atctccaaca    5940
tgctccctct agcaagagct ctttgggctt gaataatgag tcatgaccaa tacacgtgtc    6000
catttaccgt atactgaact cagtttatat gtaaaaaata tagactacaa gaatttaata    6060
cttgagtgct tggtcataga agtctagtat cacattagac ttctttgaaa tcatagaagt    6120
ctaatgtgat aaaaaaacta acctaatact cctatttaca aaaacactaa actattatag    6180
gtcttgtata agtctgctac ataacaatga taacataaca tattaataag actcctgaaa    6240
ctatatgatt ctaataacaa atgcagaagt tcatgaataa catccaataa gcagtgtctc    6300
tgagcatagg tttcgaaggc atgtcattta ttttgcatt atgtgcattc attctgtatg     6360
aaactttctt gtctaattga tcttgaaagg tctacccatt taaaatgttt gatctggcaa    6420
atttttttat aatgtttggt ggttcaatat ttctgatttt gaaatgatat attatgcatt    6480
ttttgagttt gagctcactt acctttttca ttttcttttt ttcttttat actggtttat      6540 tgaacgtttc tatggattta ttaggtataa aactgaaaac ggtcagaagc ttgagcccgt    6600
agaagaagtt acaattgagg taattccact tgtccttcat agtatgcttg ttcaagagtt    6660
tggacttcta acatcataat ggatctattc caggtaaatg atgagcatgt tggcttgata    6720
atggaggcct tgtctcatag acgagcagag gttacagaca tgggtcctgt ctcaggaact    6780
gttggtcgaa ctagattgtg tttgacttgt ccatcaaggt tagcttggtt atctttctct    6840
tgtattgaac ttatctcttt gatttgtttc cctcccagca cttaaatgtt attaatgttg    6900
atattgtatt atcataggta aatatataac tatttaatgg gaatactata gatgcatgtt    6960
tttgaagaaa tcgcattaag ttatttgttt cttattatcc tttgcctgtt ttggagggtg    7020
```

```
atgataacct ctttccatcc tagtggtagt ggctttctaa ataaacccttt ctcctagaca    7080 atcaagaaag agaaacaaga gaataatctc taagtgccct ttcaatttat tgacatcagt    7140
ttaacactca attataattt ttatatagtt tttatatctc tcaaaaatag cttttggtag    7200
cgtgattgaa tccagaaggc ataactcact aatacataat ccagatttct ggttgcttcc    7260
gtactgtggt tggatcccag agatataatt tctttggcat tatggttcta gtgaaatctg    7320
atcttatgaa gcatgcaagg aatttagtaa cttccttaat gctgtttgtt caggggctg    7380 gttgggtaca ggagcgtgtt cagcagtgac acacgtggaa ctggattcat gcatcgtgct    7440
ttccatggta tgtgttctct gcttaaaatt aatatctttt tcttccaact ggcatgtaat    7500
gatatgccaa ttttcaattt gtttgctata tgttctgcaa atcatgttta attgccccca    7560
tgagatttta tgttagcagg gctttgttgt ttcttatttt accatccaca gtttgtttga    7620
gcctttccct cttgcaatgc agcatagttt atcgtctgat gtctttttta agtatttat     7680 tttttataat tgcattttat tgtaatgttg cagcatatga aaattttcga ggccctcttg    7740
gcaatgtcag gaaggagta ctggtatgtt tggtggttgt tattcttact taaaagggtt    7800
taaaaataat taaattacac tgagttacta cctactcaca tgatatactt ctgtgtttca    7860
aattattaaa cttgtattga gtgtggttct atttcttgtg gaatgctgtt tgcttaattg    7920
aacaggtgtc aatgggtttt ggtacaatca cagctcatgc actgatgagc ttagaagctc    7980
gagggactct ttttgtcaag ttgtattata tggcaaacaa ggtcactatc tatcttcttt    8040
ctgtgtcttc cgggaagttc aagatcaaga attatatgag agcataaata gtgaagttcc    8100
actatggaaa aaagaacaa agtttaatac aagaagaaat caacaggggga ttgtccttta    8160 ttaggtcctt gaataattgg caaatttgga tgggaaagga gcaaaaagac agattttcca    8220
aaacgccctc cttgtaccaa tgaaattgta cgtaacatta attggccccc aaagaaataa    8280
aagtgaatgt ttattctttt aaaagtcaag cacacttag ttacctgttt atgatgtgac     8340
taaatttact ttttagaaaa tgagcgagta ataaatgggg gtgttgaaag agtgtattat    8400
taccgtttct ctttgaaaaa ttatgaccac tttttttttt ttttataaag tgtatgtgac    8460 caccttttgtt agttatggag taccaaggaa agttatcgac aagtcataaa atttaaattc   8520
aaatcttggt ctcaaaagga aaaaaaatgt tgataatttt gttgctacaa gttaatgtaa    8580 aagttttac atgattaatt aactattaaa aaatcacgtt aggtatatat gtttcatcac     8640
gtaagaaact attggattta agttgggttc catagttttc catagttttc atgtaaaaaa    8700
atttaatgag agaaaatccg tgtcttgaat ttttaagtaa tttttatgtt tttctttag     8760 tcccaacatt aattgggttt catagttttc atgtaaaaaa atctaatgag agaagatccg    8820
tgtcttgaat ttttaagtaa ttttcatatt tcctttccca acattagttg ggtttcatag    8880
ttttcatgta aaaaatcta atgaaattta atgagagaag atccatatct tgaatcaatc     8940
aaagaaagtt caaatcatg tttcaaactt gaaaatggtc aattttcaa aaaaagatca      9000 atgtgctata aagccctct atgttggtcg ttgagttctg tttggaatat caatgctcag     9060
cattaataaa agggcctata acaaattatt aatactatgt ctaatatatt cactagtcac    9120
gtatttacta gtcatgatat caaagtacgt attccttgat atacttctaa acccgattct    9180
gctagtatcc tctgggaagg gatctctact tcaaatggga gtaccacttc cattccataa    9240
accaaggaat acggtgttgc cccagtagaa gttcgtactg aagttcggta tccatgcaag    9300
gcaaaaggca acatctcatg ccaatctttg tatgatactg tcatcttctg aataattttc    9360
ttaatattct tgttggctgc ttccacggct ccgttcatct ttggccggta gggcgtggag    9420
```

```
ttgtgatgct ggattttgaa atccgcacac atttccttca tcatcttgtt attcaggttg   9480
gtgccattgc cagtaataat ctttgtaggg agtccatacc gacaaatcag ctccttcttt   9540
atgaacctga ccactacact cctcgtgaca ttggtgtaag aagccgcctc gacccacttg   9600
gtgaaataat ctattgccac gagaatgaag cagtgaccgt tcgaagcctt gggctcgatg   9660
gccccgatga catctattcc ccacatggaa aaaggccaag gggtggacat gacattcaaa   9720
ggatgtggcg gagcattgac attgtccgcg aacgcttgac acttgtggca tttccttaca   9780
tggacgcagc aatcaccttc catggtgagc cagtaataac ctgccctcag gatcttcctg   9840
gccatagcat gcccattggc gtgcgttcca acgaaccct cgtggacttc ctcgatcatg    9900
tggttcgcct cttttggcatc cacgcatcgc aggagagtca tgccatggtt tcttttatat  9960
agtatgctcc cgctcatgaa gaaaccgacc gccaatctcc tcaatgtcct tttatcattg  10020
tcggaagcct ctggtgggta ctatttgctt tcgacatatc gcttgatatc gaaataccaa  10080
ggcttaccgt cccattcctc ttccacctgg caataatgtg cgggtttgcc acgacaccag  10140
aactcaatgt atggtagatc ctcgtgcggc gttagctgga acatggacgc caaagtggca  10200
ggtgcatcag ccatttgatt ttcctcctgg ggaacatgat ggaaggagat ctcatcaaag  10260
gaattagcca tctccttgat ataggctttg taaggcatca gcttgggtc tttagttttcc   10320
cattcccctc ttagctgatg gatcaccaac gctgagtccc cgtacacctt gagtagcttg  10380
acattggagt caatcgctgc ctggacgacc agggcacatg cttcatactc agccatattg  10440
ttggtgcagt cgaaccccag cctggctgtg aaaggtatac attgattgtc tggagagacc  10500
aatactgctc caatgccatg gcctagaaca tttgacgctc catcaaacca cacggtccat  10560
ttgtcccggt ccttgtctag ttttttcctca acaaggcca tgatgtcctc atccgggaat  10620
tcgggatgca tgggctgata gtcgttgaga ggctgctaaa ccaaataatc tgctaaggcg  10680
cttcctttta tcgcctttg ggcgacgtaa actatatcaa actcggatag caagacttgc   10740
caccgggcga tccgtcccgt aagagttgga ttttcaaaga tgtacttaac cgggtccatc  10800
ttggatatca accaggtggt atggcttagc atgtattgtc ttaggcgatg ggatgcccag  10860
actaaagcac aacacgttct ttcgagcagg aagtaattca tttcacaggc cgtgaacttc  10920
ttactcaagt agtagacatc gcgatctttc tttccggact tgtcatgttg ccccagcata  10980
catcccatcg actcgtccaa aatcgtcata tacaagatga gaggccttcc gggtaccggt  11040
ggcataagca caggaggatt catgagacac tttttgatcc tcccaaatgc ctctcgacaa  11100
tcctcattcc aacggtcggt ttggcttttg cgtaagagtt taaacaacgg ctcacaaata  11160
gcagtgagct gtgatatgaa tctggcaata taattcaaac gtcccaggaa acctcggaca  11220
tgcctctcgg tacggggttc cggcatctca aggatgacct tcacctttc ggggtctacc   11280
tctatccctt tttggcttac gatgaaacct agcaatttcc ctgatttgac cccaaaagtg  11340
cacttagcgg ggttcaacct caattgatac ttcctaagcc tttcgaacaa cttctgcagg  11400
ttgacaaggt gttcctcctc ggatttagat ttggcaatta tgtcgtctac atagacctca  11460
atctcttggt gcatcatatt gtggaacaaa gctaccatag cccgttgata agttgccccg  11520
acattcttga gtccaaagga catcaccttg taacataaca ttccccacag agtgacgaag  11580
gtagtctttt ccttatcctc tggcgctatc tttatctgat tgtaaccgga gaacccatcc  11640
atgaaggaaa ataaatcaaa attggccgta ttatccacaa ggatatcgat gtgcggcaaa  11700
ggaaagttgt ctttgggact ggcccgattc aggtcccgat aatccacaca cattcgcaca  11760
ttcccatcct tcttagggac tgatacaatg ttggcaaccc attctgggta ccgagcgaca  11820
```

```
gccaaaaacc cggcgtcaaa ttgtttcttt acctcttctt ttattttcaa ggatgtctag   11880
ggcttcatcc ttctcagttt ctgttttacc gggggacatt cgggattag  gggtaatcgg   11940 tgttgtacaa tgtcagaact caaaccgggc atatcttggt actaccaagc aaaaatgtct   12000
tggtagtctc ttagcagggc tgttaattct tcacgaatgg gtgcggtcat acccgtgcct   12060
atctttactt ccctttttcc actaccagtt cccaagtcta ctagttctgt ctcttcttga   12120
tgaggtccca tttcttggtc ctcatgggcg actatccttt ccaaatatgg tccatgggta   12180
catgcatggt taaattaggt ggccaacttt gttgtgaacg atagaatttt ttttatatt    12240 aagtaaacta ttttatatt  atgaaataat aataaaaaaa atattttatc attattaaca   12300
aaatcatatt agttaatttg ttaactctat aataaaagaa atactgtaac attcacatta   12360
catggtaaca tctttccacc ctttcatttg ttttttgttt gatgacttt  tttcttgttt   12420 aaatttattt cccttctttt aaatttggaa tacattatca tcatatataa actaaaatac   12480
taaaaacagg attacacaaa tgataaataa taacacaaat atttataaat ctagctgcaa   12540
tatatttaaa ctagctatat cgatattgta aaataaaact agctgcattg atactgataa   12600
aaaaatatca tgtgctttct ggactgatga tgcagtatac ttttgacatt gcctttattt   12660 tattttttcag aaaagctttc ttagttctgg gttcttcatt atttgtttcc catctccatt   12720
gtgaattgaa tcatttgctt cgtgtcacaa atacatttag ctaggtacat gcattggtca   12780
gattcacggt ttattatgtc atgacttaag ttcatggtag tacattacct gccacgcatg   12840
cattatattg gttagatttg ataggcaaat ttggttgtca acaatataaa tataaataat   12900
gtttttatat tacgaaataa cagtgatcaa aacaaacagt tttatcttta ttaacaagat   12960 tttgttttg  tttgatgacg ttttttaatg tttacgcttt ccccctttctt ttgaatttag   13020 aacactttat catcataaaa tcaaatacta aaaaaattac atatttcata aataataaca   13080
caaatatttt taaaaaatct gaaataataa tgaacaatat tacatattat cacgaaaatt   13140
cattaataaa aatattatat aaataaaatg taatagtagt tatatgtagg aaaaaagtac   13200
tgcacgcata atatatacaa aaagattaaa atgaactatt ataaataata acactaaatt   13260
aatggtgaat catatcaaaa taatgaaaaa gtaaataaaa tttgtaatta acttctatat   13320
gtattacaca cacaaataat aaataatagt aaaaaaaatt atgataaata tttaccatct   13380
cataaagata tttaaaataa tgataaaaat atagattatt ttttatgcaa ctagctagcc   13440
aaaaagagaa cacgggtata tataaaaaga gtacctttaa attctactgt acttcctta    13500 ttcctgacgt ttttatatca agtggacata cgtgaagatt ttaattatca gtctaaatat   13560
ttcattagca cttaatactt ttctgtttta ttcctatcct ataagtagtc ccgattctcc   13620
caacattgct tattcacaca actaactaag aaagtcttcc atagcccccc aagcggccgc   13680
tgagtgattg ctcacgagtg tggtcaccat gccttcagca agtaccaatg ggttgatgat   13740
gttgtgggtt tgacccttca ctcaacactt ttagtccctt atttctcatg gaaaataagc   13800
catcgccgcc atcactccaa cacaggttcc cttgaccgtg atgaagtgtt tgtcccaaaa   13860
ccaaaatcca aagttgcatg ttttccaag  tacttaaaca accctctagg aagggctgtt   13920
tctcttctcg tcacactcac aataggtgg  cctatgtatt tagccttcaa tgtctctggt   13980
agaccctatg atagttttgc aagccactac caccttatg  ctcccatata ttctaaccgt   14040
gagaggcttc tgatctatgt ctctgatgtt gctttgtttt ctgtgactta ctctctctac   14100
cgtgttgcaa ccctgaaagg gttggtttgg ctgctatgtg tttatggggt gcctttgctc   14160
attgtgaacg gttttcttgt gactatcaca tatttgcagc acacacactt tgccttgcct   14220
```

```
cattacgatt catcagaatg ggactggctg aagggagctt tggcaactat ggacagagat   14280
aagcggccgc gacacaagtg tgagagtact aaataaatgc tttggttgta cgaaatcatt   14340
acactaaata aaataatcaa agcttatata tgccttccgc taaggccgaa tgcaaagaaa   14400
ttggttcttt ctcgttatct tttgccactt ttactagtac gtattaatta ctacttaatc   14460
atctttgttt acggctcatt atatccgtcg acggtaactt ttacttagat aatattttct   14520
taaaattcaa cattaaattg aaagtctatt tgacataaat ctcatatgca aaattttata   14580
ttaatcaaaa atcattttac ttcattcata taaattaata ttgatataat ataaatattt   14640
taaaatacac taaaatatag atcacttaat tatctattta ttgttattaa attttgataa   14700
aatttaacat aaataatctt aataatatat agatataatt caacaactag atcaataaaa   14760
attacatttt atattatact aagtaataat ataacagcta gatcttaata gtatattgat   14820
atatatatat atatatatat atatatatat atatatatat atatatatat atatatatat   14880
atatatatat aattttgaga aaaggaaaat tctgattaaa aaattgaagt tacatcttac   14940
ttctacgttg tgagttttag cttttgattt ttttttaaaca ccaaaagtgt ataaatattt   15000
taataaataa atttaattaa agaaatttaa aataatttat aataaaatct tgtattatat   15060
tggttatcta attatcatat aatgttgacc agtcattgca aaaatcatgt catgacaatt   15120
gttagtgatt atcgataaca tttggaggga atcagattat atatctttaa agcttcattc   15180
taaacataga atttgctata aaaaaaatta caatttaagt ttaaaatccg atattttgtg   15240
tccaagtttc tcaaaattat agttaagata ttgttgtcaa atttgattcc aacaaattga   15300
atactgattg aaatttactc actaattaaa tggaaactaa ttgagtccag attttaattg   15360
attcaagcct tcaagttgaa agcgcaatac tgatcattca tcacaaagaa ctcattacta   15420
gtgattgact taagtgtctc acatataaaa tatctattgt ttgaattaaa aagaaaagtt   15480
atctatggaa aaaaaatatt cacacaaggc taaaaacaat attcacacaa cttattcgat   15540
tttgatagta ttatagctaa caacattttc ttttcttttaa gtaatgaagg caattatata   15600 tttttttatac ataattatgt ttgatatgga tataattatt atgagaaaaa ttcttcgttt   15660
aagtatttaa gtttggacta tctcatgtta attaattatg tgtttaatga caacaacggc   15720
atatttaata agtttaattg tacattttac tactaacttt tattattttg taaattgtat   15780
tatccaaact ttttttcacga attgaacttt atcacccata ttttcaattt ttgtatattt   15840
agccatgatg acatgctatt aaaaaagtta tcaattttta tgaaacaaca ttgttttgtt   15900
atcaacatga tcattggctg atttagacat ttttcatggt aggggtaaga aaaaatttct   15960
aattttttca caaattaaaa tatcacaagg cactacaaaa tatataatat catgataaaa   16020
gaaatctaca gttaaatttt tacacgttat aaattgtcctc tacatatttt catattttga   16080
aagtattcta tgatttttttt attgtcaata ctaatttagt atgtgaaatg taatgtctttt  16140 cgttaaaata attagcacta aaatattatt aatcataatt tctttatatc aagaacacaa   16200
taaaagaaaa acacgtactc ctaaaataat tatgccatga agttttgaa aaggaatgta    16260 ttttactcac ctctagaaga agtaattgag ttctttgtta tttttgtctc gatagagttt   16320 ctttcattt tattctttct tctcaatcct tgagaatatg aataatgtca agagaaatat    16380
tttatttgtg tgattctaga aaaataaatg atctattctt atataaacgt tgtacttaat   16440
ttgaaattat atctttgaga ttgaaaaggt atgtgcttta ctcacatatg gaagcaagta   16500
attgtgttct ttattatttt tgtttcaaca aaatttcttt cctttattat ttcttctcaa   16560
tcctagagaa actcactaat gtcaagaggg acaatttatt tgtgtgattc tagaaaaata   16620
```

```
aatggtctat tcttatataa gtgtaatacg taatttgaaa ttatatttt gaatttatt    16680 taactaattt ttctttattt cttatttta ttatttttat ctgatctaat atattattat    16740
attatagttt ttaaaaaaat aacaatataa tatattaaaa taatttaatt tatacattct    16800
tttactaaaa tatatattta gataatcttt atctaaataa ttattaaatt attttggga    16860 tgttatacaa aacggtgtat tctattctat gtagtgtggg gtgtttttg ttgtgttact    16920 gtaataatac tgaaaattga gataaatgcg ttggactta acacgaaatt tttatattga    16980
atggattatg tttatttgag ttttacgatt aagaaaaatc caatgaggta atatatatt    17040 ttataggggg gattttttt atatacatta accaataaaa aaaatatatg atgcatttac    17100
caatgaacat gatggtaaaa ttaatgcaag aaaattgaaa acattagttg taaaattaat    17160
gggcaaaaac ttaaatgata aaatttataa aattatgata gccaggtggt aaaatgtgaa    17220
attaataaat aatttagttt ttaaattaaa cacacactca cacatacttg tattttagtt    17280
agtatattgc tcatgataaa tatttttta aaatcaaatt tataataata aatgattttg    17340
aaagtcaaaa tgatcctgta gtagagattt ataataaata tatttgaata tatatacata    17400
tatatattgt ttattggatt tataataatt aatttaaatt atgatataa gttataatca    17460 actattgata atttttgcttt atagatattc ttcaaattta atttaaaaat aagataaaag    17520
agagtttatt gaaaacacc atcaattaag aagattaaat atatagataa taatagaaaa    17580
agattgtagt ttgagatact tgagagaaaa aaattctaga tagatgtgaa attattgtat    17640
aaaatacacc tccaaaaaga aaaaaatat atagaaaata atatatatta gccctcaac    17700 atttttctct tcttttctat attaacacct ctatgaaagt atgacacaat gatcctccca    17760
aagtcgcatt taaatatac atatcaaat gctagtagat ttatacatga ataaatctat    17820
gatacattat tagaaaatag acttttaaca tcagttatta aagacttta atattgttta    17880 ttaattcatg ctgaaactac cgatattaaa agtatcaatg ttaataaaaa atttaataaa    17940
aattgatgtt gttgttttct tttcaccaac atcagttttt agaaaaatcg atgttgtcag    18000
taaacaacaa catcaatttt tataaaaatc gatgttgttt ttcacaacaa tatcaattt    18060 tctaaaaaaa tgatatttt tgaatttttt taatatccta tccattttt aattaccaat    18120 tctaattatt catatcaagc ttatcaatta aagttgtaaa taactctaaa aataaaccaa    18180
acttataaac aaaatatacc accaagagta catataaaca aaaatttaca gataaatgta    18240
taatataatg taatttaatt acaaacaaat ccaaaataaa aaagttagaa gttgtatctg    18300
agaactcaaa taccagcttg caaatttat gattgtgcaa aagtgcttca tctatttcca    18360 attttttgtag tcttcctcca attattataa acaatcttgc actctgtaat cccatccaaa    18420
ttcagatagg tgaaacatac ggctttcata aatgagtaca tggtactcga cacattctaa    18480
aattaacatt aaattcatct tagatatgta tatgattta aaatttgaca tacagatgag    18540
tgtttaatta ctcaccaaat tgttgcaagt cactttatac tcactcagca ggactttaaa    18600
agtgatcaag ttaggaactt ggtggtacaa agagtgttat ttaggacaag cttttggttc    18660
agagttcctt ttaaaaatgg taagaagaa aacacttgc ccaaaatggg tcatgattac    18720
ttgataattt acagtgagtt catagaaatc tttgagtttt gttcatccag ccaatatagt    18780
tggattcacc agatttggtt gtatgtaaca aagtgcatgt tgccattact gtctaccaaa    18840
tgccaagtat gctctagttc atccttgcca ttactgtcta gcagatgcca agtatgctct    18900
agttcatcct ttcatcttac agaaaaagga tctactcaat tcaccataag actacgttta    18960
acaaagaaac taatataagc aaatgtgtta tatcatgtca tgtttatttg aaaatagtgt    19020
```

```
tgaaatttct aacctgatcc ataatatgaa ctatgttgaa catttcatct aattttttgt    19080
taatcttcat cattgtttta gtcattttct tccaattcta ttaatcttca ctcatcattt    19140
gtaaactcca tttacaatgt aaaagttact attaaaaata aatatatgca tccctaccta    19200
ctagtagtaa accaagacat atgagtttgg tcgagtacat accacgaagt tgaaagacac    19260
agtgcatata tctatttttg aaaatcaaga atgatattcc tattttgaaa aaaaaattgg    19320
gggcttcagg ctttggcaaa attctcacac cagcgcaaag tctcattaac aagtattttc    19380
atgttagtaa tgcgcacaaa gtctcattat cggtatttgt atatccagaa aataacacat    19440
gctttcaaca acatacacag aaacaagcat tttcatgtta gtaatacgca cattaacaag    19500 aactttcat gttagtaatg cactgaacat ttagattagt gaccgagaag attgactaac    19560
ctttatagaa acaagtatat atagaagaat aacctttcat gcccaagaat gagaatgaga    19620
gtgggtagag ctgtgagtga gagcaagaat aagagcgcaa gagtaagagc gagaacaaga    19680
gagagagggt gagagttaga gatgacgagt gtcgttgcac tgccacagag agtgcgtgag    19740
agtaagaatg agaacgagag cacgagaatg agagatgatt caaagagaaa gtgagaagag    19800
gaagaaacaa atttaattta acaaacacaa cattggtttt ttaaaaaact gacgttaaca    19860
taatttcgtt aatatcagtt ttttcaaaaa ccgatgttaa catagtgatg ttatatccat    19920
tctttctagt agtggtaggt aatgtacaaa taaaatgttg attataaagc accaattaaa    19980
ttaatctata tataaatgaa tataatggta tcataactaa ataaagagct ctaacactac    20040
taacaaagac tacaataaca attttaaaag actttcaata atggttttga aatgatatta    20100
agatcattgt cattaaaaat taaacacttt taatgatgat ttttaaaata ataacacctt    20160
ctatattgat tttatctaaa atcaatgtaa aaagtgtgat aaaatgttta aatatatcaa    20220
cgctctatat aagttgtgta aatattatta taaaaactaa gaattttatt caagaaaaag    20280
gaaaaaaaat attattataa aatttagacc taatcatcaa gtgagaaacg atggaacata    20340
aaatttacaa aattttattt aataatttat tggatggaat gagatatgga gaagggacta    20400
ttaaaatatc aaaatgttag ctgttttact cactttttgt ggttggttga tagacattga    20460
aactagacat gacaatgagg tgtggcgagg acaagtattg tctccccaat ccccgatttc    20520
aactctttcc caacatgttt ccatacccgt atccgatact cgatgggtta aaatttatta    20580
ttccatctcc gtactcgttg ggtatcgggt atccccgacc ccgttccgta ttagattcaa    20640
attagaaaaa taattttttt ttgtaaagaa aatattaaaa atttgatttt agaaaaaata    20700
aattgattga tatacatta tttttaacta cttatatatc aataaattta ttatagtgca    20760
tgtgtctaca aaaaccatta agaaaaaaat gttaaattat gtaaaaattc taaaataaaa    20820
ttaactagta ataaaaattc tatccttttt gattaaatta tgcaaaaatt caaaaattaa    20880
gtggcgggac aggtctgggt tcgaggctga ggtagacgta gtaattccat acccataccc    20940
gacttttgat tatcgagaaa aatctaaacc tgaactcata accgatcaac tcggatatta    21000
tagtgcatgt gtttacaaaa atcattaaga aaaaatgtt aaattatgta aaaattttaa    21060
aataaaatta actagtaata aaaattctag gccttttgat taaattatgc aaaaattcaa    21120
aaattaagtg gcgggacggg tctgggttcg aggctgaggt agatgtagta attcaatact    21180
catacccgac ttttgattat cgagaaaaat ccaaacccga acacataacc gatcaactcg    21240
gatattaccc gtcaaagtcg ggaaaaatac ctacagatgc gggttttctt gtcttaaaaa    21300
agttgcattt caaatttccg gttttaacgt agttattatg ctgtaagtaa aataaaaaat    21360
aaaaaaacat catcgtaatg gtttcaaatt atttgattcc acttttttcct ttcgctttgt    21420
```

```
tctccgatca ccactttaac ttccttctcc tgtcgtcatt accgattctg atgatattgt   21480
cgtcgatcta ctccattctc tatctgatct cttgaaagtg aaaaatacag tcttgtcaat   21540
gcgacattac atcaagactt gatgacgcga tgaggataaa tgtcggggtg atggtgcaaa   21600
tctctgccaa tgtagcaagg caccgaggcg aaacaaaagg tagcttgtga gtttgctgaa   21660
atggaaaagg aagaaattgg gttaagggag acacttgact taaagatgtt ttaatctaaa   21720
tttaaaatac aaattttatt aatacacatg gcattggtgg gataggaaat ggacaagttt   21780
ggagacaggt gatttcatta atcccgcttt tagatgttaa ttattccctg caaacagaa    21840
atgtccttga agcaaataaa tgcaacatta ttaaggagga gggttattat ttttaaagtt   21900
gtattattct tctttatgtt tttttttataa tattatctta tatattgttt ttctatctct  21960
ctaggatcaa atctcacatc ttattctgct ttcgaaaaat cttaatgtct atcatatttt   22020
gggacgaatt ggggtgaaag aaagaaaaag aaaaaaataa agatagataa aaataatgtg   22080
aaatagtact atgatggaaa agaacaaaga cataaaaaag aaaacaaatt aaaattaata   22140
atatgaagaa aaaagtgaac aagagaatat attaacacct caacattttt ttcttctttt   22200
ctatatttt  tagctattaa gaaaatatca tatgaataaa tttctcttat ttttattaat   22260
aatacataat tgttgataat agcaattgaa tttttttcaat aacatatttt aaatttagag  22320
tctgaatata ttcagtaaca tttacttgaa ttgagttcga ctatgacgag ttaaactcat   22380
aaatatattt aatagaattc agctttaatt atggtttaaa gtattttat  attaaaaatt   22440
aatcaaaatt agtgtcttta aagataaagt ggcaatggaa tttcgtctca cacagaccac   22500
agtctcatga aaattacaca gcatgcattc acaattaata gaggtgtatt tgtttgtggt   22560
gggatgatgc cacatcaaca tgctcaaagt ggaagatgca acaagttagt ggggaagaca   22620
tagcacaaat tgcttgtttg ataactttat cacgttgggg aatcaattac tgcactgtat   22680
caccgatcca tcatttgata tcagcattct cctttaagtg aatcagtgtt tttggaagaa   22740
ttaataattt tattttcact taaaaaaata tttttttttat cactctcaat cattcacatt  22800
atccatttt  ctttatatct ctttgtggta aaaagtgtta taaaaatgaa ataagactat   22860
atattactat tattctttaa aaaaaagtt taactcacta aattccattt gaagatatcc    22920
cagtttctct gattcaaatc aaacgacaaa catgaacatg ctgtttcaga gcaactcaag  22980
gtgcaacatt aacaatattt aatttatttt gacactgaac ataacaggtt ttttactttg   23040
aatatcacca cgcgtcacac gaaggtagga aattccatat actctggtgg agtataatgt   23100
gagaacatga caggttagaa gaagttaata aatattgacc aaattataac aaccacaata   23160
atttatataa gatcaaatga tcaataattt ataaatgtcc gcataaggta gatgatttcc   23220
aactactgag gtggagccgt ggagtatgcg tgtttatgct cctcctttg  cataacctat   23280
taagtgaggc caccaagagc ccacatgaac agatgttttt ttattgcttt ataaattgct   23340
ccaattagac gtacatccac accaagaccc ttctcgtact tgttcaatta aaaacaatga   23400
tgaagaattt tgcctactac ttcagtcaaa acaacaaca  tcaacgtttt tgtaggtttt   23460
tcccacacag ccttggattc ttggttcgtt ttctagcctt ccatgtccac cccttcttta   23520
ttcaactttg ttattttgtg attctttctc tgcttggtta cctcggtctc aaggcctcca   23580
agccaaggac cccccttaga ccaaatgact tggacctctt ttacacctca gtttctgctt   23640
ccacagtttc tagcatggta gccgttgaaa tggaggtttt ctccaattct caactaattc   23700
tcctaaccct tctcatgttt gttggtggcg aagtttttcac ttccatgctc gaccttgtat  23760
ttgctaggta taaattcacc cggagtgtcc aaaataaagt tagcaccaat cattcttacc   23820
```

```
tgactcgaac aagattacct ccggtagatg atacttctgg tttagaccaa attttttta    23880
gcagcaatcc ttttttatcc acaaagaagc cctcgattaa tgccaatcaa attgaacttg    23940
gtttagtttc tattcatcac tcagaatcag aaaaccacaa accaagtgat agtaataata    24000
ctaacgttcc aaagggcacg gtagtgtcct taacgacagt tgatagactt aagtataact    24060
gtcttagtta cctgacttat ttagttttag gttaccttgt ggtggttcaa tttgttggct    24120
ttagttctgt gtctttgtac ataaccctgg taccgagtgc aagacaagta ctgaaaaata    24180
aaggcattaa gattgcaacg ttttctttgt ttaccatagt ttccacgttt gctagttgtg    24240
gtttcatccc caccaacgag aacatgatgg ttttcaagaa gaactcgggg cttcttctcc    24300
ttgttctccc acacatcctt ctaggtaaca ccctttaccc accgtgtttg aggcttgtga    24360
taatggttct ggaaaggatt actaaaagag aggaatactc gcacttgctt aagaatttca    24420
aagacgtggg ttatgatcac atgctttctg ctcttcattg ttgcctcctg gttgctactg    24480
tgttgggttt taatcttata cagtttgtga tgctttgctc tatggagtgg aacaccaaaa    24540
tcatggaggg tttgaatgtg tatgagaaag tggtggcgtc cttgtttcaa gttacaaacg    24600
cgagacacgc cggtgaatct gttttgatc tctcctccat ctcttcagtc atattggtac    24660
tcttcgttgt catgatgtaa gtcactactc tatctttccc gccagaaaat attagatgat    24720
ccagcatgtg atttatgatc ccaatcaacg tgttatcaat gtgatacata attatcaatt    24780
cacaaatgac atgatatctc taataatttc tcctcactat atataatcca taccaattaa    24840
tgatcgagaa tgaataatta attatactga acaatgtcag ttcaacacca caattagtat    24900
ttaagtaata tcaactctta cattctcatg tatataggca tgaaactagt tattgaattg    24960
gtattatttt taatatatca aaattatatt atattcacat tttcacacgt ttaaatttt     25020
actctacttt catatttcat ctttctgttt tttttttcct ctgtctttct taacataaac    25080
ggaaggggtt aaaataatgc aacaaattaa attaagaata taaataaat atcatttaaa     25140
atcatatgat atgtaaagaa aataaaaatg taaaactaat gtaaagctga ctgtgaaaat    25200
atcaaattaa ttgattaata acactttggg ttccgattga tttattaaaa attatggtat    25260
tgaaatctat aatttttatt atttaaaaat catgatataa ttttttttatc tcatgtacaa   25320
agaattaaaa ggacatatat tcctatttat atctatttaa taactaaaat aataataatt    25380
aacaaactca attattttat aaaaaaactc catattattt attctaatat ctttttttat    25440
aaatttatca agcttgatat catttgtatt aaaataatta atattatata ttttagtata    25500
ttttatttta ttttacttgt attatttatt attcgtcaaa tgatatatat gacaaaagat    25560
tattcaatgt tatattttgt tctataatat ttttcttctc tttgtctaat atcataattt    25620
taacatgtat cggaattatt atgtttttt tcttaattt ttttgctac attccttaat      25680
attttttca ggttgtctga taattaatta tttaatttag taactttgtc gtcaccatga    25740
gcatggcctg gcccacttct gattttccta atacatgtag tatttcctag ttgacattaa    25800
tcacattgcg tgattggaca tgaaacaaaa ttttgtgatc cgt                      25843
```

<210> SEQ ID NO 7
<211> LENGTH: 12465
<212> TYPE: DNA
<213> ORGANISM: Artificial
<220> FEATURE:
<223> OTHER INFORMATION: Contig-3

<400> SEQUENCE: 7

```
atgaatcatt aatttgaatg acattatgtt cgaattttgt aattaagttc ctaagtttaa       60
```

```
atttagagaa cgaaaacagt ttttaaaaaa ttatattaaa aataatcagt taaatttatt    120
atcattaaaa attaattgtg gtttaaactc acagataatt tacattaata ttacaataaa    180
aagaaaacat cacatcatag aagtactctt cataatttat aactattgga atggaaccgt    240
ctattttgaa ggcagaaaaa tgagattcta gagcctagag gctcttgttt cggttaatta    300
agttagaaat gttttgcata ttatactaaa aatttaatga ataaaaataa aatcaaagaa    360
aaaaaaaata agattttga tcctttaata aaattatttt tatttcaaaa atacatttta    420
atcttaaaac caaacatgca caattgcaca tattcgtgga agttgctatt acaccaacca    480
ttatactaag tagtgcatat ggccatcttt ggtcttcacc cttcggtatc ggtctcatct    540
ttgtcacttc cagtaatttt ataataaaac ataccaacat aaatcacttc aaaatcaatt    600
ttataaaatc aattacattt aaaattaatt ttgttaacac ccaaggagca tacacttcaa    660
caacccatct cacacgtaaa ccaacattca tttcccaacc cttcattac gttatctctc    720 ggtcgtgccc agtattttca tttgaattaa tttggaattc tttgcaaaca tgatttattt    780 tattttcta cttcatattt ctattttatc gttttaattt ttctctttaa aatgcatttt    840
gtaatttgta aaccttcaga cttcagtgaa ggcggataat caattttagc aagtagctag    900
ctgactgaaa ttaaatagca ctgaataaat taaattaata aactaaataa tttgtcaatt    960 aaaaagaat gaaccttat tatagtaata gagttatata gtttttatct tttagaactt    1020
acatgcataa tcggtatttg tatcccaaaa agttttgaaa tcataatcgc ataaattagc    1080
caaagaaatc ctgcaaatga gtttgttaat ggattactaa aaaattaat ttgttaatgg    1140 ggtgattata atttacttat ttattagtaa aagacaaagc aaatatcatc tatggagaga    1200
atgagaggga tagaaagcgt gttatgggcg agtagaggtt tctttagcaa aagagttctg    1260
acacacagtt tcccattttc taccccattc aaaacgttat agtgtctttt gttttgcatt    1320
gacttggaag tcaatttatg caaagaagga acgcagatat gtcaaagaag ttattaaggt    1380
tgttacaaca ttgccatcga aattgatttg gaggtcacta ttagataatg tgttattccc    1440
aaatttgaaa tttgatttta ttttagttta atttgttatt gccaaattta aaatagagat    1500
agcaatattt ttgtaaaata ttagaaatga acaaaaatta tattaggaga tttgtgctca    1560
aattgagaaa accaatagtt tatctatacc gtatgtatac aaatagatgt gctcacaggt    1620
cactgtacta acaattaact atattgtctg ataaacaata atgcgaatcg atttatagga    1680
tcatgttaaa ttcatgcaag atgaacaagt agaatttgat cataaccgca atatgttaat    1740
agaatcaaag ttattagaga agaacaactc tcacaatgaa gagaatactc aaattattat    1800
ccaaattcaa cttattctag ttctctatta tatgacttct tatttacaag aagtgtcttg    1860
ttaactacta gtactcttgg gacattaaat aaaaagtatt gcagaaagca aaacaataa    1920 gataacgtaa aaaattataa acaatacaat tttattcaat atttcttttt gttttctttt    1980
aatttcttgc ttaacatttt tttccagcat agtttacttt ttctcctatt tataagacct    2040
tccaataaag ctacaccttg aaaagagttt gtcatatgat atgtttaatt tttcaattcc    2100
cttgaataaa taggagttag gggaataagg tgccgtaaca ttacaaaaat ttcttttaa    2160 taaaatataa taagaaaaaa ttatattta tttatttaat aaaaaattta atttctacaa    2220
aatattaggt tttaaaaaag aaaaaaatta aattgttacg acagttgacc caaattaatc    2280
cattaaaata taattgaatt gagtgatgga tttgattaaa tcctacctaa agtgatttgc    2340
ttagacctct gaattgaagg gcaagaggta ccctgcattg gaaacttcat ttgaccaaat    2400
tagggaaccc cgacaactac tcaacattac attaatcgat agagagtacg cttgatcagt    2460
```

```
tgtatagggc tgtagatatc ctaaattgag aaatttaagt ttatctatgg aatataaggg    2520 ttttttgtcat gagttgaggt atatgtactg ttgatcttct aatcgggctt gtgtctagaa   2580
gttttagttg ttaagagttg gaaagctatg tttagataaa gagtgctgct aggtgcatcc    2640
aacattattg ttggtgcact caatattaat cgtaaaaaga taaaaatact ccttacggat    2700
caagttgatc tataagttaa tttttaagac ttacgaatta acttaatctg taagtctttt    2760
acagatcaag ttgattcgta agttgatttt taagacttac ggatcaacat gattcgtaag    2820 tttttatgg atcaagttga tccgtaagaa gaaaaattag cagggacaat tttatcattt     2880
tcaaaaaata ccggatgcat ctaacaacac tcctaaataa atcctatgtc ccaccccaa     2940 ctattattca attgacagag ttttatatat atatatatat atatatatat atatatatat   3000
attcttcaat ctctgtttgt ttttgtatca tgagtttatt ttattttttgg aagataattc  3060 tctatataat gcttttacat cgcttttact aatccatcat ttttaaataa gtttattaaa   3120
tattttgttt gtcatgaatt cttttgatga taattaaagc aaattttttt tactatgaat   3180
aatgtttaat gtagcaaggt attataacgg cgatgatgaa ataataata atggaggtga    3240 tccaaaggaa aacaatctat acatatacaa agaccaacaa cttgaagcca tatattggac   3300
tatttcattt tttgtctcat gtgattgact gacttagttt tctaccgcag aaagcatgct   3360
acatatcatt cagaaaacaa aacatgtata aaccaattta gttaaaccaa acagttgttt   3420
tccgagtctt ccaaccttta aaatatgggt tagaaaatta gacactctaa tcacatcaaa   3480
agaagattaa aggatccaag cttgtctctc aatactatga aactgttcac cttcaagcct   3540
tttgtgagaa tatccactag ttgcatttca gtactgcagt agttcaagtc aagctatttt   3600
ttgctcactt tttcacaaag aaagtgaaat cttgtctcta tgtgttttga ccttccgtgt   3660
gctactggat tcatggccaa gttgataatg gatttgttgt ccacatacat ttcgattggc   3720
ctatgaattt ctatcttcaa ttcttcaagt aaaaagtcta gccacagtgc ttggcatgca   3780
acatagcatg ctacaatgta ctcagcctcg caggaagata atgtcattac aggttgtttc   3840
tttgaacacc agcttattgg tgtacctagg aactttaaga gatatcccgt agtgctcttc   3900 cttccactt tgtctccaca ccagtctgag tctgagaaac ccatcaacat agttgtagat    3960
tctgaaattc caaccaggct tgtgagagca gtttgataag atttttttagg aaatagaaca  4020 ccatagctta gtgttcctct gagatatctc agaattctct tagcagtagc ccaatgaaag   4080
gctttaggat cgtccaaaaa cctactaatt agaccaactg caaaagaaat gcctggtctt   4140
gtgttgtaga ggtatctcaa tgaccctaca acctgcttga atagggtact atccactgac   4200
ttttctgact catctttcac taatctcaag cctggttcaa cttgagtgga tgttaggttg   4260
cagcacatca tctaaaatct cttcaacagg tctattgcat acttctgttg gtgcataatc   4320
agaagtcctt tggcttcctt gaactcaatt ccaaggaaat aagacaatat ccccaggtct   4380
gtcatctcaa attcaagctt caaactcctc ttgaatttct ctatatgaat ctgattactc   4440
cctgtgatca atagatcatc aacatacaag cacataatta tcagatcatc tttgtcactc   4500
ttctttacat aaaactccata ttccttctca cacttatgga aaccttattt gacaagaaag  4560
gaatctattc tcttgttcca ggcccttgga gcctgcttta ggccatacaa tgccttgtat   4620
aaccttaaca ccttgtcttc ttcaaccttg atctcaaagc caggaggttg tttcacaaag   4680
acctcctctt ccaaagtacc attgaggaat gtcgacttta catcaagctg gtatagggtc   4740
caatctctac tgtgggctag agctataacc aaccttatgg tttctagcct agatactgga   4800
gcaaacactt ctgaataatc caaactagct cttggtagga atcctcttgc aactagcctt   4860
```

```
gttttatgct tggcaacagt tccatcaggc tttaatttca tcacccactt cacatctatt   4920
ggagacttgt ttggaggcaa gtcaacaagt ttccagatct gattactttc aaatgctctc   4980
aattcctctt ccattgcagc cttccaatga tcttgttgca gtgcatctct gtgatcaatt   5040
ggttcaatgt ctgccaaaaa ggcaaaatgc acaaactcac ttgctttcct ctttgcttct   5100
gccttctttt catcatctgg aactgcagct tgcccaagga tgttaggcat atcaacatga   5160
taatctttat acttcaaagg caagtgctta tttctctatg gtttctattg cacaacagga   5220
ggttcctcat gattagcttc tatttctgtt gcttcactga gtccagtctc attgttctct   5280
tctccaaaca aggtgttggt agtgcacttc ctcttccagt cccaggagcc atcttcatca   5340
atcacaacat ctctgctgat gaagattttg tgagttaacg aatcatacaa cctataggca   5400
ccagttggat gatattcaac ctgtatcata ggtacactct tgtcctgaag cttttcctc   5460 ctctcatcag gcacattctt gaaacataat gacccaaaca ctctcaaatg cttcactgga   5520
ggcttccttt gggtccatac ttcttcaagc actctatatt ttagcttctt tgtgggacac   5580
ttattcaaaa tgtatgctgt agtggacatt gcttctcccc aaaaagttaa tgacaagtgc   5640
ttctctttca acatacacct tgccatgttc atcattgttc tgttcctcca ctcagccaaa   5700
ccattatact gaggagtata aggagcaatg atctcgtgta ttataccatg ttcgtgataa   5760
tatgtaatat tgttcattat tatttcagat ttttaaaaa tatttgtgtt attatttatg   5820
aaatatgtaa ttttttagt atttgatttt atgatgataa agtgttctaa attcaaaaga   5880
agggggaaag cgtaaacatt aaaaaacgtc atcaaacaaa acaaaatct tgttaataaa   5940 gataaaactg tttgttttga tcactgttat ttcgtaatat aaaaacatta tttatattta   6000
tattgttgac aaccaaattt gcctatcaaa tctaaccaat ataatgcatg cgtggcaggt   6060
aatgtactac catgaactta agtcatgaca taataaaccg tgaatctgac caatgcatgt   6120
acctagctaa atgtatttgt gacacgaagc aaatgattca attcacaatg gagatgggaa   6180
acaaataatg aagaacccag aactaagaaa gcttttctga aaaataaaat aaaggcaatg   6240
tcaaaagtat actgcatcat cagtccagaa agcacatgat atttttttat cagtatcaat   6300
gcagctagtt ttatttaca atatcgatat agctagttta aatatattgc agctagattt   6360
ataaatattt gtgttattat ttatcatttg tgtaatcctg tttttagtat tttagtttat   6420
atatgatgat aatgtattcc aaatttaaaa gaagggaaat aaatttaaac aagaaaaaaa   6480
gtcatcaaac aaaaaacaaa tgaaagggtg gaaagatgtt accatgtaat gtgaatgtta   6540
cagtatttct tttattatag agttaacaaa ttaactaata tgattttgtt aataatgatg   6600
aaatattttt tttattatta tttcataata taaaaatagt ttacttaata taaaaaaaaa   6660
ttctatcgtt cacaacaaag ttggccacct aatttaacca tgcatgtacc catgaccat   6720 attaggtaac catcaaacct gatgaagaga taaagagatg aagacttaag tcataacaca   6780
aaaccataaa aaacaaaaat acaatcaacc gtcaatctga ccaatgcatg aaaaagctgc   6840
aatagtgagt ggcgacacaa agcacatgat tttcttacaa cggagataaa accaaaaaa   6900 tatttcatga acaacctaga acaaataaag cttttatata ataaatatat aaataaataa   6960
aggctatgga ataatatact tcaatatatt tggattaaat aaattgttgg cggggttgat   7020
atatttatac acacctaaag tcacttcaat ctcattttca cttaactttt atttttttt   7080 tcttttatt tatcataaag agaatattga taatatactt tttaacatat ttttatgaca   7140
ttttttattg gtgaaaactt attaaaaatc ataaattttg taagttagat ttatttaaag   7200
agttcctctt cttatttaa atttttaat aaatttttaa ataactaaaa tttgtgttaa   7260
```

```
aaatgttaaa aaagtgtgtt attaaccctt ctcttcgagg atataatgat catttttcact    7320 tatccggtaa ctatcgtctt gagtccaacc cggtaagaca cgacttatcg ccactggcag    7380
cagccactgg taacaggatt agcagagcga ggtatgtagg cggtgctaca gagttcttga    7440
agtggtggcc taactacggc tacactagaa gaacagtatt tggtatctgc gctctgctga    7500
agccagttac cttcggaaaa agagttggta gctcttgatc cggcaaacaa accaccgctg    7560
gtagcggtgg tttttttgtt tgcaagcagc agattacgcg cagaaaaaaa ggatctcaaa    7620
aagatccttt gatcttttct acggggtctg acgctcagtg gaacgaaaac tcacgttaag    7680
ggattttggt catgacatta acctataaaa ataggcgtat cacgaggccc tttcgtctcg    7740
cgcgtttcgg tgatgacggt gaaaacctct gacacatgca gctcccggag acggtcacag    7800
cttgtctgta agcatcaaga ggaatcaggg aaggcaaaat gtatatcaac tggaacaagt    7860
gagatgggat tttactcttt ttattgcttt gtattttctt catactttag gggatgcttg    7920
gtttgagaag aatgtttctt attttcattt ttgctttcac ttttaattac aaaattaaca    7980
ccttgtttcc atcttgtttc ttattttcaa aagtttgtat aagtggaaac aacttttatt    8040
gttatcctta atattttttcc ctttatattt cttttctctca gtgtgcttct tcatcccatt    8100
gtataaaaag caatgcatat tggtaaaact ctaagacatt attttaattt ttttaaaaaa    8160
aagacattct aagacggtta tttgaaaaac cgtcttagaa gggtaccatt ctaagatggt    8220
ttttcaaaga accatcttag aatgtcttag aaggatatca ttctaagacg gtttttagct    8280
aagaatcgcc ttagaagaag ttctctgaaa aatcatctta gaagaatatc attctaagac    8340
ggttcttgta gttttctaag acgattttta gctaacaacc gtcttaaaaa gacacccttt    8400
tctaaaatgg tttttttgtt gaaactgtca tcaaaagtct taactttcaa cgatgttgac    8460
tacaaagacg gttcaaaatc gtctttgaat gtcttataca atcgttgttg tatatgcctt    8520
ttgtagtagt gtataattga ttgtttttat ttcgatgttt gactagtgag gttttattta    8580
taaacaattc aacaaagtat tttgaaacat tttaccggtc aaagttgaaa aactctagtt    8640
taactagagt tatcaattct caaaaaaaaa aaaaaactag agttattagt catattattt    8700 tttttttaaga aaaaattatt tattaatgcc acctgagaga ctacattgtc agtaatgttt    8760
ttcaaaaaat gttactaaag ttgtagtatt ccacacgaca ttaataatta aaaattattt    8820
tttaaacaaa atattggttg tgatattgtt tttcagcatt gattgttcca atttggtaca    8880
atatctcaaa agaacatact ttggtaatta acttttaaat tttcctttgg tcaacttaat    8940
attgctaata ctccttgtac tgtactattt gtgtggctta ataataattt tttgtcttca    9000
tctttcacat tttcaccct aaactataaa atttgcatat tttcactgct agaaaaacat    9060 tttttttatga cgattatttt ggatattatg tcggttatta actgtcgtta tatgatacat    9120
cgtagaatgt ttgcatctac aacagcagtt ctcaaaaaat agtcttagga aagttacaat    9180
tctaagacag tttaaaaaat aatcatctta gaatgtctac aatctaagat gattttcaaa    9240
taaccgtctt agaatgtatt tattttttat aaaaaattaa aaattgagga ttttaaggcg    9300 attttttccat gtcaaacaat tttttcaaag accatcttag aattcaaaca ttgtaagacg    9360 gttttttcaaa gaaccatctt agaatttttt tttttaaaat attttatttt tttactgcca    9420
taataatcaa tgattatttt atttttttat tggcataata ataaagtaat aaagtaagga    9480
attttataca tgatgacggt agaaagcata aaatgttcca attaaaaagc acaaaaatgc    9540
ctaaaaattt gcaatttcca attagaaagc tttgccaacg agaactgaat gcagaaaaca    9600
atcaattata atgtgtggaa aaaaatatgc actaattttt aattaattaa tttttacaat    9660
```

```
acataaatgt actaataatt ttaaataata aaatcaatta taaattaaaa ataattttag    9720
tgtgaaaagt ataaagcaat atattatgaa aaaatagttt aatttgtaaa caataaatga    9780
atctaaatta ttgaaattga agcttacctt tgttgaccta atattcctca gtgatgcctc    9840
cagttgattc tcaagctcat ttgtattcgt ttaggcaaga tctttcccaa gtaggttcct    9900
acatatttta tatatatata tatatagtat aaatatagaa tatatagaat atcaacttta    9960
agtttgaaaa catagcaagt aagttatata attacctttg agaagatccg gtataatgta   10020
tgcaataact aggcagtcct cagttctaag ccatgatgac ccactagtga gacatggaaa   10080
tgcagtactt cctagcattc ttgagcctag aaagcacaga tatatcaatc ccaaatacac   10140
ttctcggcca tcggcctgaa acctgggtgg aaggttgaca ttgttatcta ccattgaagc   10200
caatagaggc aaggggggat gaaggtgggt ttggaaagga tgaaaaatgt tgatagagat   10260
tgtttgtcaa tcttatgaag ttcaaagcta aattcttgag cctagaaagc acggatatat   10320
caatcccaaa tacacttctc ggccatcggc ctgaaacctg ggtggaaggt tgacattgtt   10380
atctaccatt gaagccaata gaggcaaggg gggatgaagg tgggtttgga aaggatgaaa   10440
aatgttgata gagattgttt gtcaatctta tgaagttcaa agctaaattc ttcatagaaa   10500
aaggagtgat gctcacacaa aattatcatg cagggtacca atttcaggat gattaggaaa   10560
cttggtcact agctgtagag gagatcgtac agatttgcca gaaacccga ttaactagac   10620
ataaaatgtt aattagagat ctacacttat gacacatgca attgttgcat tgtattgcag   10680
gagcaacatg tgtgaccaac ttgatggtca attctagttc cccatactta actcctcgaa   10740
gccttaacca aacattctgc accacctcac cattcacaca gttggtattt ctttcacgga   10800
caagatagtt ttcaccatca ggtatgacct tccttaatgt cgtctcaata gaggacactc   10860
ttaagatgtc tcttaatctg gctacagaga ctattggttg aaggttcagg aaagtattcc   10920
ccatcttgtc atcaaccttc aaaagatctt tatcaaacac ttcctctctc tctctctcta   10980
tctctctctc tctctatata tatatatata tatatatata tatatatata tataaacaac   11040
atcttagtta tacaacataa gatctaataa acagtaccta gtattcaaga ttttagaatg   11100
ggtaaaatat gttttaagtc ccacaatttt ttttgtcaaa attgatttta gtccatactt   11160
tagaaacatg gttttagtgc tcatattttt ataattggtt tcctttatgg aacttagaat   11220
acttgagtga gggacaagat taaccaagat tgaagaaaac aagaatgaag cggcatacta   11280
aatatcatgg agctcaccaa attcaaaact cccaagggtt ctgtcaaagt gaaatttagc   11340
tcttcattcc aaacaggatt caagcagcta ttaattacct tggtctttgt agtatggtac   11400
aatttaataa catttcaagg ttaaaatatg ctacataatg ttaatgttat tgttaataga   11460
aacaagccaa aaatgaaatt aacatataaa taagtcttat ttacctgatt ccctagcttg   11520
agcacaacat aaggatcact agtcttgaaa tcctggatca ccaacctttt cccttgcata   11580
acaattattt ttagcaaccc taattgttta cccattatac tccttctaac aagttaaact   11640
aatagtcaaa caaataaatt tctttatttg ttgttcaaag ttggtgaaat gaatttccaa   11700
actcacccta cgcatgagca agttccacca tcaaaattta ctctaaaacg aaataatgct   11760
ttgaaccagg aaaaaatagt atctcccaag cagcgtatct cagcgcaata taagcaacat   11820
ttagatttgg cttctataaa catccttta caaaataata tactagttat attttattca   11880
agtattacat tgaaacatcg ctctggatcc aggacatcaa tgcctcaaaa aaattatttc   11940
ctagatcact actaggcaag gccctatccc ttgtattaca taaattgact acgaaactag   12000
tattactaaa tcgtctctca tgcatgaact gaaggtggtg ttaaatcaca aaatcttcca   12060
```

-continued

```
ctttctctca agggcaccag taatccttgt aatacaataa gcaacactta gaggtacccc   12120
gaaactgcaa tcaggaaaca cgatgatgta agaaatagaa aatatcttga ctagtgcatg   12180
ttaaataaac aattagctga ggtagcattt tgtatatatc caagttttga caacagtttt   12240
tttagggaaa atgaaaaggg tcttgcaaac taatgcttag ttaaggaatt aagatagaaa   12300
gtatttttat tgctcctacc tgaaattaga atatattagc atgtacttac ttagacaata   12360
ggtacaaaaa ttaaaagttg agctagtatg agtaccacaa agacaaggtc catattgcta   12420
agaataattg atacttagtc atccatatct acaagcttgt ttggg                  12465

<210> SEQ ID NO 8
<211> LENGTH: 20
<212> TYPE: DNA
<213> ORGANISM: Artificial
<220> FEATURE:
<223> OTHER INFORMATION: Contig-1 20-nt 5' junction

<400> SEQUENCE: 8
atacgaaatc attaagtagt                                               20

<210> SEQ ID NO 9
<211> LENGTH: 20
<212> TYPE: DNA
<213> ORGANISM: Artificial
<220> FEATURE:
<223> OTHER INFORMATION: Contig-1 20-nt 3' junction

<400> SEQUENCE: 9
gctagctagt gttttttcct                                               20

<210> SEQ ID NO 10
<211> LENGTH: 40
<212> TYPE: DNA
<213> ORGANISM: Artificial
<220> FEATURE:
<223> OTHER INFORMATION: Contig-1 40-nt 5' junction

<400> SEQUENCE: 10
tggtactaac atacgaaatc attaagtagt aattaatacg                         40

<210> SEQ ID NO 11
<211> LENGTH: 40
<212> TYPE: DNA
<213> ORGANISM: Artificial
<220> FEATURE:
<223> OTHER INFORMATION: Contig-1 40-nt 3' junction

<400> SEQUENCE: 11 tctcttttg gctagctagt gttttttcct cgactttgt                           40

<210> SEQ ID NO 12
<211> LENGTH: 60
<212> TYPE: DNA
<213> ORGANISM: Artificial
<220> FEATURE:
<223> OTHER INFORMATION: Contig-1 60-nt 5' junction

<400> SEQUENCE: 12
aatccaagct tggtactaac atacgaaatc attaagtagt aattaatacg tactagtaaa   60

<210> SEQ ID NO 13
<211> LENGTH: 60
<212> TYPE: DNA
<213> ORGANISM: Artificial
<220> FEATURE:
```

```
<223> OTHER INFORMATION: Contig-1 60-nt 3' junction

<400> SEQUENCE: 13
atacccgtgt tctcttttg gctagctagt gttttttct cgactttgt atgaaaatca      60

<210> SEQ ID NO 14
<211> LENGTH: 20
<212> TYPE: DNA
<213> ORGANISM: Artificial
<220> FEATURE:
<223> OTHER INFORMATION: Contig-2 20-nt 5' junction

<400> SEQUENCE: 14
atcctttcca aatatggtcc                                                20

<210> SEQ ID NO 15
<211> LENGTH: 20
<212> TYPE: DNA
<213> ORGANISM: Artificial
<220> FEATURE:
<223> OTHER INFORMATION: Contig-2 20-nt 3' junction

<400> SEQUENCE: 15
ccgtcgacgg taacttttac                                                20

<210> SEQ ID NO 16
<211> LENGTH: 40
<212> TYPE: DNA
<213> ORGANISM: Artificial
<220> FEATURE:
<223> OTHER INFORMATION: Contig-2 40-nt 5' junction

<400> SEQUENCE: 16
atgggcgact atcctttcca aatatggtcc atgggtacat                          40

<210> SEQ ID NO 17
<211> LENGTH: 40
<212> TYPE: DNA
<213> ORGANISM: Artificial
<220> FEATURE:
<223> OTHER INFORMATION: Contig-2 40-nt 3' junction

<400> SEQUENCE: 17
ctcattatat ccgtcgacgg taacttttac ttagataata                          40

<210> SEQ ID NO 18
<211> LENGTH: 60
<212> TYPE: DNA
<213> ORGANISM: Artificial
<220> FEATURE:
<223> OTHER INFORMATION: Contig-2 60-nt 5' junction

<400> SEQUENCE: 18
cttggtcctc atgggcgact atcctttcca aatatggtcc atgggtacat gcatggttaa    60

<210> SEQ ID NO 19
<211> LENGTH: 60
<212> TYPE: DNA
<213> ORGANISM: Artificial
<220> FEATURE:
<223> OTHER INFORMATION: Contig-2 60-nt 3' junction

<400> SEQUENCE: 19
ttgtttacgg ctcattatat ccgtcgacgg taacttttac ttagataata ttttcttaaa    60

<210> SEQ ID NO 20
```

-continued

```
<211> LENGTH: 20
<212> TYPE: DNA
<213> ORGANISM: Artificial
<220> FEATURE:
<223> OTHER INFORMATION: Contig-3 20-nt 5' junction

<400> SEQUENCE: 20
ttataccatg ttcgtgataa                                                    20

<210> SEQ ID NO 21
<211> LENGTH: 20
<212> TYPE: DNA
<213> ORGANISM: Artificial
<220> FEATURE:
<223> OTHER INFORMATION: Contig-3 20-nt 3' junction

<400> SEQUENCE: 21
gtctgtaagc atcaagagga                                                    20

<210> SEQ ID NO 22
<211> LENGTH: 40
<212> TYPE: DNA
<213> ORGANISM: Artificial
<220> FEATURE:
<223> OTHER INFORMATION: Contig-3 40-nt 5' junction

<400> SEQUENCE: 22
atctcgtgta ttataccatg ttcgtgataa tatgtaatat                              40

<210> SEQ ID NO 23
<211> LENGTH: 40
<212> TYPE: DNA
<213> ORGANISM: Artificial
<220> FEATURE:
<223> OTHER INFORMATION: Contig-3 40-nt 3' junction

<400> SEQUENCE: 23
gtcacagctt gtctgtaagc atcaagagga atcagggaag                              40

<210> SEQ ID NO 24
<211> LENGTH: 60
<212> TYPE: DNA
<213> ORGANISM: Artificial
<220> FEATURE:
<223> OTHER INFORMATION: Contig-3 60-nt 5' junction

<400> SEQUENCE: 24
aggagcaatg atctcgtgta ttataccatg ttcgtgataa tatgtaatat tgttcattat        60

<210> SEQ ID NO 25
<211> LENGTH: 60
<212> TYPE: DNA
<213> ORGANISM: Artificial
<220> FEATURE:
<223> OTHER INFORMATION: Contig-3 60-nt 3' junction

<400> SEQUENCE: 25
cccggagacg gtcacagctt gtctgtaagc atcaagagga atcagggaag gcaaaatgta        60

<210> SEQ ID NO 26
<211> LENGTH: 27
<212> TYPE: DNA
<213> ORGANISM: Artificial
<220> FEATURE:
<223> OTHER INFORMATION: 05-O-975 Contig-1 5' junction forward primer

<400> SEQUENCE: 26
```

-continued tgtcacatta caagtgagat gtcatca                                    27

<210> SEQ ID NO 27
<211> LENGTH: 28
<212> TYPE: DNA
<213> ORGANISM: Artificial
<220> FEATURE:
<223> OTHER INFORMATION: 05-O-977 Contig-1 5' junction reverse primer

<400> SEQUENCE: 27
tctcgttatc ttttgccact tttactag                                   28

<210> SEQ ID NO 28
<211> LENGTH: 19
<212> TYPE: DNA
<213> ORGANISM: Artificial
<220> FEATURE:
<223> OTHER INFORMATION: 05-QP22 Contig-1 5' junction probe

<400> SEQUENCE: 28
caagcttggt actaacata                                             19

<210> SEQ ID NO 29
<211> LENGTH: 35
<212> TYPE: DNA
<213> ORGANISM: Artificial
<220> FEATURE:
<223> OTHER INFORMATION: 06-O-1573 Contig-1 5' junction forward primer

<400> SEQUENCE: 29
ttttggtgaa atcatgctta cttttgtgat gggac                           35

<210> SEQ ID NO 30
<211> LENGTH: 20
<212> TYPE: DNA
<213> ORGANISM: Artificial
<220> FEATURE:
<223> OTHER INFORMATION: 06-O-1487 Contig-1 5' junction reverse primer

<400> SEQUENCE: 30
cgctaaggcc gaatgcaaag                                            20

<210> SEQ ID NO 31
<211> LENGTH: 29
<212> TYPE: DNA
<213> ORGANISM: Artificial
<220> FEATURE:
<223> OTHER INFORMATION: 06-O-1414 Contig-1 3' junction forward primer

<400> SEQUENCE: 31
gtgtgaataa gcaatgttgg gagaatcgg                                  29

<210> SEQ ID NO 32
<211> LENGTH: 31
<212> TYPE: DNA
<213> ORGANISM: Artificial
<220> FEATURE:
<223> OTHER INFORMATION: 06-O-1579 Contig-1 3' junction reverse primer

<400> SEQUENCE: 32
gctcgagaag atgaagccta gaggagagca c                               31

<210> SEQ ID NO 33
<211> LENGTH: 35
<212> TYPE: DNA
<213> ORGANISM: Artificial
<220> FEATURE:

<223> OTHER INFORMATION: 06-O-1577 Contig-1 3' junction forward primer

<400> SEQUENCE: 33
aacccttctc ttcgaggatc caagcttgga ttttg                             35

<210> SEQ ID NO 34
<211> LENGTH: 31
<212> TYPE: DNA
<213> ORGANISM: Artificial
<220> FEATURE:
<223> OTHER INFORMATION: 06-O-1579 Contig-1 3' junction reverse primer

<400> SEQUENCE: 34
gctcgagaag atgaagccta gaggagagca c                                 31

<210> SEQ ID NO 35
<211> LENGTH: 35
<212> TYPE: DNA
<213> ORGANISM: Artificial
<220> FEATURE:
<223> OTHER INFORMATION: 06-O-1586 Contig-2 5' junction forward primer

<400> SEQUENCE: 35
ctggcgctat ctttatctga ttgtaaccgg agaac                             35

<210> SEQ ID NO 36
<211> LENGTH: 32
<212> TYPE: DNA
<213> ORGANISM: Artificial
<220> FEATURE:
<223> OTHER INFORMATION: 06-O-1585 Contig-2 5' junction reverse primer

<400> SEQUENCE: 36
catgcatgta cccatggacc atatttggaa ag                                32

<210> SEQ ID NO 37
<211> LENGTH: 30
<212> TYPE: DNA
<213> ORGANISM: Artificial
<220> FEATURE:
<223> OTHER INFORMATION: 06-O-1404 Contig-2 3' junction forward primer

<400> SEQUENCE: 37
cgaatgcaaa gaaattggtt ctttctcgtt                                   30

<210> SEQ ID NO 38
<211> LENGTH: 35
<212> TYPE: DNA
<213> ORGANISM: Artificial
<220> FEATURE:
<223> OTHER INFORMATION: 06-O-1590 Contig-2 3' junction reverse primer

<400> SEQUENCE: 38
atcagtattg cgctttcaac ttgaaggctt gaatc                             35

<210> SEQ ID NO 39
<211> LENGTH: 25
<212> TYPE: DNA
<213> ORGANISM: Artificial
<220> FEATURE:
<223> OTHER INFORMATION: 06-O-1626 Contig-3 5' junction forward primer

<400> SEQUENCE: 39
aatgtatgct gtagtggaca ttgct                                        25

<210> SEQ ID NO 40

```
<211> LENGTH: 27
<212> TYPE: DNA
<213> ORGANISM: Artificial
<220> FEATURE:
<223> OTHER INFORMATION: 06-O-1366 Contig-3 5' junction reverse primer

<400> SEQUENCE: 40
agtcttcatc tctttatctc ttcatca                                              27

<210> SEQ ID NO 41
<211> LENGTH: 32
<212> TYPE: DNA
<213> ORGANISM: Artificial
<220> FEATURE:
<223> OTHER INFORMATION: 06-O-1569 Contig-3 3' junction forward primer

<400> SEQUENCE: 41
ggcgacacaa agcacatgat tttcttacaa cg                                        32

<210> SEQ ID NO 42
<211> LENGTH: 29
<212> TYPE: DNA
<213> ORGANISM: Artificial
<220> FEATURE:
<223> OTHER INFORMATION: 06-O-1551 Contig-3 3' junction reverse primer

<400> SEQUENCE: 42
acattcttct caaaccaagc atcccctaa                                            29

<210> SEQ ID NO 43
<211> LENGTH: 35
<212> TYPE: DNA
<213> ORGANISM: Artificial
<220> FEATURE:
<223> OTHER INFORMATION: 06-O-1571 Contig-1 5' junction forward primer

<400> SEQUENCE: 43
tagcaaccga agcagagaat gagtgagagg taatc                                     35

<210> SEQ ID NO 44
<211> LENGTH: 35
<212> TYPE: DNA
<213> ORGANISM: Artificial
<220> FEATURE:
<223> OTHER INFORMATION: 06-O-1572 Contig-1 5' junction reverse primer

<400> SEQUENCE: 44
caaagcttat atatgccttc cgctaaggcc gaatg                                     35

<210> SEQ ID NO 45
<211> LENGTH: 28
<212> TYPE: DNA
<213> ORGANISM: Artificial
<220> FEATURE:
<223> OTHER INFORMATION: 06-O-1351 Contig-1 5' junction forward primer

<400> SEQUENCE: 45
gatgtcatca cacaactctg acttagtt                                             28

<210> SEQ ID NO 46
<211> LENGTH: 22
<212> TYPE: DNA
<213> ORGANISM: Artificial
<220> FEATURE:
<223> OTHER INFORMATION: 06-O-1367 Contig-1 5' junction reverse primer

<400> SEQUENCE: 46
```

-continued

```
ccatcactcc aacacaggtt cc                                             22

<210> SEQ ID NO 47
<211> LENGTH: 22
<212> TYPE: DNA
<213> ORGANISM: Artificial
<220> FEATURE:
<223> OTHER INFORMATION: 06-O-1357 Contig-1 insert forward primer

<400> SEQUENCE: 47
tgaatcgtaa tgaggcaagg ca                                             22

<210> SEQ ID NO 48
<211> LENGTH: 23
<212> TYPE: DNA
<213> ORGANISM: Artificial
<220> FEATURE:
<223> OTHER INFORMATION: 06-O-1368 Contig-1 insert reverse primer

<400> SEQUENCE: 48
tcacactcac aatagggtgg cct                                            23

<210> SEQ ID NO 49
<211> LENGTH: 23
<212> TYPE: DNA
<213> ORGANISM: Artificial
<220> FEATURE:
<223> OTHER INFORMATION: 06-O-1369 Contig-1 insert reverse primer

<400> SEQUENCE: 49
agcgaagttc ctattccgaa gtt                                            23

<210> SEQ ID NO 50
<211> LENGTH: 25
<212> TYPE: DNA
<213> ORGANISM: Artificial
<220> FEATURE:
<223> OTHER INFORMATION: 06-O-1356 Contig-1 insert forward primer

<400> SEQUENCE: 50
gaccatatta ggtaaccatc aaacc                                          25

<210> SEQ ID NO 51
<211> LENGTH: 20
<212> TYPE: DNA
<213> ORGANISM: Artificial
<220> FEATURE:
<223> OTHER INFORMATION: 06-O-1371 Contig-1 insert reverse primer

<400> SEQUENCE: 51
ccatctcagt cagcacaagg                                                20

<210> SEQ ID NO 52
<211> LENGTH: 21
<212> TYPE: DNA
<213> ORGANISM: Artificial
<220> FEATURE:
<223> OTHER INFORMATION: 06-O-1360 Contig-1 insert forward primer

<400> SEQUENCE: 52
gccttgtgct gactgagatg g                                              21

<210> SEQ ID NO 53
<211> LENGTH: 25
<212> TYPE: DNA
<213> ORGANISM: Artificial
<220> FEATURE:
```

<223> OTHER INFORMATION: 06-O-1423 Contig-1 insert reverse primer

<400> SEQUENCE: 53
agttccaaga cccattaaag tgcta                                          25

<210> SEQ ID NO 54
<211> LENGTH: 24
<212> TYPE: DNA
<213> ORGANISM: Artificial
<220> FEATURE:
<223> OTHER INFORMATION: 06-O-1363 Contig-1 insert forward primer

<400> SEQUENCE: 54
aactcactgg tattcccgtt gcta                                           24

<210> SEQ ID NO 55
<211> LENGTH: 20
<212> TYPE: DNA
<213> ORGANISM: Artificial
<220> FEATURE:
<223> OTHER INFORMATION: 06-O-1421 Contig-1 insert forward primer

<400> SEQUENCE: 55
tgcccacagg ccgtcgagtt                                                20

<210> SEQ ID NO 56
<211> LENGTH: 34
<212> TYPE: DNA
<213> ORGANISM: Artificial
<220> FEATURE:
<223> OTHER INFORMATION: 06-O-1578 Contig-1 3' junction reverse primer

<400> SEQUENCE: 56
tttcattgac aacattgtgg atgtgaaagc ggac                                34

<210> SEQ ID NO 57
<211> LENGTH: 37
<212> TYPE: DNA
<213> ORGANISM: Artificial
<220> FEATURE:
<223> OTHER INFORMATION: 07-O-1889 Contig-1 5' region forward primer

<400> SEQUENCE: 57
caatactagc aaaagaaaaa gaaattatac ggaacaa                             37

<210> SEQ ID NO 58
<211> LENGTH: 35
<212> TYPE: DNA
<213> ORGANISM: Artificial
<220> FEATURE:
<223> OTHER INFORMATION: 07-O-1940 Contig-1 5' region reverse primer

<400> SEQUENCE: 58
ctgatagttt taaagaaaaa agtcagagtt gtatt                               35

<210> SEQ ID NO 59
<211> LENGTH: 34
<212> TYPE: DNA
<213> ORGANISM: Artificial
<220> FEATURE:
<223> OTHER INFORMATION: 07-O-1892 Contig-1 3' region reverse primer

<400> SEQUENCE: 59
accaaaccat tttaattcaa atatttttca ttca                                34

<210> SEQ ID NO 60

-continued

```
<211> LENGTH: 34
<212> TYPE: DNA
<213> ORGANISM: Artificial
<220> FEATURE:
<223> OTHER INFORMATION: 07-O-1894 Contig-1 3' region forward primer

<400> SEQUENCE: 60
gaaaatcatt tgtgtcaata gtttgtgtta tgta                                34

<210> SEQ ID NO 61
<211> LENGTH: 35
<212> TYPE: DNA
<213> ORGANISM: Artificial
<220> FEATURE:
<223> OTHER INFORMATION: 06-O-1588 Contig-2 5' junction forward primer

<400> SEQUENCE: 61
gcgcatgaga caattatgct aagactcaag cctac                               35

<210> SEQ ID NO 62
<211> LENGTH: 29
<212> TYPE: DNA
<213> ORGANISM: Artificial
<220> FEATURE:
<223> OTHER INFORMATION: 06-O-1403 Contig-2 5' junction reverse primer

<400> SEQUENCE: 62
aaccaatttc tttgcattcg gccttagcg                                      29

<210> SEQ ID NO 63
<211> LENGTH: 35
<212> TYPE: DNA
<213> ORGANISM: Artificial
<220> FEATURE:
<223> OTHER INFORMATION: 06-O-1592 Contig-2 3' junction reverse primer

<400> SEQUENCE: 63
tatttattaa tttcacattt taccacctgg ctatc                               35

<210> SEQ ID NO 64
<211> LENGTH: 32
<212> TYPE: DNA
<213> ORGANISM: Artificial
<220> FEATURE:
<223> OTHER INFORMATION: 07-O-1895 Contig-2 5' region forward primer

<400> SEQUENCE: 64
ttttcaagga tgtctagggc ttcatccttc tc                                  32

<210> SEQ ID NO 65
<211> LENGTH: 31
<212> TYPE: DNA
<213> ORGANISM: Artificial
<220> FEATURE:
<223> OTHER INFORMATION: 07-O-1898 Contig-2 5' region reverse primer

<400> SEQUENCE: 65
ggaccaagaa atgggacctc atcaagaaga g                                   31

<210> SEQ ID NO 66
<211> LENGTH: 27
<212> TYPE: DNA
<213> ORGANISM: Artificial
<220> FEATURE:
<223> OTHER INFORMATION: 07-O-1905 Contig-2 3' region forward primer

<400> SEQUENCE: 66
```

```
caacattaaa ttgaaagtct atttgac                                    27

<210> SEQ ID NO 67
<211> LENGTH: 34
<212> TYPE: DNA
<213> ORGANISM: Artificial
<220> FEATURE:
<223> OTHER INFORMATION: 07-O-1903 Contig-2 3' region reverse primer

<400> SEQUENCE: 67
gctgttatat tattacttag tataatataa aatg                             34

<210> SEQ ID NO 68
<211> LENGTH: 35
<212> TYPE: DNA
<213> ORGANISM: Artificial
<220> FEATURE:
<223> OTHER INFORMATION: 06-O-1669 Contig-3 5' junction forward primer

<400> SEQUENCE: 68
ttgtctcatg tgattgactg acttagtttt ctacc                            35

<210> SEQ ID NO 69
<211> LENGTH: 24
<212> TYPE: DNA
<213> ORGANISM: Artificial
<220> FEATURE:
<223> OTHER INFORMATION: 06-O-1426 Contig-3 5' junction reverse primer

<400> SEQUENCE: 69
cattggtcag attcacggtt tatt                                        24

<210> SEQ ID NO 70
<211> LENGTH: 25
<212> TYPE: DNA
<213> ORGANISM: Artificial
<220> FEATURE:
<223> OTHER INFORMATION: 06-O-1355 Contig-3 insert forward primer

<400> SEQUENCE: 70
gtggcaggta atgtactacc atgaa                                       25

<210> SEQ ID NO 71
<211> LENGTH: 26
<212> TYPE: DNA
<213> ORGANISM: Artificial
<220> FEATURE:
<223> OTHER INFORMATION: 06-O-1459 Contig-3 insert reverse primer

<400> SEQUENCE: 71
tggctgctgc cagtggcgat aagtcg                                      26

<210> SEQ ID NO 72
<211> LENGTH: 23
<212> TYPE: DNA
<213> ORGANISM: Artificial
<220> FEATURE:
<223> OTHER INFORMATION: 05-O-1182 Contig-3 3' junction forward primer

<400> SEQUENCE: 72
ctgcgctctg ctgaagccag tta                                         23

<210> SEQ ID NO 73
<211> LENGTH: 33
<212> TYPE: DNA
<213> ORGANISM: Artificial
<220> FEATURE:
```

```
<223> OTHER INFORMATION: 06-O-1672 Contig-3 3' junction reverse primer

<400> SEQUENCE: 73
gaatgctagg aagtactgca tttccatgtc tca                                    33

<210> SEQ ID NO 74
<211> LENGTH: 31
<212> TYPE: DNA
<213> ORGANISM: Artificial
<220> FEATURE:
<223> OTHER INFORMATION: 07-O-1881 Contig-3 5' region forward primer

<400> SEQUENCE: 74
cttttccctc ctctcatcag gcacattctt g                                      31

<210> SEQ ID NO 75
<211> LENGTH: 30
<212> TYPE: DNA
<213> ORGANISM: Artificial
<220> FEATURE:
<223> OTHER INFORMATION: 07-O-1882 Contig-3 5' region reverse primer

<400> SEQUENCE: 75
tcagtataat ggtttggctg agtggaggaa                                        30

<210> SEQ ID NO 76
<211> LENGTH: 35
<212> TYPE: DNA
<213> ORGANISM: Artificial
<220> FEATURE:
<223> OTHER INFORMATION: 07-O-1886 Contig-3 3' region forward primer

<400> SEQUENCE: 76
ggcaaaatgt atatcaactg aacaagtga gatgg                                   35

<210> SEQ ID NO 77
<211> LENGTH: 36
<212> TYPE: DNA
<213> ORGANISM: Artificial
<220> FEATURE:
<223> OTHER INFORMATION: 07-O-1884 Contig-3 3' region reverse primer

<400> SEQUENCE: 77 tgcttttat acaatgggat gaagaagcac actgag                                  36

<210> SEQ ID NO 78
<211> LENGTH: 25
<212> TYPE: DNA
<213> ORGANISM: Artificial
<220> FEATURE:
<223> OTHER INFORMATION: HOS-A Contig-4 5' junction forward primer

<400> SEQUENCE: 78
cctgctctgt ccccttcaga ttacg                                             25

<210> SEQ ID NO 79
<211> LENGTH: 21
<212> TYPE: DNA
<213> ORGANISM: Artificial
<220> FEATURE:
<223> OTHER INFORMATION: HOS-B Contig-4 5' junction reverse primer

<400> SEQUENCE: 79
gggtggaaag atgttaccat g                                                 21

<210> SEQ ID NO 80
```

```
<211> LENGTH: 34
<212> TYPE: DNA
<213> ORGANISM: Artificial
<220> FEATURE:
<223> OTHER INFORMATION: HOS-C Contig-4 3' junction reverse primer

<400> SEQUENCE: 80
gaaacgccac catcaattta tatagacagc aagg                              34

<210> SEQ ID NO 81
<211> LENGTH: 27
<212> TYPE: DNA
<213> ORGANISM: Artificial
<220> FEATURE:
<223> OTHER INFORMATION: HOS-D Contig-4 3' junction forward primer

<400> SEQUENCE: 81
ggcggggttg atatatttat acacacc                                     27

<210> SEQ ID NO 82
<211> LENGTH: 10058
<212> TYPE: DNA
<213> ORGANISM: Artificial
<220> FEATURE:
<223> OTHER INFORMATION: Contig-4

<400> SEQUENCE: 82
actagtttat ttaacaacag gttgttatta tatgaaatta tgaattaatt ttagctgaag    60
actttaaatt aaaagattta aaatacttgt caattttttt aaggtcaaaa gttaaaatat   120
ataacttaaa aataaaacat catataatat atatacacat acaatattat agtaatccaa   180
atctcataaa aatatacata taaatataaa tcacattata aggataaatt atataagttc   240
taagtcactc aatattatac ataactttta atagaaaaca aaaactgata acacatcttc   300
acgctaaagt acacacatca atgaaccctc caaaggcaaa gaatcacctc ctatccattt   360
gctcctcaca tatgtcaggg gttatctctt agaaattcat ataataaagc atatcataat   420
aatcattagt tcatcaacca ttacataaag gttcaatcat attacataat cctcatcatc   480
aatccataaa ttattaaaca tcaaagtatg tccatgactc atcgagtaac acatcattct   540
caagacaaaa ttatcaatgc acctagccat gctagctctt gactctcgaa agatttcacc   600
tcttgagcaa ttaacctaag tacatccatt aacatattca cacattgacc atttaggaaa   660
acccgaatta tcctacgga gaaagtgtga ctttattgaa aatagatgag catgggtagt   720
aacttgcctc gttaaaactt gcaaagacct taacttatct aaggattcgt tcaccaatgc   780
aatctatagg tccattcttg ttagccatca tcaataacct ccaacactag gttgagggcc   840
accaagcacc ctcaacttgc gtgctactca catgcaatgt tattcatcaa agcatttagg   900
ttatgattat tcaaaatcaa tatcatacat catcacaaat tcattcaccg attttaacac   960
cataagaagt cataatatca tagattcacc attcacatgt tcatcactct catgaactca  1020
cctatggttc aataaatata gcaagacatt ccaacacctt aaaatcctac aaacaactca  1080
ctaaaaactt atatgaatgt gaatctcatg aatctcaaca ttaatttaat tctaataata  1140
aaacaatatc atctcaacca catctcatat catcatcgag aaatcaataa acacaattta  1200
agacatccat caataaacat aattatgagc atttcttact acaataatta tatacatgta  1260
tcatcacttc aacaattagc atttatgggt cttcttcatg tacatagagt tactcaacat  1320
aacatataat tattttatat tagtttgtaa aacaaagtta attatatgat aataacacga  1380
catcaacatc atacatctca ttcaacttat caccaattca tcactcacat cttgctcaat  1440
```

```
tcctcatcaa ttcactattc atatcattat caccaatcac atgaactctc acatagttta   1500
tctacacatc atgagacttt tcacaccaca agttttcatg atccaacact atcaaatctc   1560
aacatataaa agcataagaa caaattcaag gaatagagtt ttaatgtctt tcttgaaata   1620
ttcataagct taaggacaat ccaaaggaaa atataagaag aggtttacca cttgaggaaa   1680
aagatgtgtt tgatgtcacc atgtcaacac tattcccaac acttttctca ttttgctttg   1740
tgttcttact ccattttgc ttcaatgtgc ttgaagtttg ccacaacaaa acaaagaaca   1800
aaaactcgac tcaaattttc actataactt aatagattct cactatagtg aaaatatgtg   1860
attttagttg tagcaaaata attttagtcg caatgaaaaa aatttcaacc atagcgaaaa   1920
ttttagtcgc aacaaaaata attttagcca tcataaaata aggtttgcag aatcacgatt   1980
ttctactatt cttgtccttc taataagttc caatctatat ctaattcaaa tatttcattt   2040
acaaacatga acatcaaatt aaacaacatt aataatcaaa aataatgat caaatacatc   2100 aaacatacat gagattaaag ttggtttaag tttccatacc tatcaaactc aaggaactct   2160
ctttgatatg aagaaagaaa ggaaatgagg aaataaattt tccctcacct tcactatatt   2220
tctacatcat ttccaccacc caaacccca aaaactagca taaacacac aatattgaaa     2280 tagaccacct ttatgaaatt ttaaaaattg tctatggaag aaaatgaaaa tggaggaaga   2340
aaggaaaaaa aataaggatt tcttacctct gaaattttaa aacacatcaa gttttattct   2400
taatagtact cttttaatt attttgtata tttttaaaat aataatatta atacgtatgt     2460
taaaggaaaa acgtgtacga caagagaaat ataaaagaa aatgtgttaa gatgaatata    2520
aaaaatgctc tataaaacag atagtaattt cttaaaaaat ttaatatgat cttaaattct   2580
taatagattt tttttctgca gtgaaaaata ttcttcttct tcttaaaagc ttaacaatta   2640 acaaacttt ttatacaatg attttgaaat gtatcttaaa ggaaaaattt attttaattt    2700
tgatattagt ttaataaaaa aatcctttat cataagttca tatattttaa ttaatttatt   2760
tttttcaaaa aataaaagtc gggatttttt ttgtcatttt ctcatttatt acaaccttag   2820
ccaaatatca acataaagtt acctgctctg tcccttcag attacgtcct acgtgtctcc    2880
ttcccaaaca tgaaaatcct ttttatatta agtaaactat ttttatatta tgaataata    2940 ataaaaaaaa tattttatca ttattaacaa aatcatatta gttaatttgt taactctata   3000
ataaaagaaa tactgtaaca ttcacattac atggtaacat ctttccaccc tttcatttgt   3060
tttttgtttg atgacttttt ttcttgttta aatttatttc ccttcttta aatttggaat    3120 acattatcat catatataaa ctaaaatact aaaaacagga ttacacaaat gataaataat   3180
aacacaaata tttataaatc tagctgcaat atatttaaac tagctatatc gatattgtaa   3240
aataaaacta gctgcattga tactgataaa aaaatatcat gtgctttctg gactgatgat   3300
gcagtatact tttgacattg cctttatttt attttttcaga aaagctttct tagttctggg   3360
ttcttcatta tttgttccc atctccattg tgaattgaat catttgcttc gtgtcacaaa    3420
tacatttagc taggtacgtg cattggtcag attcacggtt tattatgtca tgacttaagt   3480
tcatggtagt acattacctg ccacgcatgc attatattgg ttagatttga taggcaaatt   3540
tggttgtcaa caatataaat ataataatg ttttatatt acgaaataac agtgatcaaa    3600
acaaacagtt ttatctttat taacaagatt ttgtttttgt ttgatgacgt ttttttaatgt  3660 ttacgctttc cccttcttt tgaatttaga acactttatc atcataaaat caaatactaa   3720
aaaaattaca tatttcataa ataataacac aaatattttt aaaaaatctg aaataataat   3780
gaacaatatt acatattatc acgaaaattc attaataaaa atattatata aataaaatgt   3840
```

```
aatagtagtt atatgtagga aaaaagtact gcacgcataa tatatacaaa aagattaaaa   3900
tgaactatta taaataataa cactaaatta atggtgaatc atatcaaaat aatgaaaaag   3960
taaataaaat ttgtaattaa cttctatatg tattacacac acaaataata aataatagta   4020
aaaaaaatta tgataaatat ttaccatctc ataaagatat ttaaaataat gataaaaata   4080
tagattattt tttatgcaac tagctagcca aaaagagaac acgggtatat ataaaaagag   4140
tacctttaaa ttctactgta cttcctttat tcctgacgtt tttatatcaa gtggacatac   4200
gtgaagattt taattatcag tctaaatatt tcattagcac ttaatacttt tctgttttat   4260
tcctatccta taagtagtcc cgattctccc aacattgctt attcacacaa ctaactaaga   4320
aagtcttcca tagcccccca agcggccgct gagtgattgc tcacgagtgt ggtcaccatg   4380
ccttcagcaa gtaccaatgg gttgatgatg ttgtgggttt gacccttcac tcaacacttt   4440
tagtccctta tttctcatgg aaaataagcc atcgccgcca tcactccaac acaggttccc   4500
ttgaccgtga tgaagtgttt gtcccaaaac caaaatccaa agttgcatgg ttttccaagt   4560
acttaaacaa ccctctagga agggctgttt ctcttctcgt cacactcaca atagggtggc   4620
ctatgtattt agccttcaat gtctctggta gaccctatga tagttttgca agccactacc   4680
acccttatgc tcccatatat attaaccgtg agaggcttct gatctatgtc tctgatgttg   4740
ctttgttttc tgtgacttac tctctctacc gtgttgcaac cctgaaaggg ttggtttggc   4800
tgctatgtgt ttatggggtg cctttgctca ttgtgaacgg ttttcttgtg actatcacat   4860
atttgcagca cacacacttt gccttgcctc attacgattc atcagaatgg gactggctga   4920
agggagcttt ggcaactatg gacagagata agcggccgcg cacaagtgt gagagtacta    4980 aataaatgct ttggttgtac gaaatcatta cactaaataa aataatcaaa gcttatatat   5040
gccttccgct aaggccgaat gcaaagaaat tggttctttc tcgttatctt ttgccacttt   5100
tactagtacg tattaattac tacttaatca tctttgttta cggctcatta tatccgtcga   5160
cggatataat gagccgtaaa caaagatgat taagtagtaa ttaatacgta ctagtaaaag   5220
tggcaaaaga taacgagaaa gaaccaattt cttttgcattc ggccttagcg gaaggcatat   5280
ataagctttg attattttat ttagtgtaat gatttcgtac aaccaaagca tttatttagt   5340
actctcacac ttgtgtcgcg gccgcttatc tctgtccata gttgccaaag ctcccttcag   5400
ccagtcccat tctgatgaat cgtaatgagg caaggcaaag tgtgtgtgct gcaaatatgt   5460
gatagtcaca agaaaaccgt tcacaatgag caaaggcacc ccataaacac atagcagcca   5520
aaccaaccct ttcagggttg caacacggta gagagagtaa gtcacagaaa acaaagcaac   5580
atcagagaca tagatcagaa gcctctcacg gttagaatat atgggagcat aagggtggta   5640
gtggcttgca aaactatcat agggtctacc agagacattg aaggctaaat acataggcca   5700
ccctattgtg agtgtgacga gaagagaaac agcccttcct agagggttgt ttaagtactt   5760
ggaaaaccat gcaactttgg attttggttt tgggacaaac acttcatcac ggtcaaggga   5820
acctgtgttg gagtgatggc ggcgatggct tattttccat gagaaataag ggactaaaag   5880
tgttgagtga agggtcaaac ccacaacatc atcaacccat tggtacttgc tgaaggcatg   5940
gtgaccacac tcgtgagcaa tcactcagcg gccgcttggg gggctatgga agactttctt   6000
agttagttgt gtgaataagc aatgttggga gaatcgggac tacttatagg ataggaataa   6060
aacagaaaag tattaagtgc taatgaaata tttagactga taattaaaat cttcacgtat   6120
gtccacttga tataaaaacg tcaggaataa aggaagtaca gtagaattta aaggtactct   6180
ttttatatat acccgtgttc tctttttggc tagctagttg cataaaaaat aatctatatt   6240
```

```
tttatcatta ttttaaatat ctttatgaga tggtaaatat ttatcataat ttttttttact    6300 attatttatt atttgtgtgt gtaatacata tagaagttaa ttacaaattt tatttacttt    6360
ttcattattt tgatatgatt caccattaat ttagtgttat tatttataat agttcattttt   6420 aatcttttttg tatatattat gcgtgcagta cttttttcct acatataact actattacat   6480
tttatttata taatattttt attaatgaat tttcgtgata atatgtaata ttgttcatta    6540
ttatttcaga ttttttaaaa atatttgtgt tattatttat gaaatatgta attttttttag   6600 tatttgattt tatgatgata aagtgttcta aattcaaaag aagggggaaa gcgtaaacat    6660
taaaaaacgt catcaacaa aaacaaaatc ttgttaataa agataaaact gtttgttttg     6720
atcactgtta tttcgtaata taaaaacatt atttatattt atattgttga caaccaaatt    6780
tgcctatcaa atctaaccaa tataatgcat gcgtggcagg taatgtacta ccatgaactt    6840
aagtcatgac ataataaacc gtgaatctga ccaatgcatg tacctagcta aatgtatttg    6900
tgacacgaag caaatgattc aattcacaat ggagatggga aacaaataat gaagaaccca    6960
gaactaagaa agcttttctg aaaaataaaa taaaggcaat gtcaaaagta tactgcatca    7020
tcagtccaga aagcacatga tatttttttta tcagtatcaa tgcagctagt tttattttac    7080
aatatcgata tagctagttt aaatatattg cagctagatt tataaatatt tgtgttatta    7140
tttatcattt gtgtaatcct gttttttagta ttttagttta tatatgatga taatgtattc    7200
caaatttaaa agaagggaaa taaatttaaa caagaaaaaa agtcatcaaa caaaaaacaa    7260
atgaaagggt ggaaagatgt taccatgtaa tgtgaatgtt acagtatttc ttttattata    7320
gagttaacaa attaactaat atgatttttgt taataatgat aaaatattttt ttttattatt   7380 atttcataat ataaaaatag tttacttaat ataaaaaaaa attctatcgt tcacaacaaa    7440
gttggccacc taatttaacc atgcatgtac ccatggacca tattaggtaa ccatcaaacc    7500
tgatgaagag ataagagat gaagacttaa gtcataacac aaaaccataa aaaacaaaaa     7560
tacaatcaac cgtcaatctg accaatgcat gaaaaagctg caatagtgag tggcgacaca    7620
aagcacatga ttttcttaca acggagataa aaccaaaaaa atatttcatg aacaacctag    7680
aacaaataaa gcttttatat aataaatata taaataaata aaggctatgg aataatatac    7740
ttcaatatat ttggattaaa taaattgttg gcggggttga tatatttata cacacctaaa    7800
gtcacttcaa tctcattttc acttaacttt tattttttttt ttcttttttat ttatcataaa  7860 gagaatattg ataatatact ttttaacata tttttatgac attttttata cttctatatg    7920
taattgtatg gtggcgatct ttgatatttg ttatctacct tgctgtctat ataaattgat    7980
ggtggcgttt caaaaaacta gtagggcaca ttttctttttt ttgaagaaag tagagcgaca   8040
gtaaaggggg gtttggtaaa aaataaatgt gcataaagaa tattatattg taacagaaac    8100
agaaacagat tagagtctac aaatgctaat taatcttgtc atttgaatca atgtaatatc    8160
ctatgaaata ttttttttac atgtaagaat aaaaacagat attaaaaatt tataataatt    8220
tatatttctt gttcaattaa ctgaattaaa ttccatcgat tctaatgtaa aatatatgtt    8280
gagaattcca atgaaacaag catcatattc gtgaatagca tgcatgtaaa aatcgttgat    8340
gcaaataaat tgaatgtaat taacaaataa ataaagtatt aaattttagg cggataatat    8400
tttttggtta tacataatag aataggtaat ataaaatcgt tttttttatc taacatgaag    8460
cttaagcttt tggtattctt gactcatgac atgttaataa gagattatttt gcttcacata   8520 cattttttctt atccattttc aatatggata ccactgctac ctccgatgct aacgtttgag   8580
cttccaactc tccaaaactt atcattgtta caaattaaac ccttgaaatg atagcaacag    8640
```

```
caatcatgca cttatattct taaacacagt ggcactcaac tttattcaaa actctctagg    8700
tctctaatta tcatgattta ggatagttca ataaaaggtt gtacttgtct ataagaggtc    8760
tcatagattg tgttgatggt aatttgacca aattcaaaca tgttaaaatt gcatgcttca    8820
cctttaaccc tgaatgtaat cactaatcac tagattcgct cggacctgct tattgttctt    8880
gtaattgtca attaacactc attaccatac tagtaggacc gcagatcaac tctcaagatg    8940
ctttggtgga cattttgaag acaatatatg tatgcaaatc gccctcatac ttggatcttg    9000
tctcttgatc gaggatcgaa aagttttttc gcgttgaact ataaaggaga aatttctatc    9060
catatttatt agtttgcaac aaattaaagc tcttcctgat gaactatcaa tcaacattgg    9120
gacaattgat cttgttaaca attatcccat gacattccta ataacatgaa aaacgtatgg    9180
actttgaaac ataataacta ttggagatat atatattaat taatttcaag ttaggagcag    9240
tctcgaggag ccccaactcc ggtgggggag gctcccccgc caggaacgga agaccgaggc    9300
tccagcaaac actcgctggc aaaggcgaga tatcattatc catgagcccg aagggaaata    9360
gcgtattgac cacaaaatca acacgtgccg taacagaacc gtcatagcca caaactcaac    9420
tctaaattag cccaagtaat aagtgttgat ggaggtcatt atttggcata agatcacccc    9480
ttgacctgga gaaaaattac catattatat caagacagga aattattgcc tgaggtgcta    9540
ggaaccaacc caccttaaac tagtataagt acaaacaatg tcattgtata ctgggttacc    9600
ggaaaaaaag aagcaaccca gcatgactcg aacccacgag cgtgctttac cactatgttg    9660
gagcgttgga ggctattcat tgatacatta ttatcaaatg taatatttaa tatatatata    9720
tatataacat ccaacatgac tcaaagccac aacgatgctc cttcttcctt ttcctgttgt    9780
tgtgctattg tatggtaaat cattaaaaaa agatttaatt aaaaaaatatt ataaattatt    9840
tataactaac atagtttgtt tcaaaaattg gagattttga taattatttc aattgtaatt    9900
ttactgtata tttgcctaac taactaacac tcaccaacca agcataacat gtgtcatgta    9960
gtattgcacc atgcacatta atcatattcc tttggtattt ttgttttcaa gaaataaaaa   10020
aaaatatggg tgcttactcg agcaacttgc tttgatca                           10058
```

```
<210> SEQ ID NO 83
<211> LENGTH: 20
<212> TYPE: DNA
<213> ORGANISM: Artificial
<220> FEATURE:
<223> OTHER INFORMATION: Contig-4 20-nt 5' junction

<400> SEQUENCE: 83
atgaaaatcc tttttatatt                                                 20

<210> SEQ ID NO 84
<211> LENGTH: 20
<212> TYPE: DNA
<213> ORGANISM: Artificial
<220> FEATURE:
<223> OTHER INFORMATION: Contig-4 20-nt 3' junction

<400> SEQUENCE: 84
cattttttat acttctatat                                                 20

<210> SEQ ID NO 85
<211> LENGTH: 40
<212> TYPE: DNA
<213> ORGANISM: Artificial
<220> FEATURE:
<223> OTHER INFORMATION: Contig-4 40-nt 5' junction
```

-continued

<210> SEQ ID NO 85

<400> SEQUENCE: 85
cttcccaaac atgaaaatcc tttttatatt aagtaaacta                     40

<210> SEQ ID NO 86
<211> LENGTH: 40
<212> TYPE: DNA
<213> ORGANISM: Artificial
<220> FEATURE:
<223> OTHER INFORMATION: Contig-4 40-nt 3' junction

<400> SEQUENCE: 86 attttatga catttttat acttctatat gtaattgtat                       40

<210> SEQ ID NO 87
<211> LENGTH: 60
<212> TYPE: DNA
<213> ORGANISM: Artificial
<220> FEATURE:
<223> OTHER INFORMATION: Contig-4 60-nt 5' junction

<400> SEQUENCE: 87
tacgtgtctc cttcccaaac atgaaaatcc tttttatatt aagtaaacta tttttatatt    60

<210> SEQ ID NO 88
<211> LENGTH: 60
<212> TYPE: DNA
<213> ORGANISM: Artificial
<220> FEATURE:
<223> OTHER INFORMATION: Contig-4 60-nt 3' junction

<400> SEQUENCE: 88
tttttaacat attttatga catttttat acttctatat gtaattgtat ggtggcgatc    60

<210> SEQ ID NO 89
<211> LENGTH: 27
<212> TYPE: DNA
<213> ORGANISM: Artificial
<220> FEATURE:
<223> OTHER INFORMATION: Contig-1 5' junction QPCR forward primer

<400> SEQUENCE: 89
tgtcacatta caagtgagat gtcatca                                   27

<210> SEQ ID NO 90
<211> LENGTH: 28
<212> TYPE: DNA
<213> ORGANISM: Artificial
<220> FEATURE:
<223> OTHER INFORMATION: Contig-1 5' junction QPCR reverse primer

<400> SEQUENCE: 90
tctcgttatc ttttgccact tttactag                                  28

<210> SEQ ID NO 91
<211> LENGTH: 19
<212> TYPE: DNA
<213> ORGANISM: Artificial
<220> FEATURE:
<223> OTHER INFORMATION: Contig-1 5' junction QPCR probe

<400> SEQUENCE: 91
caagcttggt actaacata                                            19

<210> SEQ ID NO 92
<211> LENGTH: 22
<212> TYPE: DNA

```
<213> ORGANISM: Artificial
<220> FEATURE:
<223> OTHER INFORMATION: SAMS-HRA QPCR forward primer

<400> SEQUENCE: 92
ggcttgttgt gcagttttg aa                                              22

<210> SEQ ID NO 93
<211> LENGTH: 22
<212> TYPE: DNA
<213> ORGANISM: Artificial
<220> FEATURE:
<223> OTHER INFORMATION: SAMS-HRA QPCR reverse primer

<400> SEQUENCE: 93
ggaagaagag aatcgggtgg tt                                             22

<210> SEQ ID NO 94
<211> LENGTH: 16
<212> TYPE: DNA
<213> ORGANISM: Artificial
<220> FEATURE:
<223> OTHER INFORMATION: SAMS-HRA QPCR probe

<400> SEQUENCE: 94
caacacaatg gcggcc                                                    16
```

US 8,609,935 B2

SOYBEAN EVENT DP-305423-1 AND COMPOSITIONS AND METHODS FOR THE IDENTIFICATION AND/OR DETECTION THEREOF

This application claims the benefit of U.S. Provisional Application No. 60/863,721, filed Oct. 31, 2006, and U.S. Provisional Application No. 60/942,676, filed Jun. 8, 2007, the entire contents of each are herein incorporated by reference.

FIELD OF THE INVENTION

This invention is in the field of molecular biology. More specifically, this invention pertains to plants that display both a high oleic acid phenotype and a herbicide tolerance phenotype conferred by suppression of a FAD2 gene in conjunction with the expression of a sequence that confers tolerance to inhibitors of ALS.

BACKGROUND OF THE INVENTION

The expression of foreign genes in plants is known to be influenced by their location in the plant genome, perhaps due to chromatin structure (e.g., heterochromatin) or the proximity of transcriptional regulatory elements (e.g., enhancers) close to the integration site (Weising et al. (1988) *Ann. Rev. Genet.* 22: 421-477). At the same time the presence of the transgene at different locations in the genome influences the overall phenotype of the plant in different ways. For this reason, it is often necessary to screen a large number of events in order to identify an event characterized by optimal expression of an introduced gene of interest. For example, it has been observed in plants and in other organisms that there may be a wide variation in levels of expression of an introduced gene among events. There may also be differences in spatial or temporal patterns of expression, for example, differences in the relative expression of a transgene in various plant tissues, that may not correspond to the patterns expected from transcriptional regulatory elements present in the introduced gene construct. It is also observed that the transgene insertion can affect the endogenous gene expression. For these reasons, it is common to produce hundreds to thousands of different events and screen those events for a single event that has desired transgene expression levels and patterns for commercial purposes. An event that has desired levels or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

It would be advantageous to be able to detect the presence of a particular event in order to determine whether progeny of a sexual cross contain a transgene of interest. In addition, a method for detecting a particular event would be helpful for complying with regulations requiring the pre-market approval and labeling of foods derived from recombinant crop plants, or for use in environmental monitoring, monitoring traits in crops in the field, or monitoring products derived from a crop harvest, as well as, for use in ensuring compliance of parties subject to regulatory or contractual terms.

In the commercial production of crops, it is desirable to easily and quickly eliminate unwanted plants (i.e., "weeds") from a field of crop plants. An ideal treatment would be one which could be applied to an entire field but which would eliminate only the unwanted plants while leaving the crop plants unharmed. One such treatment system would involve the use of crop plants which are tolerant to a herbicide so that when the herbicide was sprayed on a field of herbicide-tolerant crop plants, the crop plants would continue to thrive while non-herbicide-tolerant weeds were killed or severely damaged.

Plant lipids find their major use as edible oils in the form of triacylglycerols. The specific performance and health attributes of edible oils are determined largely by their fatty acid composition. Most vegetable oils derived from commercial plant varieties are composed primarily of palmitic (16:0), stearic (18:0), oleic (18:1), linoleic (18:2) and linolenic (18:3) acids. Palmitic and stearic acids are, respectively, 16- and 18-carbon-long, saturated fatty acids. Oleic, linoleic, and linolenic acids are 18-carbon-long, unsaturated fatty acids containing one, two, and three double bonds, respectively. Oleic acid is referred to as a mono-unsaturated fatty acid, while linoleic and linolenic acids are referred to as poly-unsaturated fatty acids.

A vegetable oil low in total saturates and high in mono-unsaturates would provide significant health benefits to consumers as well as economic benefits to oil processors. As an example, canola oil is considered a very healthy oil. However, in use, the high level of poly-unsaturated fatty acids in canola oil renders the oil unstable, easily oxidized, and susceptible to development of disagreeable odors and flavors (Gailliard, 1980, Vol. 4, pp. 85-116 In: Stumpf, P. K., Ed., The Biochemistry of Plants, Academic Press, New York). The levels of poly-unsaturates may be reduced by hydrogenation, but the expense of this process and the concomitant production of nutritionally questionable trans isomers of the remaining unsaturated fatty acids reduces the overall desirability of the hydrogenated oil (Mensink et al., *New England J. Medicine* (1990) N323: 439-445). Similar problems exist with soybean and corn oils.

SUMMARY OF THE INVENTION

Compositions and methods related to transgenic high oleic acid/ALS inhibitor-tolerant soybean plants are provided. Specifically, the present invention provides soybean plants containing a DP-305423-1 event which imparts a high oleic acid phenotype and tolerance to at least one ALS-inhibiting herbicide. The soybean plant harboring the DP-305423-1 event at the recited chromosomal location comprises genomic/transgene junctions having at least the polynucleotide sequence of SEQ ID NO:8, 9, 14, 15, 20, 21, 83 or 84. The characterization of the genomic insertion site of the DP-305423-1 event provides for an enhanced breeding efficiency and enables the use of molecular markers to track the transgene insert in the breeding populations and progeny thereof. Various methods and compositions for the identification, detection, and use of the soybean DP-305423-1 event are provided.

In one embodiment, the present invention includes an isolated polynucleotide comprising SEQ ID NO:5, 6, 7, 8, 9, 10, 11, 12, 13, 14, 15, 16, 17, 18, 19, 20, 21, 22, 23, 24, 25, 82, 83, 84, 85, 86, 87 or 88.

In another embodiment, the present invention includes a soybean plant or a soybean seed comprising SEQ ID NO:5, 6, 7, 8, 9, 10, 11, 12, 13, 14, 15, 16, 17, 18, 19, 20, 21, 22, 23, 24, 25, 82, 83, 84, 85, 86, 87 or 88.

In another embodiment, the present invention includes a method for identifying a biological sample comprising: a) contacting said biological sample with a first and a second primer; b) amplifying a polynucleotide comprising any of SEQ ID NO:5, 6, 7, 8, 9, 10, 11, 12, 13, 14, 15, 16, 17, 18, 19, 20, 21, 22, 23, 24, 25, 82, 83, 84, 85, 86, 87 or 88; and c) confirming said biological sample comprises a polynucleotide comprising any of SEQ ID NO:5, 6, 7, 8, 9, 10, 11, 12, 13, 14, 15, 16, 17, 18, 19, 20, 21, 22, 23, 24, 25, 82, 83, 84, 85, 86, 87 or 88. The method may further comprise detecting a polynucleotide comprising SEQ ID NO:5, 6, 7, 8, 9, 10, 11, 12, 13, 14, 15, 16, 17, 18, 19, 20, 21, 22, 23, 24, 25, 82, 83, 84, 85, 86, 87 or 88 by hybridization to a probe, wherein said probe hybridizes under stringent hybridization conditions with a polynucleotide comprising SEQ ID NO:5, 6, 7, 8, 9, 10, 11, 12, 13, 14, 15, 16, 17, 18, 19, 20, 21, 22, 23, 24, 25, 82, 83, 84, 85, 86, 87 or 88. The first or second primer may comprise a fragment of a 5' genomic region, a 3' genomic region or an insert region of SEQ ID NO:5, 6, 7 or 82. The first or second primer may comprise at least 8 consecutive nucleotides of a 5' genomic region, a 3' genomic region or an insert region of SEQ ID NO:5, 6, 7 or 82. One of the first or second primers may comprise a fragment of a 5' genomic region of SEQ ID NO:5, 6, 7 or 82 and the other of the first or second primers may comprise a fragment of a 3' genomic region of SEQ ID NO:5, 6, 7 or 82. The first or second primer may comprise SEQ ID NO:26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 89, 90, 91, 92, 93 or 94.

In another embodiment, the present invention includes a method of detecting the presence of a polynucleotide comprising SEQ ID NO:5, 6, 7, 8, 9, 10, 11, 12, 13, 14, 15, 16, 17, 18, 19, 20, 21, 22, 23, 24, 25, 82, 83, 84, 85, 86, 87 or 88 in a biological sample comprising DNA, comprising: (a) extracting a DNA sample from said biological sample; (b) contacting said DNA sample with at least one pair of DNA primer molecules selected from the group consisting of: i) the sequences comprising SEQ ID NO:26 and SEQ ID NO:27; ii) the sequences comprising SEQ ID NO:29 and SEQ ID NO:30; iii) the sequences comprising SEQ ID NO:31 and SEQ ID NO:32; iv) the sequences comprising SEQ ID NO:33 and SEQ ID NO:34; v) the sequences comprising SEQ ID NO:35 and SEQ ID NO:36; vi) the sequences comprising SEQ ID NO:37 and SEQ ID NO:38; vii) the sequences comprising SEQ ID NO:39 and SEQ ID NO:40; viii) the sequences comprising SEQ ID NO:41 and SEQ ID NO:42; ix) the sequences comprising SEQ ID NO:43 and SEQ ID NO:44; x) the sequences comprising SEQ ID NO:45 and SEQ ID NO:46; xi) the sequences comprising SEQ ID NO:47 and SEQ ID NO:48; xii) the sequences comprising SEQ ID NO:47 and SEQ ID NO:49; xiii) the sequences comprising SEQ ID NO:50 and SEQ ID NO:51; xiv) the sequences comprising SEQ ID NO:52 and SEQ ID NO:53; xv) the sequences comprising SEQ ID NO:54 and SEQ ID NO:49; xvi) the sequences comprising SEQ ID NO:55 and SEQ ID NO:46; xvii) the sequences comprising SEQ ID NO:33 and SEQ ID NO:56; xviii) the sequences comprising SEQ ID NO:57 and SEQ ID NO:58; xix) the sequences comprising SEQ ID NO:59 and SEQ ID NO:60; xx) the sequences comprising SEQ ID NO:61 and SEQ ID NO:36; xxi) the sequences comprising SEQ ID NO:35 and SEQ ID NO:62; xxii) the sequences comprising SEQ ID NO:37 and SEQ ID NO:63; xxiii) the sequences comprising SEQ ID NO:64 and SEQ ID NO:65; xxiv) the sequences comprising SEQ ID NO:66 and SEQ ID NO:67; xxv) the sequences comprising SEQ ID NO:68 and SEQ ID NO:69; xxvi) the sequences comprising SEQ ID NO:70 and SEQ ID NO:71; xxvii) the sequences comprising SEQ ID NO:72 and SEQ ID NO:73; xxviii) the sequences comprising SEQ ID NO:74 and SEQ ID NO:75; xxix) the sequences comprising SEQ ID NO:76 and SEQ ID NO:77; xxx) the sequences comprising SEQ ID NO:78 and SEQ ID NO:79; xxxi) the sequences comprising SEQ ID NO:80 and SEQ ID NO:81; and xxxii) the sequences comprising SEQ ID NO:89 and SEQ ID NO:90 (c) providing DNA amplification reaction conditions; (d) performing said DNA amplification reaction, thereby producing a DNA amplicon molecule; and (e) detecting said DNA amplicon molecule, wherein the detection of said DNA amplicon molecule in said DNA amplification reaction indicates the presence of a polynucleotide comprising SEQ ID NO:5, 6, 7, 8, 9, 10, 11, 12, 13, 14, 15, 16, 17, 18, 19, 20, 21, 22, 23, 24, 25, 82, 83, 84, 85, 86, 87 or 88.

In another embodiment, the present invention includes a method of detecting the presence of SEQ ID NO:5, 6, 7, 8, 9, 10, 11, 12, 13, 14, 15, 16, 17, 18, 19, 20, 21, 22, 23, 24, 25, 82, 83, 84, 85, 86, 87 or 88 in a biological sample, the method comprising: (a) contacting the biological sample comprising DNA under stringent hybridization conditions with a polynucleotide probe wherein said probe hybridizes under stringent hybridization conditions with a polynucleotide comprising SEQ ID NO:5, 6, 7, 8, 9, 10, 11, 12, 13, 14, 15, 16, 17, 18, 19, 20, 21, 22, 23, 24, 25, 82, 83, 84, 85, 86, 87 or 88; (b) detecting hybridization of the probe to the DNA. The biological sample may comprise soybean tissue.

In another embodiment, the present invention includes an isolated DNA primer comprising at least one sequence selected from the group consisting of SEQ ID NO:26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 89, 90, 91, 92, 93 or 94 or its complement.

In another embodiment, the present invention includes a pair of DNA primers comprising a first DNA primer and a second DNA primer, wherein the DNA primers are of a sufficient length of contiguous nucleotides of SEQ ID NO:5, 6, 7 or 82, to function as DNA primers diagnostic of DNA comprising SEQ ID NO:5, 6, 7, 8, 9, 10, 11, 12, 13, 14, 15, 16, 17, 18, 19, 20, 21, 22, 23, 24, 25, 82, 83, 84, 85, 86, 87 or 88.

In another embodiment, the present invention includes a DNA probe wherein the DNA probe is of a sufficient length of contiguous nucleotides of SEQ ID NO:5, 6, 7 or 82, to function as a DNA probe diagnostic of DNA comprising SEQ ID NO:5, 6, 7, 8, 9, 10, 11, 12, 13, 14, 15, 16, 17, 18, 19, 20, 21, 22, 23, 24, 25, 82, 83, 84, 85, 86, 87 or 88.

In another embodiment, the present invention includes a method for screening seed for a polynucleotide comprising SEQ ID NO:5, 6, 7, 8, 9, 10, 11, 12, 13, 14, 15, 16, 17, 18, 19, 20, 21, 22, 23, 24, 25, 82, 83, 84, 85, 86, 87 or 88, comprising: a) contacting a sample comprising DNA from said seed with a first and a second DNA primer; b) amplifying a polynucleotide comprising a polynucleotide comprising SEQ ID NO:5, 6, 7, 8, 9, 10, 11, 12, 13, 14, 15, 16, 17, 18, 19, 20, 21, 22, 23, 24, 25, 82, 83, 84, 85, 86, 87 or 88; and c) detecting said amplified polynucleotide.

In another embodiment, the present invention includes a method for screening seed for the presence of a polynucleotide comprising SEQ ID NO:5, 6, 7, 8, 9, 10, 11, 12, 13, 14, 15, 16, 17, 18, 19, 20, 21, 22, 23, 24, 25, 82, 83, 84, 85, 86, 87 or 88 comprising: (a) contacting a sample comprising DNA from said seed under stringent hybridization conditions with a polynucleotide probe that hybridizes under stringent hybridization conditions with a polynucleotide comprising SEQ ID NO:5, 6, 7, 8, 9, 10, 11, 12, 13, 14, 15, 16, 17, 18, 19, 20, 21, 22, 23, 24, 25, 82, 83, 84, 85, 86, 87 or 88; and (b) detecting hybridization of the probe to the DNA.

In another embodiment, the present invention includes a method of producing a high oleic acid and ALS inhibitor tolerant plant comprising breeding a plant comprising a polynucleotide comprising SEQ ID NO:5, 6, 7, 8, 9, 10, 11, 12, 13, 14, 15, 16, 17, 18, 19, 20, 21, 22, 23, 24, 25, 82, 83, 84, 85, 86, 87 or 88, and selecting progeny by analyzing for progeny that comprise a polynucleotide comprising SEQ ID NO: 5, 6, 7, 8, 9, 10, 11, 12, 13, 14, 15, 16, 17, 18, 19, 20, 21, 22, 23, 24, 25, 82, 83, 84, 85, 86, 87 or 88.

In another embodiment, the present invention includes an isolated DNA sequence comprising at least one nucleotide sequence selected from the group consisting of: (a) a nucleotide sequence set forth in SEQ ID NO:26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 89, 90, 91, 92, 93 or 94; and (b) a full-length complement of the nucleotide sequence of (a).

In another embodiment, the present invention includes a pair of isolated DNA primer sequences, each comprising at least ten nucleotides and which when used together in a DNA amplification procedure will produce a DNA amplicon comprising a polynucleotide comprising SEQ ID NO:5, 6, 7, 8, 9, 10, 11, 12, 13, 14, 15, 16, 17, 18, 19, 20, 21, 22, 23, 24, 25, 82, 83, 84, 85, 86, 87 or 88. The pair of isolated DNA primer sequences may comprise a first primer sequence chosen from the group consisting of: a) a 5' genomic region of SEQ ID NO: 5, 6, 7 or 82; and b) a 3' genomic region of SEQ ID NO: 5, 6, 7 or 82; and a second primer sequence chosen from an insert region of SEQ ID NO: 5, 6, 7 or 82.

In another embodiment, the present invention includes a method for controlling weeds in an area of cultivation comprising applying an effective amount of an ALS inhibitor to the area of cultivation comprising soybean plants comprising a polynucleotide comprising SEQ ID NO:5, 6, 7, 8, 9, 10, 11, 12, 13, 14, 15, 16, 17, 18, 19, 20, 21, 22, 23, 24, 25, 82, 83, 84, 85, 86, 87 or 88. The ALS inhibitor may be a sulfonylurea herbicide or an imidazolinone herbicide. A combination of different ALS inhibitors may be used. The ALS inhibitor or combination of ALS inhibitors may be used in further combination with one or more non-ALS inhibitor herbicides.

In another embodiment, the present invention includes a DNA expression construct comprising the isolated polynucleotide of the invention operably linked to at least one regulatory sequence.

In another embodiment, the present invention includes transgenic progeny plants obtained from the transgenic seed of the invention.

In another embodiment, the present invention includes a recombinant DNA construct comprising: a first and second expression cassette, wherein said first expression cassette in operable linkage comprises: (a) a soybean KTi3 promoter; (b) a gm-fad2-1 fragment; and (c) a soybean KTi3 transcriptional terminator; and said second expression cassette comprises in operable linkage: (i) a soybean SAMS promoter; (ii) a soybean SAMS 5' untranslated leader and intron; (iii) a soybean gm-hra encoding DNA molecule; and (iv) a soybean als transcriptional terminator.

In another embodiment, the present invention includes a plant or seed comprising the recombinant DNA construct of claim 27. The plant or seed may be a soybean plant or a soybean seed.

BRIEF DESCRIPTION OF THE FIGURES AND SEQUENCE LISTING

FIG. 1 provides a schematic map of fragment PHP19340A indicating various genetic elements and restriction enzyme sites for NcoI and HindIII.

FIG. 2 provides a schematic map of fragment PHP17752A indicating various genetic elements and restriction enzyme sites for NcoI and HindIII.

FIG. 3 provides a schematic map of expression vector PHP19340 indicating various genetic elements and restriction enzyme sites for AscI, NcoI and HindIII.

FIG. 4 provides a schematic map of expression vector PHP17752 indicating various genetic elements and restriction enzyme sites for AscI, NcoI and HindIII.

Figure 9:
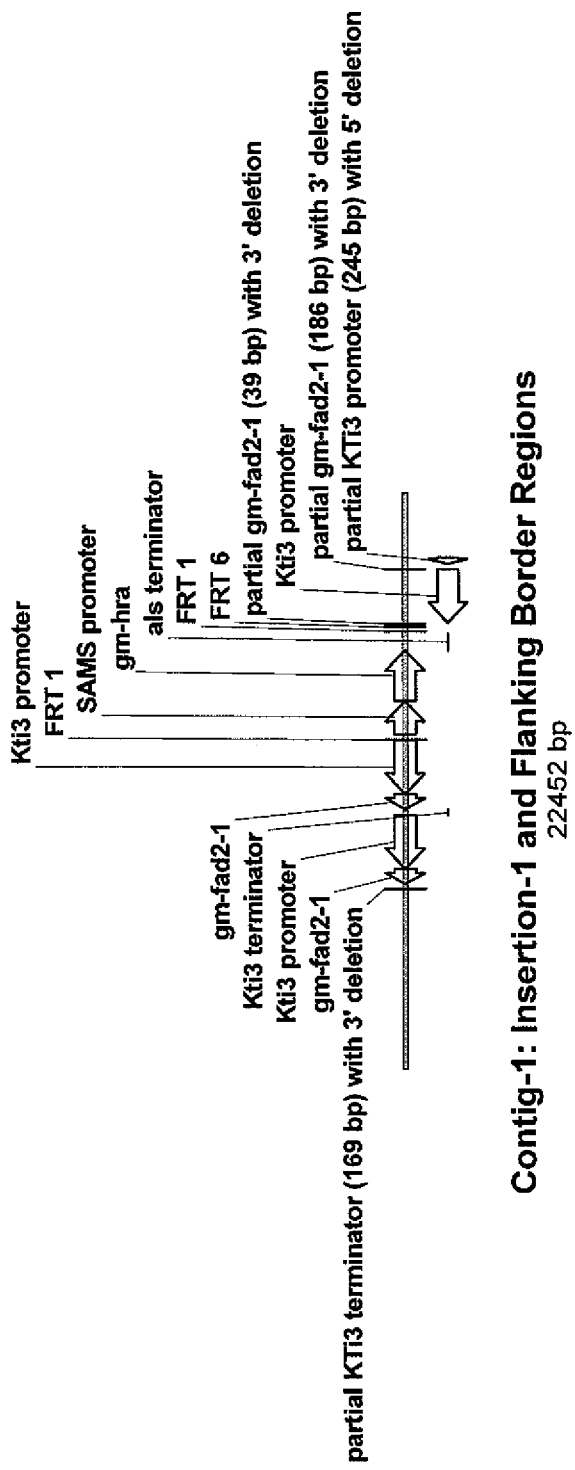

FIG. 9 provides a schematic map of Contig-1 indicating various genetic elements within Insertion-1.

Figure 10:
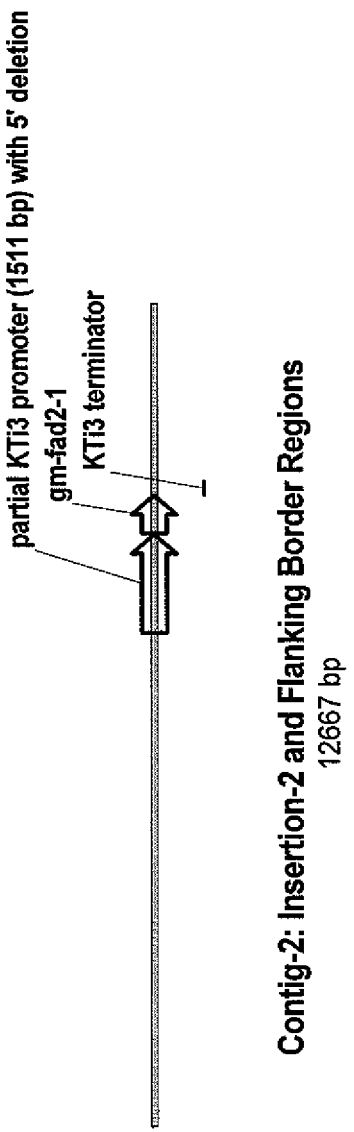

FIG. 10 provides a schematic map of Contig-2 indicating various genetic elements within Insertion-2.

Figure 11:
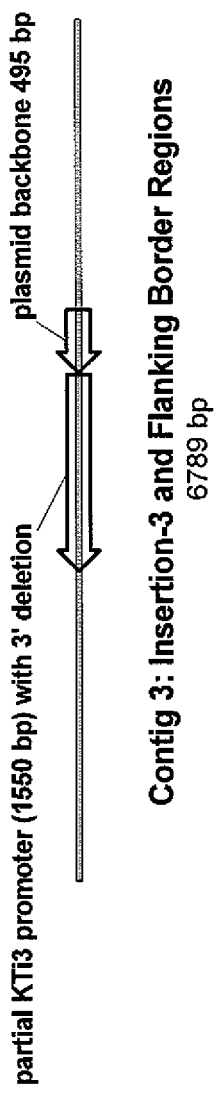

FIG. 11 provides a schematic map of Contig-3 indicating various genetic elements within Insertion-3.

Figure 12:
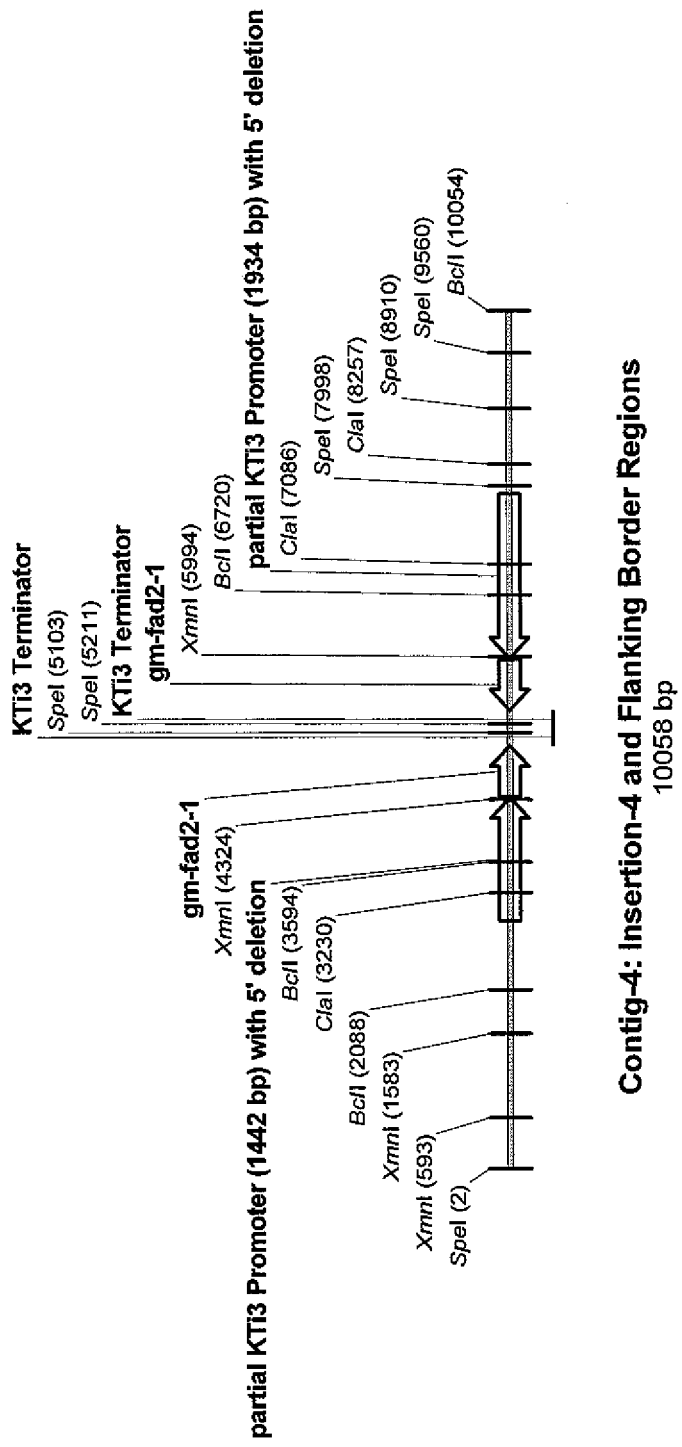

FIG. 12 provides a schematic map of Contig-4 indicating various genetic elements within Insertion-4.

Table 1 presents a description of the following sequences that are present in the Sequence Listing: (1) the insert sequences used to create the DP-305423-1 event and the vectors from which they are derived; (2) the genomic DNA sequences present in Contig-1, Contig-2, Contig-3 and Contig-4; (3) the 5' and 3' junction sequences, at which transgenic insert and endogenous soybean genomic sequence are joined, for each of the four contigs; and (4) primer sequences that can be used to amply 5' and 3' junction sequences from each of the four contigs.

TABLE 1

Summary Table of SEQ ID NOS

| SEQ ID NO | Description |
| --- | --- |
| 1 | PHP19340A |
| 2 | PHP17752A |
| 3 | PHP19340 |
| 4 | PHP17752 |
| 5 | DP-305423-1 Contig-1 |
| 6 | DP-305423-1 Contig-2 |
| 7 | DP-305423-1 Contig-3 |
| 8 | Contig-1 20-nt 5' junction (5' genomic/5' transgene; 10-nt/10-nt) |
| 9 | Contig-1 20-nt 3' junction (3' transgene/3' genomic; 10-nt/10-nt) |
| 10 | Contig-1 40-nt 5' junction (5' genomic/5' transgene; 20-nt/20-nt) |
| 11 | Contig-1 40-nt 3' junction (3' transgene/3' genomic; 20-nt/20-nt) |

TABLE 1-continued

Summary Table of SEQ ID NOS

| SEQ ID NO | Description |
|---|---|
| 12 | Contig-1 60-nt 5' junction (5' genomic/5' transgene; 30-nt/30-nt) |
| 13 | Contig-1 60-nt 3' junction (3' transgene/3' genomic; 30-nt/30-nt) |
| 14 | Contig-2 20-nt 5' junction (5' genomic/5' transgene; 10-nt/10-nt) |
| 15 | Contig-2 20-nt 3' junction (3' transgene/3' genomic; 10-nt/10-nt) |
| 16 | Contig-2 40-nt 5' junction (5' genomic/5' transgene; 20-nt/20-nt) |
| 17 | Contig-2 40-nt 3' junction (3' transgene/3' genomic; 20-nt/20-nt) |
| 18 | Contig-2 60-nt 5' junction (5' genomic/5' transgene; 30-nt/30-nt) |
| 19 | Contig-2 60-nt 3' junction (3' transgene/3' genomic; 30-nt/30-nt) |
| 20 | Contig-3 20-nt 5' junction (5' genomic/5' transgene; 10-nt/10-nt) |
| 21 | Contig-3 20-nt 3' junction (3' transgene/3' genomic; 10-nt/10-nt) |
| 22 | Contig-3 40-nt 5' junction (5' genomic/5' transgene; 20-nt/20-nt) |
| 23 | Contig-3 40-nt 3' junction (3' transgene/3' genomic; 20-nt/20-nt) |
| 24 | Contig-3 60-nt 5' junction (5' genomic/5' transgene; 30-nt/30-nt) |
| 25 | Contig-3 60-nt 3' junction (3' transgene/3' genomic; 30-nt/30-nt) |
| 26 | 05-O-975 Contig-1 5' junction forward primer |
| 27 | 05-O-977 Contig-1 5' junction reverse primer |
| 28 | 05-QP22 Contig-1 5' junction probe |
| 29 | 06-O-1573 Contig-1 5' junction forward primer |
| 30 | 06-O-1487 Contig-1 5' junction reverse primer |
| 31 | 06-O-1414 Contig-1 3' junction forward primer |
| 32 | 06-O-1579 Contig-1 3' junction reverse primer |
| 33 | 06-O-1577 Contig-1 3' junction forward primer |
| 34 | 06-O-1579 Contig-1 3' junction reverse primer |
| 35 | 06-O-1586 Contig-2 5' junction forward primer |
| 36 | 06-O-1585 Contig-2 5' junction reverse primer |
| 37 | 06-O-1404 Contig-2 3' junction forward primer |
| 38 | 06-O-1590 Contig-2 3' junction reverse primer |
| 39 | 06-O-1626 Contig-3 5' junction forward primer |
| 40 | 06-O-1366 Contig-3 5' junction reverse primer |
| 41 | 06-O-1569 Contig-3 3' junction forward primer |
| 42 | 06-O-1551 Contig-3 3' junction reverse primer |
| 43 | 06-O-1571 Contig-1 5' junction forward primer |
| 44 | 06-O-1572 Contig-1 5' junction reverse primer |
| 45 | 06-O-1351 Contig-1 5' junction forward primer |
| 46 | 06-O-1367 Contig-1 5' junction reverse primer |
| 47 | 06-O-1357 Contig-1 insert forward primer |
| 48 | 06-O-1368 Contig-1 insert reverse primer |
| 49 | 06-O-1369 Contig-1 insert reverse primer |
| 50 | 06-O-1356 Contig-1 insert forward primer |
| 51 | 06-O-1371 Contig-1 insert reverse primer |
| 52 | 06-O-1360 Contig-1 insert forward primer |
| 53 | 06-O-1423 Contig-1 insert reverse primer |
| 54 | 06-O-1363 Contig-1 insert forward primer |
| 55 | 06-O-1421 Contig-1 insert forward primer |
| 56 | 06-O-1578 Contig-1 3' junction reverse primer |
| 57 | 07-O-1889 Contig-1 5' region forward primer |
| 58 | 07-O-1940 Contig-1 5' region reverse primer |
| 59 | 07-O-1892 Contig-1 3' region reverse primer |
| 60 | 07-O-1894 Contig-1 3' region forward primer |
| 61 | 06-O-1588 Contig-2 5' junction forward primer |
| 62 | 06-O-1403 Contig-2 5' junction reverse primer |
| 63 | 06-O-1592 Contig-2 3' junction reverse primer |
| 64 | 07-O-1895 Contig-2 5' region forward primer |
| 65 | 07-O-1898 Contig-2 5' region reverse primer |
| 66 | 07-O-1905 Contig-2 3' region forward primer |
| 67 | 07-O-1903 Contig-2 3' region reverse primer |
| 68 | 06-O-1669 Contig-3 5' junction forward primer |
| 69 | 06-O-1426 Contig-3 5' junction reverse primer |
| 70 | 06-O-1355 Contig-3 insert forward primer |
| 71 | 06-O-1459 Contig-3 insert reverse primer |
| 72 | 05-O-1182 Contig-3 3' junction forward primer |
| 73 | 06-O-1672 Contig-3 3' junction reverse primer |
| 74 | 07-O-1881 Contig-3 5' region forward primer |
| 75 | 07-O-1882 Contig-3 5' region reverse primer |
| 76 | 07-O-1886 Contig-3 3' region forward primer |
| 77 | 07-O-1884 Contig-3 3' region reverse primer |
| 78 | HOS-A Contig-4 5' junction forward primer |
| 79 | HOS-B Contig-4 5' junction reverse primer |
| 80 | HOS-C Contig-4 3' junction reverse primer |
| 81 | HOS-D Contig-4 3' junction forward primer |
| 82 | DP-305423-1 Contig-4 |
| 83 | Contig-4 20-nt 5' junction (5' genomic/5' transgene; 10-nt/10-nt) |
| 84 | Contig-4 20-nt 3' junction (3' transgene/3' genomic; 10-nt/10-nt) |
| 85 | Contig-4 40-nt 5' junction (5' genomic/5' transgene; 20-nt/20-nt) |
| 86 | Contig-4 40-nt 3' junction (3' transgene/3' genomic; 20-nt/20-nt) |
| 87 | Contig-4 60-nt 5' junction (5' genomic/5' transgene; 30-nt/30-nt) |
| 88 | Contig-4 60-nt 3' junction (3' transgene/3' genomic; 30-nt/30-nt) |
| 89 | Contig-1 5' junction QPCR forward primer |
| 90 | Contig-1 5' junction QPCR reverse primer |
| 91 | Contig-1 5' junction QPCR probe |
| 92 | SAMS-HRA QPCR forward primer |
| 93 | SAMS-HRA QPCR reverse primer |
| 94 | SAMS-HRA QPCR probe |

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The following abbreviations are used in describing the present invention.

| | |
|---|---|
| ALS | acetolactate synthase protein |
| bp | base pair |
| FAD2 | microsomal omega-6 desaturase protein |
| gm-fad2-1 | soybean microsomal omega-6 desaturase gene 1 |
| gm-als | wild type acetolactate synthase gene from soybean |
| gm-hra | modified version of acetolactate synthase gene from soybean |
| kb | kilobase |
| PCR | polymerase chain reaction |
| UTR | untranslated region |

Compositions and methods related to transgenic high oleic acid/ALS inhibitor-tolerant soybean plants are provided. Specifically, the present invention provides soybean plants having event DP-305423-1. A soybean plant having "event DP-305423-1" has been modified by the insertion of a suppression cassette containing a 597 bp fragment of the soybean microsomal omega-6 desaturase gene 1 (gm-fad2-1) and an expression cassette containing a modified version of the soybean acetolactate synthase gene (gm-hra). The insertion of the gm-fad2-1 suppression cassette in the plant confers a high oleic acid phenotype. The insertion of the gm-hra gene produces a modified form of the acetolactate synthase (ALS) enzyme. ALS is essential for branched chain amino acid biosynthesis and is inhibited by certain herbicides. The modification in the gm-hra gene overcomes this inhibition and thus provides tolerance to a wide range of ALS-inhibiting herbicides. Thus, a soybean plant having a DP-305423-1 event has a high oleic acid phenotype and is tolerant at least one ALS-inhibiting herbicide.

The polynucleotides conferring the high oleic acid phenotype and ALS inhibitor tolerance are genetically linked in the soybean genome in the DP-305423-1 soybean event. The soybean plant harboring the DP-305423-1 event comprises genomic/transgene junctions having at least the polynucleotide sequence of SEQ ID NO: 8, 9, 14, 15, 20, 21, 83, and 84. The characterization of the genomic insertion site of the DP-305423-1 event provides for an enhanced breeding efficiency and enables the use of molecular markers to track the transgene insert in the breeding populations and progeny thereof. Various methods and compositions for the identification, detection, and use of the soybean DP-305423-1 events are provided herein. As used herein, the term "event DP-305423-1 specific" refers to a polynucleotide sequence which is suitable for discriminatively identifying event DP-305423-1 in plants, plant material, or in products such as, but not limited to, food or feed products (fresh or processed) comprising, or derived from plant material.

As used herein, the term "soybean" means *Glycine max* and includes all plant varieties that can be bred with soybean. As used herein, the term plant includes plant cells, plant organs, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise a DP-305423-1 event.

A transgenic "event" is produced by transformation of plant cells with a heterologous DNA construct(s), including a nucleic acid expression cassette that comprises a transgene of interest, the regeneration of a population of plants resulting from the insertion of the transgene into the genome of the plant, and selection of a particular plant characterized by insertion into a particular genome location. An event is characterized phenotypically by the expression of the transgene(s). At the genetic level, an event is part of the genetic makeup of a plant. The term "event" also refers to progeny produced by a sexual outcross between the transformant and another variety that include the heterologous DNA. Even after repeated back-crossing to a recurrent parent, the inserted DNA and flanking DNA from the transformed parent is present in the progeny of the cross at the same chromosomal location. The term "event" also refers to DNA from the original transformant comprising the inserted DNA and flanking sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

As used herein, "insert DNA" refers to the heterologous DNA within the expression cassettes used to transform the plant material while "flanking DNA" can comprise either genomic DNA naturally present in an organism such as a plant, or foreign (heterologous) DNA introduced via the transformation process which is extraneous to the original insert DNA molecule, e.g. fragments associated with the transformation event. A "flanking region" or "flanking sequence" as used herein refers to a sequence of at least 20, 50, 100, 200, 300, 400, 1000, 1500, 2000, 2500, or 5000 base pair or greater which is located either immediately upstream of and contiguous with or immediately downstream of and contiguous with the original foreign insert DNA molecule. Non-limiting examples of the flanking regions of the DP-305423-1 event are set forth in SEQ ID NO:5, 6, 7 and 82, and variants and fragments thereof.

Transformation procedures leading to random integration of the foreign DNA will result in transformants containing different flanking regions characteristic of and unique for each transformant. A "junction" is a point where two specific DNA fragments join. For example, a junction exists where insert DNA joins flanking genomic DNA. A junction point also exists in a transformed organism where two DNA fragments join together in a manner that is modified from that found in the native organism. As used herein, "junction DNA" refers to DNA that comprises a junction point. Non-limiting examples of junction DNA from the DP-305423-1 event set are forth in SEQ ID NO:5, 6, 7, 8, 9, 10, 11, 12, 13, 14, 15, 16, 17, 18, 19, 20, 21, 22, 23, 24, 25, 82, 83, 84, 85, 86, 87 or 88, or variants and fragments thereof.

A DP-305423-1 plant can be bred by first sexually crossing a first parental soybean plant grown from the transgenic DP-305423-1 soybean plant (or progeny thereof derived from transformation with the expression cassettes of the embodiments of the present invention that confer herbicide tolerance) and a second parental soybean plant that lacks the herbicide tolerance phenotype, thereby producing a plurality of first progeny plants; and then selecting a first progeny plant that displays the desired herbicide tolerance; and selfing the first progeny plant, thereby producing a plurality of second progeny plants; and then selecting from the second progeny plants which display the desired herbicide tolerance. These steps can further include the back-crossing of the first herbicide tolerant progeny plant or the second herbicide tolerant progeny plant to the second parental soybean plant or a third parental soybean plant, thereby producing a soybean plant that displays the desired herbicide tolerance. It is further recognized that assaying progeny for phenotype is not required. Various methods and compositions, as disclosed elsewhere herein, can be used to detect and/or identify the DP-305423-1 event.

It is also to be understood that two different transgenic plants can also be mated to produce offspring that contain two independently segregating added, exogenous genes. Selfing of appropriate progeny can produce plants that are homozygous for both added, exogenous genes. Back-crossing to a parental plant and out-crossing with a non-transgenic plant are also contemplated, as is vegetative propagation. Descriptions of other breeding methods that are commonly used for different traits and crops can be found in one of several references, e.g., Fehr, in *Breeding Methods for Cultivar Development*, Wilcos J. ed., American Society of Agronomy, Madison Wis. (1987).

One particularly useful application of the claimed invention is to combine the high oleic acid trait of the DP-305423-1 event with other soybean lines that have altered fatty acid compositions to obtain progeny lines with novel fatty acid compositions and/or improved agronomic traits. The other soybean lines may be mutant lines, transgenic lines, or transgenic lines that also comprise a mutated gene. The transgenes of DP-305423-1 may be combined with mutant genes or other transgenes either by making a genetic cross or by transforming the other soybean line with the recombinant DNA constructs of the invention.

As examples, the high oleic acid trait of the invention can be combined with a mutant line having a high stearic acid phenotype, such as soybean line A6 [Hammond, E. G. and Fehr, W. R. (1983)] or with a mutant line having a low linolenic acid phenotype such as soybean mutant lines A5, A23, A16 and C1640 [Fehr, W. R. et al. (1992) in *Crop Science* 32:903-906]. Oils produced from such combinations would provide improved feedstocks for production of margarines, shortenings, spray coating and frying oils and would eliminate or reduce the need for hydrogenation. Furthermore, these oils would provide a health benefit for consumers, for example by reducing or eliminating trans fatty acids which have been found to be associated with high risk to cardiovascular diseases.

The high oleic acid trait of the invention also can be combined with mutant lines that have a high oleic acid phenotype. Examples of high oleic acid mutant lines include soybean lines A5 and N782245 [Martin, B. A. and Rinne, R. W. (1985) *Crop Science* 25:1055-1058].

As used herein, the use of the term "polynucleotide" is not intended to limit the present invention to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

A DP-305423-1 plant comprises a suppression cassette containing a 597 bp fragment of the soybean microsomal omega-6 desaturase gene 1 (gm-fad2-1) and an expression cassette containing a modified version of the soybean acetolactate synthase gene (gm-hra). The cassette can include 5' and 3' regulatory sequences operably linked to the gm-fad2-1 and the gm-hra polynucleotides. "Operably linked" is intended to mean a functional linkage between two or more elements. For example, an operable linkage between a polynucleotide of interest and a regulatory sequence (i.e., a promoter) is functional link that allows for the expression of the polynucleotide of interest. Operably linked elements may be contiguous or non-contiguous. When used to refer to the joining of two protein coding regions, by operably linked it is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the polynucleotide to be under the transcriptional regulation of the regulatory regions. The expression cassette may additionally contain selectable marker genes.

The expression cassette will include in the 5'-3' direction of transcription, a transcriptional and translational initiation region (i.e., a promoter), a coding region, and a transcriptional and translational termination region functional in plants. "Promoter" refers to a nucleotide sequence capable of controlling the expression of a coding sequence or functional RNA. In general, a coding sequence is located 3' to a promoter sequence. The promoter sequence can comprise proximal and more distal upstream elements, the latter elements are often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters that cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15: 1-82. It is further recognized that since in most cases the exact boundaries of regulatory sequences have not been completely defined, nucleic acid fragments of different lengths may have identical promoter activity.

The expression cassettes may also contain 5' leader sequences. Such leader sequences can act to enhance translation. The regulatory regions (i.e., promoters, transcriptional regulatory regions, RNA processing or stability regions, introns, polyadenylation signals, and translational termination regions) and/or the coding region may be native/analogous or heterologous to the host cell or to each other.

The "translation leader sequence" refers to a nucleotide sequence located between the promoter sequence of a gene and the coding sequence. The translation leader sequence is present in the fully processed mRNA upstream of the translation start sequence. The translation leader sequence may affect numerous parameters including, processing of the primary transcript to mRNA, mRNA stability and/or translation efficiency. Examples of translation leader sequences have been described (Turner and Foster (1995) *Mol. Biotechnol.* 3: 225-236). The "3'non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1: 671-680.

As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved. The expression cassette can also comprise a selectable marker gene for the selection of transformed cells. Selectable marker genes are utilized for the selection of transformed cells or tissues.

Isolated polynucleotides are provided that can be used in various methods for the detection and/or identification of the soybean DP-305423-1 event. An "isolated" or "purified" polynucleotide, or biologically active portion thereof, is substantially or essentially free from components that normally accompany or interact with the polynucleotide as found in its naturally occurring environment. Thus, an isolated or purified polynucleotide is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived.

In specific embodiments, the polynucleotides of the invention comprise the junction DNA sequence set forth in SEQ ID NO:8, 9, 14, 15, 20, 21, 83 or 84. In other embodiments, the polynucleotides of the invention comprise the junction DNA sequences set forth in SEQ ID NO:5, 6, 7, 8, 9, 10, 11, 12, 13, 14, 15, 16, 17, 18, 19, 20, 21, 22, 23, 24, 25, 82, 83, 84, 85, 86, 87 or 88 or variants and fragments thereof. Fragments and variants of junction DNA sequences are suitable for discriminatively identifying event DP-305423-1. As discussed elsewhere herein, such sequences find use as primer and/or probes.

Another embodiment is a DNA expression construct comprising the isolated polynucleotide of the invention operably linked to at least one regulatory sequence.

Another embodiment is a recombinant DNA construct comprising: a first and second expression cassette, wherein said first expression cassette in operable linkage comprises: (a) a soybean KTi3 promoter; (b) a gm-fad2-1 fragment; and (c) a soybean KTi3 transcriptional terminator; and said second expression cassette comprising in operable linkage: (i) a soybean SAMS promoter; (ii) a soybean SAMS 5' untranslated leader and intron; (iii) a soybean gm-hra encoding DNA molecule; and (iv) a soybean als transcriptional terminator.

Another embodiment is a transgenic soybean plant having stably integrated into its genome the polynucleotide or the recombinant DNA construct of the invention, and transgenic seed and transgenic progeny derived from said transgenic soybean plant, each also comprising the polynucleotide or recombinant DNA construct of the invention.

In other embodiments, the polynucleotides of the invention comprise polynucleotides that can detect a DP-305423-1 event or a DP-305423-1 specific region. Such sequences include any polynucleotide set forth in SEQ ID NOS:1-94 or variants and fragments thereof. Fragments and variants of polynucleotides that detect a DP-305423-1 event or a DP-305423-1 specific region are suitable for discriminatively identifying event DP-305423-1. As discussed elsewhere herein, such sequences find us as primer and/or probes. Further provided are isolated DNA nucleotide primer sequences comprising or consisting of a sequence set forth in SEQ ID NO:26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 89, 90, 91, 92, 93 or 94, or a complement thereof.

"Variants" is intended to mean substantially similar sequences. For polynucleotides, a variant comprises a polynucleotide having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide.

As used herein, a "probe" is an isolated polynucleotide to which is attached a conventional detectable label or reporter molecule, e.g., a radioactive isotope, ligand, chemiluminescent agent, enzyme, etc. Such a probe is complementary to a strand of a target polynucleotide, in the case of the present invention, to a strand of isolated DNA from soybean event DP-305423-1 whether from a soybean plant or from a sample that includes DNA from the event. Probes according to the present invention include not only deoxyribonucleic or ribonucleic acids but also polyamides and other probe materials that can specifically detect the presence of the target DNA sequence.

As used herein, "primers" are isolated polynucleotides that are annealed to a complementary target DNA strand by nucleic acid hybridization to form a hybrid between the primer and the target DNA strand, then extended along the target DNA strand by a polymerase, e.g., a DNA polymerase. Primer pairs of the invention refer to their use for amplification of a target polynucleotide, e.g., by the polymerase chain reaction (PCR) or other conventional nucleic-acid amplification methods. "PCR" or "polymerase chain reaction" is a technique used for the amplification of specific DNA segments (see, U.S. Pat. Nos. 4,683,195 and 4,800,159; herein incorporated by reference). Any combination of primers disclosed herein can be used such that the pair allows for the detection a DP-305423-1 event or specific region. Non-limiting examples of primer pairs include SEQ ID NOS:26 and 27; SEQ ID NOS:29 and 30; SEQ ID NOS:31 and 32; SEQ ID NOS:33 AND 34; SEQ ID NOS:35 and 36; SEQ ID NOS:37 and 38; SEQ ID NOS:39 and 40; SEQ ID NO:41 and 42; SEQ ID NOS:43 and 44; SEQ ID NOS:45 and 46; SEQ ID NOS:47 and 48; SEQ ID NOS:47 and 49; SEQ ID NOS:50 and 51; SEQ ID NOS:52 and 53; SEQ ID NOS:54 and 49; SEQ ID NOS:55 and 46; SEQ ID NOS:33 and 56; SEQ ID NOS:57 and 58; SEQ ID NOS:59 and 60; SEQ ID NOS:61 and 36; SEQ ID NOS:35 and 62; SEQ ID NOS:37 and 63; SEQ ID NOS:64 and 65; SEQ ID NOS:66 and 67; SEQ ID NOS:68 and 69; SEQ ID NOS:70 and 71; SEQ ID NOS:72 and 73; SEQ ID NOS:74 and 75; SEQ ID NOS:76 and 77; SEQ ID NOS:78 and 79; SEQ ID NOS:80 and 81; and SEQ ID NOS: 89 and 90.

Probes and primers are of sufficient nucleotide length to bind to the target DNA sequence and specifically detect and/or identify a polynucleotide having a DP-305423-1 event. It is recognized that the hybridization conditions or reaction conditions can be determined by the operator to achieve this result. This length may be of any length that is of sufficient length to be useful in a detection method of choice. Generally, 8, 11, 14, 16, 18, 20, 22, 24, 26, 28, 30, 40, 50, 75, 100, 200, 300, 400, 500, 600, 700 nucleotides or more, or between about 11-20, 20-30, 30-40, 40-50, 50-100, 100-200, 200-300, 300-400, 400-500, 500-600, 600-700, 700-800, or more nucleotides in length are used. Such probes and primers can hybridize specifically to a target sequence under high stringency hybridization conditions. Probes and primers according to embodiments of the present invention may have complete DNA sequence identity of contiguous nucleotides with the target sequence, although probes differing from the target DNA sequence and that retain the ability to specifically detect and/or identify a target DNA sequence may be designed by conventional methods. Accordingly, probes and primers can share about 80%, 85%, 90%, 91%, 92%, 93%, 94%, 95%, 96%, 97%, 98%, 99% or greater sequence identity or complementarity to the target polynucleotide (i.e., SEQ ID NO:1-94), or can differ from the target sequence (i.e., SEQ ID NO:1-94) by 1, 2, 3, 4, 5, 6 or more nucleotides. Probes can be used as primers, but are generally designed to bind to the target DNA or RNA and are not used in an amplification process.

Specific primers can be used to amplify an integration fragment to produce an amplicon that can be used as a "specific probe" or can itself be detected for identifying event DP-305423-1 in biological samples. Alternatively, a probe of the invention can be used during the PCR reaction to allow for the detection of the amplification event (i.e., a taqman probe). When the probe is hybridized with the polynucleotides of a biological sample under conditions which allow for the binding of the probe to the sample, this binding can be detected and thus allow for an indication of the presence of event DP-305423-1 in the biological sample. Such identification of a bound probe has been described in the art. In an embodiment of the invention, the specific probe is a sequence which, under optimized conditions, hybridizes specifically to a region within the 5' or 3' flanking region of the event and also comprises a part of the foreign DNA contiguous therewith. The specific probe may comprise a sequence of at least 80%, between 80 and 85%, between 85 and 90%, between 90 and 95%, and between 95 and 100% identical (or complementary) to a specific region of the DP-305423-1 event.

As used herein, "amplified DNA" or "amplicon" refers to the product of polynucleotide amplification of a target polynucleotide that is part of a nucleic acid template. For example, to determine whether a soybean plant resulting from a sexual cross contains the DP-305423-1 event, DNA extracted from the soybean plant tissue sample may be subjected to a polynucleotide amplification method using a DNA primer pair that includes a first primer derived from flanking sequence adjacent to the insertion site of inserted heterologous DNA, and a second primer derived from the inserted heterologous DNA to produce an amplicon that is diagnostic for the presence of the DP-305423-1 event DNA. By "diagnostic" for a DP-305423-1 event the use of any method or assay which discriminates between the presence or the absence of a DP-305423-1 event in a biological sample is intended. Alternatively, the second primer may be derived from the flanking sequence. In still other embodiments, primer pairs can be derived from flanking sequence on both sides of the inserted DNA so as to produce an amplicon that includes the entire insert polynucleotide of the expression construct as well as the sequence flanking the transgenic insert. The amplicon is of a length and has a sequence that is also diagnostic for the event (i.e., has a junction DNA from a DP-305423-1 event). The amplicon may range in length from the combined length of the primer pairs plus one nucleotide base pair to any length of amplicon producible by a DNA amplification protocol. A member of a primer pair derived from the flanking sequence may be located a distance from the inserted DNA sequence, this distance can range from one nucleotide base pair up to the limits of the amplification reaction, or about twenty thousand nucleotide base pairs. The use of the term "amplicon" specifically excludes primer dimers that may be formed in the DNA thermal amplification reaction.

Methods for preparing and using probes and primers are described, for example, in *Molecular Cloning: A Laboratory Manual*, 2.sup.nd ed, vol. 1-3, ed. Sambrook et al., Cold Spring Harbor Laboratory Press, Cold Spring Harbor, N.Y. 1989 (hereinafter, "Sambrook et al., 1989"); *Current Protocols in Molecular Biology*, ed. Ausubel et al., Greene Publishing and Wiley-Interscience, New York, 1992 (with periodic updates) (hereinafter, "Ausubel et al., 1992"); and Innis et al., PCR Protocols: A Guide to Methods and Applications, Academic Press: San Diego, 1990. PCR primer pairs can be derived from a known sequence, for example, by using computer programs intended for that purpose such as the PCR primer analysis tool in Vector NTI version 6 (Informax Inc., Bethesda Md.); PrimerSelect (DNASTAR Inc., Madison, Wis.); and Primer (Version 0.5.COPYRGT., 1991, Whitehead Institute for Biomedical Research, Cambridge, Mass.). Additionally, the sequence can be visually scanned and primers manually identified using guidelines known to one of skill in the art.

It is to be understood that as used herein the term "transgenic" includes any cell, cell line, callus, tissue, plant part, or plant, the genotype of which has been altered by the presence of a heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143: 277) and particle-accelerated or "gene gun" transformation technology (Klein et al. (1987) *Nature* (London) 327: 70-73; U.S. Pat. No. 4,945,050, incorporated herein by reference). Additional transformation methods are disclosed below.

Thus, isolated polynucleotides of the invention can be incorporated into recombinant constructs, typically DNA constructs, which are capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al. (1985; Supp. 1987) *Cloning Vectors: A Laboratory Manual*, Weissbach and Weissbach (1989) *Methods for Plant Molecular Biology* (Academic Press, New York); and Flevin et al. (1990) *Plant Molecular Biology Manual* (Kluwer Academic Publishers). Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Various methods and compositions for identifying event DP-305423-1 are provided. Such methods find use in identifying and/or detecting a DP-305423-1 event in any biological material. Such methods include, for example, methods to confirm seed purity and methods for screening seeds in a seed lot for a DP-305423-1 event. In one embodiment, a method for identifying event DP-305423-1 in a biological sample is provided and comprises contacting the sample with a first and a second primer; and, amplifying a polynucleotide comprising a DP-305423-1 specific region.

A biological sample can comprise any sample in which one desires to determine if DNA having event DP-305423-1 is present. For example, a biological sample can comprise any plant material or material comprising or derived from a plant material such as, but not limited to, food or feed products. As used herein, "plant material" refers to material which is obtained or derived from a plant or plant part. In specific embodiments, the biological sample comprises a soybean tissue.

Primers and probes based on the flanking DNA and insert sequences disclosed herein can be used to confirm (and, if necessary, to correct) the disclosed sequences by conventional methods, e.g., by re-cloning and sequencing such sequences. The polynucleotide probes and primers of the present invention specifically detect a target DNA sequence. Any conventional nucleic acid hybridization or amplification method can be used to identify the presence of DNA from a transgenic event in a sample. By "specifically detect" it is intended that the polynucleotide can be used either as a primer to amplify a DP-305423-1 specific region or the polynucleotide can be used as a probe that hybridizes under stringent conditions to a polynucleotide having a DP-305423-1 event or a DP-305423-1 specific region. The level or degree of hybridization which allows for the specific detection of a DP-305423-1 event or a specific region of a DP-305423-1 event is sufficient to distinguish the polynucleotide with the DP-305423-1 specific region from a polynucleotide lacking this region and thereby allow for discriminately identifying a DP-305423-1 event. By "shares sufficient sequence identity or complementarity to allow for the amplification of a DP-305423-1 specific event" is intended the sequence shares at least 80%, 85%, 90%, 91%, 92%, 93%, 94%, 95%, 96%, 97%, 98%, 99% or 100% identity or complementarity to a fragment or across the full length of the polynucleotide having the DP-305423-1 specific region.

Regarding the amplification of a target polynucleotide (e.g., by PCR) using a particular amplification primer pair, "stringent conditions" are conditions that permit the primer pair to hybridize to the target polynucleotide to which a primer having the corresponding wild-type sequence (or its complement) would bind and preferably to produce an identifiable amplification product (the amplicon) having a DP-305423-1 specific region in a DNA thermal amplification reaction. In a PCR approach, oligonucleotide primers can be designed for use in PCR reactions to amplify a DP-305423-1 specific region. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Methods of amplification are further described in U.S. Pat. Nos. 4,683,195, 4,683,202 and Chen et al. (1994) *PNAS* 91:5695-5699. These methods as well as other methods known in the art of DNA amplification may be used in the practice of the embodiments of the present invention. It is understood that a number of parameters in a specific PCR protocol may need to be adjusted to specific laboratory conditions and may be slightly modified and yet allow for the collection of similar results. These adjustments will be apparent to a person skilled in the art.

The amplified polynucleotide (amplicon) can be of any length that allows for the detection of the DP-305423-1 event or a DP-305423-1 specific region. For example, the amplicon can be about 10, 50, 100, 200, 300, 500, 700, 100, 2000, 3000, 4000, 5000 nucleotides in length or longer.

In specific embodiments, the specific region of the DP-305423-1 event is detected.

Any primer can be employed in the methods of the invention that allows a DP-305423-1 specific region to be amplified and/or detected. For example, in specific embodiments, the first primer comprises a fragment of a polynucleotide of SEQ ID NO:5, 6, 7 or 82, wherein the first or the second primer shares sufficient sequence identity or complementarity to the polynucleotide to amplify the DP-305423-1 specific region. The primer pair can comprise a first primer that comprises a fragment of a 5' genomic region of SEQ ID NO:5, 6, 7 or 82, and a second primer that comprises a fragment of a 3' genomic region of SEQ ID NO:5, 6, 7 or 82, or an insert region of SEQ ID NO:5, 6, 7 or 82, or alternatively, the primer pair can comprise a first primer that comprises a fragment of a 3' genomic region of SEQ ID NO:5, 6, 7 or 82, and a second primer that comprises a fragment of a 5' genomic region of SEQ ID NO:5, 6, 7 or 82, or an insert region of SEQ ID NO:5, 6, 7 or 82. In still further embodiments, the first and the second primer can comprise any one or any combination of the sequences set forth in SEQ ID NO:26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 89, 90, 91, 92, 93 or 94. The primers can be of any length sufficient to amplify a DP-305423-1 region including, for example, at least 6, 7, 8, 9, 10, 15, 20, 15, or 30 or about 7-10, 10-15, 15-20, 20-25, 25-30, 30-35, 35-40, 40-45 nucleotides or longer.

As discussed elsewhere herein, any method to PCR amplify the DP-305423-1 event or specific region can be employed, including for example, real time PCR. See, for example, Livak et al. (1995a) Oligonucleotides with fluorescent dyes at opposite ends provide a quenched probe system for detecting PCR product and nucleic acid hybridization. PCR methods and Applications. 4:357-362; U.S. Pat. No. 5,538,848; U.S. Pat. No. 5,723,591; Applied Biosystems User Bulletin No. 2, "Relative Quantitation of Gene Expression," P/N 4303859; and, Applied Biosystems User Bulletin No. 5, "Multiplex PCR with Taqman VIC probes," P/N 4306236; each of which is herein incorporated by reference.

Thus, in specific embodiments, a method of detecting the presence of soybean event DP-305423-1 or progeny thereof in a biological sample is provided. The method comprises (a) extracting a DNA sample from the biological sample; (b) providing a pair of DNA primer molecules, including, but not limited to, i) the sequences comprising SEQ ID NO:26 and SEQ ID NO:27; ii) the sequences comprising SEQ ID NO:29 and SEQ ID NO:30; iii) the sequences comprising SEQ ID NO:31 and SEQ ID NO:32; iv) the sequences comprising SEQ ID NO:33 and SEQ ID NO:34; v) the sequences comprising SEQ ID NO:35 and SEQ ID NO:36; vi) the sequences comprising SEQ ID NO:37 and SEQ ID NO:38; vii) the sequences comprising SEQ ID NO:39 and SEQ ID NO:40; viii) the sequences comprising SEQ ID NO:41 and SEQ ID NO:42; ix) the sequences comprising SEQ ID NO:43 and SEQ ID NO:44; x) the sequences comprising SEQ ID NO:45 and SEQ ID NO:46; xi) the sequences comprising SEQ ID NO:47 and SEQ ID NO:48; xii) the sequences comprising SEQ ID NO:47 and SEQ ID NO:49; xiii) the sequences comprising SEQ ID NO:50 and SEQ ID NO:51; xiv) the sequences comprising SEQ ID NO:52 and SEQ ID NO:53; xv) the sequences comprising SEQ ID NO:54 and SEQ ID NO:49; xvi) the sequences comprising SEQ ID NO:55 and SEQ ID NO:46; xvii) the sequences comprising SEQ ID NO:33 and SEQ ID NO:56; xviii) the sequences comprising SEQ ID NO:57 and SEQ ID NO:58; xix) the sequences comprising SEQ ID NO:59 and SEQ ID NO:60; xx) the sequences comprising SEQ ID NO:61 and SEQ ID NO:36; xxi) the sequences comprising SEQ ID NO:35 and SEQ ID NO:62; xxii) the sequences comprising SEQ ID NO:37 and SEQ ID NO:63; xxiii) the sequences comprising SEQ ID NO:64 and SEQ ID NO:65; xxiv) the sequences comprising SEQ ID NO:66 and SEQ ID NO:67; xxv) the sequences comprising SEQ ID NO:68 and SEQ ID NO:69; xxvi) the sequences comprising SEQ ID NO:70 and SEQ ID NO:71; xxvii) the sequences comprising SEQ ID NO:72 and SEQ ID NO:73; xxviii) the sequences comprising SEQ ID NO:74 and SEQ ID NO:75; xxix) the sequences comprising SEQ ID NO:76 and SEQ ID NO:77; xxx) the sequences comprising SEQ ID NO:78 and SEQ ID NO:79; xxxi) the sequences comprising SEQ ID NO:80 and SEQ ID NO:81; and xxxii) the sequences comprising SEQ ID NO:89 and SEQ ID NO:90 (c) providing DNA amplification reaction conditions; (d) performing the DNA amplification reaction, thereby producing a DNA amplicon molecule; and (e) detecting the DNA amplicon molecule, wherein the detection of said DNA amplicon molecule in the DNA amplification reaction indicates the presence of soybean event DP-305423-1. In order for a nucleic acid molecule to serve as a primer or probe it need only be sufficiently complementary in sequence to be able to form a stable double-stranded structure under the particular solvent and salt concentrations employed.

In hybridization techniques, all or part of a polynucleotide that selectively hybridizes to a target polynucleotide having a DP-305423-1 specific event is employed. By "stringent conditions" or "stringent hybridization conditions" when referring to a polynucleotide probe conditions under which a probe will hybridize to its target sequence to a detectably greater degree than to other sequences (e.g., at least 2-fold over background) are intended. Regarding the amplification of a target polynucleotide (e.g., by PCR) using a particular amplification primer pair, "stringent conditions" are conditions that permit the primer pair to hybridize to the target polynucleotide to which a primer having the corresponding wild-type. Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of identity are detected (heterologous probing). Generally, a probe is less than about 1000 nucleotides in length or less than 500 nucleotides in length.

As used herein, a substantially identical or complementary sequence is a polynucleotide that will specifically hybridize to the complement of the nucleic acid molecule to which it is being compared under high stringency conditions. Appropriate stringency conditions which promote DNA hybridization, for example, 6× sodium chloride/sodium citrate (SSC) at about 45° C., followed by a wash of 2×SSC at 50° C., are known to those skilled in the art or can be found in Current Protocols in Molecular Biology, John Wiley & Sons, N.Y. (1989), 6.3.1-6.3.6. Typically, stringent conditions for hybridization and detection will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

In hybridization reactions, specificity is typically the function of post-hybridization washes, the critical factors being the ionic strength and temperature of the final wash solution. For DNA-DNA hybrids, the $T_m$ can be approximated from the equation of Meinkoth and Wahl (1984) Anal. Biochem. 138: 267-284: $T_m=81.5°$ C.$+16.6$ (log M)$+0.41$ (% GC)$-0.61$ (% form)$-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) Laboratory Techniques in Biochemistry and Molecular Biology—Hybridization with Nucleic Acid Probes, Part I, Chapter 2 (Elsevier, New York); and Ausubel et al., eds. (1995) Current Protocols in Molecular Biology, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.) and Haymes et al. (1985) In: *Nucleic Acid Hybridization, a Practical Approach*, IRL Press, Washington, D.C.

A polynucleotide is said to be the "complement" of another polynucleotide if they exhibit complementarity. As used herein, molecules are said to exhibit "complete complementarity" when every nucleotide of one of the polynucleotide molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions.

Further provided are methods of detecting the presence of DNA corresponding to the DP-305423-1 event in a sample. In one embodiment, the method comprises (a) contacting the biological sample with a polynucleotide probe that hybridizes under stringent hybridization conditions with DNA from soybean event DP-305423-1 and specifically detects the DP-305423-1 event; (b) subjecting the sample and probe to stringent hybridization conditions; and (c) detecting hybridization of the probe to the DNA, wherein detection of hybridization indicates the presence of the DP-305423-1 event.

Various method can be used to detect the DP-305423-1 specific region or amplicon thereof, including, but not limited to, Genetic Bit Analysis (Nikiforov et al. (1994) *Nucleic Acid Res.* 22: 4167-4175) where a DNA oligonucleotide is designed which overlaps both the adjacent flanking DNA sequence and the inserted DNA sequence. The oligonucleotide is immobilized in wells of a microwell plate. Following PCR of the region of interest (using one primer in the inserted sequence and one in the adjacent flanking sequence) a single-stranded PCR product can be hybridized to the immobilized oligonucleotide and serve as a template for a single base extension reaction using a DNA polymerase and labeled ddNTPs specific for the expected next base. Readout may be fluorescent or ELISA-based. A signal indicates presence of the insert/flanking sequence due to successful amplification, hybridization, and single base extension.

Another detection method is the Pyrosequencing technique as described by Winge ((2000) *Innov. Pharma. Tech.* 00: 18-24). In this method, an oligonucleotide is designed that overlaps the adjacent DNA and insert DNA junction. The oligonucleotide is hybridized to a single-stranded PCR product from the region of interest (one primer in the inserted sequence and one in the flanking sequence) and incubated in the presence of a DNA polymerase, ATP, sulfurylase, luciferase, apyrase, adenosine 5' phosphosulfate and luciferin. dNTPs are added individually and the incorporation results in a light signal which is measured. A light signal indicates the presence of the transgene insert/flanking sequence due to successful amplification, hybridization, and single or multi-base extension.

Fluorescence Polarization as described by Chen et al. ((1999) *Genome Res.* 9: 492-498, 1999) is also a method that can be used to detect an amplicon of the invention. Using this method, an oligonucleotide is designed which overlaps the flanking and inserted DNA junction. The oligonucleotide is hybridized to a single-stranded PCR product from the region of interest (one primer in the inserted DNA and one in the flanking DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

Taqman® (PE Applied Biosystems, Foster City, Calif.) is described as a method of detecting and quantifying the presence of a DNA sequence and is fully understood in the instructions provided by the manufacturer. Briefly, a FRET oligonucleotide probe is designed which overlaps the flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

Molecular Beacons have been described for use in sequence detection as described in Tyangi et al. ((1996) *Nature Biotech.* 14: 303-308). Briefly, a FRET oligonucleotide probe is designed that overlaps the flanking and insert DNA junction. The unique structure of the FRET probe results in it containing secondary structure that keeps the fluorescent and quenching moieties in close proximity. The FRET probe and PCR primers (one primer in the insert DNA sequence and one in the flanking sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking/transgene insert sequence due to successful amplification and hybridization.

A hybridization reaction using a probe specific to a sequence found within the amplicon is yet another method used to detect the amplicon produced by a PCR reaction.

As used herein, "kit" refers to a set of reagents for the purpose of performing the method embodiments of the invention, more particularly, the identification and/or the detection of the DP-305423-1 event in biological samples. The kit of the invention can be used, and its components can be specifically adjusted, for purposes of quality control (e.g. purity of seed lots), detection of event DP-305423-1 in plant material, or material comprising or derived from plant material, such as but not limited to food or feed products.

In specific embodiments, a kit for identifying event DP-305423-1 in a biological sample is provided. The kit comprises a first and a second primer, wherein the first and second primer amplify a polynucleotide comprising a DP-305423-1 specific region. In further embodiments, the kit also comprises a polynucleotide for the detection of the DP-305423-1 specific region. The kit can comprise, for example, a first primer comprising a fragment of a polynucleotide of SEQ ID NO:5, 6, 7 or 82, wherein the first or the second primer shares sufficient sequence homology or complementarity to the polynucleotide to amplify said DP-305423-1 specific region. For example, in specific embodiments, the first primer comprises a fragment of a polynucleotide of SEQ ID NO:5, 6, 7 or 82, wherein the first or the second primer shares sufficient sequence homology or complementarity to the polynucleotide to amplify said DP-305423-1 specific region. The primer pair can comprises a first primer that comprises a fragment of a 5' genomic region of SEQ ID NO:5, 6, 7 or 82, and a second primer that comprises a fragment of a 3' genomic region of SEQ ID NO:5, 6, 7 or 82, or an insert region of SEQ ID NO:5, 6, 7 or 82, or alternatively, the primer pair can comprise a first primer that comprises a fragment of a 3' genomic region of SEQ ID NO:5, 6, 7 or 82, and a second primer that comprises a fragment of a 5' genomic region of SEQ ID NO:5, 6, 7 or 82, or an insert region of SEQ ID NO:5, 6, 7 or 82. In still further embodiments, the first and the second primer can comprise any one or any combination of the sequences set forth in SEQ ID NO:26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 89, 90, 91, 92, 93 or 94. The primers can be of any length sufficient to amplify the DP-305423-1 region including, for example, at least 6, 7, 8, 9, 10, 15, 20, 15, or 30 or about 7-10, 10-15, 15-20, 20-25, 25-30, 30-35, 35-40, 40-45 nucleotides or longer.

Further provided are DNA detection kits comprising at least one polynucleotide that can specifically detect a DP-305423-1 specific region, wherein said polynucleotide comprises at least one DNA molecule of a sufficient length of contiguous nucleotides homologous or complementary to SEQ ID NO:5, 6, 7 or 82. In specific embodiments, the DNA detection kit comprises a polynucleotide having SEQ ID NO:8, 9, 14, 15, 20, 21, 83 or 84, or comprises a sequence which hybridizes with at least one sequence selected from the group consisting of: a) the sequences of a 5' genomic region of SEQ ID NO:5, 6, 7 or 82, and the sequences of an insert region of SEQ ID NO:5, 6, 7 or 82; and, b) the sequences of a 3' genomic region of SEQ ID NO:5, 6, 7 or 82, and the sequences of an insert region of SEQ ID NO:5, 6, 7 or 82.

Any of the polynucleotides and fragments and variants thereof employed in the methods and compositions of the invention can share sequence identity to a region of the transgene insert of the DP-305423-1 event, a junction sequence of the DP-305423-1 event or a flanking sequence of the DP-305423-1 event. Methods to determine the relationship of various sequences are known. As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence. As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local-alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

Sequence alignments and percent identity calculations may be determined using a variety of comparison methods designed to detect homologous sequences including, but not limited to, the Megalign® program of the LASERGENE® bioinformatics computing suite (DNASTAR® Inc., Madison, Wis.). For example, multiple alignment of the sequences provided herein can be performed using the Clustal V method of alignment (Higgins and Sharp (1989) *CABIOS.* 5:151-153) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" any sequence comparison program that, for any two sequences in question, generates an alignment having identical nucleotide or amino acid residue matches and an identical percent sequence identity when compared to the corresponding alignment generated by GAP Version 10 is intended.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the Quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The present invention provides methods for controlling weeds in an area of cultivation, preventing the development or the appearance of herbicide resistant weeds in an area of cultivation, producing a crop, and increasing crop safety. The term "controlling," and derivations thereof, for example, as in "controlling weeds" refers to one or more of inhibiting the growth, germination, reproduction, and/or proliferation of; and/or killing, removing, destroying, or otherwise diminishing the occurrence and/or activity of a weed.

As used herein, an "area of cultivation" comprises any region in which one desires to grow a plant. Such areas of cultivations include, but are not limited to, a field in which a plant is cultivated (such as a crop field, a sod field, a tree field, a managed forest, a field for culturing fruits and vegetables, etc), a greenhouse, a growth chamber, etc.

The methods of the invention comprise planting the area of cultivation with the soybean DP-305423-1 seeds or plants, and in specific embodiments, applying to the crop, seed, weed or area of cultivation thereof an effective amount of a herbicide of interest. It is recognized that the herbicide can be applied before or after the crop is planted in the area of cultivation. Such herbicide applications can include an application of an inhibitor of ALS. In specific embodiments, an inhibitor of ALS is applied to the soybean DP-305423-1 event, wherein the effective concentration of the ALS inhibitor would significantly damage an appropriate control plant. In one non-limiting embodiment, the herbicide comprises at least one of a sulfonylaminocarbonyltriazolinone; a triazolopyrimidine; a pyrimidinyl(thio)benzoate; an imidazolinone; a triazine; and/or a phosphinic acid.

In another non-limiting embodiment, the herbicide comprises imazapyr, chlorimuron-ethyl, quizalofop, or fomesafen, wherein an effective amount is tolerated by the crop and controls weeds. As disclosed elsewhere herein, any effective amount of these herbicides can be applied. In specific embodiments, an effective amount of imazapyr comprising about 7.5 to about 27.5 g ai/hectare; an effective amount of chlorimuron-ethyl comprising about 7.5 to about 27.5 g ai/hectare; an effective amount of quizalofop comprising about 50 to about 70 g ai/hectare; and, an effective amount of fomesafen comprising about 240 to about 260 g ai/hectare.

In other embodiments, a combination of at least two herbicides are applied. More details regarding the various herbicide combinations that can be employed in the methods of the invention are discussed elsewhere herein.

A "control" or "control plant" or "control plant cell" provides a reference point for measuring changes in phenotype of the subject plant or plant cell, and may be any suitable plant or plant cell. A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell which is genetically identical to the subject plant or plant cell but which is not exposed to the same treatment (e.g., herbicide treatment) as the subject plant or plant cell; (e) the subject plant or plant cell itself, under conditions in which the gene of interest is not expressed; or (f) the subject plant or plant cell itself, under conditions in which it has not been exposed to a particular treatment such as, for example, a herbicide or combination of herbicides and/or other chemicals. In some instances, an appropriate control plant or control plant cell may have a different genotype from the subject plant or plant cell but may share the herbicide-sensitive characteristics of the starting material for the genetic alteration(s) which resulted in the subject plant or cell (see, e.g., Green (1998) *Weed Technology* 12: 474-477; Green and Ulrich (1993) *Weed Science* 41: 508-516. In some instances, an appropriate control soybean plant is a "Jack" soybean plant (Illinois Foundation Seed, Champaign, Ill.). In other embodiments, the null segregant can be used as a control, as they are genetically identical to DP-305423-1 with the exception of the transgenic insert DNA.

Any herbicide can be applied to the DP-305423-1 soybean crop, crop part, or the area of cultivation containing the crop plant. Classifications of herbicides (i.e., the grouping of herbicides into classes and subclasses) is well-known in the art and includes classifications by HRAC (Herbicide Resistance Action Committee) and WSSA (the Weed Science Society of America) (see also, Retzinger and Mallory-Smith (1997) *Weed Technology* 11: 384-393). An abbreviated version of the HRAC classification (with notes regarding the corresponding WSSA group) is set forth below in Table 2.

Herbicides can be classified by their mode of action and/or site of action and can also be classified by the time at which they are applied (e.g., preemergent or postemergent), by the method of application (e.g., foliar application or soil application), or by how they are taken up by or affect the plant. For example, thifensulfuron-methyl and tribenuron-methyl are applied to the foliage of a crop and are generally metabolized there, while rimsulfuron and chlorimuron-ethyl are generally taken up through both the roots and foliage of a plant. "Mode of action" generally refers to the metabolic or physiological process within the plant that the herbicide inhibits or otherwise impairs, whereas "site of action" generally refers to the physical location or biochemical site within the plant where the herbicide acts or directly interacts. Herbicides can be classified in various ways, including by mode of action and/or site of action (see, e.g., Table 2).

Often, a herbicide-tolerance gene that confers tolerance to a particular herbicide or other chemical on a plant expressing it will also confer tolerance to other herbicides or chemicals in the same class or subclass, for example, a class or subclass set forth in Table 2. Thus, in some embodiments of the invention, a transgenic plant of the invention is tolerant to more than one herbicide or chemical in the same class or subclass, such as, for example, an inhibitor of PPO, a sulfonylurea, or a synthetic auxin.

The invention provides a transgenic soybean plant which can be selected for use in crop production based on the prevalence of herbicide-tolerant weed species in the area where the transgenic crop is to be grown. Methods are known in the art for assessing the herbicide tolerance of various weed species. Weed management techniques are also known in the art, such as for example, crop rotation using a crop that is tolerant to a herbicide to which the local weed species are not tolerant. A number of entities monitor and publicly report the incidence and characteristics of herbicide-tolerant weeds, including the Herbicide Resistance Action Committee (HRAC), the Weed Science Society of America, and various state agencies (see, e.g., see, for example, herbicide tolerance scores for various broadleaf weeds from the 2004 Illinois Agricultural Pest Management Handbook), and one of skill in the art would be able to use this information to determine which crop and herbicide combinations should be used in a particular location.

These entities also publish advice and guidelines for preventing the development and/or appearance of and controlling the spread of herbicide tolerant weeds (see, e.g., Owen and Hartzler (2004), 2005 *Herbicide Manual for Agricultural Professionals*, Pub. WC 92 Revised (Iowa State University Extension, Iowa State University of Science and Technology, Ames, Iowa); *Weed Control for Corn, Soybeans, and Sorghum*, Chapter 2 of "2004 Illinois Agricultural Pest Management Handbook" (University of Illinois Extension, University of Illinois at Urbana-Champaign, Ill.); *Weed Control Guide for Field Crops*, MSU Extension Bulletin E434 (Michigan State University, East Lansing, Mich.)).

TABLE 2

| Abbreviated version of HRAC Herbicide Classification |
|---|
| I. ALS Inhibitors (WSSA Group 2) |
|   A. Sulfonylureas |
|     1. Azimsulfuron |
|     2. Chlorimuron-ethyl |
|     3. Metsulfuron-methyl |
|     4. Nicosulfuron |
|     5. Rimsulfuron |
|     6. Sulfometuron-methyl |
|     7. Thifensulfuron-methyl |
|     8. Tribenuron-methyl |
|     9. Amidosulfuron |
|     10. Bensulfuron-methyl |
|     11. Chlorsulfuron |
|     12. Cinosulfuron |
|     13. Cyclosulfamuron |
|     14. Ethametsulfuron-methyl |
|     15. Ethoxysulfuron |
|     16. Flazasulfuron |
|     17. Flupyrsulfuron-methyl |
|     18. Foramsulfuron |
|     19. Imazosulfuron |
|     20. Iodosulfuron-methyl |
|     21. Mesosulfuron-methyl |
|     22. Oxasulfuron |
|     23. Primisulfuron-methyl |
|     24. Prosulfuron |
|     25. Pyrazosulfuron-ethyl |
|     26. Sulfosulfuron |
|     27. Triasulfuron |
|     28. Trifloxysulfuron |
|     29. Triflusulfuron-methyl |
|     30. Tritosulfuron |
|     31. Halosulfuron-methyl |
|     32. Flucetosulfuron |
|   B. Sulfonylaminocarbonyltriazolinones |
|     1. Flucarbazone |
|     2. Procarbazone |
|   C. Triazolopyrimidines |
|     1. Cloransulam-methyl |
|     2. Flumetsulam |
|     3. Diclosulam |
|     4. Florasulam |
|     5. Metosulam |

TABLE 2-continued

Abbreviated version of HRAC Herbicide Classification

6. Penoxsulam
  7. Pyroxsulam
 D. Pyrimidinyloxy(thio)benzoates
  1. Bispyribac
  2. Pyriftalid
  3. Pyribenzoxim
  4. Pyrithiobac
  5. Pyriminobac-methyl
 E. Imidazolinones
  1. Imazapyr
  2. Imazethapyr
  3. Imazaquin
  4. Imazapic
  5. Imazamethabenz-methyl
  6. Imazamox
II. Other Herbicides-Active Ingredients/Additional Modes of Action
 A. Inhibitors of Acetyl CoA carboxylase (ACCase)
    (WSSA Group 1)
  1. Aryloxyphenoxypropionates ('FOPs')
    a. Quizalofop-P-ethyl
    b. Diclofop-methyl
    c. Clodinafop-propargyl
    d. Fenoxaprop-P-ethyl
    e. Fluazifop-P-butyl
    f. Propaquizafop
    g. Haloxyfop-P-methyl
    h. Cyhalofop-butyl
    i. Quizalofop-P-ethyl
  2. Cyclohexanediones ('DIMs')
    a. Alloxydim
    b. Butroxydim
    c. Clethodim
    d. Cycloxydim
    e. Sethoxydim
    f. Tepraloxydim
    g. Tralkoxydim
 B. Inhibitors of Photosystem II-HRAC Group C1/WSSA Group 5
  1. Triazines
    a. Ametryne
    b. Atrazine
    c. Cyanazine
    d. Desmetryne
    e. Dimethametryne
    f. Prometon
    g. Prometryne
    h. Propazine
    i. Simazine
    j. Simetryne
    k. Terbumeton
    l. Terbuthylazine
    m. Terbutryne
    n. Trietazine
  2. Triazinones
    a. Hexazinone
    b. Metribuzin
    c. Metamitron
  3. Triazolinone
    a. Amicarbazone
  4. Uracils
    a. Bromacil
    b. Lenacil
    c. Terbacil
  5. Pyridazinones
    a. Pyrazon
  6. Phenyl carbamates
    a. Desmedipham
    b. Phenmedipham
 C. Inhibitors of Photosystem II-HRAC Group C2/WSSA Group 7
  1. Ureas
    a. Fluometuron
    b. Linuron
    c. Chlorbromuron
    d. Chlorotoluron
    e. Chloroxuron
    f. Dimefuron
    g. Diuron
    h. Ethidimuron
    i. Fenuron TABLE 2-continued Abbreviated version of HRAC Herbicide Classification j. Isoproturon
    k. Isouron
    l. Methabenzthiazuron
    m. Metobromuron
    n. Metoxuron
    o. Monolinuron
    p. Neburon
    q. Siduron
    r. Tebuthiuron
  2. Amides
    a. Propanil
    b. Pentanochlor
 D. Inhibitors of Photosystem II-HRAC Group C3/WSSA Group 6
  1. Nitriles
    a. Bromofenoxim
    b. Bromoxynil
    c. Ioxynil
  2. Benzothiadiazinone (Bentazon)
    a. Bentazon
  3. Phenylpyridazines
    a. Pyridate
    b. Pyridafol
 E. Photosystem-I-electron diversion (Bipyridyliums)
    (WSSA Group 22)
  1. Diquat
  2. Paraquat
 F. Inhibitors of PPO (protoporphyrinogen oxidase)
    (WSSA Group 14)
  1. Diphenylethers
    a. Acifluorfen-Na
    b. Bifenox
    c. Chlomethoxyfen
    d. Fluoroglycofen-ethyl
    e. Fomesafen
    f. Halosafen
    g. Lactofen
    h. Oxyfluorfen
  2. Phenylpyrazoles
    a. Fluazolate
    b. Pyraflufen-ethyl
  3. N-phenylphthalimides
    a. Cinidon-ethyl
    b. Flumioxazin
    c. Flumiclorac-pentyl
  4. Thiadiazoles
    a. Fluthiacet-methyl
    b. Thidiazimin
  5. Oxadiazoles
    a. Oxadiazon
    b. Oxadiargyl
  6. Triazolinones
    a. Carfentrazone-ethyl
    b. Sulfentrazone
  7. Oxazolidinediones
    a. Pentoxazone
  8. Pyrimidindiones
    a. Benzfendizone
    b. Butafenicil
  9. Others
    a. Pyrazogyl
    b. Profluazol
 G. Bleaching: Inhibition of carotenoid biosynthesis at the
    phytoene desaturase step (PDS) (WSSA Group 12)
  1. Pyridazinones
    a. Norflurazon
  2. Pyridinecarboxamides
    a. Diflufenican
    b. Picolinafen
  3. Others
    a. Beflubutamid
    b. Fluridone
    c. Flurochloridone
    d. Flurtamone
 H. Bleaching: Inhibition of 4-hydroxyphenyl-pyruvate-dioxygenase
    (4-HPPD) (WSSA Group 28)
  1. Triketones
    a. Mesotrione
    b. Sulcotrione TABLE 2-continued Abbreviated version of HRAC Herbicide Classification 2. Isoxazoles
        a. Isoxachlortole
        b. Isoxaflutole
    3. Pyrazoles
        a. Benzofenap
        b. Pyrazoxyfen
        c. Pyrazolynate
    4. Others
        a. Benzobicyclon
I. Bleaching: Inhibition of carotenoid biosynthesis (unknown target) (WSSA Group 11 and 13)
    1. Triazoles (WSSA Group 11)
        a. Amitrole
    2. Isoxazolidinones (WSSA Group 13)
        a. Clomazone
    3. Ureas
        a. Fluometuron
    4. Diphenylether
        a. Aclonifen
J. Inhibition of EPSP Synthase
    1. Glycines (WSSA Group 9)
        a. Glyphosate
        b. Sulfosate
K. Inhibition of glutamine synthetase
    1. Phosphinic Acids
        a. Glufosinate-ammonium
        b. Bialaphos
L. Inhibition of DHP (dihydropteroate) synthase (WSSA Group 18)
    1. Carbamates
        a. Asulam
M. Microtubule Assembly Inhibition (WSSA Group 3)
    1. Dinitroanilines
        a. Benfluralin
        b. Butralin
        c. Dinitramine
        d. Ethalfluralin
        e. Oryzalin
        f. Pendimethalin
        g. Trifluralin
    2. Phosphoroamidates
        a. Amiprophos-methyl
        b. Butamiphos
    3. Pyridines
        a. Dithiopyr
        b. Thiazopyr
    4. Benzamides
        a. Pronamide
        b. Tebutam
    5. Benzenedicarboxylic acids
        a. Chlorthal-dimethyl
N. Inhibition of mitosis/microtubule organization WSSA Group 23)
    1. Carbamates
        a. Chlorpropham
        b. Propham
        c. Carbetamide
O. Inhibition of cell division (Inhibition of very long chain fatty acids as proposed mechanism; WSSA Group 15)
    1. Chloroacetamides
        a. Acetochlor
        b. Alachlor
        c. Butachlor
        d. Dimethachlor
        e. Dimethanamid
        f. Metazachlor
        g. Metolachlor
        h. Pethoxamid
        i. Pretilachlor
        j. Propachlor
        k. Propisochlor
        l. Thenylchlor
    2. Acetamides
        a. Diphenamid
        b. Napropamide
        c. Naproanilide
    3. Oxyacetamides
        a. Flufenacet
        b. Mefenacet
    4. Tetrazolinones
        a. Fentrazamide
    5. Others
        a. Anilofos
        b. Cafenstrole
        c. Indanofan
        d. Piperophos
P. Inhibition of cell wall (cellulose) synthesis
    1. Nitriles (WSSA Group 20)
        a. Dichlobenil
        b. Chlorthiamid
    2. Benzamides (isoxaben (WSSA Group 21))
        a. Isoxaben
    3. Triazolocarboxamides (flupoxam)
        a. Flupoxam
Q. Uncoupling (membrane disruption): (WSSA Group 24)
    1. Dinitrophenols
        a. DNOC
        b. Dinoseb
        c. Dinoterb
R. Inhibition of Lipid Synthesis by other than ACC inhibition
    1. Thiocarbamates (WSSA Group 8)
        a. Butylate
        b. Cycloate
        c. Dimepiperate
        d. EPTC
        e. Esprocarb
        f. Molinate
        g. Orbencarb
        h. Pebulate
        i. Prosulfocarb
        j. Benthiocarb
        k. Tiocarbazil
        l. Triallate
        m. Vernolate
    2. Phosphorodithioates
        a. Bensulide
    3. Benzofurans
        a. Benfuresate
        b. Ethofumesate
    4. Halogenated alkanoic acids (WSSA Group 26)
        a. TCA
        b. Dalapon
        c. Flupropanate
S. Synthetic auxins (IAA-like) (WSSA Group 4)
    1. Phenoxycarboxylic acids
        a. Clomeprop
        b. 2,4-D
        c. Mecoprop
    2. Benzoic acids
        a. Dicamba
        b. Chloramben
        c. TBA
    3. Pyridine carboxylic acids
        a. Clopyralid
        b. Fluroxypyr
        c. Picloram
        d. Tricyclopyr
    4. Quinoline carboxylic acids
        a. Quinclorac
        b. Quinmerac
    5. Others (benazolin-ethyl)
        a. Benazolin-ethyl
T. Inhibition of Auxin Transport
    1. Phthalamates; semicarbazones (WSSA Group 19)
        a. Naptalam
        b. Diflufenzopyr-Na
U. Other Mechanism of Action
    1. Arylaminopropionic acids
        a. Flamprop-M-methyl/-isopropyl
    2. Pyrazolium
        a. Difenzoquat
    3. Organoarsenicals
        a. DSMA
        b. MSMA
    4. Others
        a. Bromobutide
        b. Cinmethylin

TABLE 2-continued

Abbreviated version of HRAC Herbicide Classification c. Cumyluron
    d. Dazomet
    e. Daimuron-methyl
    f. Dimuron
    g. Etobenzanid
    h. Fosamine
    i. Metam
    j. Oxaziclomefone
    k. Oleic acid
    l. Pelargonic acid
    m. Pyributicarb In one embodiment, one ALS inhibitor or at least two ALS inhibitors are applied to the DP-305423-1 soybean crop or area of cultivation. The ALS inhibitor can be applied at any effective rate that selectively controls weeds and does not significantly damage the crop. In specific embodiments, at least one ALS inhibitor is applied at a level that would significantly damage an appropriate control plant. In other embodiments, at least one ALS inhibitor is applied above the recommended label use rate for the crop. In still other embodiments, a mixture of ALS inhibitors is applied at a lower rate than the recommended use rate and weeds continue to be selectively controlled. Herbicides that inhibit acetolactate synthase (also known as acetohydroxy acid synthase) and are therefore useful in the methods of the invention include sulfonylureas as listed in Table 2, including agriculturally suitable salts (e.g., sodium salts) thereof; sulfonylaminocarbonyltriazolinones as listed in Table 2, including agriculturally suitable salts (e.g., sodium salts) thereof; triazolopyrimidines as listed in Table 2, including agriculturally suitable salts (e.g., sodium salts) thereof; pyrimidinyloxy(thio)benzoates as listed in Table 2, including agriculturally suitable salts (e.g., sodium salts) thereof; and imidazolinones as listed in Table 2, including agriculturally suitable salts (e.g., sodium salts) thereof. In some embodiments, methods of the invention comprise the use of a sulfonylurea which is not chlorimuron-ethyl, chlorsulfuron, rimsulfuron, thifensulfuron-methyl, or tribenuron-methyl.

Thus, in some embodiments, a transgenic plant of the invention is used in a method of growing a DP-305423-1 soybean crop by the application of herbicides to which the plant is tolerant. In this manner, treatment with a combination of one of more herbicides which include, but are not limited to: acetochlor, acifluorfen and its sodium salt, aclonifen, acrolein (2-propenal), alachlor, alloxydim, ametryn, amicarbazone, amidosulfuron, aminopyralid, amitrole, ammonium sulfamate, anilofos, asulam, atrazine, azimsulfuron, beflubutamid, benazolin, benazolin-ethyl, bencarbazone, benfluralin, benfuresate, bensulfuron-methyl, bensulide, bentazone, benzobicyclon, benzofenap, bifenox, bilanafos, bispyribac and its sodium salt, bromacil, bromobutide, bromofenoxim, bromoxynil, bromoxynil octanoate, butachlor, butafenacil, butamifos, butralin, butroxydim, butylate, cafenstrole, carbetamide, carfentrazone-ethyl, catechin, chlomethoxyfen, chloramben, chlorbromuron, chlorflurenol-methyl, chloridazon, chlorimuron-ethyl, chlorotoluron, chlorpropham, chlorsulfuron, chlorthal-dimethyl, chlorthiamid, cinidon-ethyl, cinmethylin, cinosulfuron, clethodim, clodinafop-propargyl, clomazone, clomeprop, clopyralid, clopyralid-olamine, cloransulam-methyl, CUH-35 (2-methoxyethyl 2-[[[4-chloro-2-fluoro-5-[(1-methyl-2-propynyl)oxy]phenyl](3-fluorobenzoyl)amino]carbonyl]-1-cyclohexene-1-carboxylate), cumyluron, cyanazine, cycloate, cyclosulfamuron, cycloxydim, cyhalofop-butyl, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, diclosulam, difenzoquat metilsulfate, diflufenican, diflufenzopyr, dimefuron, dimepiperate, dimethachlor, dimethametryn, dimethenamid, dimethenamid-P, dimethipin, dimethylarsinic acid and its sodium salt, dinitramine, dinoterb, diphenamid, diquat dibromide, dithiopyr, diuron, DNOC, endothal, EPTC, esprocarb, ethalfluralin, ethametsulfuron-methyl, ethofumesate, ethoxyfen, ethoxysulfuron, etobenzanid, fenoxaprop-ethyl, fenoxaprop-P-ethyl, fentrazamide, fenuron, fenuron-TCA, flamprop-methyl, flamprop-M-isopropyl, flamprop-M-methyl, flazasulfuron, florasulam, fluazifop-butyl, fluazifop-P-butyl, flucarbazone, flucetosulfuron, fluchloralin, flufenacet, flufenpyr, flufenpyr-ethyl, flumetsulam, flumiclorac-pentyl, flumioxazin, fluometuron, fluoroglycofen-ethyl, flupyrsulfuron-methyl and its sodium salt, flurenol, flurenol-butyl, fluridone, fluorochloridone, fluoroxypyr, flurtamone, fluthiacet-methyl, fomesafen, foramsulfuron, fosamine-ammonium, glufosinate, glufosinate-ammonium, glyphosate and its salts such as ammonium, isopropylammonium, potassium, sodium (including sesquisodium) and trimesium (alternatively named sulfosate), halosulfuron-methyl, haloxyfop-etotyl, haloxyfop-methyl, hexazinone, HOK-201 (N-(2,4-difluorophenyl)-1,5-dihydro-N-(1-methylethyl)-5-oxo-1-[(tetrahydro-2H-pyran-2-yl)methyl]-4H-1,2,4-triazole-4-carboxamide), imazamethabenz-methyl, imazamox, imazapic, imazapyr, imazaquin, imazaquin-ammonium, imazethapyr, imazethapyr-ammonium, imazosulfuron, indanofan, iodosulfuron-methyl, ioxynil, ioxynil octanoate, ioxynil-sodium, isoproturon, isouron, isoxaben, isoxaflutole, isoxachlortole, lactofen, lenacil, linuron, maleic hydrazide, MCPA and its salts (e.g., MCPA-dimethylammonium, MCPA-potassium and MCPA-sodium, esters (e.g., MCPA-2-ethylhexyl, MCPA-butotyl) and thioesters (e.g., MCPA-thioethyl), MCPB and its salts (e.g., MCPB-sodium) and esters (e.g., MCPB-ethyl), mecoprop, mecoprop-P, mefenacet, mefluidide, mesosulfuron-methyl, mesotrione, metam-sodium, metamifop, metamitron, metazachlor, methabenzthiazuron, methylarsonic acid and its calcium, monoammonium, monosodium and disodium salts, methyldymron, metobenzuron, metobromuron, metolachlor, S-metholachlor, metosulam, metoxuron, metribuzin, metsulfuron-methyl, molinate, monolinuron, naproanilide, napropamide, naptalam, neburon, nicosulfuron, norflurazon, orbencarb, oryzalin, oxadiargyl, oxadiazon, oxasulfuron, oxaziclomefone, oxyfluorfen, paraquat dichloride, pebulate, pelargonic acid, pendimethalin, penoxsulam, pentanochlor, pentoxazone, perfluidone, pethoxyamid, phenmedipham, picloram, picloram-potassium, picolinafen, pinoxaden, piperofos, pretilachlor, primisulfuron-methyl, prodiamine, profoxydim, prometon, prometryn, propachlor, propanil, propaquizafop, propazine, propham, propisochlor, propoxycarbazone, propyzamide, prosulfocarb, prosulfuron, pyraclonil, pyraflufen-ethyl, pyrasulfotole, pyrazogyl, pyrazolynate, pyrazoxyfen, pyrazosulfuron-ethyl, pyribenzoxim, pyributicarb, pyridate, pyriftalid, pyriminobac-methyl, pyrimisulfan, pyrithiobac, pyrithiobac-sodium, pyroxsulam, quinclorac, quinmerac, quinoclamine, quizalofop-ethyl, quizalofop-P-ethyl, quizalofop-P-tefuryl, rimsulfuron, sethoxydim, siduron, simazine, simetryn, sulcotrione, sulfentrazone, sulfometuron-methyl, sulfosulfuron, 2,3,6-TBA, TCA, TCA-sodium, tebutam, tebuthiuron, tefuryltrione, tembotrione, tepraloxydim, terbacil, terbumeton, terbuthylazine, terbutryn, thenylchlor, thiazopyr, thiencarbazone, thifensulfuron-methyl, thiobencarb, tiocarbazil, topramezone, tralkoxydim, tri-allate, triasulfuron, triaziflam, tribenuron-methyl, triclopyr, triclopyr-butotyl, triclopyr-triethylammonium, tridiphane, trietazine, trifloxysulfuron, trifluralin, triflusulfuron-methyl, tritosulfuron and vernolate is disclosed.

Other suitable herbicides and agricultural chemicals are known in the art, such as, for example, those described in WO 2005/041654. Other herbicides also include bioherbicides such as *Alternaria destruens* Simmons, *Colletotrichum gloeosporiodes* (Penz.) Penz. & Sacc., *Drechsiera monoceras* (MTB-951), *Myrothecium verrucaria* (Albertini & Schweinitz) Ditmar: Fries, *Phytophthora palmivora* (Butyl.) Butyl. and *Puccinia thlaspeos* Schub. Combinations of various herbicides can result in a greater-than-additive (i.e., synergistic) effect on weeds and/or a less-than-additive effect (i.e. safening) on crops or other desirable plants. Herbicidally effective amounts of any particular herbicide can be easily determined by one skilled in the art through simple experimentation.

Herbicides may be classified into groups and/or subgroups as described herein above with reference to their mode of action, or they may be classified into groups and/or subgroups in accordance with their chemical structure.

Sulfonamide herbicides have as an essential molecular structure feature a sulfonamide moiety (—S(O)$_2$NH—). As referred to herein, sulfonamide herbicides particularly comprise sulfonylurea herbicides, sulfonylaminocarbonyltriazolinone herbicides and triazolopyrimidine herbicides. In sulfonylurea herbicides the sulfonamide moiety is a component in a sulfonylurea bridge (—S(O)$_2$NHC(O)NH(R)—). In sulfonylurea herbicides the sulfonyl end of the sulfonylurea bridge is connected either directly or by way of an oxygen atom or an optionally substituted amino or methylene group to a typically substituted cyclic or acyclic group. At the opposite end of the sulfonylurea bridge, the amino group, which may have a substituent such as methyl (R being CH$_3$) instead of hydrogen, is connected to a heterocyclic group, typically a symmetric pyrimidine or triazine ring, having one or two substituents such as methyl, ethyl, trifluoromethyl, methoxy, ethoxy, methylamino, dimethylamino, ethylamino and the halogens. In sulfonylaminocarbonyltriazolinone herbicides, the sulfonamide moiety is a component of a sulfonylaminocarbonyl bridge (—S(O)$_2$NHC(O)—). In sulfonylaminocarbonyltriazolinone herbicides the sulfonyl end of the sulfonylaminocarbonyl bridge is typically connected to substituted phenyl ring. At the opposite end of the sulfonylaminocarbonyl bridge, the carbonyl is connected to the 1-position of a triazolinone ring, which is typically substituted with groups such as alkyl and alkoxy. In triazolopyrimidine herbicides the sulfonyl end of the sulfonamide moiety is connected to the 2-position of a substituted [1,2,4]triazolopyrimidine ring system and the amino end of the sulfonamide moiety is connected to a substituted aryl, typically phenyl, group or alternatively the amino end of the sulfonamide moiety is connected to the 2-position of a substituted [1,2,4]triazolopyrimidine ring system and the sulfonyl end of the sulfonamide moiety is connected to a substituted aryl, typically pyridinyl, group.

Representative of the sulfonylurea herbicides useful in the present invention are those of the formula:

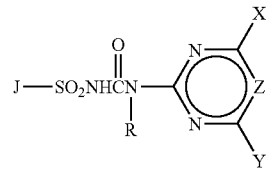

wherein:

J is selected from the group consisting of

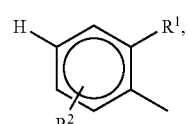
J-1

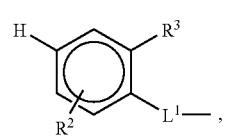
J-2

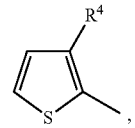
J-3

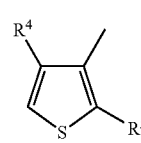
J-4

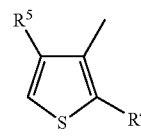
J-5

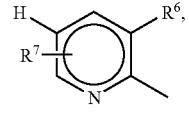
J-6

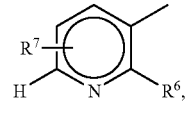
J-7

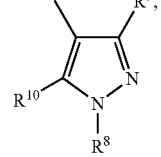
J-8

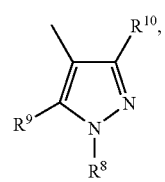
J-9

-continued

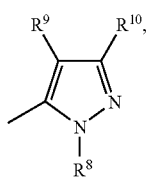
J-10

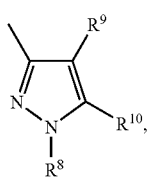
J-11

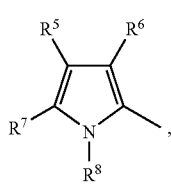
J-12

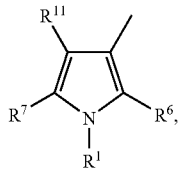
J-13

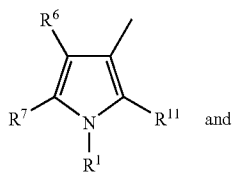
J-14

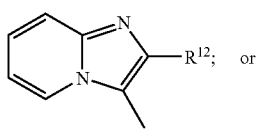 or
J-15

J is $R^{13}SO_2N(CH_3)-$;
R is H or $CH_3$;
$R^1$ is F, Cl, Br, $NO_2$, $C_1$-$C_4$ alkyl, $C_1$-$C_4$ haloalkyl, $C_3$-$C_4$ cycloalkyl, $C_2$-$C_4$ haloalkenyl, $C_1$-$C_4$ alkoxy, $C_1$-$C_4$ haloalkoxy, $C_2$-$C_4$ alkoxyalkoxy, $CO_2R^{14}$, $C(O)NR^{15}R^{16}$, $SO_2NR^{17}R^{18}$, $S(O)_nR^{19}$, $C(O)R^{20}$, $CH_2CN$ or L;
$R^2$ is H, F, Cl, Br, I, CN, $CH_3$, $OCH_3$, $SCH_3$, $CF_3$ or $OCF_2H$;
$R^3$ is Cl, $NO_2$, $CO_2CH_3$, $CO_2CH_2CH_3$, $C(O)CH_3$, $C(O)CH_2CH_3$, $C(O)$-cyclopropyl, $SO_2N(CH_3)_2$, $SO_2CH_3$, $SO_2CH_2CH_3$, $OCH_3$ or $OCH_2CH_3$;
$R^4$ is $C_1$-$C_3$ alkyl, $C_1$-$C_2$ haloalkyl, $C_1$-$C_2$ alkoxy, $C_2$-$C_4$ haloalkenyl, F, Cl, Br, $NO_2$, $CO_2R^{14}$, $C(O)NR^{15}R^{16}$, $SO_2NR^{17}R^{18}$, $S(O)_nR^{19}$, $C(O)R^{20}$ or L;
$R^5$ is H, F, Cl, Br or $CH_3$;
$R^6$ is $C_1$-$C_3$ alkyl optionally substituted with 0-3 F, 0-1 Cl and 0-1 $C_3$-$C_4$ alkoxyacetyloxy, or $R^6$ is $C_1$-$C_2$ alkoxy, $C_2$-$C_4$ haloalkenyl, F, Cl, Br, $CO_2R^{14}$, $C(O)NR^{15}R^{16}$, $SO_2NR^{17}R^{18}$, $S(O)_nR^{19}$, $C(O)R^{20}$ or L;
$R^7$ is H, F, Cl, $CH_3$ or $CF_3$;
$R^8$ is H, $C_1$-$C_3$ alkyl or pyridinyl;
$R^9$ is $C_1$-$C_3$ alkyl, $C_1$-$C_2$ alkoxy, F, Cl, Br, $NO_2$, $CO_2R^{14}$, $SO_2NR^{17}R^{18}$, $S(O)_nR^{19}$, $OCF_2H$, $C(O)R^{20}$, $C_2$-$C_4$ haloalkenyl or L;
$R^{10}$ is H, Cl, F, Br, $C_1$-$C_3$ alkyl or $C_1$-$C_2$ alkoxy;
$R^{11}$ is H, $C_1$-$C_3$ alkyl, $C_1$-$C_2$ alkoxy, $C_2$-$C_4$ haloalkenyl, F, Cl, Br, $CO_2R^{14}$, $C(O)NR^{15}R^{16}$, $SO_2NR^{17}R^{18}$, $S(O)_nR^{19}$, $C(O)R^{20}$ or L;
$R^{12}$ is halogen, $C_1$-$C_4$ alkyl or $C_1$-$C_3$ alkylsulfonyl;
$R^{13}$ is $C_1$-$C_4$ alkyl;
$R^{14}$ is allyl, propargyl or oxetan-3-yl; or $R^{14}$ is $C_1$-$C_3$ alkyl optionally substituted by at least one member independently selected from halogen, $C_1$-$C_2$ alkoxy and CN;
$R^{15}$ is H, $C_1$-$C_3$ alkyl or $C_1$-$C_2$ alkoxy;
$R^{16}$ is $C_1$-$C_2$ alkyl;
$R^{17}$ is H, $C_1$-$C_3$ alkyl, $C_1$-$C_2$ alkoxy, allyl or cyclopropyl;
$R^{18}$ is H or $C_1$-$C_3$ alkyl;
$R^{19}$ is $C_1$-$C_3$ alkyl, $C_1$-$C_3$ haloalkyl, allyl or propargyl;
$R^{20}$ is $C_1$-$C_4$ alkyl, $C_1$-$C_4$ haloalkyl or $C_3$-$C_5$ cycloalkyl optionally substituted by halogen;
n is 0, 1 or 2;
L is

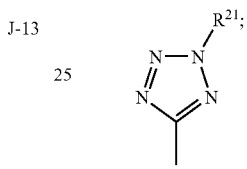

$L^1$ is $CH_2$, NH or O;
$R^{21}$ is H or $C_1$-$C_3$ alkyl;
X is H, $C_1$-$C_4$ alkyl, $C_1$-$C_4$ alkoxy, $C_1$-$C_4$ haloalkoxy, $C_1$-$C_4$ haloalkyl, $C_1$-$C_4$ haloalkylthio, $C_1$-$C_4$ alkylthio, halogen, $C_2$-$C_5$ alkoxyalkyl, $C_2$-$C_5$ alkoxyalkoxy, amino, $C_1$-$C_3$ alkylamino or di($C_1$-$C_3$ alkyl)amino;
Y is H, $C_1$-$C_4$ alkyl, $C_1$-$C_4$ alkoxy, $C_1$-$C_4$ haloalkoxy, $C_1$-$C_4$ alkylthio, $C_1$-$C_4$ haloalkylthio, $C_2$-$C_5$ alkoxyalkyl, $C_2$-$C_5$ alkoxyalkoxy, amino, $C_1$-$C_3$ alkylamino, di($C_1$-$C_3$ alkyl)amino, $C_3$-$C_4$ alkenyloxy, $C_3$-$C_4$ alkynyloxy, $C_2$-$C_5$ alkylthioalkyl, $C_2$-$C_5$ alkylsulfinylalkyl, $C_2$-$C_5$ alkylsulfonylalkyl, $C_1$-$C_4$ haloalkyl, $C_2$-$C_4$ alkynyl, $C_3$-$C_5$ cycloalkyl, azido or cyano; and
Z is CH or N;
provided that (i) when one or both of X and Y is $C_1$ haloalkoxy, then Z is CH; and (ii) when X is halogen, then Z is CH and Y is $OCH_3$, $OCH_2CH_3$, $N(OCH_3)CH_3$, $NHCH_3$, $N(CH_3)_2$ or $OCF_2H$. Of note is the present single liquid herbicide composition comprising one or more sulfonylureas of Formula I wherein when $R^6$ is alkyl, said alkyl is unsubstituted.

Representative of the triazolopyrimidine herbicides contemplated for use in this invention are those of the formula:

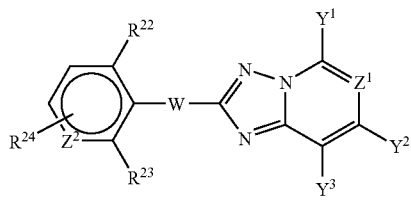

wherein:
$R^{22}$ and $R^{23}$ each independently halogen, nitro, $C_1$-$C_4$ alkyl, $C_1$-$C_4$ haloalkyl, $C_1$-$C_4$ alkoxy, $C_1$-$C_4$ haloalkoxy or $C_2$-$C_3$ alkoxycarbonyl;

$R^{24}$ is H, halogen, $C_1$-$C_2$ alkyl or $C_1$-$C_2$ alkoxy;

W is —NHS(O)$_2$— or —S(O)$_2$NH—;

$Y^1$ is H, $C_1$-$C_2$ alkyl or $C_1$-$C_2$ alkoxy;

$Y^2$ is H, F, Cl, Br, $C_1$-$C_2$ alkyl or $C_1$-$C_2$ alkoxy;

$Y^3$ is H, F or methoxy;

$Z^1$ is CH or N; and $Z^2$ is CH or N;

provided that at least one of $Y^1$ and $Y^2$ is other than H.

In the above Markush description of representative triazolopyrimidine herbicides, when W is —NHS(O)$_2$— the sulfonyl end of the sulfonamide moiety is connected to the [1,2,4]triazolopyrimidine ring system, and when W is —S(O)$_2$NH— the amino end of the sulfonamide moiety is connected to the [1,2,4]triazolopyrimidine ring system.

In the above recitations, the term "alkyl", used either alone or in compound words such as "alkylthio" or "haloalkyl" includes straight-chain or branched alkyl, such as, methyl, ethyl, n-propyl, i-propyl, or the different butyl isomers. "Cycloalkyl" includes, for example, cyclopropyl, cyclobutyl and cyclopentyl. "Alkenyl" includes straight-chain or branched alkenes such as ethenyl, 1-propenyl, 2-propenyl, and the different butenyl isomers. "Alkenyl" also includes polyenes such as 1,2-propadienyl and 2,4-butadienyl. "Alkynyl" includes straight-chain or branched alkynes such as ethynyl, 1-propynyl, 2-propynyl and the different butynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkoxyalkoxy" denotes alkoxy substitution on alkoxy. "Alkenyloxy" includes straight-chain or branched alkenyloxy moieties. Examples of "alkenyloxy" include $H_2C=CHCH_2O$, $(CH_3)CH=CHCH_2O$ and $CH_2=CHCH_2CH_2O$. "Alkynyloxy" includes straight-chain or branched alkynyloxy moieties. Examples of "alkynyloxy" include $HC\equiv CCH_2O$ and $CH_3C\equiv CCH_2O$. "Alkylthio" includes branched or straight-chain alkylthio moieties such as methylthio, ethylthio, and the different propylthio isomers. "Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2CH_2SCH_2$ and $CH_3CH_2SCH_2CH_2$; "alkylsulfinylalkyl" and "alkylsulfonylalkyl" include the corresponding sulfoxides and sulfones, respectively. Other substituents such as "alkylamino", "dialkylamino" are defined analogously.

The total number of carbon atoms in a substituent group is indicated by the "$C_i$-$C_j$" prefix where i and j are numbers from 1 to 5. For example, $C_1$-$C_4$ alkyl designates methyl through butyl, including the various isomers. As further examples, $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. The terms "haloalkoxy", "haloalkylthio", and the like, are defined analogously to the term "haloalkyl". Examples of "haloalkoxy" include $CF_3O$, $CCl_3CH_2O$, $HCF_2CH_2CH_2O$ and $CF_3CH_2O$. Examples of "haloalkylthio" include $CCl_3S$, $CF_3S$, $CCl_3CH_2S$ and $ClCH_2CH_2CH_2S$.

The following sulfonylurea herbicides illustrate the sulfonylureas useful for this invention: amidosulfuron (N-[[[[(4,6-dimethoxy-2-pyrimdinyl)amino]carbonyl]amino]-sulfonyl]-N-methylmethanesulfonamide), azimsulfuron (N-[[(4,6-dimethoxy-2-pyrimidinyl)amino]carbonyl]-1-methyl-4-(2-methyl-2H-tetrazol-5-yl)-1H-pyrazole-5-sulfonamide), bensulfuron-methyl (methyl 2-[[[[[(4,6-dimethoxy-2-pyrimidinyl)amino]carbonyl]amino]sulfonyl]methyl]benzoate), chlorimuron-ethyl (ethyl 2-[[[[(4-chloro-6-methoxy-2-pyrimidinyl)amino]carbonyl]amino]sulfonyl]-benzoate), chlorsulfuron (2-chloro-N-[[(4-methoxy-6-methyl-1,3,5-triazin-2-yl)amino]-carbonyl]benzenesulfonamide), cinosulfuron (N-[[(4,6-dimethoxy-1,3,5-triazin-2-yl)amino]carbonyl]-2-(2-methoxyethoxy)benzenesulfonamide), cyclosulfamuron (N-[[[2-(cyclopropylcarbonyl)phenyl]amino]sulfonyl]-$N^1$-(4,6-dimethoxypyrimidin-2-yl)urea), ethametsulfuron-methyl (methyl 2-[[[[[4-ethoxy-6-(methylamino)-1,3,5-triazin-2-yl]amino]carbonyl]amino]sulfonyl]benzoate), ethoxysulfuron (2-ethoxyphenyl [[(4,6-dimethoxy-2-pyrimidinyl)amino]carbonyl]sulfamate, flazasulfuron (N-[[(4,6-dimethoxy-2-pyrimidinyl)amino]carbonyl]-3-(trifluoromethyl)-2-pyridinesulfonamide), flucetosulfuron (1-[3-[[[[(4,6-dimethoxy-2-pyrimidinyl)-amino]carbonyl]amino] sulfonyl]-2-pyridinyl]-2-fluoropropyl methoxyacetate), flupyrsulfuron-methyl (methyl 2-[[[[(4,6-dimethoxy-2-pyrimidinyl)amino]carbonyl]-amino]sulfonyl]-6-(trifluoromethyl)-3-pyridinecarboxylate), foramsulfuron (2-[[[[(4,6-dimethoxy-2-pyrimidinyl)amino]carbonyl]amino]sulfonyl]-4-(formylamino)-N,N-dimethylbenzamide), halosulfuron-methyl (methyl 3-chloro-5-[[[[(4,6-dimethoxy-2-pyrimidinyl)amino]carbonyl]amino]sulfonyl]-1-methyl-1H-pyrazole-4-carboxylate), imazosulfuron (2-chloro-N-[[(4,6-dimethoxy-2-pyrimidinyl)amino]carbonyl]-imidazo[1,2-a]pyridine-3-sulfonamide), iodosulfuron-methyl (methyl 4-iodo-2-[[[[(4-methoxy-6-methyl-1,3,5-triazin-2-yl)amino]carbonyl]amino]sulfonyl]benzoate), mesosulfuron-methyl (methyl 2-[[[[(4,6-dimethoxy-2-pyrimidinyl)amino]carbonyl]-amino]sulfonyl]-4-[[(methylsulfonyl)amino]methyl]benzoate), metsulfuron-methyl (methyl 2-[[[[(4-methoxy-6-methyl-1,3,5-triazin-2-yl)amino]carbonyl]amino]sulfonyl]-benzoate), nicosulfuron (2-[[[[(4,6-dimethoxy-2-pyrimidinyl)amino]carbonyl]amino]-sulfonyl]-N,N-dimethyl-3-pyridinecarboxamide), oxasulfuron (3-oxetanyl 2-[[[[(4,6-dimethyl-2-pyrimidinyl)amino]carbonyl]amino]sulfonyl]benzoate), primisulfuron-methyl (methyl 2-[[[[[4,6-bis(trifluoromethoxy)-2-pyrimidinyl]amino]carbonyl]amino]sulfonyl]benzoate), prosulfuron (N-[[(4-methoxy-6-methyl-1,3,5-triazin-2-yl)amino]carbonyl]-2-(3,3,3-trifluoro-propyl)benzenesulfonamide), pyrazosulfuron-ethyl (ethyl 5-[[[[(4,6-dimethoxy-2-pyrimidinyl)amino]carbonyl]amino]sulfonyl]-1-methyl-1H-pyrazole-4-carboxylate), rimsulfuron (N-[[(4,6-dimethoxy-2-pyrimidinyl)amino]carbonyl]-3-(ethylsulfonyl)-2-pyridinesulfonamide), sulfometuron-methyl (methyl 2-[[[[(4,6-dimethyl-2-pyrimidinyl)amino]carbonyl]amino] sulfonyl]benzoate), sulfosulfuron (N-[[(4,6-dimethoxy-2-pyrimidinyl)amino]carbonyl]-2-(ethylsulfonyl)imidazo[1,2-a]pyridine-3-sulfonamide), thifensulfuron-methyl (methyl 3-[[[[(4-methoxy-6-methyl-1,3,5-triazin-2-yl)amino]carbonyl]amino]sulfonyl]-2-thiophenecarboxylate), triasulfuron (2-(2-chloroethoxy)-N-[[(4-methoxy-6-methyl-1,3,5-triazin-2-yl)amino]carbonyl]benzenesulfonamide), tribenuron-methyl (methyl 2-[[[[N-(4-methoxy-6-methyl-1,3,5-triazin-2-yl)-N-methylamino]carbonyl]amino]-sulfonyl]

benzoate), trifloxysulfuron (N-[[(4,6-dimethoxy-2-pyrimidinyl)amino]-carbonyl]-3-(2,2,2-trifluoroethoxy)-2-pyridinesulfonamide), triflusulfuron-methyl (methyl 2-[[[[(4-dimethylamino)-6-(2,2,2-trifluoroethoxy)-1,3,5-triazin-2-yl]amino]-carbonyl]amino]sulfonyl]-3-methylbenzoate) and tritosulfuron (N-[[[4-methoxy-6-(trifluoromethyl)-1,3,5-triazin-2-yl]amino]carbonyl]-2-(trifluoromethyl)benzene-sulfonamide).

The following triazolopyrimidine herbicides illustrate the triazolopyrimidines useful for this invention: cloransulam-methyl (methyl 3-chloro-2-[[(5-ethoxy-7-fluoro-[1,2,4]triazolo[1,5-c]pyrimidin-2-yl)sulfonyl]amino]benzoate, diclosulam (N-(2,6-dichlorophenyl)-5-ethoxy-7-fluoro[1,2,4]triazolo[1,5-c]pyrimidine-2-sulfonamide, florasulam (N-(2,6-difluorophenyl)-8-fluoro-5-methoxy[1,2,4]triazolo[1,5-c]pyrimidine-2-sulfonamide), flumetsulam (N-(2,6-difluorophenyl)-5-methyl[1,2,4]triazolo[1,5-a]pyrimidine-2-sulfonamide), metosulam (N-(2,6-dichloro-3-methylphenyl)-5,7-dimethoxy[1,2,4]triazolo[1,5-a]pyrimidine-2-sulfonamide), penoxsulam (2-(2,2-difluoroethoxy)-N-(5,8-dimethoxy[1,2,4]triazolo[1,5-c]pyrimidin-2-yl)-6-(trifluoromethyl)benzenesulfonamide) and pyroxsulam (N-(5,7-dimethoxy[1,2,4]triazolo[1,5-a]pyrimidin-2-yl)-2-methoxy-4-(trifluoromethyl)-3-pyridinesulfonamide).

The following sulfonylaminocarbonyltriazolinone herbicides illustrate the sulfonylaminocarbonyltriazolinones useful for this invention: flucarbazone (4,5-dihydro-3-methoxy-4-methyl-5-oxo-N-[[2-(trifluoromethoxy)phenyl]sulfonyl]-H-1,2,4-triazole-1-carboxamide) and procarbazone (methyl 2-[[[(4,5-dihydro-4-methyl-5-oxo-3-propoxy-1H-1,2,4-triazol-1-yl)carbonyl]amino]sulfonyl]benzoate).

Additional herbicides include phenmedipham, triazolinones, and the herbicides disclosed in WO2006/012981, herein incorporated by reference in its entirety.

The methods further comprise applying to the crop and the weeds in a field a sufficient amount of at least one herbicide to which the crop seeds or plants is tolerant, such as, for example, glyphosate, a hydroxyphenylpyruvatedioxygenase inhibitor (e.g., mesotrione or sulcotrione), a phytoene desaturase inhibitor (e.g., diflufenican), a pigment synthesis inhibitor, sulfonamide, imidazolinone, bialaphos, phosphinothricin, azafenidin, butafenacil, sulfosate, glufosinate, triazolopyrimidine, pyrimidinyloxy(thio)benzoate, or sulonylaminocarbonyltriazolinone, an acetyl Co-A carboxylase inhibitor such as quizalofop-P-ethyl, a synthetic auxin such as quinclorac, or a protox inhibitor to control the weeds without significantly damaging the crop plants.

Generally, the effective amount of herbicide applied to the field is sufficient to selectively control the weeds without significantly affecting the crop. "Weed" as used herein refers to a plant which is not desirable in a particular area. Conversely, a "crop plant" as used herein refers to a plant which is desired in a particular area, such as, for example, a soybean plant. Thus, in some embodiments, a weed is a non-crop plant or a non-crop species, while in some embodiments, a weed is a crop species which is sought to be eliminated from a particular area, such as, for example, an inferior and/or non-transgenic soybean plant in a field planted with soybean event DP-305423-1, or a maize plant in a field planted with DP-305423-1. Weeds can be either classified into two major groups: monocots and dicots.

Many plant species can be controlled (i.e., killed or damaged) by the herbicides described herein. Accordingly, the methods of the invention are useful in controlling these plant species where they are undesirable (i.e., where they are weeds). These plant species include crop plants as well as species commonly considered weeds, including but not limited to species such as: blackgrass (*Alopecurus myosuroides*), giant foxtail (*Setaria faberi*), large crabgrass (*Digitaria sanguinalis*), Surinam grass (*Brachiaria decumbens*), wild oat (*Avena fatua*), common cocklebur (*Xanthium pensylvanicum*), common lambsquarters (*Chenopodium album*), morning glory (*Ipomoea coccinea*), pigweed (*Amaranthus* spp.), velvetleaf (*Abutilion theophrasti*), common barnyardgrass (*Echinochloa crus-galli*), bermudagrass (*Cynodon dactylon*), downy brome (*Bromus tectorum*), goosegrass (*Eleusine indica*), green foxtail (*Setaria viridis*), Italian ryegrass (*Lolium multiflorum*), Johnsongrass (*Sorghum halepense*), lesser canarygrass (*Phalaris minor*), windgrass (*Apera spica-venti*), wooly cupgrass (*Erichloa villosa*), yellow nutsedge (*Cyperus esculentus*), common chickweed (*Stellaria media*), common ragweed (*Ambrosia artemisiifolia*), *Kochia scoparia*, horseweed (*Conyza canadensis*), rigid ryegrass (*Lolium rigidum*), goosegrass (*Eleucine indica*), hairy fleabane (*Conyza bonariensis*), buckhorn plantain (*Plantago lanceolata*), tropical spiderwort (*Commelina benghalensis*), field bindweed (*Convolvulus arvensis*), purple nutsedge (*Cyperus rotundus*), redvine (*Brunnichia ovata*), hemp sesbania (*Sesbania exaltata*), sicklepod (*Senna obtusifolia*), Texas blueweed (*Helianthus ciliaris*), and Devil's claws (*Proboscidea louisianica*). In other embodiments, the weed comprises a herbicide-resistant ryegrass, for example, a glyphosate resistant ryegrass, a paraquat resistant ryegrass, a ACCase-inhibitor resistant ryegrass, and a non-selective herbicide resistant ryegrass. In some embodiments, the undesired plants are proximate the crop plants.

As used herein, by "selectively controlled" it is intended that the majority of weeds in an area of cultivation are significantly damaged or killed, while if crop plants are also present in the field, the majority of the crop plants are not significantly damaged. Thus, a method is considered to selectively control weeds when at least 55%, 60%, 65%, 70%, 75%, 80%, 85%, 90%, 95%, or more of the weeds are significantly damaged or killed, while if crop plants are also present in the field, less than 45%, 40%, 35%, 30%, 25%, 20%, 15%, 10%, 5%, or 1% of the crop plants are significantly damaged or killed.

In some embodiments, a soybean DP-305423-1 plant of the invention is not significantly damaged by treatment with a particular herbicide applied to that plant at a dose equivalent to a rate of at least 0.5, 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 110, 120, 150, 170, 200, 300, 400, 500, 600, 700, 800, 800, 1000, 2000, 3000, 4000, 5000 or more grams or ounces (1 ounce=29.57 ml) of active ingredient or commercial product or herbicide formulation per acre or per hectare, whereas an appropriate control plant is significantly damaged by the same treatment.

In specific embodiments, an effective amount of an ALS inhibitor herbicide comprises at least about 0.1, 1, 5, 10, 25, 50, 75, 100, 150, 200, 250, 300, 350, 400, 450, 500, 600, 700, 750, 800, 850, 900, 950, 1000, 2000, 3000, 4000, 5000, or more grams or ounces (1 ounce=29.57 ml) of active ingredient per hectare. In other embodiments, an effective amount of an ALS inhibitor comprises at least about 0.1-50, about 25-75, about 50-100, about 100-110, about 110-120, about 120-130, about 130-140, about 140-150, about 150-200, about 200-500, about 500-600, about 600-800, about 800-1000, or greater grams or ounces (1 ounce=29.57 ml) of active ingredient per hectare. Any ALS inhibitor, for example, those listed in Table 2 can be applied at these levels.

In other embodiments, an effective amount of a sulfonylurea comprises at least 0.1, 1, 5, 10, 25, 50, 75, 100, 150, 200, 250, 300, 350, 400, 450, 500, 600, 700, 800, 900, 1000, 5000 or more grams or ounces (1 ounce=29.57 ml) of active ingredient per hectare. In other embodiments, an effective amount of a sulfonylurea comprises at least about 0.1-50, about 25-75, about 50-100, about 100-110, about 110-120, about 120-130, about 130-140, about 140-150, about 150-160, about 160-170, about 170-180, about 190-200, about 200-250, about 250-300, about 300-350, about 350-400, about 400-450, about 450-500, about 500-550, about 550-600, about 600-650, about 650-700, about 700-800, about 800-900, about 900-1000, about 1000-2000, or more grams or ounces (1 ounce=29.57 ml) of active ingredient per hectare. Representative sulfonylureas that can be applied at this level are set forth in Table 2.

In other embodiments, an effective amount of a sulfonylaminocarbonyltriazol inones, triazolopyrimidines, pyrimidinyloxy(thio)benzoates, and imidazolinones can comprise at least about 0.1, 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1500, 1550, 1600, 1650, 1700, 1800, 1850, 1900, 1950, 2000, 2500, 3500, 4000, 4500, 5000 or greater grams or ounces (1 ounce=29.57 ml) active ingredient per hectare. In other embodiments, an effective amount of a sulfonyluminocarbonyltriazolines, triazolopyrimidines, pyrimidinyloxy(thio) benzoates, or imidazolinones comprises at least about 0.1-50, about 25-75, about 50-100, about 100-110, about 110-120, about 120-130, about 130-140, about 140-150, about 150-160, about 160-170, about 170-180, about 190-200, about 200-250, about 250-300, about 300-350, about 350-400, about 400-450, about 450-500, about 500-550, about 550-600, about 600-650, about 650-700, about 700-800, about 800-900, about 900-1000, about 1000-2000, or more grams or ounces (1 ounce=29.57 ml) active ingredient per hectare.

Additional ranges of the effective amounts of herbicides can be found, for example, in various publications from University Extension services. See, for example, Bernards et al. (2006) *Guide for Weed Management in Nebraska* (www.ianrpubs.url.edu/sendlt/ec130); Regher et al. (2005) *Chemical Weed Control for Fields Crops, Pastures, Rangeland, and Noncropland*, Kansas State University Agricultural Extension Station and Corporate Extension Service; Zollinger et al. (2006) *North Dakota Weed Control Guide*, North Dakota Extension Service, and the Iowa State University Extension at www.weeds.iastate.edu, each of which is herein incorporated by reference.

Herbicides known to inhibit ALS vary in their active ingredient as well as their chemical formulations. One of skill in the art is familiar with the determination of the amount of active ingredient and/or acid equivalent present in a particular volume and/or weight of herbicide preparation.

Rates at which the ALS inhibitor herbicide is applied to the crop, crop part, seed or area of cultivation can be any of the rates disclosed herein. In specific embodiments, the rate for the ALS inhibitor herbicide is about 0.1 to about 5000 g ai/hectare, about 0.5 to about 300 g ai/hectare, or about 1 to about 150 g ai/hectare.

Generally, a particular herbicide is applied to a particular field (and any plants growing in it) no more than 1, 2, 3, 4, 5, 6, 7, or 8 times a year, or no more than 1, 2, 3, 4, or 5 times per growing season.

By "treated with a combination of" or "applying a combination of" herbicides to a crop, area of cultivation or field" it is intended that a particular field, crop or weed is treated with each of the herbicides and/or chemicals indicated to be part of the combination so that a desired effect is achieved, i.e., so that weeds are selectively controlled while the crop is not significantly damaged. In some embodiments, weeds which are susceptible to each of the herbicides exhibit damage from treatment with each of the herbicides which is additive or synergistic. The application of each herbicide and/or chemical may be simultaneous or the applications may be at different times, so long as the desired effect is achieved. Furthermore, the application can occur prior to the planting of the crop.

The proportions of herbicides used in the methods of the invention with other herbicidal active ingredients in herbicidal compositions are generally in the ratio of 5000:1 to 1:5000, 1000:1 to 1:1000, 100:1 to 1:100, 10:1 to 1:10 or 5:1 to 1:5 by weight. The optimum ratios can be easily determined by those skilled in the art based on the weed control spectrum desired. Moreover, any combinations of ranges of the various herbicides disclosed in Table 2 can also be applied in the methods of the invention.

Thus, in some embodiments, the invention provides improved methods for selectively controlling weeds in a field wherein the total herbicide application may be less than 90%, 85%, 80%, 75%, 70%, 65%, 60%, 55%, 50%, 45%, 40%, 35%, 30%, 25%, 20%, 15%, 10%, 5%, or 1% of that used in other methods. Similarly, in some embodiments, the amount of a particular herbicide used for selectively controlling weeds in a field may be less than 90%, 85%, 80%, 75%, 70%, 65%, 60%, 55%, 50%, 45%, 40%, 35%, 30%, 25%, 20%, 15%, 10%, 5%, or 1% of the amount of that particular herbicide that would be used in other methods, i.e., methods not utilizing a plant of the invention.

As used herein, the terms "synergy," "synergistic," "synergistically" and derivations thereof, such as in a "synergistic effect" or a "synergistic herbicide combination" or a "synergistic herbicide composition" refer to circumstances under which the biological activity of a combination of herbicides, such as at least a first herbicide and a second herbicide, is greater than the sum of the biological activities of the individual herbicides. Synergy, expressed in terms of a "Synergy Index (SI)," generally can be determined by the method described by Kull et al. *Applied Microbiology* 9, 538 (1961). See also Colby "Calculating Synergistic and Antagonistic Responses of Herbicide Combinations," *Weeds* 15, 20-22 (1967).

In the same manner, in some embodiments, a DP-305423-1 soybean plant of the invention shows improved tolerance to a particular formulation of a herbicide active ingredient in comparison to an appropriate control plant. Herbicides are sold commercially as formulations which typically include other ingredients in addition to the herbicide active ingredient; these ingredients are often intended to enhance the efficacy of the active ingredient. Such other ingredients can include, for example, safeners and adjuvants (see, e.g., Green and Foy (2003) "Adjuvants: Tools for Enhancing Herbicide Performance," in *Weed Biology and Management*, ed. Inderjit (Kluwer Academic Publishers, The Netherlands)). Thus, a DP-305423-1 soybean plant of the invention can show tolerance to a particular formulation of a herbicide (e.g., a particular commercially available herbicide product) that is at least 1%, 2%, 3%, 4%, 5%, 6%, 7%, 8%, 9%, 10%, 12%, 15%, 17%, 20%, 22%, 25%, 27%, 30%, 35%, 40%, 45%, 50%, 55%, 60%, 65%, 70%, 80%, 90%, 100%, 125%, 150%, 175%, 200%, 300%, 400%, 500%, 600%, 700%, 800%, 900%, 1000%, 1100%, 1200%, 1300%, 1400%, 1500%, 1600%, 1700%, 1800%, 1900%, or 2000% or more higher than the tolerance of an appropriate control plant that contains only a single herbicide tolerance gene which confers tolerance to the same herbicide formulation.

In other methods, a herbicide combination is applied over a DP-305423-1 soybean plant, where the herbicide combination produces either an additive or a synergistic effect for controlling weeds. Such combinations of herbicides can allow the application rate to be reduced, a broader spectrum of undesired vegetation to be controlled, improved control of the undesired vegetation with fewer applications, more rapid onset of the herbicidal activity, or more prolonged herbicidal activity.

An "additive herbicidal composition" has a herbicidal activity that is about equal to the observed activities of the individual components. A "synergistic herbicidal combination" has a herbicidal activity higher than what can be expected based on the observed activities of the individual components when used alone. Accordingly, the presently disclosed subject matter provides a synergistic herbicide combination, wherein the degree of weed control of the mixture exceeds the sum of control of the individual herbicides. In some embodiments, the degree of weed control of the mixture exceeds the sum of control of the individual herbicides by any statistically significant amount including, for example, about 1% to 5%, about 5% to about 10%, about 10% to about 20%, about 20% to about 30%, about 30% to 40%, about 40% to about 50%, about 50% to about 60%, about 60% to about 70%, about 70% to about 80%, about 80% to about 90%, about 90% to about 100%, about 100% to 120% or greater. Further, a "synergistically effective amount" of a herbicide refers to the amount of one herbicide necessary to elicit a synergistic effect in another herbicide present in the herbicide composition. Thus, the term "synergist," and derivations thereof, refer to a substance that enhances the activity of an active ingredient (ai), i.e., a substance in a formulation from which a biological effect is obtained, for example, a herbicide.

Plants of the current invention can be crossed with transgenic plants that are tolerant to glyphosate, to produce progeny that have tolerance to both glyphosate and inhibitors of ALS.

Weeds that can be difficult to control with glyphosate alone in fields where a crop is grown (such as, for example, a soybean crop) include but are not limited to the following: horseweed (e.g., *Conyza canadensis*); rigid ryegrass (e.g., *Lolium rigidum*); goosegrass (e.g., *Eleusine indica*); Italian ryegrass (e.g., *Lolium multiflorum*); hairy fleabane (e.g., *Conyza bonariensis*); buckhorn plantain (e.g., *Plantago lanceolata*); common ragweed (e.g., *Ambrosia artemisifolia*); morning glory (e.g., *Ipomoea* spp.); waterhemp (e.g., *Amaranthus* spp.); field bindweed (e.g., *Convolvulus arvensis*); yellow nutsedge (e.g., *Cyperus esculentus*); common lambsquarters (e.g., *Chenopodium album*); wild buckwheat (e.g., *Polygonium convolvulus*); velvetleaf (e.g., *Abutilon theophrasti*); kochia (e.g., *Kochia scoparia*); and Asiatic dayflower (e.g., *Commelina* spp.). In areas where such weeds are found, the DP-305423-1 soybeans are particularly useful in allowing the treatment of a field (and therefore any crop growing in the field) with combinations of herbicides that would cause unacceptable damage to crop plants that did not contain both of these polynucleotides. Plants of the invention that are tolerant to glyphosate and other herbicides such as, for example, sulfonylurea, imidazolinone, triazolopyrimidine, pyrimidinyl(thio)benzoate, and/or sulfonylaminocarbonyltriazolinone herbicides in addition to being tolerant to at least one other herbicide with a different mode of action or site of action are particularly useful in situations where weeds are tolerant to at least two of the same herbicides to which the plants are tolerant. In this manner, plants of the invention make possible improved control of weeds that are tolerant to more than one herbicide.

In the methods of the invention, a herbicide may be formulated and applied to an area of interest such as, for example, a field or area of cultivation, in any suitable manner. A herbicide may be applied to a field in any form, such as, for example, in a liquid spray or as solid powder or granules. In specific embodiments, the herbicide or combination of herbicides that are employed in the methods comprise a tankmix or a premix. A herbicide may also be formulated, for example, as a "homogenous granule blend" produced using blends technology (see, e.g., U.S. Pat. No. 6,022,552, entitled "Uniform Mixtures of Pesticide Granules"). The blends technology of U.S. Pat. No. 6,022,552 produces a nonsegregating blend (i.e., a "homogenous granule blend") of formulated crop protection chemicals in a dry granule form that enables delivery of customized mixtures designed to solve specific problems. A homogenous granule blend can be shipped, handled, subsampled, and applied in the same manner as traditional premix products where multiple active ingredients are formulated into the same granule.

Briefly, a "homogenous granule blend" is prepared by mixing together at least two extruded formulated granule products. In some embodiments, each granule product comprises a registered formulation containing a single active ingredient which is, for example, a herbicide, a fungicide, and/or an insecticide. The uniformity (homogeneity) of a "homogenous granule blend" can be optimized by controlling the relative sizes and size distributions of the granules used in the blend. The diameter of extruded granules is controlled by the size of the holes in the extruder die, and a centrifugal sifting process may be used to obtain a population of extruded granules with a desired length distribution (see, e.g., U.S. Pat. No. 6,270, 025).

A homogenous granule blend is considered to be "homogenous" when it can be subsampled into appropriately sized aliquots and the composition of each aliquot will meet the required assay specifications. To demonstrate homogeneity, a large sample of the homogenous granule blend is prepared and is then subsampled into aliquots of greater than the minimum statistical sample size.

Blends also afford the ability to add other agrochemicals at normal, labeled use rates such as additional herbicides (a $3^{rd}/4^{th}$ mechanism of action), fungicides, insecticides, plant growth regulators and the like thereby saving costs associated with additional applications.

Any herbicide formulation applied over the DP-305423-1 soybean plant can be prepared as a "tank-mix" composition. In such embodiments, each ingredient or a combination of ingredients can be stored separately from one another. The ingredients can then be mixed with one another prior to application. Typically, such mixing occurs shortly before application. In a tank-mix process, each ingredient, before mixing, typically is present in water or a suitable organic solvent. For additional guidance regarding the art of formulation, see T. S. Woods, "The Formulator's Toolbox—Product Forms for Modern Agriculture" *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; and Hance et al., *Weed Control Handbook*, 8th Ed., Blackwell Scientific Publications, Oxford, 1989, each of which is incorporated herein by reference in their entirety.

The methods of the invention further allow for the development of herbicide combinations to be used with the DP-305423-1 soybean plants. In such methods, the environmental conditions in an area of cultivation are evaluated. Environmental conditions that can be evaluated include, but are not limited to, ground and surface water pollution concerns, intended use of the crop, crop tolerance, soil residuals, weeds present in area of cultivation, soil texture, pH of soil, amount of organic matter in soil, application equipment, and tillage practices. Upon the evaluation of the environmental conditions, an effective amount of a combination of herbicides can be applied to the crop, crop part, seed of the crop or area of cultivation.

In some embodiments, the herbicide applied to the DP-305423-1 soybean plants of the invention serves to prevent the initiation of growth of susceptible weeds and/or serve to cause damage to weeds that are growing in the area of interest. In some embodiments, the herbicide or herbicide mixture exert these effects on weeds affecting crops that are subsequently planted in the area of interest (i.e., field or area of cultivation). In the methods of the invention, the application of the herbicide combination need not occur at the same time. So long as the field in which the crop is planted contains detectable amounts of the first herbicide and the second herbicide is applied at some time during the period in which the crop is in the area of cultivation, the crop is considered to have been treated with a mixture of herbicides according to the invention. Thus, methods of the invention encompass applications of herbicide which are "preemergent," "postemergent," "preplant incorporation" and/or which involve seed treatment prior to planting.

In one embodiment, methods are provided for coating seeds. The methods comprise coating a seed with an effective amount of a herbicide or a combination of herbicides (as disclosed elsewhere herein). The seeds can then be planted in an area of cultivation. Further provided are seeds having a coating comprising an effective amount of a herbicide or a combination of herbicides (as disclosed elsewhere herein).

"Preemergent" refers to a herbicide which is applied to an area of interest (e.g., a field or area of cultivation) before a plant emerges visibly from the soil. "Postemergent" refers to a herbicide which is applied to an area after a plant emerges visibly from the soil. In some instances, the terms "preemergent" and "postemergent" are used with reference to a weed in an area of interest, and in some instances these terms are used with reference to a crop plant in an area of interest. When used with reference to a weed, these terms may apply to only a particular type of weed or species of weed that is present or believed to be present in the area of interest. While any herbicide may be applied in a preemergent and/or postemergent treatment, some herbicides are known to be more effective in controlling a weed or weeds when applied either preemergence or postemergence. For example, rimsulfuron has both preemergence and postemergence activity, while other herbicides have predominately preemergence (metolachlor) or postemergence (glyphosate) activity. These properties of particular herbicides are known in the art and are readily determined by one of skill in the art. Further, one of skill in the art would readily be able to select appropriate herbicides and application times for use with the transgenic plants of the invention and/or on areas in which transgenic plants of the invention are to be planted. "Preplant incorporation" involves the incorporation of compounds into the soil prior to planting.

The time at which a herbicide is applied to an area of interest (and any plants therein) may be important in optimizing weed control. The time at which a herbicide is applied may be determined with reference to the size of plants and/or the stage of growth and/or development of plants in the area of interest, e.g., crop plants or weeds growing in the area. The stages of growth and/or development of plants are known in the art. For example, soybean plants normally progress through vegetative growth stages known as $V_E$ (emergence), $V_C$ (cotyledon), $V_1$ (unifoliate), and $V_2$ to $V_N$. Soybeans then switch to the reproductive growth phase in response to photoperiod cues; reproductive stages include $R_1$ (beginning bloom), $R_2$ (full bloom), $R_3$ (beginning pod), $R_4$ (full pod), $R_5$ (beginning seed), $R_6$ (full seed), $R_7$ (beginning maturity), and $R_8$ (full maturity). Thus, for example, the time at which a herbicide or other chemical is applied to an area of interest in which plants are growing may be the time at which some or all of the plants in a particular area have reached at least a particular size and/or stage of growth and/or development, or the time at which some or all of the plants in a particular area have not yet reached a particular size and/or stage of growth and/or development.

The term "safener" refers to a substance that when added to a herbicide formulation eliminates or reduces the phytotoxic effects of the herbicide to certain crops. One of ordinary skill in the art would appreciate that the choice of safener depends, in part, on the crop plant of interest and the particular herbicide or combination of herbicides included in the synergistic herbicide composition. Exemplary safeners suitable for use with the presently disclosed herbicide compositions include, but are not limited to, those disclosed in U.S. Pat. Nos. 4,808,208; 5,502,025; 6,124,240 and U.S. Patent Application Publication Nos. 2006/0148647; 2006/0030485; 2005/0233904; 2005/0049145; 2004/0224849; 2004/0224848; 2004/0224844; 2004/0157737; 2004/0018940; 2003/0171220; 2003/0130120; 2003/0078167, the disclosures of which are incorporated herein by reference in their entirety. The methods of the invention can involve the use of herbicides in combination with herbicide safeners such as benoxacor, BCS (1-bromo-4-[(chloromethyl)sulfonyl]benzene), cloquintocet-mexyl, cyometrinil, dichlormid, 2-(dichloromethyl)-2-methyl-1,3-dioxolane (MG 191), fenchlorazole-ethyl, fenclorim, flurazole, fluxofenim, furilazole, isoxadifen-ethyl, mefenpyr-diethyl, methoxyphenone ((4-methoxy-3-methylphenyl)(3-methylphenyl)-methanone), naphthalic anhydride (1,8-naphthalic anhydride) and oxabetrinil to increase crop safety. Antidotally effective amounts of the herbicide safeners can be applied at the same time as the compounds of this invention, or applied as seed treatments.

Seed treatment is particularly useful for selective weed control, because it physically restricts antidoting to the crop plants. Therefore a particularly useful embodiment of the present invention is a method for selectively controlling the growth of weeds in a field comprising treating the seed from which the crop is grown with an antidotally effective amount of safener and treating the field with an effective amount of herbicide to control weeds. Antidotally effective amounts of safeners can be easily determined by one skilled in the art through simple experimentation. An antidotally effective amount of a safener is present where a desired plant is treated with the safener so that the effect of a herbicide on the plant is decreased in comparison to the effect of the herbicide on a plant that was not treated with the safener; generally, an antidotally effective amount of safener prevents damage or severe damage to the plant treated with the safener. One of skill in the art is capable of determining whether the use of a safener is appropriate and determining the dose at which a safener should be administered to a crop.

In specific embodiments, the combination of safening herbicides comprises a first ALS inhibitor and a second ALS inhibitor.

Such mixtures provide increased crop tolerance (i.e., a decrease in herbicidal injury). This method allows for increased application rates of the chemistries post or pretreatment. Such methods find use for increased control of unwanted or undesired vegetation. In still other embodiments, a safening affect is achieved when the DP-305423-1 soybean crops, crop part, crop seed, weed, or area of cultivation is treated with at least one herbicide from the sulfonylurea family of chemistry in combination with at least one herbicide from the imidazolinone family. This method provides increased crop tolerance (i.e., a decrease in herbicidal injury). In specific embodiments, the sulfonylurea comprises rimsulfuron and the imidazolinone comprises imazethapyr.

As used herein, an "adjuvant" is any material added to a spray solution or formulation to modify the action of an agricultural chemical or the physical properties of the spray solution. See, for example, Green and Foy (2003) "Adjuvants: Tools for Enhancing Herbicide Performance," in *Weed Biology and Management*, ed. Inderjit (Kluwer Academic Publishers, The Netherlands). Adjuvants can be categorized or subclassified as activators, acidifiers, buffers, additives, adherents, antiflocculants, antifoamers, defoamers, antifreezes, attractants, basic blends, chelating agents, cleaners, colorants or dyes, compatibility agents, cosolvents, couplers, crop oil concentrates, deposition agents, detergents, dispersants, drift control agents, emulsifiers, evaporation reducers, extenders, fertilizers, foam markers, formulants, inerts, humectants, methylated seed oils, high load COCs, polymers, modified vegetable oils, penetrators, repellants, petroleum oil concentrates, preservatives, rainfast agents, retention aids, solubilizers, surfactants, spreaders, stickers, spreader stickers, synergists, thickeners, translocation aids, uv protectants, vegetable oils, water conditioners, and wetting agents.

In addition, methods of the invention can comprise the use of a herbicide or a mixture of herbicides, as well as, one or more other insecticides, fungicides, nematocides, bactericides, acaricides, growth regulators, chemosterilants, semiochemicals, repellents, attractants, pheromones, feeding stimulants or other biologically active compounds or entomopathogenic bacteria, virus, or fungi to form a multi-component mixture giving an even broader spectrum of agricultural protection. Examples of such agricultural protectants which can be used in methods of the invention include: insecticides such as abamectin, acephate, acetamiprid, amidoflumet (S-1955), avermectin, azadirachtin, azinphos-methyl, bifenthrin, bifenazate, buprofezin, carbofuran, cartap, chlorfenapyr, chlorfluazuron, chlorpyrifos, chlorpyrifos-methyl, chromafenozide, clothianidin, cyflumetofen, cyfluthrin, beta-cyfluthrin, cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, esfenvalerate, ethiprole, fenothiocarb, fenoxycarb, fenpropathrin, fenvalerate, fipronil, flonicamid, flubendiamide, flucythrinate, tau-fluvalinate, flufenerim (UR-50701), flufenoxuron, fonophos, halofenozide, hexaflumuron, hydramethylnon, imidacloprid, indoxacarb, isofenphos, lufenuron, malathion, metaflumizone, metaldehyde, methamidophos, methidathion, methomyl, methoprene, methoxychlor, metofluthrin, monocrotophos, methoxyfenozide, nitenpyram, nithiazine, novaluron, noviflumuron (XDE-007), oxamyl, parathion, parathion-methyl, permethrin, phorate, phosalone, phosmet, phosphamidon, pirimicarb, profenofos, profluthrin, pymetrozine, pyrafluprole, pyrethrin, pyridalyl, pyriprole, pyriproxyfen, rotenone, ryanodine, spinosad, spirodiclofen, spiromesifen (BSN 2060), spirotetramat, sulprofos, tebufenozide, teflubenzuron, tefluthrin, terbufos, tetrachlorvinphos, thiacloprid, thiamethoxam, thiodicarb, thiosultap-sodium, tralomethrin, triazamate, trichlorfon and triflumuron; fungicides such as acibenzolar, aldimorph, amisulbrom, azaconazole, azoxystrobin, benalaxyl, benomyl, benthiavalicarb, benthiavalicarb-isopropyl, binomial, biphenyl, bitertanol, blasticidin-S, Bordeaux mixture (Tribasic copper sulfate), boscalid/nicobifen, bromuconazole, bupirimate, buthiobate, carboxin, carpropamid, captafol, captan, carbendazim, chloroneb, chlorothalonil, chlozolinate, clotrimazole, copper oxychloride, copper salts such as copper sulfate and copper hydroxide, cyazofamid, cyflunamid, cymoxanil, cyproconazole, cyprodinil, dichlofluanid, diclocymet, diclomezine, dicloran, diethofencarb, difenoconazole, dimethomorph, dimoxystrobin, diniconazole, diniconazole-M, dinocap, discostrobin, dithianon, dodemorph, dodine, econazole, etaconazole, edifenphos, epoxiconazole, ethaboxam, ethirimol, ethridiazole, famoxadone, fenamidone, fenarimol, fenbuconazole, fencaramid, fenfuram, fenhexamide, fenoxanil, fenpiclonil, fenpropidin, fenpropimorph, fentin acetate, fentin hydroxide, ferbam, ferfurazoate, ferimzone, fluazinam, fludioxonil, flumetover, fluopicolide, fluoxastrobin, fluquinconazole, fluquinconazole, flusilazole, flusulfamide, flutolanil, flutriafol, folpet, fosetyl-aluminum, fuberidazole, furalaxyl, furametapyr, hexaconazole, hymexazole, guazatine, imazalil, imibenconazole, iminoctadine, iodicarb, ipconazole, iprobenfos, iprodione, iprovalicarb, isoconazole, isoprothiolane, kasugamycin, kresoxim-methyl, mancozeb, mandipropamid, maneb, mapanipyrin, mefenoxam, mepronil, metalaxyl, metconazole, methasulfocarb, metiram, metominostrobin/fenominostrobin, mepanipyrim, metrafenone, miconazole, myclobutanil, neo-asozin (ferric methanearsonate), nuarimol, octhilinone, ofurace, orysastrobin, oxadixyl, oxolinic acid, oxpoconazole, oxycarboxin, paclobutrazol, penconazole, pencycuron, penthiopyrad, perfurazoate, phosphonic acid, phthalide, picobenzamid, picoxystrobin, polyoxin, probenazole, prochloraz, procymidone, propamocarb, propamocarb-hydrochloride, propiconazole, propineb, proquinazid, prothioconazole, pyraclostrobin, pryazophos, pyrifenox, pyrimethanil, pyrifenox, pyrolnitrine, pyroquilon, quinconazole, quinoxyfen, quintozene, silthiofam, simeconazole, spiroxamine, streptomycin, sulfur, tebuconazole, techrazene, tecloftalam, tecnazene, tetraconazole, thiabendazole, thifluzamide, thiophanate, thiophanate-methyl, thiram, tiadinil, tolclofos-methyl, tolyfluanid, triadimefon, triadimenol, triarimol, triazoxide, tridemorph, trimoprhamide tricyclazole, trifloxystrobin, triforine, triticonazole, uniconazole, validamycin, vinclozolin, zineb, ziram, and zoxamide; nematocides such as aldicarb, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents including entomopathogenic bacteria, such as *Bacillus thuringiensis* subsp. *Aizawai*, *Bacillus thuringiensis* subsp. *Kurstaki*, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CPGV. The weight ratios of these various mixing partners to other compositions (e.g., herbicides) used in the methods of the invention typically are between 100:1 and 1:100, or between 30:1 and 1:30, between 10:1 and 1:10, or between 4:1 and 1:4.

The present invention also pertains to a composition comprising a biologically effective amount of a herbicide of interest or a mixture of herbicides, and an effective amount of at least one additional biologically active compound or agent and can further comprise at least one of a surfactant, a solid diluent or a liquid diluent. Examples of such biologically active compounds or agents are: insecticides such as abamectin, acephate, acetamiprid, amidoflumet (S-1955), avermectin, azadirachtin, azinphos-methyl, bifenthrin, binfenazate, buprofezin, carbofuran, chlorfenapyr, chlorfluazuron, chlorpyrifos, chlorpyrifos-methyl, chromafenozide, clothianidin, cyfluthrin, beta-cyfluthrin, cyhalothrin, lambda-cyhalothrin, cypermethrin, cyromazine, deltamethrin, diafenthiuron, diazinon, diflubenzuron, dimethoate, diofenolan, emamectin, endosulfan, esfenvalerate, ethiprole, fenothicarb, fenoxycarb, fenpropathrin, fenvalerate, fipronil, flonicamid, flucythrinate, tau-fluvalinate, flufenerim (UR-50701), flufenoxuron, fonophos, halofenozide, hexaflumuron, imidacloprid, indoxacarb, isofenphos, lufenuron, malathion, metaldehyde, methamidophos, methidathion, methomyl, methoprene, methoxychlor, monocrotophos, methoxyfenozide, nithiazin, novaluron, noviflumuron (XDE-007), oxamyl, parathion, parathion-methyl, permethrin, phorate, phosalone, phosmet, phosphamidon, pirimicarb, profenofos, pymetrozine, pyridalyl, pyriproxyfen, rotenone, spinosad, spiromesifin (BSN 2060), sulprofos, tebufenozide, teflubenzuron, tefluthrin, terbufos, tetrachlorvinphos, thiacloprid, thiamethoxam, thiodicarb, thiosultap-sodium, tralomethrin, trichlorfon and triflumuron; fungicides such as acibenzolar, azoxystrobin, benomyl, blasticidin-S, Bordeaux mixture (tribasic copper sulfate), bromuconazole, carpropamid, captafol, captan, carbendazim, chloroneb, chlorothalonil, copper oxychloride, copper salts, cyflufenamid, cymoxanil, cyproconazole, cyprodinil, (S)-3,5-dichloro-N-(3-chloro-1-ethyl-1-methyl-2-oxopropyl)-4-methylbenzamide (RH 7281), diclocymet (S-2900), diclomezine, dicloran, difenoconazole, (S)-3,5-dihydro-5-methyl-2-(methylthio)-5-phenyl-3-(phenyl-amino)-4H-imidazol-4-one (RP 407213), dimethomorph, dimoxystrobin, diniconazole, diniconazole-M, dodine, edifenphos, epoxiconazole, famoxadone, fenamidone, fenarimol, fenbuconazole, fencaramid (SZX0722), fenpiclonil, fenpropidin, fenpropimorph, fentin acetate, fentin hydroxide, fluazinam, fludioxonil, flumetover (RPA 403397), flumorf/flumorlin (SYP-L190), fluoxastrobin (HEC 5725), fluquinconazole, flusilazole, flutolanil, flutriafol, folpet, fosetyl-aluminum, furalaxyl, furametapyr (S-82658), hexaconazole, ipconazole, iprobenfos, iprodione, isoprothiolane, kasugamycin, kresoxim-methyl, mancozeb, maneb, mefenoxam, mepronil, metalaxyl, metconazole, metomino-strobin/fenominostrobin (SSF-126), metrafenone (AC375839), myclobutanil, neoasozin (ferric methanearsonate), nicobifen (BAS 510), orysastrobin, oxadixyl, penconazole, pencycuron, probenazole, prochloraz, propamocarb, propiconazole, proquinazid (DPX-KQ926), prothioconazole (JAU 6476), pyrifenox, pyraclostrobin, pyrimethanil, pyroquilon, quinoxyfen, spiroxamine, sulfur, tebuconazole, tetraconazole, thiabendazole, thifluzamide, thiophanate-methyl, thiram, tiadinil, triadimefon, triadimenol, tricyclazole, trifloxystrobin, triticonazole, validamycin and vinclozolin; nematocides such as aldicarb, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents including entomopathogenic bacteria, such as Bacillus thuringiensis subsp. Aizawai, Bacillus thuringiensis subsp. Kurstaki, and the encapsulated delta-endotoxins of Bacillus thuringiensis (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CPGV. Methods of the invention may also comprise the use of plants genetically transformed to express proteins toxic to invertebrate pests (such as Bacillus thuringiensis delta-endotoxins). In such embodiments, the effect of exogenously applied invertebrate pest control compounds may be synergistic with the expressed toxin proteins.

General references for these agricultural protectants include *The Pesticide Manual*, 13*th Edition*, C. D. S. Tomlin, Ed., British Crop Protection Council, Farnham, Surrey, U.K., 2003 and *The BioPesticide Manual*, 2$^{nd}$ *Edition*, L. G. Copping, Ed., British Crop Protection Council, Farnham, Surrey, U.K., 2001.

In certain instances, combinations with other invertebrate pest control compounds or agents having a similar spectrum of control but a different mode of action will be particularly advantageous for resistance management. Thus, compositions of the present invention can further comprise a biologically effective amount of at least one additional invertebrate pest control compound or agent having a similar spectrum of control but a different mode of action. Contacting a plant genetically modified to express a plant protection compound (e.g., protein) or the locus of the plant with a biologically effective amount of a compound of this invention can also provide a broader spectrum of plant protection and be advantageous for resistance management.

Thus, methods of the invention employ a herbicide or herbicide combination and may further comprise the use of insecticides and/or fungicides, and/or other agricultural chemicals such as fertilizers. The use of such combined treatments of the invention can broaden the spectrum of activity against additional weed species and suppress the proliferation of any resistant biotypes.

Methods of the invention can further comprise the use of plant growth regulators such as aviglycine, N-(phenylmethyl)-1H-purin-6-amine, ethephon, epocholeone, gibberellic acid, gibberellin $A_4$ and $A_7$, harpin protein, mepiquat chloride, prohexadione calcium, prohydrojasmon, sodium nitrophenolate and trinexapac-methyl, and plant growth modifying organisms such as *Bacillus cereus* strain BP01.

Embodiments of the present invention are further defined in the following Examples. It should be understood that these Examples are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

EXAMPLE 1

Genetic Material Used to Produce the DP-305423-1 Event

Figure 1:
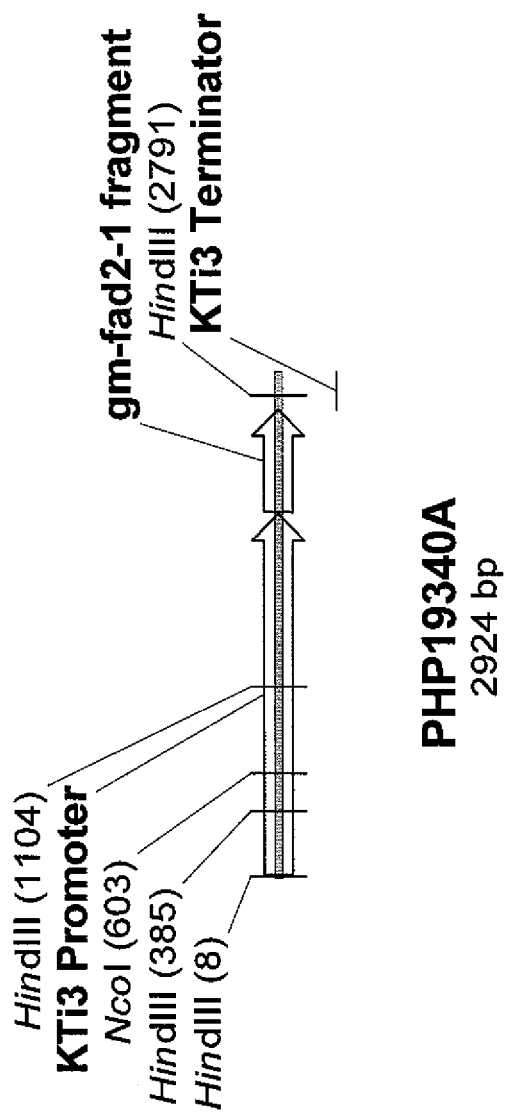
Figure 3:
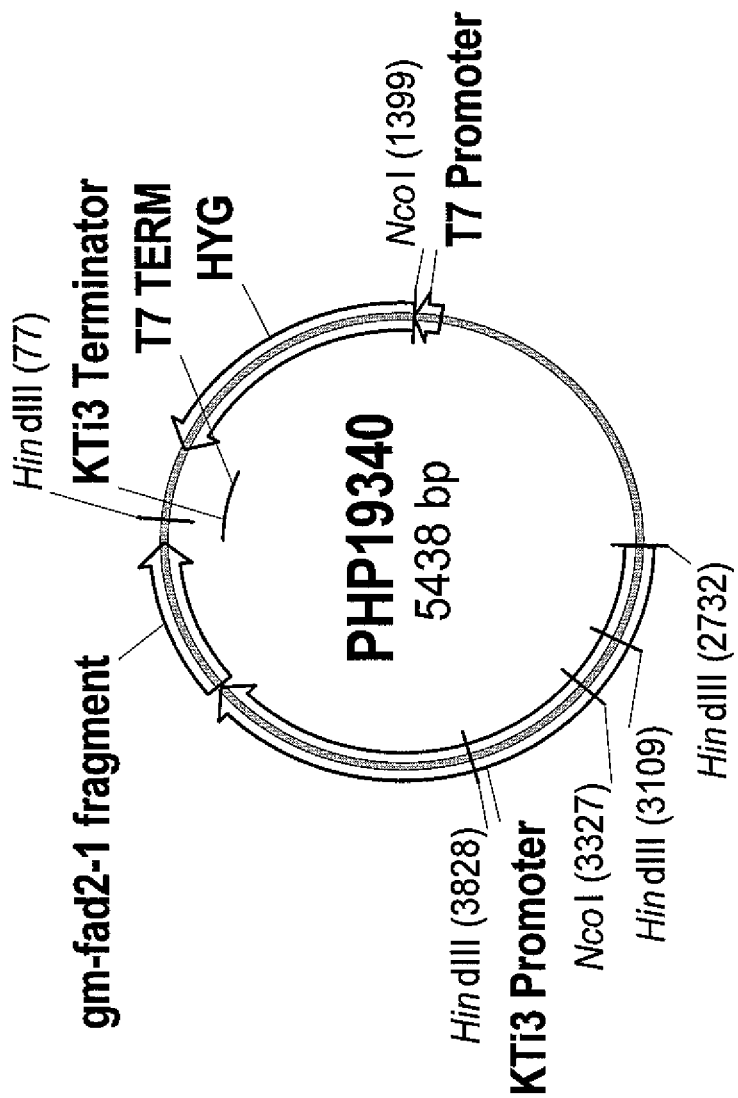
Figure 4:
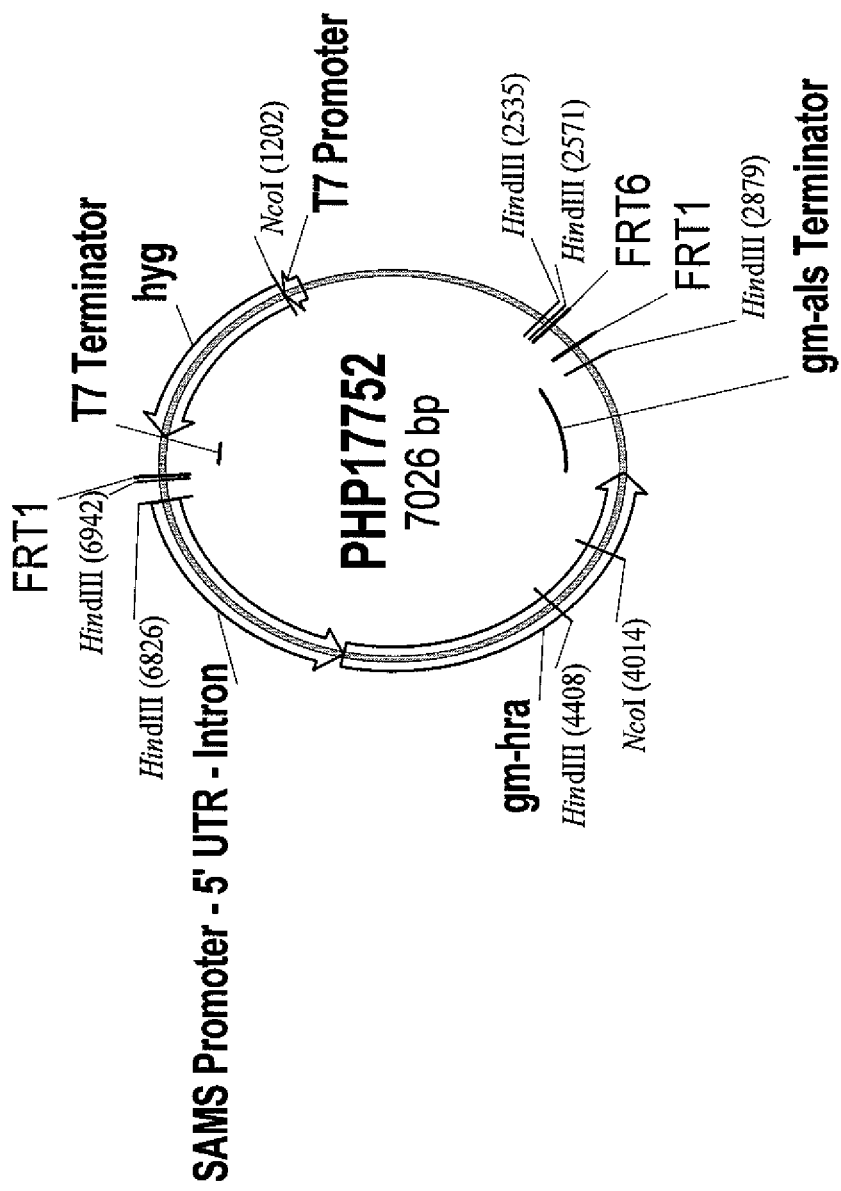

Soybean (*Glycine max*) event DP-305423-1 was produced by particle co-bombardment with fragments PHP19340A (FIG. 1; SEQ ID NO:1) and PHP17752A (FIG. 2; SEQ ID NO:2). A summary of the elements and their position on the PHP19340A fragment is presented in Table 3 and for the PHP17752A fragment in Table 4. These fragments were obtained by Asc I digestion from a source plasmid. Fragment PHP19340A was obtained from plasmid PHP19340 (FIG. 3; SEQ ID NO:3) and fragment PHP17752A was obtained from plasmid PHP17752 (FIG. 4; SEQ ID NO:4). A summary of the elements and their position on each of the plasmids, PHP19340 and PHP17752, are described in Tables 5 and 6, respectively.

The PHP19340A fragment contains a cassette with a 597 bp fragment of the soybean microsomal omega-6 desaturase gene 1 (gm-fad2-1) (Heppard et al., 1996). The presence of the gm-fad2-1 fragment in the expression cassette acts to suppress expression of the endogenous omega-6 desaturases, resulting in an increased level of oleic acid and decreased levels of palmitic, linoleic, and linolenic acid levels. Upstream of the gm-fad2-1 fragment is the promoter region from the Kunitz trypsin inhibitor gene 3 (KTi3) (Jofuku and Goldberg, 1989; Jofuku et al., 1989) regulating expression of the transcript. The KTi3 promoter is highly active in soy embryos and 1000-fold less active in leaf tissue (Jofuku and Goldberg, 1989). The 3' untranslated region of the KTi3 gene (KTi3 terminator) (Jofuku and Goldberg, 1989) terminates expression from this cassette.

The PHP17752A fragment contains a cassette with a modified version of the soybean acetolactate synthase gene (gm-hra) encoding the GM-HRA protein with two amino acid residues modified from the endogenous enzyme and five additional amino acids at the N-terminal region of the protein derived from the translation of the soybean acetolactate synthase gene 5' untranslated region (Falco and Li, 2003). The gm-hra gene encodes a form of acetolactate synthase, which is tolerant to the sulfonylurea class of herbicides. The GM-HRA protein is comprised of 656 amino acids and has a molecular weight of approximately 71 kDa.

The expression of the gm-hra gene is controlled by the 5' promoter region of the S-adenosyl-L-methionine synthetase (SAMS) gene from soybean (Falco and Li, 2003). This 5' region consists of a constitutive promoter and an intron that interrupts the SAMS 5' untranslated region (Falco and Li, 2003). The terminator for the gm-hra gene is the endogenous soybean acetolactate synthase terminator (gm-als terminator) (Falco and Li, 2003).

TABLE 3

Description of Genetic Elements in the Fragment PHP19340A

| Location on DNA Fragment (base pair position) | Genetic Element | Size (base pairs) | Description |
|---|---|---|---|
| 1 to 18 | polylinker region | 18 | Region required for cloning genetic elements |
| 19 to 2102 | KTi3 promoter | 2084 | Promoter region from the soybean Kunitz trypsin inhibitor gene 3 (Jofuku and Goldberg, 1989; Jofuku et al., 1989). |
| 2103 to 2113 | polylinker region | 11 | Region required for cloning genetic elements. |
| 2114 to 2710 | gm-fad2-1 fragment | 597 | Fragment of the soybean microsomal omega-6 desaturase gene (Heppard et al., 1996) |
| 2711 to 2720 | polylinker region | 10 | Region required for cloning genetic elements. |
| 2721 to 2916 | KTi3 terminator | 196 | Terminator region from the soybean Kunitz trypsin inhibitor gene 3 (Jofuku and Goldberg, 1989; Jofuku et al., 1989). |
| 2917 to 2924 | polylinker region | 8 | Region required for cloning genetic elements |

TABLE 4

Description of Genetic Elements in the Fragment PHP17752A

| Location on DNA Fragment (base pair position) | Genetic Element | Size (base pairs) | Description |
|---|---|---|---|
| 1 to 25 | polylinker region | 25 | Region required for cloning genetic elements |
| 26 to 76 | FRT1 | 51 | Flp recombinase recombination site (GenBank ID: AY737006.1). |
| 77 to 222 | polylinker region | 145 | Region required for cloning genetic elements |
| 223 to 867 | SAMS promoter | 645 | Promoter portion of the regulatory region of the SAMS gene (Falco and Li, 2003). |
| 868 to 926 | SAMS 5'-UTR | 59 | 5' untranslated region of the SAMS gene (Falco and Li, 2003). |
| 927 to 1517 | SAMS intron | 591 | Intron within the 5'-UTR of the SAMS gene (Falco and Li, 2003). |

TABLE 4-continued

Description of Genetic Elements in the Fragment PHP17752A

| Location on DNA Fragment (base pair position) | Genetic Element | Size (base pairs) | Description |
|---|---|---|---|
| 1518 to 1533 | SAMS 5'-UTR | 16 | 5' untranslated region of the SAMS gene (Falco and Li, 2003). |
| 1534 to 3504 | gm-hra gene | 1971 | Modified version of the acetolactate synthase gene from soybean with 15 additional nucleotides on the 5' end (1534 to 1548) derived from the als 5' UTR and two nucleotide changes within the coding sequence (Falco and Li, 2003). |
| 3505 to 4156 | als terminator | 652 | Native terminator from the soybean acetolactate synthase gene (Falco and Li, 2003). |
| 4157 to 4231 | polylinker region | 75 | Region required for cloning genetic elements |
| 4232 to 4282 | FRT1 | 51 | Flp recombinase recombination site (GenBank ID: AY737006.1). |
| 4283 to 4396 | polylinker region | 114 | Region required for cloning genetic elements |
| 4397 to 4447 | FRT6 | 51 | Modified Flp recombinase recombination site (94% homology to GenBank ID: AY737006.1) |
| 4448 to 4512 | polylinker region | 65 | Region required for cloning genetic elements |

TABLE 5

Description of Genetic Elements of Plasmid PHP19340

| Region | Location on plasmid (base pair position) | Known Genetic Element | Size (base pairs) | Description |
|---|---|---|---|---|
| PHP19340A fragment | 2725 to 5438 1 to 210 | | 2924 | see Table 3 for elements and description of fragment (complement strand) |
| plasmid construct | 211 to 2724 | includes elements below | 2514 | Vector DNA from various sources for plasmid construction and replication. |
| | 228 to 351 | T7 terminator | 124 | Terminator derived from the Enterobacteria phage T7 genome (GenBank V01146; Dunn and Studier, 1983). (complement strand) |
| | 376 to 1326 | Hyg | 951 | Hygromycin resistance gene from *Trypanosoma brucei* (GenBank AL671259; Gritz and Davies, 1983). (complement strand) |
| | 1404 to 1487 | T7 promoter | 84 | Promoter derived from the Enterobacteria phage T7 genome (GenBank V01146; Dunn and Studier, 1983). (complement strand) |
| | 1561 to 1930 | Ori | 370 | Hae II fragment containing bacterial origin of replication (colE1 derived) (Tomizawa et al., 1977). |

TABLE 6

Description of Genetic Elements of Plasmid PHP17752

| Region | Location on plasmid (base pair position) | Known Genetic Element | Size (base pairs) | Description |
|---|---|---|---|---|
| PHP17752A fragment | 2528 to 7026 1 to 13 | | 4512 | see Table 4 for elements and description of fragment (complement strand) |
| plasmid construct | 14 to 2527 | includes elements below | 2514 | Vector DNA from various sources for plasmid construction and replication. |

TABLE 6-continued

Description of Genetic Elements of Plasmid PHP17752

| Region | Location on plasmid (base pair position) | Known Genetic Element | Size (base pairs) | Description |
|---|---|---|---|---|
| | 31 to 154 | T7 terminator | 124 | Terminator derived from the Enterobacteria phage T7 genome (GenBank V01146; Dunn and Studier, 1983). (complement strand) |
| | 179 to 1129 | Hyg | 951 | Hygromycin resistance gene from *Trypanosoma brucei* (GenBank AL671259; Gritz and Davies, 1983). (complement strand) |
| | 1207 to 1290 | T7 promoter | 84 | Promoter derived from the Enterobacteria phage T7 genome (GenBank V01146; Dunn and Studier, 1983). (complement strand) |
| | 1364 to 1733 | Ori | 370 | Hae II fragment containing bacterial origin of replication (colE1 derived) (Tomizawa et al., 1977). |

REFERENCES

Dunn, J. J. and Studier, F. W. 1983. Complete nucleotide sequence of bacteriophage T7 DNA and the locations of T7 genetic elements. *J. Mol. Biol* 166 (4): 477-535.

Falco, C. S. and Li, Z. 2003. S-adenosyl-L-methionine Synthetase Promoter and Its Use in Expression of Transgenic Genes in Plants. US Patent Application: 2003/0226166.

Gritz, L. and Davies, J. 1983. Plasmid-encoded hygromycin B resistance: the sequence of hygromycin B phosphotransferase gene and its expression in *E. coli* and *Saccharomyces cerevisiae*. *Gene* 25: 179-188.

Heppard, E. P., Kinney, A. J., Stecca, K. L., and Miao, G.-H. 1996. Developmental and Growth Temperature Regulation of Two Different Microsomal omega-6 Desaturase Genes in Soybeans. *Plant Physiol.* 110: 311-319.

Jofuku, K. D. and Goldberg, R. B. 1989. Kunitz Trypsin Inhibitor Genes Are Differentially Expressed during the Soybean Life Cycle and in Transformed Tobacco Plants. *Plant Cell* 1: 1079-1093.

Jofuku, K. D. and Schipper, R. D. and Goldberg, R. B. 1989. A Frameshift Mutation Prevents Kunitz Trypsin Inhibitor mRNA Accumulation in Soybean Embryos. *Plant Cell* 1: 427-435.

Tomizawa, J-I., Ohmori, H., and Bird, R. E. 1977. Origin of replication of colicin E1 plasmid DNA. *Proc. Natl. Acad. Sci.* 74 (5): 1865-1869.

EXAMPLE 2

Method of Transformation and Selection for the Soybean Event DP-305423-1

For transformation of soybean tissue, a linear portion of DNA, containing the gm-fad2-1 gene sequence and the regulatory components necessary for expression, was excised from the plasmid PHP19340 through the use of the restriction enzyme Asc I and purified using agarose gel electrophoresis. A linear portion of DNA, containing the gm-hra gene sequences and the regulatory components necessary for expression, was excised from the plasmid PHP17752 through the use of the restriction enzyme Asc I and purified using agarose gel electrophoresis. The linear portion of DNA containing the gm-fad2-1 gene is designated insert PHP19340A and is 2924 bp in size. The linear portion of DNA containing the gm-hra gene is designated insert PHP17752A and is 4511 bp in size. The only DNA introduced into transformation event DP-305423-1 was the DNA of the inserts described above.

The transgenic plants from event DP-305423-1 were obtained by microprojectile bombardment using the Biolistics™ PDS-1000He particle gun manufactured by Bio-Rad, essentially as described by Klein et al. ("High velocity microprojectiles for delivering nucleic acids into living cells", Nature 327:70-73 (1987)). The targets for transformation were clumps of secondary somatic embryos derived from explants from small, immature soybean seeds. The secondary somatic embryos were excised from immature explants after several weeks on a soybean culture initiation medium. The embryogenic clumps which were excised from the explants were transferred to a liquid soybean culture maintenance medium, and subcultured at regular intervals until prepared for bombardment.

Soybean somatic embryogenic cultures are used in transformation experiments from 2-4 months after initiation. On the day of transformation, microscopic gold particles were coated with a mixture of the DNA of the two purified fragments, PHP19340A and PHP17752A, and accelerated into the embryogenic soybean cultures, after which the insert DNAs were incorporated into some of the cells' chromosomes. Only PHP19340A and PHP17752A were used and no additional DNA (e.g., carrier DNA) was incorporated into the transformation process. After bombardment, the bombarded soybean tissue was transferred to flasks of fresh liquid culture maintenance medium for recovery. After a few days, the liquid culture medium in each flask of bombarded embryogenic soybean culture was changed to culture maintenance medium supplemented with chlorsulfuron as the selection agent. Individual flasks of tissue in liquid selective medium were kept physically separate during culture, and the majority of the somatic embryogenic clumps within each flask died in the liquid selective medium.

After several weeks in the culture maintenance medium supplemented with chlorsulfuron, small islands of healthy, chlorsulfuron-resistant green tissue became visible growing out of pieces of dying somatic embryogenic tissue. The resistant embryogenic clumps were excised from their associated pieces of dying or dead tissue, and were assigned unique identification codes representing putative transformation events. The individual putative events received regular changes to fresh liquid selection medium until the start of the regeneration process. Embryogenic tissue samples were taken for molecular analysis to confirm the presence of the gm-fad2-1 and gm-hra transgenes by Southern analysis. Plants were regenerated from tissue derived from each unique event and transferred to the greenhouse for seed production.

EXAMPLE 3

Southern Analysis of Plants Containing the DP-305423-1 Event

Materials and Methods: Genomic DNA was extracted from frozen soybean leaf tissue of individual plants of the T4 and T5 generations of DP-305423-1 and of control (variety: Jack) using a standard Urea Extraction Buffer method. Genomic DNA was quantified on a spectrofluorometer using Pico Green® reagent (Molecular Probes, Invitrogen). Approximately 4 μg of DNA per sample was digested with HindIII or NcoI. For positive control samples, approximately 3 pg (2 genome copy equivalents) of plasmid PHP19340 or PHP17752 was added to control soybean genomic DNA prior to digestion. Negative control samples consisted of unmodified soybean genomic DNA (variety: Jack). DNA fragments were separated by size using agarose gel electrophoresis.

Following agarose gel electrophoresis, the separated DNA fragments were depurinated, denatured, neutralized in situ, and transferred to a nylon membrane in 20×SSC buffer using the method as described for TURBOBLOTTER™ Rapid Downward Transfer System (Schleicher & Schuell). Following transfer to the membrane, the DNA was bound to the membrane by UV crosslinking.

DNA probes for gm-fad2-1 and gm-hra were labeled with digoxigenin (DIG) by PCR using the PCR DIG Probe Synthesis Kit (Roche).

Labeled probes were hybridized to the target DNA on the nylon membranes for detection of the specific fragments using DIG Easy Hyb solution (Roche) essentially as described by manufacturer. Post-hybridization washes were carried out at high stringency. DIG-labeled probes hybridized to the bound fragments were detected using the CDP-Star Chemiluminescent Nucleic Acid Detection System (Roche). Blots were exposed to X-ray film at room temperature for one or more time points to detect hybridizing fragments.

Summary of Southern Analysis of DP-305423-1: Schematic maps of plasmids PHP19340 (SEQ ID NO:3) and PHP17752 (SEQ ID NO:4) used as positive controls on these blots are presented in FIGS. 3 and 4, respectively. These plasmids were the sources of fragments PHP19340A (FIG. 1; SEQ ID NO:1) and PHP17752A (FIG. 2; SEQ ID NO:2). The fragments were isolated by AscI digestion of the corresponding source plasmid. DP-305423-1 was obtained by particle co-bombardment transformation using fragments PHP19340A and PHP17752A.

Figure 5:
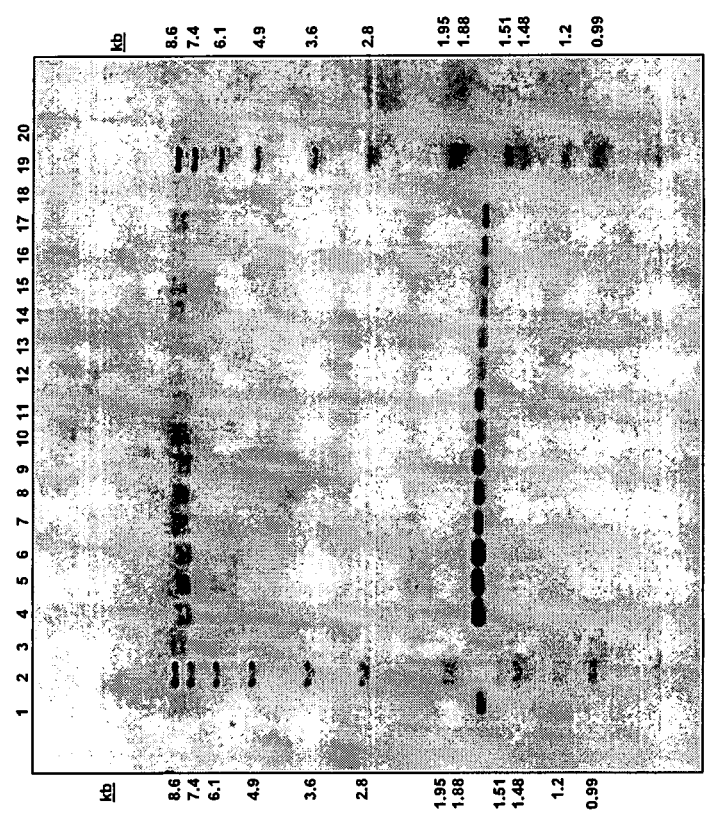
FIG. 5 shows a Southern hybridization experiment of genomic DNA from soybean leaf tissue of individual plants of DP-305423-1 (T5 and T4 generation) and of unmodified control (Jack), digested with HindIII and probed with the gm-fad2-1 gene probe.

Genomic DNA isolated from soybean leaf tissue of individual plants of DP-305423-1 (T5 and T4 generation) and of unmodified control (Jack) was digested with HindIII and probed with the gm-fad2-1 gene probe (FIG. 5; Table 7). Approximately 2 μg of genomic DNA was digested and loaded per lane. The gene copy number controls included plasmid PHP19340 and PHP17752 at the indicated approximate gene copy number and 2 μg of unmodified control DNA. Sizes of the DIG VII molecular weight markers are indicated adjacent to the blot image in kilobase pairs (kb). A description of each lane is presented in Table 7.

TABLE 7

Southern Blot Analysis of DP-3Ø5423-1; Hind III Digest, gm-fad2-1 Probe

| Lane | Sample |
|---|---|
| 1 | 2 copies PHP19340 + Control |
| 2 | DIGVII |
| 3 | Control |
| 4 | DP-3Ø5423-1/T8 (T5 generation) |
| 5 | DP-3Ø5423-1/T9 (T5 generation) |
| 6 | DP-3Ø5423-1/T10 (T5 generation) |
| 7 | DP-3Ø5423-1/T11 (T5 generation) |
| 8 | DP-3Ø5423-1/T12 (T5 generation) |
| 9 | DP-3Ø5423-1/T13 (T5 generation) |
| 10 | DP-3Ø5423-1/T14 (T5 generation) |
| 11 | DP-3Ø5423-1/T38 (T4 generation) |
| 12 | DP-3Ø5423-1/T39 (T4 generation) |
| 13 | DP-3Ø5423-1/T40 (T4 generation) |
| 14 | DP-3Ø5423-1/T41 (T4 generation) |
| 15 | DP-3Ø5423-1/T42 (T4 generation) |
| 16 | DP-3Ø5423-1/T43 (T4 generation) |
| 17 | DP-3Ø5423-1/T44 (T4 generation) |
| 18 | Control |
| 19 | DIGVII |
| 20 | 2 copies PHP17752 + Control |

Figure 6:
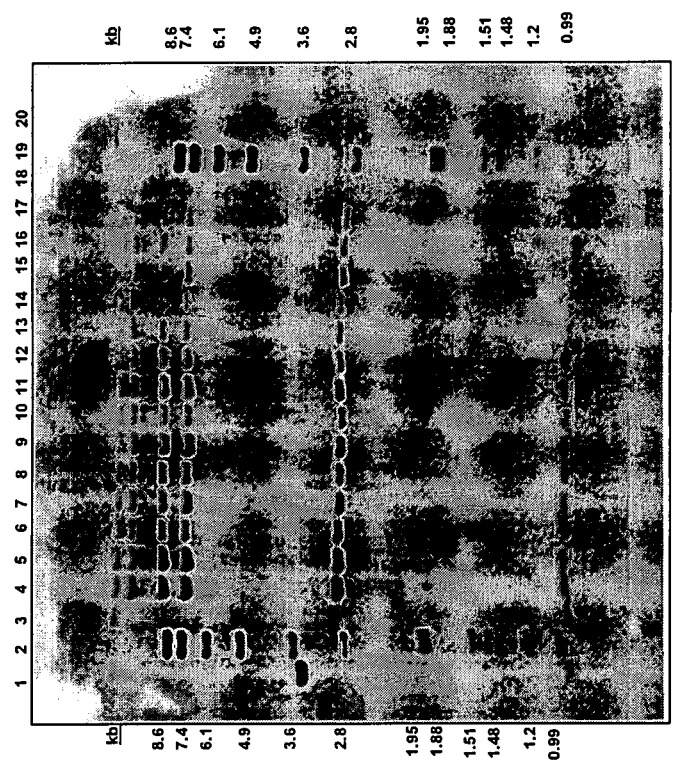
FIG. 6 shows a Southern hybridization experiment of genomic DNA isolated from soybean leaf tissue of individual plants of DP-305423-1 (T5 and T4 generation) and of unmodified control (Jack), digested with NcoI and probed with the gm-fad2-1 gene probe.

Genomic DNA isolated from soybean leaf tissue of individual plants of DP-305423-1 (T5 and T4 generation) and of unmodified control (Jack) was digested with NcoI and probed with the gm-fad2-1 gene probe (FIG. 6; Table 8). Approximately 2 μg of genomic DNA was digested and loaded per lane. The gene copy number controls included plasmid PHP19340 and PHP17752 at the indicated approximate gene copy number and 2 μg of unmodified control DNA. Sizes of the DIG VII molecular weight markers are indicated adjacent to the blot image in kilobase pairs (kb). A description of each lane is presented in Table 8.

TABLE 8

Southern Blot Analysis of DP-3Ø5423-1; Nco I Digest, gm-fad2-1 Probe

| Lane | Sample |
|---|---|
| 1 | 2 copies PHP19340 + Control |
| 2 | DIGVII |
| 3 | Control |
| 4 | DP-3Ø5423-1/T8 (T5 generation) |
| 5 | DP-3Ø5423-1/T9 (T5 generation) |
| 6 | DP-3Ø5423-1/T10 (T5 generation) |
| 7 | DP-3Ø5423-1/T11 (T5 generation) |
| 8 | DP-3Ø5423-1/T12 (T5 generation) |
| 9 | DP-3Ø5423-1/T13 (T5 generation) |
| 10 | DP-3Ø5423-1/T14 (T5 generation) |
| 11 | DP-3Ø5423-1/T38 (T4 generation) |
| 12 | DP-3Ø5423-1/T39 (T4 generation) |
| 13 | DP-3Ø5423-1/T40 (T4 generation) |
| 14 | DP-3Ø5423-1/T41 (T4 generation) |
| 15 | DP-3Ø5423-1/T42 (T4 generation) |
| 16 | DP-3Ø5423-1/T43 (T4 generation) |
| 17 | DP-3Ø5423-1/T44 (T4 generation) |
| 18 | Control |
| 19 | DIGVII |
| 20 | 2 copies PHP17752 + Control |

Figure 7:
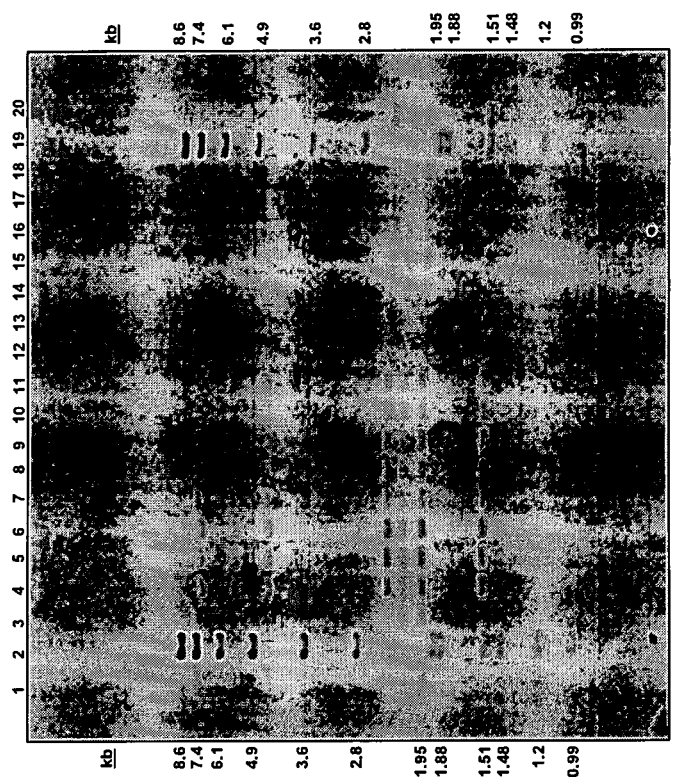
FIG. 7 shows a Southern hybridization experiment of genomic DNA isolated from soybean leaf tissue of individual plants of DP-305423-1 (T5 and T4 generation) and of unmodified control (Jack). digested with HindIII and probed with the gm-hra gene probe.
Figure 8:
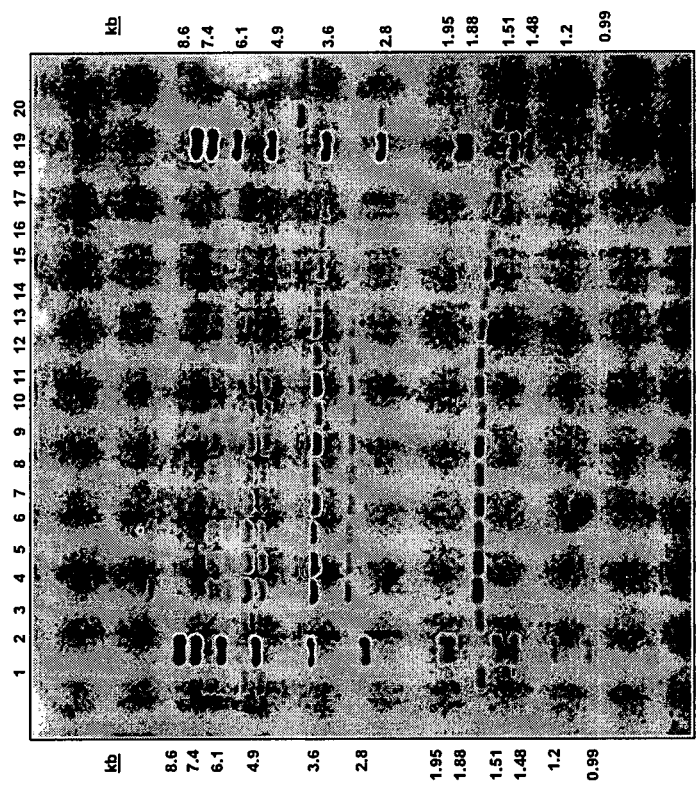
FIG. 8 shows a Southern hybridization experiment of genomic DNA isolated from soybean leaf tissue of individual plants of DP-305423-1 (T5 and T4 generation) and of unmodified control (Jack), digested with NcoI and probed with the gm-hra gene probe.

Genomic DNA isolated from soybean leaf tissue of individual plants of DP-305423-1 (T5 and T4 generation) and of unmodified control (Jack) was digested with HindIII and probed with the gm-hra gene probe (FIG. 7; Table 9). Approximately 2 μg of genomic DNA was digested and loaded per lane. The gene copy number controls included plasmid PHP19340 and PHP17752 at the indicated approximate gene copy number and 2 μg of unmodified control DNA.

Sizes of the DIG VII molecular weight markers are indicated adjacent to the blot image in kilobase pairs (kb). A description of each lane is presented in Table 9.

TABLE 9

Southern Blot Analysis of DP-3Ø5423-1; Hind III Digest, gm-hra Probe

| Lane | Sample |
|---|---|
| 1 | 2 copies PHP19340 + Control |
| 2 | DIGVII |
| 3 | Control |
| 4 | DP-3Ø5423-1/T8 (T5 generation) |
| 5 | DP-3Ø5423-1/T9 (T5 generation) |
| 6 | DP-3Ø5423-1/T10 (T5 generation) |
| 7 | DP-3Ø5423-1/T11 (T5 generation) |
| 8 | DP-3Ø5423-1/T12 (T5 generation) |
| 9 | DP-3Ø5423-1/T13 (T5 generation) |
| 10 | DP-3Ø5423-1/T14 (T5 generation) |
| 11 | DP-3Ø5423-1/T38 (T4 generation) |
| 12 | DP-3Ø5423-1/T39 (T4 generation) |
| 13 | DP-3Ø5423-1/T40 (T4 generation) |
| 14 | DP-3Ø5423-1/T41 (T4 generation) |
| 15 | DP-3Ø5423-1/T42 (T4 generation) |
| 16 | DP-3Ø5423-1/T43 (T4 generation) |
| 17 | DP-3Ø5423-1/T44 (T4 generation) |
| 18 | Control |
| 19 | DIGVII |
| 20 | 2 copies PHP17752 + Control |

Genomic DNA isolated from soybean leaf tissue of individual plants of DP-305423-1 (T5 and T4 generation) and of unmodified control (Jack) was digested with NcoI and probed with the gm-hra gene probe. Approximately 2 μg of genomic DNA was digested and loaded per lane. The gene copy number controls included plasmid PHP19340 and PHP17752 at the indicated approximate gene copy number and 2 μg of unmodified control DNA. Sizes of the DIG VII molecular weight markers are indicated adjacent to the blot image in kilobase pairs (kb). A description of each lane is presented in Table 10.

TABLE 10

Southern Blot Analysis of DP-3Ø5423-1; Nco I Digest, gm-hra Probe

| Lane | Sample |
|---|---|
| 1 | 2 copies PHP19340 + Control |
| 2 | DIGVII |
| 3 | Control |
| 4 | DP-3Ø5423-1/T8 (T5 generation) |
| 5 | DP-3Ø5423-1/T9 (T5 generation) |
| 6 | DP-3Ø5423-1/T10 (T5 generation) |
| 7 | DP-3Ø5423-1/T11 (T5 generation) |
| 8 | DP-3Ø5423-1/T12 (T5 generation) |
| 9 | DP-3Ø5423-1/T13 (T5 generation) |
| 10 | DP-3Ø5423-1/T14 (T5 generation) |
| 11 | DP-3Ø5423-1/T38 (T4 generation) |
| 12 | DP-3Ø5423-1/T39 (T4 generation) |
| 13 | DP-3Ø5423-1/T40 (T4 generation) |
| 14 | DP-3Ø5423-1/T41 (T4 generation) |
| 15 | DP-3Ø5423-1/T42 (T4 generation) |
| 16 | DP-3Ø5423-1/T43 (T4 generation) |
| 17 | DP-3Ø5423-1/T44 (T4 generation) |
| 18 | Control |
| 19 | DIGVII |
| 20 | 2 copies PHP17752 + Control |

Tables 11 and 12 summarize the results from the Southern blot analyses presented in FIGS. 5 through 8.

TABLE 11

Summary of Expected and Observed Hybridization Fragments on Southern Blots with the gm-fad2-1 Probe for DP-3Ø5423-1

| Generation | Enzyme Digestion | Expected Fragment Size[1] (bp) | Expected size of Plasmid (bp)[2] | Observed Fragment Size in DP-3Ø5423-1 (bp) |
|---|---|---|---|---|
| T4 and T5 (FIG. 5) | Hind III | 1687 | 1687 | ~8600* ~8000* ~2400 1687[3] |
| T4 and T5 (FIG. 6) | Nco I | >2300 (border) | 3510 | >8600* 3 bands >8600 ~7400 ~6100 (faint) ~2900 ~900* |

Footnotes:
*Hybridizing band that was also present in control samples. This band is determined to be from sequences endogenous to the Jack variety background and is not related to the insertion in DP-3Ø5423-1.
[1]Size based on map of fragment PHP19340A in FIG. 2.
[2]Size based on plasmid map of PHP19340 in FIG. 1.
[3]Size is same as expected because of equivalent migration with plasmid positive control.

TABLE 12

Summary of Expected and Observed Hybridization Fragments on Southern Blots with the gm-hra Probe for DP-3Ø5423-1

| Generation | Enzyme Digestion | Expected Fragment Size[1] (bp) | Expected size of Plasmid (bp)[2] | Observed Fragment Size in DP-3Ø5423-1 (bp) |
|---|---|---|---|---|
| T4 and T5 (FIG. 7) | Hind III | 2418 1529 | 2418 1529 | >8600* ~8600* ~7400* ~5700* ~4600* 2418[3] ~2300* ~2100* 1529[3] ~900* |
| T4 and T5 (FIG. 8) | Nco I | >3000 (border) >1500 (border) | 4214 2812 | >8600* ~8000* ~6900* ~6100* ~5200* ~4900* ~4500* ~3600 ~3200 ~1600* |

Footnotes:
*Hybridizing band that was also present in control samples. This band is determined to be from sequences endogenous to the Jack variety background and is not related to the insertion in DP-3Ø5423-1.
[1]Size based on map of fragment PHP17752A in FIG. 4.
[2]Size based on plasmid map of PHP17752 in FIG. 3.
[3]Size is same as expected because of equivalent migration with plasmid positive control.

HindIII digestions were conducted on the genomic DNA samples to evaluate internal fragments and integrity of both PHP19340A (FIG. 1; SEQ ID NO:1) and PHP17752A (FIG. 2; SEQ ID NO:2) across the T4 and T5 generations of DP-305423-1. Nco I was selected to evaluate the copy number of the gm-fad2-1 and gm-hra elements in DP-305423-1 because of the presence of a single restriction enzyme site in each of the transformation fragments. The single restriction enzyme site would yield a single hybridizing border fragment for each inserted copy of the gm-fad2-1 element and two hybridizing border fragments for each copy of the gm-hra gene (Tables 11 and 12, respectively). A border fragment is derived from a restriction site in the insert and the nearest corresponding restriction site within the adjacent plant genomic DNA. The number of border fragments observed with the gm-fad2-1 and gm-hra probes would provide an estimate of the number of copies of the element within the DNA insertion of DP-305423-1.

The gm-fad2-1 and gm-hra probes used for Southern analysis were highly homologous to sequences in the endogenous soybean genome and thus additional hybridizing fragments were expected. These hybridizing bands were determined by their presence in the negative control samples and are indicated in Tables 11 and 12 by an asterisk (*).

To verify the integrity of the 3' region of the PHP19340A insertion, the gm-fad2-1 was hybridized to the Hind III blot. A single internal fragment of 1687 bp would be expected based on the presence of HindIII sites in PHP19340A (Table 11, FIG. 1). The expected band of 1687 bp was observed and a second band of approximately 2400 bp was also observed (FIG. 5). In addition, the gm-fad2-1 probe hybridized to two additional bands in DP-305423-1 that were also present in controls and not due to the DP-305423-1 insertion (FIG. 5). The 2400 bp band is most likely due to a partial copy of PHP19340A containing the gm-fad2-1 region. These results indicate the presence of intact copies of PHP19340A as well as a partial copy containing gm-fad2-1 in DP-305423-1. This hybridization pattern is consistent across the T4 and T5 generations of DP-305423-1 analyzed (Table 11).

To determine the number of copies of the gm-fad2-1 element in DP-3Ø5423-1, the gm-fad2-1 probe was hybridized to the NcoI blot. A border fragment of greater than 2300 bp would be expected for each copy gm-fad2-1 (Table 11, FIG. 1). The NcoI blot hybridized to the gm-fad2-1 probe showed six hybridizing fragments (FIG. 6). Sizes of these six hybridizing fragments are given in Table 11. Two additional bands were observed and determined to be due to the endogenous soybean genome based on their presence in negative control samples (Table 11, FIG. 6). The presence of six hybridizing fragments indicates that there are approximately six inserted copies of complete or partial gm-fad2-1 elements in the DP-305423-1 genome. This hybridization pattern is consistent across the T4 and T5 generations of DP-305423-1 analyzed (Table 11), indicating stability of the inserted DNA.

Figure 2:
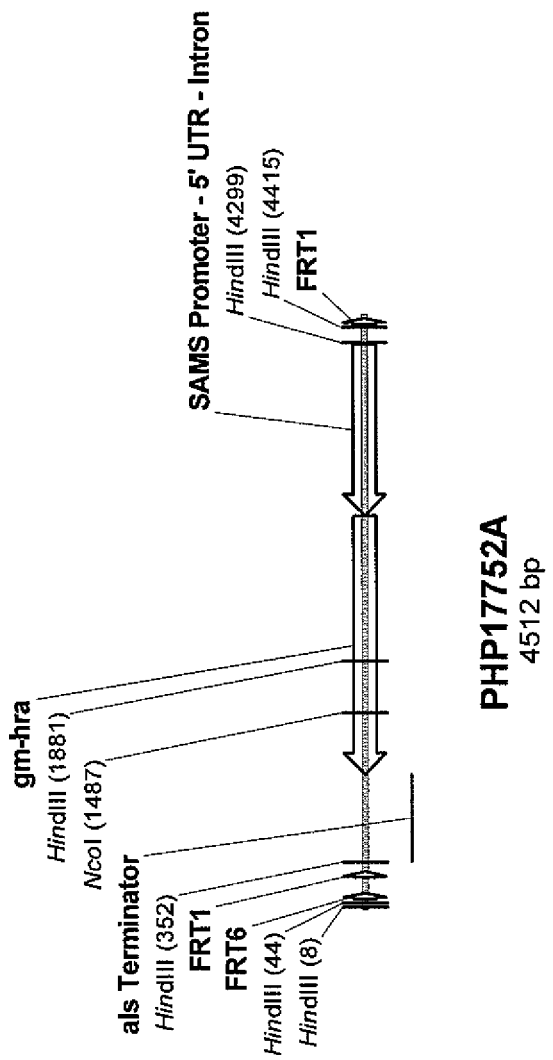

Hybridization of the gm-hra probe to the HindIII blot would verify the integrity of the inserted PHP17752A fragment as two internal bands of 1529 bp and 2418 bp would be expected based on the position of HindIII sites on the fragment (Table 12, FIG. 2). These two bands were observed in the hybridization of the HindIII blot with the gm-hra probe (Table 12, FIG. 7). Additional hybridizing bands were observed in both DP-305423-1 and control lanes, indicating that these bands were due to endogenous sequences and not due to the DP-305423-1 insertion (Table 12, FIG. 7). The presence of only the two expected transgenic bands are an indication the PHP17752A fragment inserted intact in the genome. Both the T4 and T5 generations of DP-305423-1 exhibited the same hybridization pattern (Table 12).

Hybridization of the gm-hra probe to the NcoI blot would verify the number of copies of the element in DP-305423-1. Two border fragments, one greater than 1500 bp and a second greater than 3000 bp, would be expected for each copy of the element based on the position of the NcoI restriction enzyme site within the gm-hra gene in PHP17752A (Table 12, FIG. 4). Two hybridizing bands, one of approximately 3200 bp and 3600 bp, were observed (Table 12, FIG. 8). Additional hybridizing bands were observed in both DP-305423-1 and control lanes, indicating that these bands were due to endogenous sequences and not due to the DP-305423-1 insertion (Table 12, FIG. 8). The presence of two transgenic bands indicates one insertion of the gm-hra gene in the DP-305423-1 genome. This hybridization pattern is consistent across the T4 and T5 generations of DP-305423-1 analyzed (Table 12), indicating stability of the inserted DNA.

In summary, these restriction enzyme and probe combinations showed consistent hybridization patterns throughout all individuals analyzed and across the T4 and T5 generations of DP-305423-1. Based on the analyses reported here, there appear to be approximately six copies of the partial or complete gm-fad2-1 element and a single copy of the gm-hra gene in the genome of DP-305423-1. Intact and partial copies of PHP19340A and a single intact copy of PHP17752A are likely to have inserted into the genome of DP-305423-1.

EXAMPLE 4

Confirmation of High Oleic Acid Phenotype by Gas Chromatography (CG) and Southern Blot Analysis Prior to planting, remove small seed chips (~2 mg) from the seed cotyledons using a razor blade. Prepare fatty acid methyl esters (FAMES) from single, matured, soybean seed chips by transesterification using trimethylsulfonium hydroxide (TMSH) (Butte, 1983). Place seed chips in a 1.5 mL glass gas chromatography vial containing 50 µL of TMSH and 0.5 mL of heptane and incubate for 10 minutes at room temperature while shaking. Transfer vials to the vial racks on the Gas Chromatograph. Separate and quantify fatty acid methyl esters (3 µL injected from heptane layer) using a Hewlett-Packard 6890-2 Gas Chromatograph fitted with an Omegawax 320 fused silica capillary column (Supelco Inc., Bellfonte, Pa.) and a Flame Ionization Detector (FID). The oven temperature is programmed to hold at 220° C. for 5 min, increase to 240° C. at 20° C./min and hold for an additional minute. A Whatman hydrogen generator supplies carrier gas and supplies hydrogen for the FID. Retention times are compared to those for methyl esters of commercially available standards (Nu-Chek Prep, Inc., Elysian, Minn.).

Oil profiles for all seeds are reviewed for elevated oleic acid (18:1) levels as confirmation of the phenotype. The oleic acid level as measured by GC is expected to be >70% for DP-305423-1 soybean seeds, and <30% for the control seeds.

Plants are examined by Southern blot analysis to confirm the presence of the introduced gm-fad2-1 gene fragment and gm-hra gene in DP-305423-1 soybean plants, their absence in control soybean plants, and these data are correlated with the oleic acid results.

EXAMPLE 5

Characterization of Insert and Flanking Border Sequence of Soybean Event DP-305423-1

The insert and flanking border regions of DP-305423-1 genomic DNA were isolated by PCR amplification and by cosmid cloning. PCR fragments were either sequenced directly or cloned into plasmid vectors prior to sequencing. Cosmid DNAs were isolated and sequenced.

Partial and intact copies of PHP19340A and a single copy of PHP17752A were found to be present on four contigs of genomic DNA from the DP-305423-1 event. These four contigs were designated Contig-1 (FIG. 9; SEQ ID NO:5), Contig-2 (FIG. 10; SEQ ID NO:6), Contig-3 (FIG. 11; SEQ ID NO:7) and Contig-4 (FIG. 12; SEQ ID NO:82). Contig-1 has 39,499 nucleotides. The 5' soybean genomic sequence is from nucleotide 1-18,651; the insert sequence is from nucleotide 18, 652-31579; and the 3' soybean genomic sequence is from nucleotide 31580-39,499. Contig-2 has 25,843 nucleotides. The 5' soybean genomic sequence is from nucleotide 1-12,163; the insert sequence is from nucleotide 12,164-14,494; and the 3' soybean genomic sequence is from nucleotide 14,495-25,843. Contig-3 has 12,465 nucleotides. The 5' soybean genomic sequence is from nucleotide 1-5750; the insert sequence is from nucleotide 5751-7813; and the 3' soybean genomic sequence is from nucleotide 7814-12,465. Contig-4 has 10,058 nucleotides. The 5' soybean genomic sequence is from nucleotide 1-2899; the insert sequence is from nucleotide 2899-7909; and the 3' soybean genomic sequence is from nucleotide 7910-10,058.

Genomic DNA Cloning and Primer Design:

Total genomic DNA from DP-305423-1 soybean was partially digested with restriction enzymes HindIII and MboI, and cloned into cosmid vectors to construct HindIII and MboI cosmid libraries. The cosmid libraries were screened using a KTi3 promoter fragment as probe. Total three unique clones (51-21, 51-9, and H3IIBB19) were identified from HindIII library, and two (mbo30 and mbo22) from MboI library. These five clones were analyzed by full-insert sequencing (FIS), a transposon-based sub-cloning method to facilitate bi-directional sequencing of a cloned insert from the site of the transposition event (MJ Research TGS system; Happa et al., 1999). Sequence analysis showed that 51-21 and mbo30 were overlap clones containing the identical insertion from Contig-1, 51-9 and mbo22 were overlap clones containing the identical insertion from Contig-2, and H3IIBB19 contained unique Contig-3. Primers were designed based on the sequences from the cosmid clones. Genomic PCR was performed to verify the insertions and flanking border regions in DP-305423-1 soybean.

Contig-1—Insert and Flanking Genomic Border Regions:

Primers were designed based on the sequence information obtained from the cosmid clones 51-21 and mbo30 containing sequence of Contig-1. PCR products were amplified from genomic DNA of DP-305423-1 soybean using primer pairs A (06-O-1571/06-O-1572, 7103 bp of 5' insert/genomic border junction), B (06-O-1351/06-O-1367, 731 bp of 5' insert/border junction), C (06-O-1357/06-O-1368, 3226 bp of insert), D (06-O-1357/06-O-1369, 2737 bp of insert), E (06-O-1356/06-O-1371, 1800 bp of insert), F (06-O-1360/06-O-1423, 1321 bp of insert), G (06-O-1363/06-O-06-O-1369, 1830 bp of insert), H (06-O-1421/06-O-06-O-1367, 2410 b p of insert), and I (06-O-1577/06-O-1578, 2991 bp of 3' insert/genomic border junction) (Table 13), and cloned. PCR products B, C, D, E, F, G, and H were directly sequenced to verify the insertion, and A and I were analyzed by FIS to verify 5' and 3' insert/genomic junctions and their flanking border regions. No PCR products were amplified when the control genomic DNA was used as a template.

For Contig-1, 22452 bp of DP-305423-1 genomic sequence was confirmed (nucleotides 11652-34103 of SEQ ID NO:5), comprising 7000 bp of the 5' flanking border sequence, 2524 bp of the 3' flanking genomic border sequence, and 12928 bp of inserted DNA. The insert was found to contain one intact PHP19340A fragment, a single, intact PHP17752A fragment, and three truncated PHP19340A fragments. The first truncated PHP19340A fragment contains a partial KTi3 terminator (180 bp) with 3' deletion, an intact gm-fad2-1 fragment (597 bp) and an intact KTi3 promoter (2084 bp). The second truncated PHP19340A fragment contains a partial gm-fad2-1 fragment (39 bp) with 3' deletion and an intact KTi3 promoter (2084 bp). The third truncated PHP19340A fragment contains a partial KTi3 promoter (245 bp) with 5' deletion and a partial gm-fad2-1 fragment (186 bp) with 3' deletion.

To demonstrate that the identified 5' and 3' flanking border sequences for Contig-1 are of soybean origin, PCR was performed within the 5' and 3' flanking border regions (07-O-1889/07-O-1940, 07-O-1892/07-O-1894, respectively) on both DP-305423-1 soybean genomic DNA samples and control samples. The expected PCR products (115 bp for the 5' flanking genomic region and 278 bp for the 3' flanking genomic region) were generated from both DP-305423-1 soybean and control samples, indicating that the sequences were of soybean genomic origin and not specific to DP-305423-1 soybean. These PCR products were cloned and sequenced. The sequences from both the DP-305423-1 and control genomic DNA were identical.

Contig-2—Insert and Flanking Genomic Border Regions:

Primers were designed based on the sequence information obtained from the cosmid clones 51-9 and mbo22 for Contig-2. PCR products were amplified from genomic DNA of DP-305423-1 soybean using primer pairs J (06-O-1588/06-O-1585, 7642 bp of 5' insert/genomic border junction), K (06-O-1586/06-O-1403, 2807 bp of 5' insert/genomic border junction), and L (06-O-1404/06-O-1592, 2845 bp of 3' insert/genomic border junction) (Table 13), and cloned. PCR products K and L were directly sequenced to verify the insertion and 3' insert/genomic border junction and its flanking border region, and J was analyzed by FIS to verify 5' insert/genomic border junctions and its flanking border region. No PCR products were amplified when the control genomic DNA was used as a template.

For Contig-2, 12667 bp of DP-305423-1 genomic sequence was confirmed (nucleotides 4565-17231 of SEQ ID NO:6), comprising 7599 bp of the 5' flanking genomic border sequence, 2737 bp of the 3' flanking genomic border sequence, and 2331 bp of inserted DNA. The insert was found to contain one truncated PHP19340A fragment, with a partial KTi3 promoter (1511 bp), an intact gm-fad2-1 fragment (597 bp), and an intact KTi3 terminator (196 bp).

To demonstrate that the identified 5' and 3' flanking border sequences for Contig-2 are of soybean origin, PCR was performed within the 5' and 3' flanking genomic regions (primer pairs 07-O-1895/07-O-1898 and 07-O-1905/07-O-1903, respectively) on both DP-305423-1 and control soybean genomic DNA samples. The expected PCR products (278 bp for the 5' flanking border region and 271 bp for the 3' flanking border region) were generated from both DP-305423-1 soybean and control samples, indicating that the sequences were of soybean genomic origin and not specific to DP-305423-1 soybean. These PCR products were cloned and sequenced. The sequences from both the DP-305423-1 and control genomic DNA were identical.

Contig-3—Insert and Flanking Genomic Border Regions:

Primers were designed based on the sequence information obtained from the cosmid clone H3IIB19 for Contig-3. PCR products were amplified on genomic DNA from DP-305423-1 using primer pairs M (06-O-1669/06-O-1426, 2804 bp), N (06-O-1355/06-O-1459, 1335 bp), O (06-O-1569/06-O-1551, 1085 bp), and P (05-O-1182/06-O-1672, 2614 bp) (Table 13), and cloned. PCR products M, N, O, and P were directly sequenced to verify the insertion, and the 5' and 3' insert/genomic junction and their flanking genomic regions. No PCR products were amplified when the control genomic DNA was used as a template.

For Contig-3, 6789 bp of DP-305423-1 soybean genomic sequence was confirmed (nucleotides 3312-10100 of SEQ ID NO:7), comprising 2439 bp of the 5' flanking border sequence, 2287 bp of the 3' flanking border sequence, and 2063 bp of inserted DNA. The insert was found to contain one truncated PHP19340A fragment with only a partial KTi3 promoter (1550 bp), and a 495 bp plasmid backbone fragment. This plasmid backbone fragment was identical to the regions located from 2033 bp to 2527 bp in plasmid PHP19340 and from 1836 bp to 2330 bp in plasmid PHP17752, not including the origin of replication (ori). The ori in plasmids PHP13940 and PHP1772 is located from 1561 to 1930 bp and 1364 to 1733 bp, respectively (Tomizawa et al., 1977).

To demonstrate that the identified 5' and 3' flanking border sequences for Contig-3 are of soybean origin, PCR was performed within the 5' and 3' flanking border regions (primer pairs 07-O-1881/07-O-1882 and 07-O-1886/07-O-1884, respectively) on both DP-305423-1 soybean genomic DNA samples and control samples. The expected PCR products (262 bp for the 5' flanking border region and 280 bp for the 3' flanking border region) were generated from both DP-305423-1 soybean and control samples, indicating that the sequences were of soybean genomic origin and not specific to DP-305423-1 soybean. These PCR products were cloned and sequenced. The sequences from both the DP-305423-1 and control genomic DNA were identical.

Contig-4—Insert and Flanking Genomic Border Regions:

Plasmid libraries and iPCR were used to identify the insert within and the flanking border regions of Contig-4. Total genomic DNA from DP-305423-1 soybean was digested with restriction enzymes SpeI and BclI, and run on agarose gels to separate the DNA fragments based on their molecular weights. The DNA fragments on agarose gels were transferred to nylon membrane, and hybridized with a gm-fad2-1 probe or a KTi3 promoter probe. The 2.8 kb and 5.1 kb bands were hybridized with the gm-fad2-1 probe after SpeI digestion, and 1.5 kb and 3.3 kb bands were hybridized with the KTi3 promoter probe after BclI digestion. All of these bands were only present in DP-305423-1 plants, but absent in control plants. These four bands were cloned into plasmid vectors to make plasmid libraries. Positive clones were identified after plasmid library screening with the gm-fad2-1 probe or the KTi3 promoter probe, and were directly sequenced. The sequence for Contig-4 is presented in SEQ ID NO:82.

The 2.8 kb band from SpeI digestion and the 3.3 kb band from BclI digestion were overlapping (referred to as SpeI2.8), containing one truncated PHP19340A fragment with 159 bp deletion at 3' end of the KTi3 promoter; and the 5.1 band from SpeI digestion and the 1.5 kb band from BclI digestion were overlapping (referred to as SpeI5.1), containing one truncated PHP19340A fragment with 649 bp deletion at 3' end of the KTi3 promoter. Since there is a SpeI site within the KTi3 terminator, only 148 bp KTi3 terminator sequence was obtained for both SpeI2.8 and SpeI5.1.

Based on the sequence information, primers designed for inverse PCR (iPCR) were used to obtain additional sequence information at the 3' end of the KTi3 terminator. The iPCR products were either directly sequenced, or cloned and then directly sequenced. Sequence data generated from iPCR products with NdeI digestion showed that SpeI2.8 contained an intact KTi3 terminator and 35 bp KTi3 terminator in the reverse orientation, and SpeI5.1 contained an intact KTi3 terminator and 34 bp KTi3 terminator in the reverse orientation, indicating that the two KTi3 terminators of SpeI2.8 and SpeI5.1 arranged as inverted repeats. Sequence data generated from iPCR products with PacI digestion confirmed that SpeI2.8 and Spe5.1 are arranged as inverted repeats.

Additional confirmation was done using Southern blot analysis. Total genomic DNA from DP-305423-1 and control soybean plants were digested with BclI, ClaI and XmnI, run on an agarose gel, transferred to nylon membrane, and hybridized with the gm-fad2-1 probe. The predicted size bands were hybridized with the gm-fad2-1 probe: about 3.1 kb band for BclI digestion, about 3.9 kb band for ClaI digestion, and 1.7 kb band for XmnI digestion (FIG. 12). Taken together, these results suggest that the two KTi3 terminators from SpeI2.8 and SpeI5.1 are arranged in inverted fashion.

For Contig-4, 10058 bp of DP-305423-1 genomic sequence was identified (SEQ ID NO:82), comprising 2899 bp of the 5' flanking genomic border sequence, 2149 bp of the 3' flanking genomic border sequence, and 5010 bp of inserted DNA. The insert was believed to contain two truncated PHP19340A fragments in inverted fashion. The first truncated PHP1930A fragment is located from 2900 to 5163 bp, containing a partial KTi3 promoter (1442 bp) with 5' deletion, an intact gm-fad2-1 fragment (597 bp) and an intact KTi3 terminator (196 bp). The second truncated PHP1930A fragment is located from 5164 to 7919 bp, containing a partial KTi3 promoter (1934 bp) with 5' deletion, an intact gm-fad2-1 fragment (597 bp) and an intact KTi3 terminator (196 bp) (FIG. 12).

To verify the 5' and 3' insert/genomic junctions obtained from plasmid libraries, PCR was performed on genomic DNA of DP-305423-1 soybean plants using primer pair Q (HOS-A/HOS-B) to confirm the 5' insert/genomic junction, and primer pair R(HOS-C/HOS-D) to confirm the 3' insert/junction. The expected PCR products were amplified from DP-305423-1 plants (Table 13), and not from control plants; these PCR products were cloned and sequenced. The sequence was confirmed to be the same as the sequence obtained from plasmid clones.

TABLE 13

Genomic PCR to Confirm the Inserted DNA and Flanking Genomic Border Regions in DP-305423-1 Soybean

| PCR Product (size in bp) | Primer Pair | PCR System[1] | Insert | Amplified Region |
|---|---|---|---|---|
| A (7103) | 06-O-1571/06-O-1572 | Expand Long Template | 1 | 5' flanking region and insert |
| B (731) | 06-O-1351/06-O-1367 | High Fidelity | 1 | 5' flanking region and insert |
| C (3226) | 06-O-1357/06-O-1368 | Advantage-GC-2 | 1 | Insert |
| D (2737) | 06-O-1357/06-O1369 | Advantage-GC-2 | 1 | Insert |
| E (1800) | 06-O-1356/06-O-1371 | High Fidelity | 1 | Insert |
| F (1321) | 06-O-1360/06-O-1423 | Advantage-GC-2 | 1 | Insert |
| G (1830) | 06-O-1363/06-O-1369 | Advantage-GC-2 | 1 | Insert |
| H (2410) | 06-O-1421/06-O-1367 | Advantage-GC-2 | 1 | Insert |
| I (2991) | 06-O-1577/06-O-1578 | Extensor High Fidelity | 1 | 3' flanking region and insert |

TABLE 13-continued

Genomic PCR to Confirm the Inserted DNA and
Flanking Genomic Border Regions in DP-305423-1 Soybean

| PCR Product (size in bp) | Primer Pair | PCR System[1] | Insert | Amplified Region |
| --- | --- | --- | --- | --- |
| J (7642) | 06-O-1588/06-O-1585 | Expand Long Template | 2 | 5' flanking region and insert |
| K (2817) | 06-O-1586/06-O-1403 | Advantage-GC-2 | 2 | 5' flanking region and insert |
| L (2845) | 06-O-1404/06-O-1592 | Advantage-GC-2 | 2 | 3' flanking region and insert |
| M (2804) | 06-O-1669/06-O-1426 | Expand Long Template | 3 | 5' flanking region and insert |
| N (1335) | 06-O-1355/06-O-1459 | High Fidelity | 3 | insert |
| O (1085) | 06-O-1569/06-O-1551 | Expand Long Template | 3 | 3' flanking region and insert |
| P (2614) | 05-O-1182/06-O-1672 | High Fidelity | 3 | 3' flanking region and insert |
| Q (209) | HOS-A/HOS-B | Taq polymerase | 4 | 5' flanking region and insert |
| R (222) | HOS-C/HOS-D | Taq polymerase | 4 | 3' flanking region and insert |

[1]The High Fidelity and Expand Long Template PCR systems were purchased from Roche (Mannheim, Germany), the Advantage-GC-2 PCR system was purchased from Clontech (Palo Alto, CA), the Extensor High Fidelity PCR system was purchased from ABgene (Surrey, UK), and the Taq polymerase was purchased from Fermentas (Hanover, MD).

EXAMPLE 6

Stability of Contig-1 Insert

The insert in Contig-1 was found to contain one intact PHP19340A fragment (gm-fad2-1 suppression cassette), a single, intact PHP17752A fragment (gm-hra expression cassette), and three truncated PHP19340A fragments. Southern blot analysis conducted on 100 plants from the F2 generation of DP-305423-1 identified a single plant that appeared to have undergone a recombination event that resulted in the removal of the entire gm-hra cassette along with portions of two of the multiple KTi3 promoter fragments found in the insertion. A large number of plants from segregating generations were analyzed by Polymerase Chain Reaction (PCR) to determine at what frequency this recombination occurs.

Seed was obtained from soybean DP-305423-1 segregating generations BC1F2, BC2F2, and BC3F2. Each generation consisted of DP-305423-1 in either the Elite 1 or Elite 2 background. A total of 1060 seeds were planted (Table 14).

TABLE 14

Soybean DP-305423-1 Seed

| Generation | Background | Seeds Planted | Plants Sampled |
| --- | --- | --- | --- |
| BC1F2 | Elite 1 | 175 | 166 |
| BC1F2 | Elite 2 | 150 | 142 |
| BC2F2 | Elite 1 | 65 | 62 |
| BC2F2 | Elite 2 | 40 | 36 |
| BC3F2 | Elite 1 | 420 | 402 |
| BC3F2 | Elite 2 | 210 | 201 |

Single leaf punches were collected from plants and genomic DNA was extracted from the punches utilizing a hot sodium hydroxide and tris extraction method (Truett, G. E., Heeger, P., Mynatt, R. L., Truett, A. A., Walker, J. A. and Warman, M. L. (2000) Preparation of PCR-Quality Mouse Genomic DNA with Hot Sodium Hydroxide and Tris (Hot-SHOT). *BioTechniques* 29: 52-53).

Real-time PCR was performed on each DNA sample utilizing an ABI PRISM® 7900HT Sequence Detection System and accompanying SDS software (Applied Biosystems, Inc., Foster City, Calif.). TaqMan® probe and primer sets were designed to detect two insertion target sequences: (1) the 5' junction region between genomic and insert DNA in Contig-1, which was used as a marker for the gm-fad2-1 suppression cassette (SEQ ID NOs:89, 90 and 91), and (2) the region in the insert of Contig-1 spanning the SAMS promoter and gm-hra (SEQ ID NOs:92, 93 and 94). In addition, a TaqMan® probe and primer set for a reference soybean endogenous gene was used to confirm the presence of amplifiable DNA in each reaction. The analysis consisted of quantitative real-time PCR determination of qualitative positive/negative calls. The extracted DNA was assayed using optimized and validated primer and probe concentrations in Extract-N-Amp™ PCR reaction mix containing Rox passive reference dye (Sigma-Aldrich, St. Louis, Mo.). After initial incubations at 50° C. for 2 minutes and then at 95° C. for 3 minutes, 40 cycles were conducted as follows: 95° C. for 15 seconds, 60° C. for 1 minute. Positive or negative determination for each insertion target was based on comparison of the CT (threshold cycle) of the insertion target PCR to that of the endogenous target.

A total of 1009 plants of three different segregating generations (BC1F2, BC2F2 and BC3F2) and two different backgrounds (Elite 1 and Elite 2) were analyzed by qualitative real-time PCR for the Contig-1 5' junction and the SAMS Promoter::gm-hra targets. Each reaction contained amplifiable DNA based on the endogenous gene control. Of the 1009 plants in the six segregating populations, 745 were positive and 264 were negative for both PCR assays. No plants were identified in which the PCR results were positive for one target and negative for the other. Consequently, in this sample group of 1009 plants, no recombination within the Contig-1 insertion was detected that selectively removed the SAMS Promoter::gm-hra cassette. A summary of the results is given in Table 15.

TABLE 15

Results of Real-time Qualitative PCR Analysis by Generation and Background

| Generation | Background | Contig-1 5' Junction PCR Results | | SAMS Promoter::gm-hra PCR Results | | Total Plants |
|---|---|---|---|---|---|---|
| | | Positive | Negative | Positive | Negative | |
| BC1F2 | Elite 1 | 125 | 41 | 125 | 41 | 166 |
| | Elite 2 | 108 | 34 | 108 | 34 | 142 |
| BC2F2 | Elite 1 | 39 | 23 | 39 | 23 | 62 |
| | Elite 2 | 27 | 9 | 27 | 9 | 36 |
| BC3F2 | Elite 1 | 297 | 105 | 297 | 105 | 402 |
| | Elite 2 | 149 | 52 | 149 | 52 | 201 |
| Total | | 745 | 264 | 745 | 264 | 1009 |

EXAMPLE 7

Fatty Acid Levels in Soybean Grain

Levels of 25 fatty acids were measured in DP-305423-1 and control soybean grain. Levels of ten fatty acids were below the lower limit of quantitation (LLOQ) for the assay: caprylic acid (C8:0), capric acid (C10:0), lauric acid (C12:0), myristoleic acid (C14:1), pentadecanoic acid (C15:0), pentadecenoic acid (C15:1), γ-linolenic acid (C18:3), eicosatrienoic acid (C20:3), arachidonic acid (C20:4), and erucic acid (C22:1). Therefore, no statistical analyses were conducted on these fatty acids and data are not shown. Results of the analysis for the 15 remaining fatty acid are presented in Table 16.

The mean values for oleic acid (C18:1) and linoleic acid (C18:2) fell outside the tolerance intervals and/or the combined literature ranges for conventional soybean varieties. As expected, the mean level of the oleic acid in DP-305423-1 soybean was above the upper range of both the statistical tolerance interval for the reference soybean lines and literature range for conventional soybean varieties. The mean level of the oleic acid in DP-305423-1 soybean was statistically significantly different from that of the control near isoline soybean (adjusted P-value <0.05). The mean level of linoleic acid (C18:2) in DP-305423-1 soybean was below the lower range of the statistical tolerance interval for the reference soybean lines and literature range for conventional soybean varieties. It was also statistically significantly different from that of the control near isoline soybean (adjusted P-value <0.05). The increase in the oleic acid content and the decrease in linoleic acid content in DP-305423-1 soybean are intended effects achieved through introduction of the gm-fad2-1 gene fragment. These changes have been reported previously for transgenic high oleic soybean (OECD identifier DD-Ø26ØØ5-3, AGBIOS database) generated via introduction of the FAD2-1 gene (Kinney and Knowlton, 1997; Glancey et al., 1998; Knowlton, 1999).

Though being within the literature ranges and/or statistical tolerance intervals, the mean values for palimitic acid (C16:0) and linolenic acid (C18:3) were statistically significantly different (lower) in DP-305423-1 soybean as compared to the control near isoline (adjusted P-value <0.05). Linolenic acid is produced directly from conversion of linoleic acid and therefore the decrease in the linoleic acid content was expected to affect the linolenic acid content in DP-305423-1 soybean. The decrease in both palmitic acid and linolenic acid content has been reported previously for transgenic high oleic soybean (OECD identifier DD-Ø26ØØ5-3, AGBIOS database) generated via introduction of the FAD2-1 gene (Kinney and Knowlton, 1997; Glancey et al., 1998; Knowlton, 1999).

The (9,15) isomer of linoleic acid (cis-9, cis-15-octadecadienoic acid) was detected in DP-305423-1 soybean at the mean concentration of 0.341% of the total fatty acids, while the conventional reference varieties did not contain measurable concentrations of this analyte. This was an expected finding, as the 9,15-linoleic acid isomer had been previously seen in high oleic soybean oil at less than 1% of the total fatty acid content (Kinney and Knowlton, 1997). This isomer is also found, at concentrations ranging from 0.02% to 5.4% of the total fatty acids, in many edible sources of fat including butterfat, cheese, beef and mutton tallow, partially hydrogenated vegetable oils, human milk and mango pulp (Kinney and Knowlton, 1997, and references therein). The 9,15-linoleic acid isomer is likely a result of the activity of the fatty acid desaturase encoded by the FAD3 gene that normally inserts a d-15 double bond into 9,12-linoleic acid to produce 9,12,15-linolenic acid. In the DP-305423-1 soybean, the 9,12-linoleic acid content is significantly reduced (Table 16) so that the FAD3-encoded desaturase probably creates a small amount of the 9,15-linoleic acid isomer by desaturating the abundant 9-oleic acid substrate at the d-15 position. This view is supported by the results of crossing high oleic soybeans (OECD identifier DD-Ø026ØØ5-3, AGBIOS database) with soybeans containing a silenced FAD3 gene. In the resulting progeny the 9,15-linoleic acid isomer is either reduced or eliminated (Kinney and Knowlton, 1997).

The mean values of two minor fatty acids, heptadecanoic acid (C17:0) and heptadecenoic acid (C17:1), in DP-305423-1 soybean were above the upper range of the statistical tolerance intervals and literature ranges for conventional soybean varieties. Mean values for C17:0 and C17:1 were statistically significantly different from those of control near isoline soybean. However, levels of heptadecanoic and heptadecenoic acid are in general still very low; each represents less than 1.2% of the total fatty acid content in DP-305423-1 soybean.

The detected increase in heptadecanoic acid (C17:0) and heptadecenoic acid (C17:1), in DP-305423-1 soybean is not unexpected, as expression of the GM-HRA protein likely results in a slight shift in availability of the GM-HRA enzyme substrates, pyruvate and 2-ketobutyrate. These two compounds are also substrates for the enzyme complex that initiates oil biosynthesis.

The mean values for myristic acid (C14:0), palmitoleic acid (C16:1), stearic acid (C18:0), arachidic acid (C20:0), eicosenoic acid (C20:1), behenic acid (C22:0) and lignoceric acid (C24:0) for DP-305423-1 soybean were within the statistical tolerance intervals and/or the combined literature ranges for these fatty acids in different soybean varieties. With exception of the behenic acid, the mean values for these fatty acids were statistically significantly different either above (palmitoleic, arachidic, eicosenoic, and lignoceric acids) or below (myristic and stearic acids) those in the control near isoline. Myristic, palmitoleic, arachidic, eicosenoic, behenic, and lignoceric acids are minor fatty acids, each comprising 0.05-0.5% of the total fatty acids in DP-305423-1 soybean; stearic acid comprises less then 4.5% in DP-305423-1 soybean. These fatty acids are common constituents of vegetable oils and common foodstuffs and are present at levels similar to those observed in DP-305423-1 soybean (USDA Nutrition Database, Release 19).

Eicosadienoic acid (C20:2) was undetectable in DP-305423-1 soybean. Similarly, reference soybean varieties also lacked measurable concentrations of this fatty acid. A very low level of the eicosadienoic acid was detectable in the control near isoline soybean; however, this difference with DP-305423-1 soybean was not statistically significant (adjusted P-value>0.05).

TABLE 16

Major Fatty Acids in Soybean Grain

| Fatty Acid (% Total) | | Control (Null Segregant) | 305423 Soybean | Tolerance Interval[1] | Combined Literature Ranges[2] |
|---|---|---|---|---|---|
| Myristic Acid (C14:0) | Mean[3] | 0.0742 | 0.0451 | 0-0.174 | 0.0710-0.238 |
| | Range[4] | 0.0676-0.0807 | 0.0419-0.0522 | | |
| | Adjusted P-value[5] | | 0.0007[7] | | |
| | P-value[6] | | 0.0001 | | |
| Palmitic Acid (C16:0) | Mean | 10.3 | 6.28 | 2.93-19.6 | 7.00-15.8 |
| | Range | 9.77-10.7 | 5.71-7.27 | | |
| | Adjusted P-value | | 0.0007[7] | | |
| | P-value | | 0.0001 | | |
| Palmitoleic Acid (C16:1) | Mean | 0.0860 | 0.0946 | 0.0110-0.177 | 0.0860-0.194 |
| | Range | 0.0751-0.0948 | 0.0835-0.105 | | |
| | Adjusted P-value | | 0.0248[7] | | |
| | P-value | | 0.0053 | | |
| Heptadecanoic Acid (C17:0) | Mean | 0.113 | 0.798 | 0.0722-0.131 | 0.0850-0.146 |
| | Range | 0.0993-0.127 | 0.703-0.890 | | |
| | Adjusted P-value | | 0.0007[7] | | |
| | P-value | | 0.0001 | | |
| Heptadecenoic Acid (C17:1) | Mean | 0.0614 | 1.19 | 0.0351-0.0732 | 0.0730-0.0870 |
| | Range | 0.0513-0.0762 | 1.01-1.51 | | |
| | Adjusted P-value | | 0.0007[7] | | |
| | P-value | | 0.0001 | | |
| Stearic Acid (C18:0) | Mean | 4.98 | 4.36 | 0.852-8.34 | 2.00-5.88 |
| | Range | 4.36-5.89 | 3.90-5.01 | | |
| | Adjusted P-value | | 0.0007[7] | | |
| | P-value | | 0.0001 | | |
| Oleic Acid (C18:1) | Mean | 21.1 | 76.5 | 11.3-32.6 | 14.3-34.0 |
| | Range | 18.0-24.1 | 68.7-79.4 | | |
| | Adjusted P-value | | 0.0007[7] | | |
| | P-value | | 0.0001 | | |
| Linoleic Acid (C18:2) | Mean | 52.5 | 3.62 | 41.7-64.3 | 42.3-60.0 |
| | Range | 50.2-54.3 | 1.53-8.98 | | |
| | Adjusted P-value | | 0.0007[7] | | |
| | P-value | | 0.0001 | | |
| Linoleic Acid (C18:2) Isomer (9, 15) | Mean | 0.247 | 0.341 | NA[8] | NR[9] |
| | Range | 0-0.532 | 0.143-0.456 | | |
| | Adjusted P-value | | 0.1787 | | |
| | P-value | | 0.0699 | | |
| Linolenic Acid (C18:3) | Mean | 9.35 | 5.39 | 1.15-14.7 | 2.00-12.5 |
| | Range | 7.83-11.2 | 4.03-7.32 | | |
| | Adjusted P-value | | 0.0007[7] | | |
| | P-value | | 0.0001 | | |
| Arachidic Acid (C20:0) | Mean | 0.396 | 0.450 | 0.103-0.619 | 0-1.00 |
| | Range | 0.348-0.479 | 0.393-0.528 | | |
| | Adjusted P-value | | 0.0007[7] | | |
| | P-value | | 0.0001 | | |
| Eicosenoic Acid (C20:1) | Mean | 0.170 | 0.347 | 0.0549-0.319 | 0.140-0.350 |
| | Range | 0.135-0.201 | 0.290-0.394 | | |
| | Adjusted P-value | | 0.0007[7] | | |
| | P-value | | 0.0001 | | |
| Eicosadienoic Acid (C20:2) | Mean | 0.0225 | 0 | NA[8] | 0.0770-0.245 |
| | Range | 0-0.0502 | 0-0 | | |
| | Adjusted P-value | | 0.0928 | | |
| | P-value | | 0.0298 | | |
| Behenic Acid (C22:0) | Mean | 0.414 | 0.427 | 0.188-0.458 | 0.277-0.595 |
| | Range | 0.349-0.566 | 0.382-0.546 | | |
| | Adjusted P-value | | 0.5468 | | |
| | P-value | | 0.3779 | | |

TABLE 16-continued

Major Fatty Acids in Soybean Grain

| Fatty Acid (% Total) | | Control (Null Segregant) | 305423 Soybean | Tolerance Interval[1] | Combined Literature Ranges[2] |
|---|---|---|---|---|---|
| Lignoceric Acid (C24:0) | Mean | 0.114 | 0.143 | 0-0.310 | NR[9] |
| | Range | 0.0845-0.139 | 0.115-0.173 | | |
| | Adjusted P-value | | 0.0017[7] | | |
| | P-value | | 0.0003 | | |

[1]Negative tolerance limits have been set to zero.
[2]Literature ranges are taken from published literature for soybeans (OECD, 2001; ILSI 2004).
[3]Least Square Mean
[4]Range denotes the lowest and highest individual value across locations.
[5]False Discovery Rate (FDR) adjusted P-value
[6]Non-adjusted P-value
[7]Statistically significant difference; adjusted P-value <0.05
[8]Statistical analysis was not available (NA), due to lack of measurable concentrations detected for this analyte.
[9]Analyte ranges were not reported (NR) in the published literature references.

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed:

1. A soybean plant comprising nucleotides 18,652-31,579 of SEQ ID NO:5.

2. A soybean seed comprising nucleotides 18,652-31,579 of SEQ ID NO:5.

3. The soybean plant of claim 1, further comprising nucleotides 12,164-14,494 of SEQ ID NO:6, nucleotides 5751-7813 of SEQ ID NO:7 and nucleotides 2899-7909 of SEQ ID NO:82.

4. The soybean seed of claim 2, wherein said seed has an oleic acid level of greater than 70%.

5. The soybean seed of claim 2, further comprising nucleotides 12,164-14,494 of SEQ ID NO:6, nucleotides 5751-7813 of SEQ ID NO:7 and nucleotides 2899-7909 of SEQ ID NO:82.

6. The soybean seed of claim 5, wherein said seed has an oleic acid level of greater than 70%.

7. A method of producing an ALS inhibitor tolerant plant comprising breeding a plant comprising a polynucleotide comprising nucleotides 18,652-31,579 of SEQ ID NO:5, and selecting progeny by analyzing for progeny that comprise a polynucleotide comprising nucleotides 18,652-31,579 of SEQ ID NO: 5.

8. A method for controlling weeds in an area of cultivation comprising applying an effective amount of an ALS inhibitor to the area of cultivation comprising soybean plants comprising a polynucleotide comprising nucleotides 18,652-31,579 of SEQ ID NO:5.

9. The method of claim 8 further comprising applying an effective amount of at least one herbicide selected from the group consisting of inhibitors of Acetyl CoA carboxylase, inhibitors of Photosystem II, Photosystem I electron diverters, inhibitors of PPO, inhibitors of carotenoid biosynthesis, inhibitors of 4-HPPD, inhibitors of DHP, inhibitors of EPSP synthase, inhibitors of glutamine synthetase, inhibitors of microtubule assembly, inhibitors of mitosis/microtubule organization, inhibitors of cell division, inhibitors of cell wall synthesis, membrane disruptors, inhibitors of lipid synthesis by other than ACC inhibition, synthetic auxins, inhibitors of auxin transport, and Other Mechanism of Action herbicides, as described in Table 2.

10. A method for controlling weeds in an area of cultivation comprising applying an effective amount of at least one herbicide selected from the group consisting of acetochlor, acifluorfen and its sodium salt, aclonifen, acrolein (2-propenal), alachlor, alloxydim, ametryn, amicarbazone, amidosulfuron, aminopyralid, amitrole, ammonium sulfamate, anilofos, asulam, atrazine, azimsulfuron, beflubutamid, benazolin, benazolin-ethyl, bencarbazone, benfluralin, benfuresate, bensulfuron-methyl, bensulide, bentazone, benzobicyclon, benzofenap, bifenox, bilanafos, bispyribac and its sodium salt, bromacil, bromobutide, bromofenoxim, bromoxynil, bromoxynil octanoate, butachlor, butafenacil, butamifos, butralin, butroxydim, butylate, cafenstrole, carbetamide, carfentrazone-ethyl, catechin, chlomethoxyfen, chloramben, chlorbromuron, chlorflurenol-methyl, chloridazon, chlorimuron-ethyl, chlorotoluron, chlorpropham, chlorsulfuron, chlorthal-dimethyl, chlorthiamid, cinidon-ethyl, cinmethylin, cinosulfuron, clethodim, clodinafop-ropargyl, clomazone, clomeprop, clopyralid, clopyralid-olamine, cloransulam-methyl, CUH-35 (2-methoxyethyl 2-[[[4-chloro-2-fluoro-5-[(1-methyl-2-propynyl)-oxy]-phenyl](3-fluorobenzoyl)-amino]carbonyl]-1-cyclohexene-1-carboxylate), cumyluron, cyanazine, cycloate, cyclosulfamuron, cycloxydim, cyhalofop-butyl, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, diclosulam, difenzoquat metilsulfate, diflufenican, diflufenzopyr, dimefuron, dimepiperate, dimethachlor, dimethametryn, dimethenamid, dimethenamid-P, dimethipin, dimethylarsinic acid and its sodium salt, dinitramine, dinoterb, diphenamid, diquat dibromide, dithiopyr, diuron, DNOC, endothal, EPTC, esprocarb, ethalfluralin, ethametsulfuron-methyl, ethofumesate, ethoxyfen, ethoxysulfuron, etobenzanid, fenoxaprop-ethyl, fenoxaprop-P-ethyl, fentrazamide, fenuron, fenuron-TCA, flamprop-methyl, flamprop-M-isopropyl, flamprop-M-methyl, flazasulfuron, florasulam, fluazifop-butyl, fluazifop-P-butyl, flucarbazone, flucetosulfuron, fluchloralin, flufenacet, flufenpyr, flufenpyr-ethyl, flumetsulam, flumiclorac-pentyl, flumioxazin, fluometuron, fluoroglycofen-ethyl, flupyrsulfuron-methyl and its sodium salt, flurenol, flurenol-butyl, fluridone, flurochloridone, fluroxypyr, flurtamone, fluthiacet-methyl, fomesafen, foramsulfuron, fosamine-ammonium, glufosinate, glufosinate-ammonium, glyphosate and its salts such as ammonium, isopropylammonium, potassium, sodium (including sesquisodium) and trimesium (alternatively named sulfosate), halosulfuron-methyl, haloxyfop-etotyl, haloxyfop-methyl, hexazinone, HOK-201 (N-(2,4-difluorophenyl)-1,5-dihydro-N-(1-methylethyl)-5-oxo-1-[(tetrahydro-2H-pyran-2-ylymethyl]-4H-1,2,4-triazole-4-carboxamide), imazamethabenz-methyl, imazamox, imazapic, imazapyr, imazaquin, imazaquin-ammonium, imazethapyr, imazethapyr-ammonium, imazosulfuron, indanofan, iodosulfuron-methyl, ioxynil, ioxynil octanoate, ioxynil-sodium, isoproturon, isouron, isoxaben, isoxaflutole, isoxachlortole, lactofen, lenacil, linuron, maleic hydrazide, MCPA and its salts (e.g., MCPA-dimethylammonium, MCPA-potassium and MCPA-sodium, esters (e.g., MCPA-2-ethylhexyl, MCPA-butotyl) and thioesters (e.g., MCPA-thioethyl), MCPB and its salts (e.g., MCPB-sodium) and esters (e.g., MCPB-ethyl), mecoprop, mecoprop-P, mefenacet, mefluidide, mesosulfuron-methyl, mesotrione, metam-sodium, metamifop, metamitron, metazachlor, methabenzthiazuron, methylarsonic acid and its calcium, monoammonium, monosodium and disodium salts, methyldymron, metobenzuron, metobromuron, metolachlor, S-metholachlor, metosulam, metoxuron, metribuzin, metsulfuron-methyl, molinate, monolinuron, naproanilide, napropamide, naptalam, neburon, nicosulfuron, norflurazon, orbencarb, oryzalin, oxadiargyl, oxadiazon, oxasulfuron, oxaziclomefone, oxyfluorfen, paraquat dichloride, pebulate, pelargonic acid, pendimethalin, penoxsulam, pentanochlor, pentoxazone, perfluidone, pethoxyamid, phenmedipham, picloram, picloram-potassium, picolinafen, pinoxaden, piperofos, pretilachlor, primisulfuron-methyl, prodiamine, profoxydim, prometon, prometryn, propachlor, propanil, propaquizafop, propazine, propham, propisochlor, propoxycarbazone, propyzamide, prosulfocarb, prosulfuron, pyraclonil, pyraflufen-ethyl, pyrasulfotole, pyrazogyl, pyrazolynate, pyrazoxyfen, pyrazosulfuron-ethyl, pyribenzoxim, pyributicarb, pyridate, pyriftalid, pyriminobac-methyl, pyrimisulfan, pyrithiobac, pyrithiobac-sodium, pyroxsulam, quinclorac, quinmerac, quinoclamine, quizalofop-ethyl, quizalofop-P-ethyl, quizalofop-P-tefuryl, rimsulfuron, sethoxydim, siduron, simazine, simetryn, sulcotrione, sulfentrazone, sulfometuron-methyl, sulfosulfuron, 2,3,6-TBA, TCA, TCA-sodium, tebutam, tebuthiuron, tefuryltrione, tembotrione, tepraloxydim, terbacil, terbumeton, terbuthylazine, terbutryn, thenylchlor, thiazopyr, thiencarbazone, thifensulfuron-methyl, thiobencarb, tiocarbazil, topramezone, tralkoxydim, tri-allate, triasulfuron, triaziflam, tribenuron-methyl, triclopyr, triclopyr-butotyl, triclopyr-triethylammonium, tridiphane, trietazine, trifloxysulfuron, trifluralin, triflusulfuron-methyl, tritosulfuron and vernolate to the area of cultivation comprising soybean plants comprising a polynucleotide comprising nucleotides 18,652-31,579 of SEQ ID NO:5.

11. A method for controlling weeds in an area of cultivation comprising applying an effective amount of at least one sulfonylurea herbicide and at least one imidazolinone herbicide to the area of cultivation comprising soybean plants comprising a polynucleotide comprising nucleotides 18,652-31,579 of SEQ ID NO:5.

\* \* \* \* \*